United States Patent
Yamamoto et al.

(10) Patent No.: US 10,028,983 B2
(45) Date of Patent: Jul. 24, 2018

(54) COMPOSITIONS AND METHODS FOR PROMOTING GROWTH OF BENEFICIAL MICROBES TO TREAT OR PREVENT DISEASE OR PROLONG LIFE

(71) Applicant: The Regents of the University of California, Oakland, CA (US)

(72) Inventors: Mitsuko L. Yamamoto, Alameda, CA (US); Robert H. Schiestl, Encino, CA (US); Ramune Reliene, Delmar, NY (US); James Borneman, Riverside, CA (US); Laura L. Presley, Santa Maria, CA (US); Jonathan Braun, Tarzana, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/769,734

(22) PCT Filed: Feb. 19, 2014

(86) PCT No.: PCT/US2014/017142
§ 371 (c)(1),
(2) Date: Aug. 21, 2015

(87) PCT Pub. No.: WO2014/130540
PCT Pub. Date: Aug. 28, 2014

(65) Prior Publication Data
US 2016/0000841 A1 Jan. 7, 2016

Related U.S. Application Data

(60) Provisional application No. 61/909,242, filed on Nov. 26, 2013, provisional application No. 61/956,186, filed on Feb. 22, 2013.

(51) Int. Cl.
*A61K 35/747* (2015.01)
*A61K 35/76* (2015.01)
(Continued)

(52) U.S. Cl.
CPC .......... *A61K 35/747* (2013.01); *A61K 35/741* (2013.01); *A61K 35/76* (2013.01); *A61K 45/06* (2013.01)

(58) Field of Classification Search
None
See application file for complete search history.

(56) References Cited

U.S. PATENT DOCUMENTS

2004/0005304 A1* 1/2004 Brudnak ................ A61K 31/70
424/93.45

OTHER PUBLICATIONS

Bouilly-Gauthier, D; et al; "Clinical evidence of benefits of a dietary supplement containing probiotic and carotenoids on ultraviolet-induced skin damage" British Journal of Dermatology, 163, 536-543.*

(Continued)

*Primary Examiner* — David W Berke-Schlessel
(74) *Attorney, Agent, or Firm* — Foley Hoag LLP; David P. Halstead; Allison Gilder

(57) ABSTRACT

Inoculation of ATM-deficient mice with probiotic microorganisms, such as *L. johnsonii*, changed immune parameters, decreased a marker of DNA damage and increased the lifespan of the mice. Compositions and methods described herein are useful for the treatment and prevention of Ataxia telangiectasia and other cancer-prone diseases, such as p53 deficiency-associated cancers. Compositions and methods of the present invention are also useful for treating and preventing radiation-induced toxicity to normal tissue in a subject being exposed to radiation. Compositions and methods of the invention can increase lifespan in a simple, non-invasive manner.

15 Claims, 12 Drawing Sheets

(51) Int. Cl.
*A61K 45/06* (2006.01)
*A61K 35/741* (2015.01)

(56) References Cited

OTHER PUBLICATIONS

Hsieh, Pei-Shan; et al; "Eradication of Helicobacter pylori Infection by the Probiotic Strains Lactobacillus johnsonii MH-68 and *L. salivarius* ssp. *salicinius* AP-32" Helicobacter, 17, 466-477, 2012.*
Wei, Jinxiong; et al; "Regulation of p53 tumor suppressor by Helicobacter pylori in gastric epithelial cells" Gastroenterology, 139, 1333-1343, 2010.*
Vitor, Jorge MB; Vale, Filipa F; "Alternative therapies for Helicobacter pylori: probiotics and phytomedicine" FEMS Immunology & Medical Microbiology, 63, 153-164, 2011.*
De Vrese et al., "Probiotics, Prebiotics, and Synbiotics," Adv Biochem Eng Biotechnol, 111: 1-66 (2008).
Huang et al., "Commensal Microbiota Alter the Abundance and TCR Responsiveness of Splenic Naïve CD4+ T Lymphocytes," Clin Immunol, 117: 221-230 (2005).
Li W, et al., "Kaempferol induces apoptosis in human HCT116 colon cancer cells cia the Ataxia-Telangiectasia Mutated-p53 pathway with the involvement of p53 Upregulated Modulator of Apoptosis," Chem Biol Interact, 177(2): 121-127 (2009).
Manoj Kumar, et al., "Cancer-preventing attributes of probiotics: an update," Int J Food Sci Nutr, 61(5): 473-496 (2010).
S. D. K. Kingma, et al., "Lactobacillus johnsonii N6.2 Stimulates the Innate Immune Response through Toll-Like Receptor 9 in Caco-2 Cells and Increases Intestinal Crypt Paneth Cell Number in BioBreeding Diabetes-Prone Rats," J Nutr, 141(6): 1023-1028 (2011).
Scupham et al., "Abundant and Diverse Fungal Microbiota in the Murine Intensine," Appl Environ Microbiol, 72: 793-801 (2006).

* cited by examiner

A

B

C

Survival of p53⁻/⁻ male mice developing lymphoma
Conventional Colony vs. Parental Colony all

COMPOSITIONS AND METHODS FOR PROMOTING GROWTH OF BENEFICIAL MICROBES TO TREAT OR PREVENT DISEASE OR PROLONG LIFE

CROSS-REFERENCE TO RELATED APPLICATIONS

This application is the U.S. national phase of International Patent Application No. PCT/US14/017142, filed Feb. 19, 2014, which claims the benefit of U.S. Provisional Application No. 61/956,186, filed on Feb. 22, 2013 and U.S. Provisional Application No. 61/909,242, filed on Nov. 26, 2013; the entire contents of which applications are incorporated by reference herein in their entirety.

STATEMENT REGARDING FEDERALLY SPONSORED RESEARCH

This invention was made with Government support under AI078885, CA133928, DK46763, ES009519, awarded by the National Institutes of Health. The Government has certain rights in the invention.

FIELD OF THE INVENTION

This invention relates to using intestinal bacteria to modify lymphoma penetrance and inflammation-mediated genotoxicity.

BACKGROUND OF THE INVENTION

Ataxia-telangiectasia (A-T) is an autosomal recessive disorder associated with high incidence of lymphoid malignancies, neurological degeneration, immunodeficiency, radiation sensitivity and genetic instability (Meyn, *Clin Genet*, 1999, 55:289-304). Approximately 30-40% of all A-T patients develop neoplasia during their life (Peterson et al., 1992, *Leukemia* 6 *Suppl.* 1:8-13): more than 40% of all tumors are non-Hodgkin's B cell lymphomas, about 20% acute lymphocytic leukemias, and 5% Hodgkin's lymphomas (Morrell et al., 1986, *J Natl Cancer Inst*, 77:89-92; Hecht and Hecht, 1990, *Cancer Genet Cytogenet*, 46:9-19; Taylor et al., 1996, *Blood* 87:423-438; Sandoval and Swift, 1998, *Med Pediatr Oncol* 31:491-97). Lymphoid malignancies are of both B and T cell origin. T cell tumors comprise T cell lymphoma, T acute lymphocytic leukemia and T prolymphocytic leukemia. A-T patients suffer from increased mortality due to malignancy, infections of the respiratory system and various rare complications (Boder et al., 1975, *Birth Defects Orig Artic Ser* 11(1):255-70; Crawford et al., 2006, *Arch Dis Child* 91(7):610-611; Gatti et al., 2001, *Clin Rev Allergy Immunol* 20(1):87-108). Currently, there is no therapy available to prevent cancer or progressive neurodegeneration.

A-T is caused by biallelic mutations in the ATM gene. Over 600 different ATM mutations have been described (LOVD—Leiden Open Variation Database; Curator: Patrick Concannon). The ATM gene encodes a ~350 kDa protein, phosphatidylinositol-3-like kinase, which is expressed abundantly in multiple tissues (Savitsky et al., 1995, *Science* 268:1749-1753; Chen and Lee, 1996, *J Biol Chem* 271: 33693-33697; Uziel et al., 1996, *Genomics* 33:317-320) and plays an important role in cell cycle checkpoint control as well as repair responses to DNA double strand breaks (DSBs) (Jeggo et al., 1998, *Trends Genet* 14:312-316; Rotman and Shiloh, 1998, *Hum Mol Genet* 7:1555-1563; Barzilai et al., 2002, *DNA Repair (Amst)* 1:3-25). Absence of functional ATM protein results in chromosomal breakage and rearrangements, aberrant V(D)J recombination, and heightened sensitivity to radiation and chemicals with radiomimetic and prooxidant activity.

Although investigations into A-T have been greatly enhanced by the development of mouse models, disease penetrance in genetically identical mouse colonies at different laboratories can vary widely. Some ATM-deficient (Atm$^{-/-}$) mice develop early lymphomas and have short life spans (2-5 months) (Barlow et al., 1996, *Cell*, 86:159-171; Elson et al., 1996, *Proc Natl Acad Sci USA* 106:1027-1032; Xu et al., 1996a, *Genes Dev* 10:2411-2422; Xu et al., 1996b, *Genes Dev* 10:2401-2410) while others display dramatically delayed phenotypes, where 50% of the mice remain viable after 7-12 months (Borghesani et al., 2000, *Proc Natl Acad Sci USA* 97:3336-3341; Petiniot et al., 2002, *Mol Cell Biol* 22:3174-3177; Schubert et al., 2004, *Hum Mol Genet* 13:1793-802; Reliene and Schiestl, 2006a, *DNA Repair (Amst)* 5:852-959. Lifespan studies on inbred and mixed background mice have failed to show phenotypic differences (Reliene and Schiestl, 2006b, *DNA Repair (Amst)* 5:651-653), suggesting other factors besides genetic diversity are contributing to disease penetrance. Environmental factors such as housing conditions and diet have been postulated to be contributing factors (Rao and Crockett, 2003, *Toxicol Pathol* 31:243-250). Herein, Applicants examined another potential contributor—the intestinal microbiota.

Intestinal bacteria have been implicated in several types of cancer. In animal models of colorectal cancer, lower incidences in germ-free animals point toward intestinal microbes playing a causative role (Rescigno, 2008, *Curr Drug Targets* 9:395-403; Rowland, 2009, *Curr Pharm Des* 15:1524-1527). *Helicobacter* species have been associated with enhanced carcinogenesis including liver cancer, colon cancer, and mammary carcinoma (Ward et al., 1994a, *Am J Pathol* 145:959-968; Ward et al., 1994b, *J Natl Cancer Inst* 86:1222-1227; Rao et al., 2006, *Cancer Res* 66:7395-7400). Conversely, probiotic formulations containing lactic acid bacteria have been shown to reduce the incidence of chemically mediated hepatocellular carcinoma and colon cancer in rats (Pool-Zobel et al., 1996, *Nutr Cancer* 26:365-380; Kumar et al., 2011, *Gene* 490:54-59).

According to the latest statistics reported by the American Cancer Society, the most common type of cancer currently is lung cancer, with more than 222,000 new cases expected in the United States in 2010. Prostate cancer follows with 217,730, breast cancer with 209,060, and colorectal with 142,570 new cases expected in 2010 (American Cancer Society, *Cancer Facts and Figures* 2010, 2010). It is estimated that half of all cancer patients will receive radiotherapy during the course of their treatment for cancer (Weiss and Landauer, 2003, *Toxicology* 189(1-2):1-20). Of those cancer patients who are cured it is estimated that 49% are cured by surgery, 40% by radiotherapy (RT) alone or combined with other treatments and 11% by chemotherapy alone or combined with other treatments (Levitt and Leer, 1996, *Acta Oncol* 35(8):965-6). Even in advanced or recurrent cases, radiotherapy is a highly effective option for temporary relief and control of symptoms (Levitt and Leer, 1996, *Acta Oncol* 35(8):965-6; Hoskin et al., 2001, *Clin Oncol (R Coll Radiol)* 13(2):88-90).

Radiotherapy is commonly used as a component of therapy for a wide range of malignant conditions. About half of all cancer patients receive radiation therapy as either curative or palliative treatments (American Cancer Society, *Cancer Facts and Figures* 2010, 2010). Radiotherapy is frequently used to achieve local or regional control of malignancies either alone or in combination with other treatments such as chemotherapy or surgery. Irradiation of noncancerous "normal" tissues during the course of therapeutic radiation can result in a range of side effects including self-limited acute toxicities, mild chronic symptoms, or severe organ dysfunction. The likelihood of developing these complications relates to the volume of an organ irradiated, the radiation dose delivered, fractionation of the delivered dose, the delivery of radiation modifiers, and individual radiosensitivity (Barnett et al., 2009, *Nat Rev Cancer* 9(2):134-42). Efforts to reduce the toxicities associated with therapeutic radiation have centered on both technological improvements in radiation delivery and chemical modifiers of radiation injury. Normal tissue toxicity remains a limiting factor in the treatment of many diseases with radiation therapy.

Tissue toxicity may range from no symptoms, to changes in tissue structure and function, and all the way to severe cosmetic and life-altering changes in organ function (Lee et al., 2009, *Int J Radiat Oncol Biol Phys* 73(4):1121-8). The effects of radiotherapy on normal tissue could be divided into early (acute) reactions, which occur within 90 days of radiotherapy, and late reactions that occur more than 90 days after radiotherapy, with a potential to continue for life span (Kirkpatrick et al., *Int J Radiat Oncol Biol Phys* 76(3 Suppl):S42-9). Early reactions principally affect high turnover tissues, such as skin, the gastrointestinal tract and bone marrow where the onset and severity of the reactions reflect the balance between the rate of stem/progenitor-cell killing and the rate of regeneration of surviving cells (Van der Kogel, 1993; Kirkpatrick et al., *Int J Radiat Oncol Biol Phys* 76(3 Suppl):S42-9). Severe acute reactions are rare and usually are associated with DNA DSB repair deficiency syndromes such as Ataxia Telangiectasia (ATM) and Nijmegen Breakage Syndrome (NBS).

Thus, there is a long felt need in the art for providing methods and compositions useful for the treatment, prevention and delaying onset of AT-associated conditions and cancer as well as radiation-induced toxicity to normal tissue during and/or caused by radiation treatment. The present invention described herein, provides such compositions and methods.

BRIEF SUMMARY OF THE INVENTION

The compositions and methods of the present disclosure may be used for the prognosis, treatment and/or prevention of disease, including diseases related to genome instability, for prolonging life expectancy as well as for delaying cancer onset and are applicable to a variety of cancer-prone diseases as well as for delaying cancer in the general population. Diseases related to genome instability include ataxia telangiectasia (AT).

The compositions and methods described herein may also be used for the prognosis, treatment and/or prevention of a p53-deficient cancer in a subject, for prolonging life expectancy as well as for delaying cancer onset and are applicable to a variety of p53-deficient cancers.

Further, the compositions and methods described herein may be used for the treatment and/or prevention of radiation-induced toxicity to normal tissue, e.g., occurring during radiation treatment or caused by radiation treatment in a subject.

Applicants herein provide cocktails of pre-biotics, probiotics and/or anti-biotics that can be used as to delay symptoms of genome instability syndromes, such as carcinogenesis and mortality. The mechanistic interaction between intestinal microbiota and cancer is difficult to understand; however, without being bound by theory, Applicants believe there is substantial cross-talk between microbiota and the immune system that can lead to inflammation and cytotoxicity. The immune response can both promote and mitigate carcinogenesis. In a similar manner, Applicants provide compositions and methods for promoting the growth of beneficial bacteria and inhibiting the growth of detrimental bacteria, thereby improving prognosis of diseases including, but not limited to, premature carcinogenesis as well as the health of the general population.

Using an ataxia-telangiectasia (A-T) mouse model, comparison of several isogenic mouse colonies harboring different bacterial communities demonstrated that intestinal microbiota are a major contributor to lymphoma latency and penetrance, lifespan, molecular oxidative stress, and systemic leucocyte genotoxicity. High throughput sequence analysis of rRNA genes identified mucosa-associated bacterial phylotypes that were colony-specific. *Lactobacillus johnsonii*, which was deficient in the more cancer-prone mouse colony, was causally tested for its capacity to confer reduced genotoxicity when restored by short-term oral transfer. This intervention decreased systemic genotoxicity, a response associated with reduced basal leucocyte and cytokine inflammatory state, and mechanistically linked to the host cell biology of systemic genotoxicity. Intestinal microbiota are thus a potentially modifiable trait for translational intervention in individuals at risk for B cell lymphoma and other diseases driven by genotoxicity or the oxidative molecular stress response.

An objective of Applicants' experiments was to examine the role of intestinal bacteria in the penetrance of lymphoma in Atm−/− mice. Applicants first demonstrate the effects of housing and intestinal bacteria on lifespan, lymphoma latency, oxidative stress, and systemic DNA damage (or genotoxicity). Next, high throughput sequence analysis was used to identify mucosa-associated bacteria from animals reared in two distinct housing conditions, differing in intestinal microbiota and the aforementioned ATM-deficient traits. Finally, after determining that *Lactobacillus johnsonii* was higher in abundance in a more cancer-resistant mouse colony, its ability to reduce systemic inflammation and genotoxicity when administered to animals from the more cancer-prone colony was demonstrated.

Applicants' invention described herein provides for altering the intestinal microbiota of AT patients using specific combinations of pre-biotics, pro-biotics and/or anti-biotics to establish a defined intestinal microbiota that can increase their lifespan in a simple, non-invasive manner. Furthermore, Applicants demonstrate that effects of intestinal microbiota are exacerbated in ATM-deficient mice since they are cancer-prone and changes in the intestinal microbiota may add as much as 20 to 30% to the life-span in wildtype mice or humans.

The present invention provides a method for treating, preventing, or delaying the onset of disease. The disease may be related to genome instability, such as ataxia telangiectasia, p53 deficiency, or exposure to radiation. In some embodiments, this method comprises of administering to a subject suffering from a disease related to genome instability a therapeutically effective amount of a composition comprising a probiotic microorganism. Thereby the disease in the subject is treated, prevented, or its onset is delayed.

The present application describes various compositions comprising or consisting essentially of beneficial microorganisms and useful in the method for treating, preventing, or delaying the onset of a disease may be related to genome instability, such as ataxia telangiectasia, p53 deficiency, or exposure to radiation. In some embodiments, a composition comprises a *Lactobacillus* sp. A preferred *Lactobacillus* sp is *Lactobacillus johnsonii*. A preferred *Lactobacillus johnsonii* is *Lactobacillus johnsonii* 456.

In some embodiments, the method for treating, preventing, or delaying the onset of a disease may be related to genome instability, such as ataxia telangiectasia, p53 deficiency, or exposure to radiation, comprises sustaining a beneficial level of the probiotic microorganism in the subject. In some embodiments, the method comprises restoring the presence of a beneficial level of the probiotic microorganism in the subject. In some embodiments, the method comprises selecting a subject having a disease related to genome instability, such as ataxia telangiectasia, p53 deficiency, or exposure to radiation.

In some embodiments, the method comprises inhibiting the growth of one or more detrimental microorganisms in the subject. In some embodiments this is achieved by administering to the subject a therapeutically effective amount of an antibiotic. In some embodiments, this is achieved by administering to the subject a therapeutically effective amount of a composition comprising two or more antibiotics. In some embodiments, this is achieved by administering one or more bacteriophages that target one or more detrimental microorganisms. In some embodiments, the method comprises administering to the subject a combination of one or more beneficial microorganisms and one or more antibiotics. In some embodiments, the method comprises administering to the subject a combination of one or more beneficial microorganisms and one or more bacteriophages. In some embodiments, the method comprises administering to the subject a combination of one or more bacteriophages and one or more antibiotics. In some embodiments, the method comprises administering to the subject a combination of one or more beneficial microorganisms, one or more antibiotics, and one or more bacteriophages.

In some embodiments, the disease is an ataxia telangiectasia (AT)-associated condition in a subject having AT. In some embodiments, this method comprises administering to a subject having AT and diagnosed with an AT-associated condition or at risk of developing an AT-associated condition a therapeutically effective amount of a composition comprising a probiotic microorganism. Thereby the AT-associated condition in the subject is treated, prevented, or its onset is delayed.

As one of ordinary skill in the art will appreciate various AT-associated conditions can be treated, prevented, or their onset being delayed using the teaching herein. In some embodiments, the AT-associated condition is selected from the group consisting of a cancerous condition, a neurological degeneration, an immunodeficiency, an inflammatory condition, an inflammation-induced genotoxicity, a radiation sensitivity, an abundance of hepatic and/or migratory cells and a genetic instability.

The cancerous condition may be selected from hematologic cancer and a lymphoid malignancy. The hematologic cancer may be selected from neoplasia, non-Hodgkin's B cell lymphoma, acute lymphocytic leukemia, and Hodgkin's lymphoma.

As one of ordinary skill in the art will appreciate, various inflammatory conditions can be treated, prevented, or their onset delayed using the teachings herein. In some embodiments, the inflammatory condition is selected from a substantially increased expression level of transforming growth factor type beta, a substantially increased expression level of interleukin (IL)-10, a substantially increased expression level of IL-4, a substantially decreased expression level of myeloid differentiation primary response 88, a substantially decreased expression level of IL-12, a substantially decreased expression level IL-1β, and a substantially decreased expression level of interferon gamma. When the inflammatory condition is associated with AT, the substantially increased and substantially decreased expression levels are in comparison to the respective expression levels in a subject not having AT.

As one of ordinary skill in the art will appreciate, various inflammation-induced gentotoxicities can be treated, prevented, or their onset delayed using the teachings herein. In some embodiments, the inflammation-induced genotoxicity is selected from DNA damage, DNA instability, DNA breakage, and DNA deletion.

As one of ordinary skill in the art will appreciate, various diseases related to genetic instabilities can be treated, prevented, or their onset delayed using the teachings herein. In some embodiments, the disease related to genetic instability is selected from Nijmegen Breakage Syndrome, Fanconi's anemia, Werner Syndrome, Blooms Syndrome, and Li Fraumeni Disease.

The present invention describes various compositions comprising or consisting essentially of beneficial microorganisms and useful in methods for treating, preventing, or delaying the onset of an ataxia telangiectasia (AT)-associated condition in a subject having AT. In some embodiments, a composition comprises a *Lactobacillus* sp. A preferred *Lactobacillus* sp is *Lactobacillus johnsonii*. A preferred *Lactobacillus johnsonii* is *Lactobacillus johnsonii* 456.

*Lactobacillus johnsonii* 456 was deposited at the American Type Tissue Collection Depository, having an address of 10801 University Boulevard, Manassas, Va. 20110-2209 U.S.A. and was received on May 18, 2017, in accordance with the provisions of the Budapest Treaty on the International Recognition of the Deposit of Microorganisms for the Purposes of Patent Procedure under deposit number PTA-124205. In accordance with the United States Code Of Federal Regulations (see 37 CFR § 1.808) and the United States Patent And Trademark Office's Manual Of Patent Examination ("MPEP") (see § 2410.01), all restrictions imposed by the depositor on the availability to the public of the deposited material (except as permitted by the MPEP) will be irrevocably removed upon the granting of any patent issuing from this application or from any continuing application based thereon.

In some embodiments, the method may be a method for treating, preventing, or delaying the onset of a disease related to genome instability, such as an ataxia telangiectasia (AT)-associated condition in a subject having AT, that comprises sustaining a beneficial level of the probiotic microorganism in the subject. In some embodiments, the method comprises restoring the presence of a beneficial level of the probiotic microorganism in the subject. In some embodiments, the method comprises selecting a subject having a cancerous AT-associated condition.

In some embodiments, the method comprises inhibiting the growth of one or more detrimental microorganisms in the subject. In some embodiments, this is achieved by administering to the subject a therapeutically effective amount of an antibiotic. In some embodiments, this is achieved by administering to the subject a therapeutically effective amount of a composition comprising two or more antibiotics. In some embodiments, this is achieved by administering one or more bacteriophages that target one or more detrimental microorganisms. In some embodiments, the method comprises administering to the subject a combination of one or more beneficial microorganisms and one or more antibiotics. In some embodiments, the method comprises administering to the subject a combination of one or more beneficial microorganisms and one or more bacteriophages. In some embodiments, the method comprises administering to the subject a combination of one or more bacteriophages and one or more antibiotics. In some embodiments, the method comprises administering to the subject a combination of one or more beneficial microorganisms, one or more antibiotics, and one or more bacteriophages.

The invention also provides compositions useful for treating, preventing, or delaying the onset of cancerous condition in a subject having a p53 deficiency. In some embodiments of this method, the method comprises administering to a subject having a p53 deficiency and diagnosed with a p53 deficiency-associated cancer or at risk of developing a p53 deficiency-associated cancer a therapeutically effective amount of a composition comprising a probiotic microorganism. Thereby the p53 deficiency-associated cancer in the subject is treated, prevented, or its onset is delayed.

As one of ordinary skill in the art will appreciate, various p53 deficiency-associated cancers can be treated, prevented, or their onset delayed using the teaching herein. In some embodiments, the p53 deficiency-associated cancer is selected from a lung cancer, a sarcoma, a gastrointestinal cancer, a cancer of the genitourinary tract, a liver cancer, a skin cancer, a gynecological cancer, a bone cancer, a cancer of the nervous system, a hematologic cancer, a cancer of the adrenal glands, and a cancer associated with Li Fraumeni Disease.

The present invention describes various compositions comprising or consisting essentially of beneficial microorganisms and useful in the method for treating, preventing, or delaying the onset of cancerous condition in a subject having a p53 deficiency. In some embodiments, a composition comprises a *Lactobacillus* sp. A preferred *Lactobacillus* sp is *Lactobacillus johnsonii*. A preferred *Lactobacillus johnsonii* is *Lactobacillus johnsonii* 456.

In some embodiments, the method for treating, preventing, or delaying the onset of cancerous condition in a subject having a p53 deficiency comprises sustaining a beneficial level of the probiotic microorganism in the subject. In some embodiments, the method comprises restoring the presence of a beneficial level of the probiotic microorganism in the subject. In some embodiments, the method comprises selecting a subject having a p53 deficiency.

In some embodiments, the method comprises inhibiting the growth of one or more detrimental microorganisms in the subject. In some embodiments, this is achieved by administering to the subject a therapeutically effective amount of an antibiotic. In some embodiments, this is achieved by administering to the subject a therapeutically effective amount of a composition comprising two or more antibiotics. In some embodiments, this is achieved by administering one or more bacteriophages that target one or more detrimental microorganisms. In some embodiments, the method comprises administering to the subject a combination of one or more beneficial microorganisms and one or more antibiotics. In some embodiments, the method comprises administering to the subject a combination of one or more beneficial microorganisms and one or more bacteriophages. In some embodiments, the method comprises administering to the subject a combination of one or more bacteriophages and one or more antibiotics. In some embodiments, the method comprises administering to the subject a combination of one or more beneficial microorganisms, one or more antibiotics, and one or more bacteriophages.

The present invention also provides methods for treating, mitigating, or preventing damage to normal tissue in a subject being exposed to radiation. In some embodiments of this method, the method comprises administering to a subject previously exposed, being exposed, or intended to be exposed to radiation a therapeutically effective amount of a composition comprising a probiotic microorganism. Thereby the damage to normal tissue in the subject is treated, mitigated or prevented.

In some embodiments, the subject has a condition requiring exposure to radiation. The subject may be exposed to environmental radiation or accidental radiation.

The present invention describes various compositions comprising or consisting essentially of beneficial microorganisms and useful in the method for treating, mitigating, or preventing damage to normal tissue in a subject being exposed to radiation. In some embodiments, a composition comprises a *Lactobacillus* sp. A preferred *Lactobacillus* sp is *Lactobacillus johnsonii*. A preferred *Lactobacillus johnsonii* is *Lactobacillus johnsonii* 456.

In some embodiments, the method for treating, mitigating, or preventing damage to normal tissue in a subject being exposed to radiation comprises sustaining a beneficial level of the probiotic microorganism in the subject. In some embodiments, the method comprises restoring the presence of a beneficial level of the probiotic microorganism in the subject. In some embodiments, the method comprises selecting a subject previously exposed, being exposed, or intended to be exposed to radiation.

In some embodiments, the method for treating, mitigating, or preventing damage to normal tissue in a subject being exposed to radiation comprises inhibiting the growth of one or more detrimental microorganisms in the subject. In some embodiments, this is achieved by administering to the subject a therapeutically effective amount of an antibiotic. In some embodiments, this is achieved by administering to the subject a therapeutically effective amount of a composition comprising two or more antibiotics. In some embodiments, this is achieved by administering one or more bacteriophages that target one or more detrimental microorganisms. In some embodiments, the method comprises administering to the subject a combination of one or more beneficial microorganisms and one or more antibiotics. In some embodiments, the method comprises administering to the subject a combination of one or more beneficial microorganisms and one or more bacteriophages. In some embodiments, the method comprises administering to the subject a combination of one or more bacteriophages and one or more antibiotics. In some embodiments, the method comprises administering to the subject a combination of one or more beneficial microorganisms, one or more antibiotics, and one or more bacteriophages.

Further, the present invention provides methods for preventing a spontaneous genetic instability in a subject. In some embodiments of the method for preventing a spontaneous genetic instability in a subject, the method comprises administering to a subject in need of having a spontaneous genetic instability prevented a therapeutically effective amount of a composition comprising a probiotic microorganism. Thereby the spontaneous genetic instability in the subject is prevented. The spontaneous genetic instability, for example, can cause a spontaneous cancer in the subject. In some embodiments, the spontaneous cancer is a lymphoma.

In some embodiments, this method comprises selecting a subject in need of having a spontaneous genetic instability prevented.

The present invention also provides methods for reducing the occurrence of a spontaneous genetic instability in a subject. In some embodiments of the method for reducing the occurrence of a spontaneous genetic instability in a subject, the method comprises administering to a subject in need of having the occurrence of a spontaneous genetic instability reduced a therapeutically effective amount of a composition comprising a probiotic microorganism. Thereby the occurrence of a spontaneous genetic instability in the subject is prevented. The spontaneous genetic instability for example, can cause a spontaneous cancer in the subject. In some embodiments, the spontaneous cancer is a lymphoma. In some embodiments, this method comprises selecting a subject in need of having the occurrence of a spontaneous genetic instability reduced.

The present invention describes various compositions comprising or consisting essentially of beneficial microorganisms and useful in the method for reducing the occurrence of a spontaneous genetic instability in a subject. In some embodiments, a composition comprises a *Lactobacillus* sp. A preferred *Lactobacillus* sp is *Lactobacillus johnsonii*. A preferred *Lactobacillus johnsonii* is *Lactobacillus johnsonii* 456.

In some embodiments, the method for reducing the occurrence of a spontaneous genetic instability in a subject comprises the step of sustaining a beneficial level of the probiotic microorganism in the subject. In some embodiments, the method comprises the step of restoring the presence of a beneficial level of the probiotic microorganism in the subject. In some embodiments, the method comprises the step of selecting a subject at risk for spontaneous genetic instability.

In some embodiments, the method for reducing the occurrence of a spontaneous genetic instability in a subject comprises inhibiting the growth of one or more detrimental microorganisms in the subject. In some embodiments this is achieved by administering to the subject a therapeutically effective amount of an antibiotic. In some embodiments, this is achieved by administering to the subject a therapeutically effective amount of a composition comprising two or more antibiotics. In some embodiments, this is achieved by administering one or more bacteriophages that target one or more detrimental microorganisms. In some embodiments, the method comprises administering to the subject a combination of one or more beneficial microorganisms and one or more antibiotics. In some embodiments, the method comprises administering to the subject a combination of one or more beneficial microorganisms and one or more bacteriophages. In some embodiments, the method comprises administering to the subject a combination of one or more bacteriophages and one or more antibiotics. In some embodiments, the method comprises administering to the subject a combination of one or more beneficial microorganisms, one or more antibiotics, and one or more bacteriophages.

DETAILED DESCRIPTION OF THE INVENTION

I. Definitions

Figure 1:
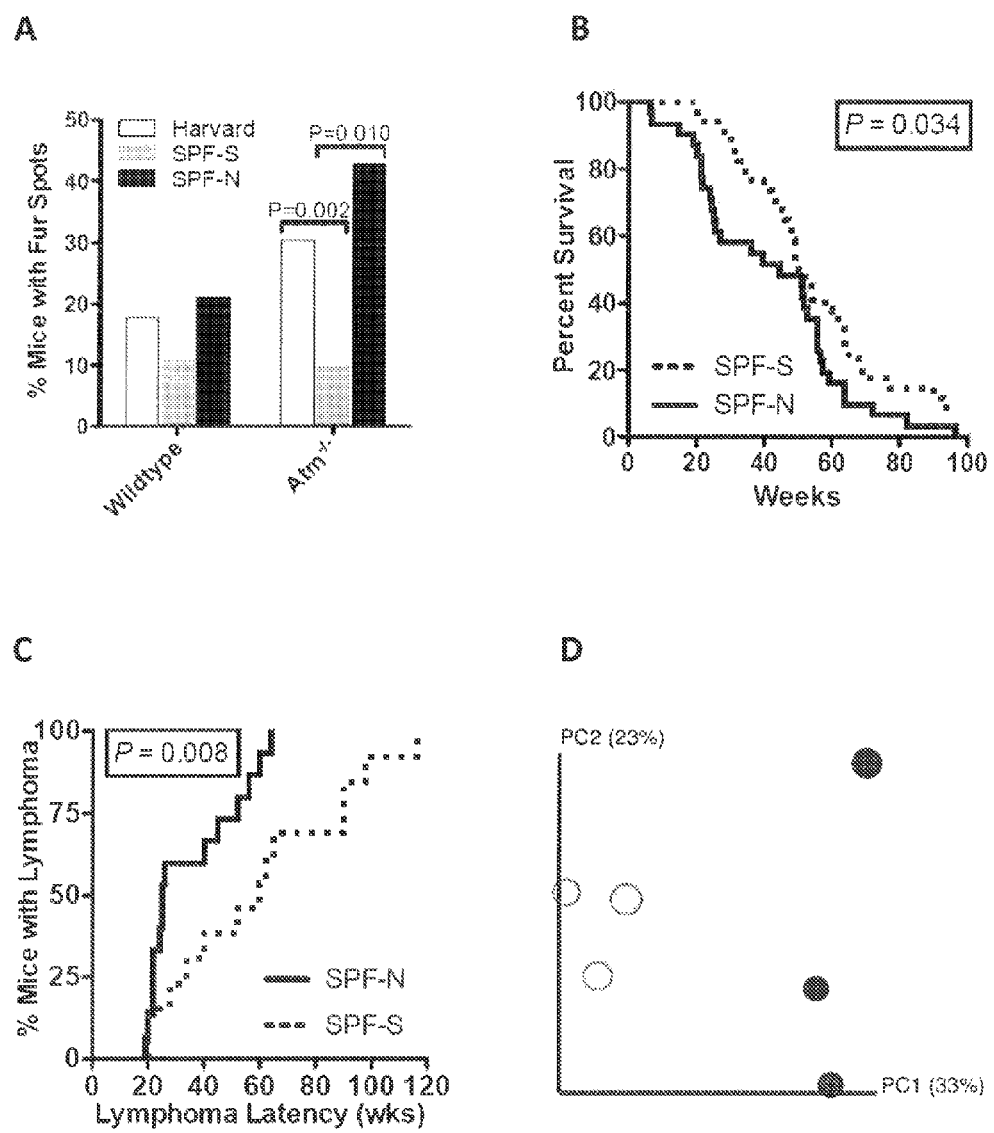
FIG. 1 depicts that genetic instability, lymphoma latency, and lifespan are increased in separate isogenic colonies of Atm$^{-/-}$ mice. (A) Genetic instability (DNA deletions) were measured by Pun reversion assay (n=220, 83 and 62 for wildtype mice with conventional microbiota (Harvard University), SPF-S and SPF-N, respectively). n=122, 40 and 28 for ATM$^{-/-}$ mice with conventional microbiota (Harvard University), in sterile (SPF-S) conditions, and semi-conventionalized, respectively. Conventional microbiota fur-spot data was adapted from Bioshop et al. (2000, Cancer Res 60:395-399). DNA deletions were increased in Atm-deficient mice in non-sterile (SPF-N) facilities but not in a sterile (SPF-S) facility. Fur-spots, which are a visual measure of DNA deletions were increased in Atm-deficient mice compared to their wildtype littermates in non-sterile (SPF-N) facilities but not in a sterile (SPF-S) facility. (B) The Kaplan-Meier survival curve (n=34 and 31 for SPF-S and SPF-N, respectively) of semi-conventional (SPF-N) ATM$^{-/-}$ mice and mice housed in sterile (SPF-S) environment is significantly different. (C) Lymphoma latency was determined for the subset of mice developing lymphoma (n=13 and 15 for SPF-S and SPF-N, respectively) using the logrank test. Lymphoma latency is decreased in mice housed in non-sterile (SPF-N) conditions. In the experiment shown, of the mice which developed lymphomas (~75% of Atm-deficient mice in both sterile (SPF-S) and non-sterile (SPF-N) conditions), the median age at which Atm-deficient mice in the non-sterile (SPF-N) conditions developed lymphomas was 25 weeks versus 60 weeks in sterile (SPF-S) conditions. (D) An unweighted UniFrac analysis of bacteria in Atm+/– mice in SPF-S and SPF-N conditions. Spheres around points indicate the 95% confidence ranges estimated by bootstrap resampling of data sets. Details are described herein, e.g., in Example B.

Throughout the present specification and the accompanying claims the words "comprise," "include," and "have" and variations thereof such as "comprises," "comprising," "includes," "including," "has," and "having" are to be interpreted inclusively. That is, these words are intended to convey the possible inclusion of other elements or integers not specifically recited, where the context allows. No language in the specification should be construed as indicating any non-claimed element essential to the practice of the invention.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximately") one particular value, and/or to "about" (or "approximately") another particular value. When such a range is expressed, another embodiment includes from the one particular value and/or to the other particular value. Similarly, when values are expressed as approximations, by use of the antecedent "about" or "approximately" it will be understood that the particular value forms another embodiment. It will be further understood that the endpoints of each of the ranges are disclosed both in relation to the other endpoint, and independently of the other endpoint.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e. g. "such as") provided herein is intended merely to better illuminate the invention and does not pose a limitation on the scope of the invention otherwise claimed.

Units, prefixes, and symbols are denoted in their Système International de Unites (SI) accepted form. Unless otherwise indicated, nucleic acids are written left to right in 5' to 3' orientation; amino acid sequences are written left to right in amino to carboxy orientation.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "about" refers to a range of values of plus or minus 10% of a specified value. For example, the phrase "about 200" includes plus or minus 10% of 200, or from 180 to 220, unless clearly contradicted by context.

As used herein, the term "administering" means the actual physical introduction of a composition into or onto (as appropriate) a host or cell. Any and all methods of introducing the composition into the host or cell are contemplated according to the invention; the method is not dependent on any particular means of introduction and is not to be so construed. Means of introduction are well-known to those skilled in the art, and also are exemplified herein.

As used herein, administration "in combination" refers to both simultaneous and sequential administration of two or more agents or compositions. Concurrent or combined administration, as used herein, means that two or more agents or compositions are administered to a subject either (a) simultaneously, or (b) at different times during the course of a common treatment schedule. In the latter case, the two or more agents or compositions are administered sufficiently close in time to achieve the intended effect.

As used herein, the terms "altering the immune response" or "regulating the immune response" or grammatical equivalents thereof, refer to any alteration in any cell type involved in the immune response. The definition is meant to include an increase or decrease in the number of cells, an increase or decrease in the activity of the cells, or any other changes which can occur within the immune system. The cells may be, but are not limited to, T lymphocytes, B lymphocytes, natural killer (NK) cells, macrophages, eosinophils, mast cells, dendritic cells, or neutrophils.

As used herein, the term "bacteriophage" refers to a virus that infects and replicates within bacteria. Bacteriophages are composed of proteins that encapsulate a genome comprising either DNA or RNA. Bacteriophages replicate within bacteria following the injection of their genome into the bacterial cytoplasm. Bacteriophages include "lytic bacteriophages," which disrupt bacterial metabolism and cause the bacterium to lyse, i.e., break open.

As used herein, the terms "cancer" "cancer cell," "tumor," "transformed" cell or "transformation" refer to spontaneous or induced phenotypic changes of a cell or tissue that do not necessarily involve the uptake of new genetic material. The phenotypic changes include, but are not limited to, immortalization of cells, aberrant growth control, nonmorphological changes, and/or malignancy. "Cancer" or "tumor" is intended to include any neoplastic growth in a patient, including an initial tumor and any metastases. The cancer can be of the liquid or solid tumor type. Specific cancers are amenable to treatment and/or prevention using methods and compositions of the invention are described herein.

As used herein, the abbreviation "CM" means conventional mice and conventional conditions.

As used herein, the terms "effective amount", "effective dose", "sufficient amount", "amount effective to", "therapeutically effective amount" or grammatical equivalents thereof mean a dosage sufficient to produce a desired result, to ameliorate, or in some manner, reduce a symptom or stop or reverse progression of a condition and provide either a subjective relief of a symptom(s) or an objectively identifiable improvement as noted by a clinician or other qualified observer. Amelioration of a symptom of a particular condition by administration of a pharmaceutical composition described herein refers to any lessening, whether permanent or temporary, lasting, or transitory, that can be associated with the administration of the pharmaceutical composition. With respect to "effective amount", "effective dose", "sufficient amount", "amount effective to", "therapeutically effective amount" of a probiotic microorganism, the dosing range varies with the probiotic microorganism used, the route of administration and the potency of the particular probiotic microorganism.

Ataxia telangiectasia is abbreviated "AT."

As used herein, the term "biologically active" when referring to a probiotic microorganism or a composition comprising a probiotic microorganism refers to a probiotic microorganism or a composition comprising a probiotic microorganism that allows for it, or a portion thereof to be administered, to be absorbed by, incorporated to, or otherwise be made physiologically available to a subject or patient to whom it is administered.

As used herein, the terms "detrimental microorganism" and "pathogen" are used interchangeably and refer to microorganisms, including some bacteria, that are harmful to human health. Preventing the growth of detrimental microorganisms may improve prognosis of diseases including, but not limited to, premature carcinogenesis as well as the health of the general population. Non-limiting examples of detrimental microorganisms include species of the *Enterobacter, Helicobacter, Pseudomonas, Escherichia, Klebsiella, Staphylococcus, Proteus, Salmonella,* and *Shigella* genera, such as *Enterobacter cloacae, Helicobacter acinonychis, Helicobacter anseris, Helicobacter aurati, Helicobacter bilis, Helicobacter bizzozeronii, Helicobacter brantae, Helicobacter canadensis, Helicobacter canis, Helicobacter cetorum, Helicobacter cholecystus, Helicobacter cinaedi, Helicobacter cynogastricus, Helicobacter felis, Helicobacter fennelliae, Helicobacter ganmani, Helicobacter hepaticus, Helicobacter mesocricetorum, Helicobacter marmotae, Helicobacter muridarum, Helicobacter mustelae, Helicobacter pametensis, Helicobacter pullorum, Helicobacter pylori, Helicobacter rappini, Helicobacter rodentium, Helicobacter salomonis, Helicobacter trogontum, Helicobacter typhlonius, Helicobacter winghamensis, Salmonella enterica, Salmonella bongori, Salmonella subterranean, Salmonella typhimurium, Shigella dysenteriae, Shigella flexneri, Shigella boydii,* and *Shigella sonnei.* The detrimental microorganism may be selected from *Enterobacter cloacae, Helicobacter pylori, Helicobacter hepaticus, Salmonella typhimurium,* and *Shigella dysenteriae.* In some embodiments, the detrimental microorganism is a microorganism listed in Table 7B.

As used herein, "disorder", "disease" or "pathological condition" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information. Preferred "disorders", "diseases" or "pathological conditions" amenable to prevention and/or treatment using compositions and methods described herein are ataxia telangiectasia (AT) and cancer as well as radiation-induced toxicity to normal tissue during and/or caused by radiation treatment.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

As used herein, the term "fraction" denotes any fragment derived from a microorganism under consideration according to the invention and also endowed with efficacy for the treatment of AT, increasing longevity, decrease of lymphoma onset, and/or prevention of genetic instability, DNA damage, or genotoxicity.

As used herein, the term "genetic instability" refers to a mutation in a nucleic acid caused by exposure of a subject to radiation, to a carcinogen, to a virus, etc. The term "spontaneous genetic instability" refers to any condition that arises spontaneously in a subject not being exposed to radiation, to a carcinogen or to a virus, etc. that leads to an increase of a risk of developing cancer in the subject or to an increase of developing cancer in the subject.

As used herein, the term "inactivated" microorganism refers to a microorganism that is no longer capable, temporarily or definitively, of forming colonies in culture. As used herein, a "dead" microorganism is a microorganism that is no longer capable, definitively, of forming colonies in culture. Dead or inactivated microorganisms may have intact or ruptured cell membranes. Thus, the term "inactivated" also denotes microorganism extracts and lysates as detailed herein below. Dead or inactivated microorganisms may be produced via any method known to those skilled in the art. As used herein, the term "at least partly inactivated or dead" microorganism means a preparation of probiotic microorganisms in accordance with the invention comprising at least 80%, in particular at least 85%, more particularly at least 90%, or even at least 95%, or at least 99% of inactivated or dead probiotic microorganisms relative to the total amount of non-inactivated live probiotic microorganisms. The degree of inactivation or of death obtained depends on the application of the method used, which are adjusted by a person skilled in the art according to the degree of inactivation or death sought to be obtained.

The terms "individual," "subject," "host," and "patient," used interchangeably herein, refer to an animal, such as a mammal, including, but not limited to, murines, simians, felines, canines, equines, bovines, mammalian farm animals, mammalian sport animals, and mammalian pets and humans. Preferred is a human.

As used herein, the terms "inhibiting the growth of a cell, "inhibiting the growth of a population of cells" or grammatical equivalents thereof refer to inhibiting cell division and may include destruction of the cell. The term also refers to any inhibition in cell growth and proliferation characteristics in vitro or in vivo of a cell, preferably a cancer cell, such as inhibiting formation of foci, inhibiting anchorage independence, inhibiting semi-solid or soft agar growth, inhibiting loss of growth factor or serum requirements, inhibiting changes in cell morphology, inhibiting immortalization, inhibiting expression of tumor specific markers, and/or inhibiting formation of tumors of the cell. See, e.g., *Freshney, Culture of Animal Cells a Manual of Basic Technique* pp. 231-241 (3rd ed. 1994). Similarly, the terms "inhibiting the growth of a microorganism, "inhibiting the growth of a population of microorganisms" or grammatical equivalents thereof refer to inhibiting division of the microorganism and may include destruction of the microorganism.

The terms "isolated," "purified" or "biologically pure" refer to material that is substantially or essentially free of components that normally accompany it as found in its native state.

As used herein, a "lysate" commonly denotes a material obtained after the destruction or dissolution of biological cells via a phenomenon known as cell lysis, thus giving rise to the release of the intracellular biological constituents naturally contained in the cells of the microorganism under consideration. As used herein, the term "lysate" is used without preference to denote the whole lysate obtained via lysis of a microorganism under consideration or only a fraction thereof. Cell lysis may be accomplished via various techniques, such as an osmotic shock, a heat shock, via ultrasonication, or alternatively under a mechanical stress of centrifugation type.

As used herein, the term "metabolite" denotes any substance derived from the metabolism of a microorganism, and especially secreted by the microorganism under consideration according to the invention and also endowed with efficacy for the treatment of AT, increasing longevity, decrease of lymphoma onset, and/or prevention of genetic instability, DNA damage, or genotoxicity.

As used herein, the term "microorganism" refers to a single-celled organism (e.g., a bacterium) and includes both live, partly or completely inactivated and attenuated microorganisms.

The terms "modulate," "modulation," or "modulating" are art-recognized and refer to up-regulation (i.e., activation, stimulation, increase), or down-regulation (i.e., inhibition, suppression, reduction, or decrease) of a response, or the two in combination or apart.

As used herein, "optional" or "optionally" means that the subsequently described event or circumstance may or may not occur, and that the description includes instances where said event or circumstance occurs and instances where it does not.

As used herein, the term "mutation" means a change in a nucleic acid sequence (in comparison to a wildtype or normal nucleic acid sequence) that alters or eliminates the function of an encoded polypeptide, that alters or eliminates the amount of an encoded polypeptide produced, or that alters or eliminates a regulatory function of the nucleic acid having acquired a mutation. Mutations include, but are not limited to, point mutations, deletions, insertions, inversions, duplications, etc. as known in the art.

As used herein, the terms "p53 deficiency" or "p53-deficient" mean (i) a lower than normal expression level of a p53 nucleic acid, (ii), a lower than normal expression level of a p53 polypeptide, (iii), a mutation in a gene encoding a p53 polypeptide that is not present in a wildtype or normal gene encoding a wildtype or normal p53 polypeptide, (iv) a mutation in a gene transcript encoding a p53 polypeptide that is not present in a wildtype or normal gene transcript encoding a wildtype or normal p53 polypeptide, and (v) a mutation in an amino acid sequence of a p53 polypeptide that is not present in an amino acid sequence of a wildtype or normal p53 polypeptide. A "p53 deficiency" may occur in an "individual," "subject" "host" or "patient" more specifically in a cell of an "individual," "subject" "host," "patient." Methods for determining a p53 deficiency are well known in the art.

As used herein, the terms "p53-deficiency cancer" or "p53 deficient cancer" mean a cancer in which at least one cell has a p53 deficiency.

As used herein, the term "parenteral" route means a route other than the oral and topical routes. A parenteral route that is suitable for use in the invention may be, for example, the nasal route.

As used herein, the term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a federal or state government or listed in the *U.S. Pharmacopeia* or other generally recognized pharmacopeia for use in animals, and more particularly in humans.

As used herein, the term "prebiotic" refers to any compound, nutrient, or additional microbe applied as a single additive or as a mixture, together with probiotics or without probiotics, in order to augment a desired probiotic health effect or to stimulate the growth and activity of those bacteria in the digestive system which are assumed to be beneficial to the health of a host.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

As used herein, the term "probiotic microorganism" or simply "probiotic" means a live microorganism, which, when consumed by a host in an adequate amount, has a positive effect on the health of its host and which may in particular improve the intestinal microbial balance. The term refers to any bacterial species, strain or their combinations, with health supportive effects, not limited to currently accepted strains or to intestinal effects.

As used herein, the term "radiation" refers to energy which may be selectively applied, including energy having a wavelength of between $10^{-14}$ and $10^4$ meters including, for example, electron beam radiation, gamma radiation, x-ray radiation, light such as ultra-violet light, visible light, and infrared light, microwave radiation, and radio waves. The radiation is in particular an ionizing radiation which comprises subatomic particles and/or ions or electromagnetic waves which are energetic enough to ionize atoms or molecules. "Irradiation" refers to the application (exposure) of radiation to a subject, e.g., in radiation oncology for the treatment of cancer and/or during accidental or environmental radiation.

As used herein, the term "radiation treatment" means a procedure including, but not limited to, radiotherapy, radiosurgery (i.e., radiation surgery) and/or any other (in particular) medical procedure, which uses ionizing radiation and in which a subject is treated by applying radiation to the subject's body. The radiation used for the treatment (the "treatment radiation") is effective for a particular part(s) of the body. Radiation treatment comprises providing an energy value which depends on the radiation energy, in particular the energy of the treatment radiation, which is applied to the patient's body, and controlling the period of time over which radiation treatment is performed in accordance with the energy value. The ionizing radiation can be emitted by an irradiation device such as an x-ray tube and/or a particle accelerator and/or an antenna and/or a radioactive material.

As used herein, the abbreviation "RM" means restricted microbiota.

As used herein, the term "radiation-induced toxicity" means any damage to a cell, tissue, or any of its components, such as a nucleic acid, caused by radiation.

As used herein, the abbreviation "SPF-M" means semi-conventional condition(s) and non-sterile condition(s).

As used herein, the abbreviation "SPF-S" means sterile condition(s). This meaning includes conditions as described previously Kadhim et al., 1992, *Nature* 355(6362):738-40; Watson et al., 2001, *Int J Radiat Biol* 77(4):409-17).

As used herein, the term "substantially decreased" and grammatical equivalents thereof refer to a level, amount, concentration of a parameter, such as a chemical compound, a metabolite, a nucleic acid, a polypeptide or a physical parameter (pH, temperature, viscosity, etc.) measured in a sample that has a decrease of at least 10%, preferably about 20%, more preferable about 40%, even more preferable about 50% and still more preferably a decrease of more than 75% when compared to the level, amount, or concentration of the same chemical compound, nucleic acid, polypeptide or physical parameter in a control sample.

As used herein, the term "substantially increased" and grammatical equivalents thereof refer to a level, amount, concentration of a parameter, such as a chemical compound, a metabolite, a nucleic acid, a polypeptide or a physical parameter (pH, temperature, viscosity, etc.) measured in a sample that has an increase of at least 30%, preferably about 50%, more preferable about 75%, and still more preferably an increase of more than 100% when compared to the level, amount, or concentration of the same chemical compound, nucleic acid, polypeptide or physical parameter in a control sample.

As used herein, the terms "treat", "treating", and "treatment" include inhibiting the pathological condition, disorder, or disease, e.g., arresting or reducing the development of the pathological condition, disorder, or disease or its clinical symptoms; or relieving the pathological condition, disorder, or disease, e.g., causing regression of the pathological condition, disorder, or disease or its clinical symptoms. These terms encompass also therapy and cure. Treatment means any manner in which the symptoms of a pathological condition, disorder, or disease are ameliorated or otherwise beneficially altered. Preferably, the subject in need of such treatment is a mammal, more preferably a human.

"w/v" refers to weight/volume.

II. Compositions

The inventors have observed, surprisingly and unexpectedly, that the administration of a food supplement comprising a probiotic microorganism, especially of the genus *Lactobacillus* sp., in particular *Lactobacillus johnsonii* and more particularly *Lactobacillus johnsonii* 456, can substantially affect genetic instability, DNA damage, genotoxicity, immunological markers, longevity and lymphoma latency in an ATM deficient subject, in a subject having a p53 deficiency, or in a subject having a p53 deficiency-associated cancer. In addition, compositions described herein are useful for treating and preventing radiation-induced toxicity to normal tissues during irradiation of a subject.

A. Probiotic, Prebiotic, and Synbiotic Microorganisms and Compositions

Probiotic, prebiotic and synbiotic microorganism useful for composition and methods of the present invention have been described by de Vrese and Schrezenmeir (*Adv Biochem Eng Biotechnol*, 2008, 111:1-66), herewith incorporated by reference in its entirety.

1. Probiotic Microorganisms

Probiotics are live microorganisms which can maintain intestinal microbial balance in the gastrointestinal tract of an animal host including a human. The probiotics, e.g., have beneficial effects in maintaining intestinal microbial balance, improving diarrhea caused by Rotavirus, alleviating antibiotic-related diarrhea, lactose intolerance and infant food allergic symptoms, and performing intestinal regulation. Applicants surprisingly and unexpectedly have found that probiotic formulations described herein are effective in treating and preventing certain disorders and conditions, including treating, preventing and delaying onset of AT-associated conditions and cancers as well as treating and/or preventing radiation-induced toxicity to normal tissue caused by exposure to radiation.

In some embodiments of the present invention, a probiotic composition is a composition that is suitable for use in the invention and useful for treating and/or preventing a disease related to genome instability, such as an AT-associated condition, a p53 deficiency, a p53 deficiency-associated cancer and radiation-induced toxicity to normal tissue due to exposure to radiation.

In some embodiments, the probiotic composition comprises at least one of the probiotic microorganisms listed in Table 6. In some embodiments, the probiotic composition comprises at least one of the probiotic microorganisms listed in Table 7A. In some embodiments, a probiotic composition advantageously comprises a *Lactobacillus* sp., especially *Lactobacillus johnsonii* and more particularly *Lactobacillus johnsonii* 456 as defined herein.

In some embodiments of the present invention, a probiotic microorganism may be used in an isolated or purified form, i.e., not mixed with one or more compound(s) typically associated with it in its medium of origin. In some embodiments, a probiotic microorganism may be used in combination with an antibacterial agent, such as an antibiotic or a bacteriophage.

In some embodiments of the present invention, a probiotic microorganism may be used in a live, semi-active, inactivated or dead form. A probiotic microorganism administered orally may advantageously be used in live form.

A probiotic microorganism according to the invention may be used in whole form, i.e., essentially in its native form, or in the form of extracts or lysates of disintegrated suspensions comprising fractions and/or metabolites of this microorganism.

In some embodiments of the present invention, a probiotic microorganism that is suitable for use in the invention may be used in the form of a lysate.

i. *Lactobacillus*

In some embodiments of the present invention, a probiotic composition that is suitable for use in the invention, for example topically or orally, and especially orally, comprises, or in some embodiments consists essentially of, a microorganism of the genus *Lactobacillus* sp., preferably selected from *L. acidophilus*, *L. alimentarius*, *L. amylovorus*, *L. brevis*, *L. bulgaricus*, *L. casei*, *L. casei* subsp. *casei*, *L. casei shirota*, *L. crispatus*, *L. curvatus*, *L. delbrueckii* subsp. *lactis*, *L. fermentum*, *L. gallinarum*, *L. gasseri*, *L. helveticus*, *L. johnsonii*, *L. paracasei*, *L. plantarum*, *L. reuteri*, *L. rhamnosus*, *L. sake* and *L. salivarius* and combinations thereof.

A preferred *Lactobacillus* sp. is *L. johnsonii*. Thus, in some embodiments of the present invention, a probiotic composition that is suitable for use in the invention comprises *L. johnsonii*. A more preferred *Lactobacillus* sp. is *L. johnsonii* 456. Thus, in some embodiments of the present invention, a probiotic composition that is suitable for use in the invention comprises *L. johnsonii* 456.

In some embodiments of the present invention, a probiotic composition comprising a *Lactobacillus* sp. does not include a *Clostridium* sp. In some embodiments of the present invention, a probiotic composition comprising a *Lactobacillus* sp. does not include a *Eubacterium* sp. In some embodiments of the present invention, a probiotic composition comprising a *Lactobacillus* sp. does not include a *Barnesiella* sp. In some embodiments of the present invention, a probiotic composition comprising a *Lactobacillus* sp. does not include an *Acetanaerobacterium* sp. In some embodiments of the present invention, a probiotic composition comprising a *Lactobacillus* sp. does not include a *Porphyromonadaceae* sp. In some embodiments of the present invention, a probiotic composition comprising a *Lactobacillus* sp. does not include a *Butyrivibrio* sp. In some embodiments of the present invention, a probiotic composition comprising a *Lactobacillus* sp. does not include a *Butyricimimonas* sp. In some embodiments of the present invention, a probiotic composition comprising a *Lactobacillus* sp. does not include a *Lachnospiraceae* sp. In some embodiments of the present invention, a probiotic composition comprising a *Lactobacillus* sp. does not include a *Porpyromonas* sp. In some embodiments of the present invention, a probiotic composition comprising a *Lactobacillus* sp. does not include a *Prevotella* sp. In some embodiments of the present invention, a probiotic composition comprising a *Lactobacillus* sp. does not include a *Rumen bacterium* sp. In some embodiments of the present invention, a probiotic composition comprising a *Lactobacillus* sp. does not include a *Filifactor* sp. In some embodiments of the present invention, a probiotic composition comprising a *Lactobacillus* sp. does not include a *Cyanobacterium* sp. In some embodiments of the present invention, a probiotic composition comprising a *Lactobacillus* sp. does not include a *Alistipes* sp. In some embodiments of the present invention, a probiotic composition comprising a *Lactobacillus* sp. does not include a microorganism listed in Table 7B.

ii. *Clostridium*

In some embodiments of the present invention, a probiotic composition that is suitable for use in the invention, for example topically or orally, and especially orally, comprises, or in some embodiments consists essentially of, a microorganism of the genus *Clostridium* sp., preferably selected from *Clostridium polysaccharaolyticum*, *Clostridium populeti*, *Clostridium oroticum*, *Clostridium fimetarium*, *Clostridium chauvoei*, and *Clostridium tyrobutyricum*.

In some embodiments of the present invention, a probiotic composition comprising a *Clostridium* sp. does not include a *Lactobacillus* sp. In some embodiments of the present invention, a probiotic composition comprising a *Clostridium* sp. does not include a *Eubacterium* sp. In some embodiments of the present invention, a probiotic composition comprising a *Clostridium* sp. does not include a *Barnesiella* sp. In some embodiments of the present invention, a probiotic composition comprising a *Clostridium* sp. does not include an *Acetanaerobacterium* sp. In some embodiments of the present invention, a probiotic composition comprising a *Clostridium* sp. does not include a *Porphyromonadaceae* sp. In some embodiments of the present invention, a probiotic composition comprising a *Clostridium* sp. does not include a *Butyrivibrio* sp. In some embodiments of the present invention, a probiotic composition comprising a *Clostridium* sp. does not include a *Butyricimonas* sp. In some embodiments of the present invention, a probiotic composition comprising a *Clostridium* sp. does not include a *Lachnospiraceae* sp. In some embodiments of the present invention, a probiotic composition comprising a *Clostridium* sp. does not include a *Porpyromonas* sp. In some embodiments of the present invention, a probiotic composition comprising a *Clostridium* sp. does not include a *Prevotella* sp. In some embodiments of the present invention, a probiotic composition comprising a *Clostridium* sp. does not include a *Rumen bacteriyum* sp. In some embodiments of the present invention, a probiotic composition comprising a *Clostridium* sp. does not include a *Filifactor* sp. In some embodiments of the present invention, a probiotic composition comprising a *Clostridium* sp. does not include a *Cyanobacterium* sp. In some embodiments of the present invention, a probiotic composition comprising a *Clostridium* sp. does not include a *Alistipes* sp. In some embodiments of the present invention, a probiotic composition comprising a *Clostridium* sp. does not include a microorganism listed in Table 7B.

iii. *Eubacterium*

In some embodiments of the present invention, a probiotic composition that is suitable for use in the invention, for example topically or orally, and especially orally, comprises, or in some embodiments consists essentially of, a microorganism of the genus *Eubacterium* sp., preferably *Eubacterium hadrum*.

In some embodiments of the present invention, a probiotic composition comprising a *Eubacterium* sp. does not include a *Lactobacillus* sp. In some embodiments of the present invention, a probiotic composition comprising a *Eubacterium* sp. does not include a *Clostridium* sp. In some embodiments of the present invention, a probiotic composition comprising a *Eubacterium* sp. does not include a *Barnesiella* sp. In some embodiments of the present invention, a probiotic composition comprising a *Eubacterium* sp. does not include an *Acetanaerobacterium* sp. In some embodiments of the present invention, a probiotic composition comprising a *Eubacterium* sp. does not include a *Porphyromonadaceae* sp. In some embodiments of the present invention, a probiotic composition comprising a *Eubacterium* sp. does not include a *Butyrivibrio* sp. In some embodiments of the present invention, a probiotic composition comprising a *Eubacterium* sp. does not include a *Butyricimonas* sp. In some embodiments of the present invention, a probiotic composition comprising a *Eubacterium* sp. does not include a *Lachnospiraceae* sp. In some embodiments of the present invention, a probiotic composition comprising a *Eubacterium* sp. does not include a *Porpyromonas* sp. In some embodiments of the present invention, a probiotic composition comprising a *Eubacterium* sp. does not include a *Prevotella* sp. In some embodiments of the present invention, a probiotic composition comprising a *Eubacterium* sp. does not include a *Rumen bacteriyum* sp. In some embodiments of the present invention, a probiotic composition comprising a *Eubacterium* sp. does not include a *Filifactor* sp. In some embodiments of the present invention, a probiotic composition comprising a *Eubacterium* sp. does not include a *Cyanobacterium* sp. In some embodiments of the present invention, a probiotic composition comprising a *Eubacterium* sp. does not include a *Alistipes* sp. In some embodiments of the present invention, a probiotic composition comprising a *Eubacterium* sp. does not include a microorganism listed in Table 7B.

iv. *Barnesiella*

In some embodiments of the present invention, a probiotic composition that is suitable for use in the invention, for example topically or orally, and especially orally, comprises, or in some embodiments consists essentially of, a microorganism of the genus *Barnesiella* sp., preferably selected from *Barnesiella intestinihominis* and *Barnesiella viscericola*.

In some embodiments of the present invention, a probiotic composition comprising a *Barnesiella* sp. does not include a *Lactobacillus* sp. In some embodiments of the present invention, a probiotic composition comprising a *Barnesiella* sp. does not include a *Clostridium* sp. In some embodiments of the present invention, a probiotic composition comprising a *Barnesiella* sp. does not include a *Eubacterium* sp. In some embodiments of the present invention, a probiotic composition comprising a *Barnesiella* sp. does not include an *Acetanaerobacterium* sp. In some embodiments of the present invention, a probiotic composition comprising a *Barnesiella* sp. does not include a *Porphyromonadaceae* sp. In some embodiments of the present invention, a probiotic composition comprising a *Barnesiella* sp. does not include a *Butyrivibrio* sp. In some embodiments of the present invention, a probiotic composition comprising a *Barnesiella* sp. does not include a *Butyricimonas* sp. In some embodiments of the present invention, a probiotic composition comprising a *Barnesiella* sp. does not include a *Lachnospiraceae* sp. In some embodiments of the present invention, a probiotic composition comprising a *Barnesiella* sp. does not include a *Porpyromonas* sp. In some embodiments of the present invention, a probiotic composition comprising a *Barnesiella* sp. does not include a *Prevotella* sp. In some embodiments of the present invention, a probiotic composition comprising a *Barnesiella* sp. does not include a *Rumen bacteriyum* sp. In some embodiments of the present invention, a probiotic composition comprising a *Barnesiella* sp. does not include a *Filifactor* sp. In some embodiments of the present invention, a probiotic composition comprising a *Barnesiella* sp. does not include a *Cyanobacterium* sp. In some embodiments of the present invention, a probiotic composition comprising a *Barnesiella* sp. does not include a *Alistipes* sp. In some embodiments of the present invention, a probiotic composition comprising a *Barnesiella* sp. does not include a microorganism listed in Table 7B.

v. *Acetanaerobacterium*

In some embodiments of the present invention, a probiotic composition that is suitable for use in the invention, for example topically or orally, and especially orally, comprises, or in some embodiments consists essentially of, a microorganism of the genus *Acetanaerobacterium* sp., preferably *Acetanaerobacterium elongatum*.

In some embodiments of the present invention, a probiotic composition comprising an *Acetanaerobacterium* sp. does not include a *Lactobacillus* sp. In some embodiments of the present invention, a probiotic composition comprising an *Acetanaerobacterium* sp. does not include a *Clostridium* sp. In some embodiments of the present invention, a probiotic composition comprising an *Acetanaerobacterium* sp. does not include a *Barnesiella* sp. In some embodiments of the present invention, a probiotic composition comprising an *Acetanaerobacterium* sp. does not include a *Eubacterium* sp. In some embodiments of the present invention, a probiotic composition comprising an *Acetanaerobacterium* sp. does not include a *Porphyromonadaceae* sp. In some embodiments of the present invention, a probiotic composition comprising an *Acetanaerobacterium* sp. does not include a *Butyrivibrio* sp. In some embodiments of the present invention, a probiotic composition comprising an *Acetanaerobacterium* sp. does not include a *Butyricimonas* sp. In some embodiments of the present invention, a probiotic composition comprising a *Acetanaerobacterium* sp. does not include a *Lachnospiraceae* sp. In some embodiments of the present invention, a probiotic composition comprising a *Acetanaerobacterium* sp. does not include a *Porpyromonas* sp. In some embodiments of the present invention, a probiotic composition comprising a *Acetanaerobacterium* sp. does not include a *Prevotella* sp. In some embodiments of the present invention, a probiotic composition comprising a *Acetanaerobacterium* sp. does not include a *Rumen bacteriyum* sp. In some embodiments of the present invention, a probiotic composition comprising a *Acetanaerobacterium* sp. does not include a *Filifactor* sp. In some embodiments of the present invention, a probiotic composition comprising a *Acetanaerobacterium* sp. does not include a *Cyanobacterium* sp. In some embodiments of the present invention, a probiotic composition comprising a *Acetanaerobacterium* sp. does not include a *Alistipes* sp. In some embodiments of the present invention, a probiotic composition comprising an *Acetanaerobacterium* sp. does not include a microorganism listed in Table 7B.

vi. *Porphyromonadaceae*

In some embodiments of the present invention, a probiotic composition that is suitable for use in the invention, for example topically or orally, and especially orally, comprises, or in some embodiments consists essentially of, a microorganism of the genus *Porphyromonadaceae* sp., preferably *Porphyromonadaceae* bacterium C941.

In some embodiments of the present invention, a probiotic composition comprising a *Porphyromonadaceae* sp. does not include a *Lactobacillus* sp. In some embodiments of the present invention, a probiotic composition comprising a *Porphyromonadaceae* sp. does not include a *Clostridium* sp. In some embodiments of the present invention, a probiotic composition comprising a *Porphyromonadaceae* sp. does not include a *Eubacterium* sp. In some embodiments of the present invention, a probiotic composition comprising a *Porphyromonadaceae* sp. does not include an *Acetanaerobacterium* sp. In some embodiments of the present invention, a probiotic composition comprising a *Porphyromonadaceae* sp. does not include a *Barnesiella* sp. In some embodiments of the present invention, a probiotic composition comprising a *Porphyromonadaceae* sp. does not include a *Butyrivibrio* sp. In some embodiments of the present invention, a probiotic composition comprising a *Porphyromonadaceae* sp. does not include a *Butyricimonas* sp. In some embodiments of the present invention, a probiotic composition comprising a *Porphyromonadaceae* sp. does not include a *Lachnospiraceae* sp. In some embodiments of the present invention, a probiotic composition comprising a *Porphyromonadaceae* sp. does not include a *Porpyromonas* sp. In some embodiments of the present invention, a probiotic composition comprising a *Porphyromonadaceae* sp. does not include a *Prevotella* sp. In some embodiments of the present invention, a probiotic composition comprising a *Porphyromonadaceae* sp. does not include a *Rumen bacteriyum* sp. In some embodiments of the present invention, a probiotic composition comprising a *Porphyromonadaceae* sp. does not include a *Filifactor* sp. In some embodiments of the present invention, a probiotic composition comprising a *Porphyromonadaceae* sp. does not include a *Cyanobacterium* sp. In some embodiments of the present invention, a probiotic composition comprising a *Porphyromonadaceae* sp. does not include a *Alistipes* sp. In some embodiments of the present invention, a probiotic composition comprising a *Porphyromonadaceae* sp. does not include a microorganism listed in Table 7B.

vii. *Butyrivibrio*

In some embodiments of the present invention, a probiotic composition that is suitable for use in the invention, for example topically or orally, and especially orally, comprises, or in some embodiments consists essentially of, a microorganism of the genus *Butyrivibrio* sp., preferably *Butyrivibrio crossotus*.

In some embodiments of the present invention, a probiotic composition comprising a *Butyrivibrio* sp. does not include a *Lactobacillus* sp. In some embodiments of the present invention, a probiotic composition comprising a *Butyrivibrio* sp. does not include a *Clostridium* sp. In some embodiments of the present invention, a probiotic composition comprising a *Butyrivibrio* sp. does not include a *Eubacterium* sp. In some embodiments of the present invention, a probiotic composition comprising a *Butyrivibrio* sp. does not include a *Barnesiella* sp. In some embodiments of the present invention, a probiotic composition comprising a *Butyrivibrio* sp. does not include an *Acetanaerobacterium* sp. In some embodiments of the present invention, a probiotic composition comprising a *Butyrivibrio* sp. does not include a *Porphyromonadaceae* sp. In some embodiments of the present invention, a probiotic composition comprising a *Butyrivibrio* sp. does not include a *Butyricimonas* sp. In some embodiments of the present invention, a probiotic composition comprising a *Butyrivibrio* sp. does not include a *Lachnospiraceae* sp. In some embodiments of the present invention, a probiotic composition comprising a *Butyrivibrio* sp. does not include a *Porpyromonas* sp. In some embodiments of the present invention, a probiotic composition comprising a *Butyrivibrio* sp. does not include a *Prevotella* sp. In some embodiments of the present invention, a probiotic composition comprising a *Butyrivibrio* sp. does not include a *Rumen bacteriyum* sp. In some embodiments of the present invention, a probiotic composition comprising a *Butyrivibrio* sp. does not include a *Filifactor* sp. In some embodiments of the present invention, a probiotic composition comprising a *Butyrivibrio* sp. does not include a *Cyanobacterium* sp. In some embodiments of the present invention, a probiotic composition comprising a *Butyrivibrio* sp. does not include a *Alistipes* sp. In some embodiments of the present invention, a probiotic composition comprising a *Butyrivibrio* sp. does not include a microorganism listed in Table 7B.

viii. *Butyricimonas*

In some embodiments of the present invention, a probiotic composition that is suitable for use in the invention, for example topically or orally, and especially orally, comprises, or in some embodiments consists essentially of, a microorganism of the genus *Butyricimonas* sp., preferably *Butyricimonas syngergistica*.

In some embodiments of the present invention, a probiotic composition comprising a *Butyricimonas* sp. does not include a *Lactobacillus* sp. In some embodiments of the present invention, a probiotic composition comprising a *Butyricimonas* sp. does not include a *Clostridium* sp. In some embodiments of the present invention, a probiotic composition comprising a *Butyricimonas* sp. does not include a *Eubacterium* sp. In some embodiments of the present invention, a probiotic composition comprising a *Butyricimonas* sp. does not include a *Barnesiella* sp. In some embodiments of the present invention, a probiotic composition comprising a *Butyricimonas* sp. does not include an *Acetanaerobacterium* sp. In some embodiments of the present invention, a probiotic composition comprising a *Butyricimonas* sp. does not include a *Porphyromonadaceae* sp. In some embodiments of the present invention, a probiotic composition comprising a *Butyricimonas* sp. does not include a *Butyrivibrio* sp. In some embodiments of the present invention, a probiotic composition comprising a *Butyricimonas* sp. does not include a *Lachnospiraceae* sp. In some embodiments of the present invention, a probiotic composition comprising a *Butyricimonas* sp. does not include a *Porpyromonas* sp. In some embodiments of the present invention, a probiotic composition comprising a *Butyricimonas* sp. does not include a *Prevotella* sp. In some embodiments of the present invention, a probiotic composition comprising a *Butyricimonas* sp. does not include a *Rumen bacteriyum* sp. In some embodiments of the present invention, a probiotic composition comprising a *Butyricimonas* sp. does not include a *Filifactor* sp. In some embodiments of the present invention, a probiotic composition comprising a *Butyricimonas* sp. does not include a *Cyanobacterium* sp. In some embodiments of the present invention, a probiotic composition comprising a *Butyricimonas* sp. does not include a *Alistipes* sp. In some embodiments of the present invention, a probiotic composition comprising a *Butyricimonas* sp. does not include a microorganism listed in Table 7B.

ix. *Lachnospiraceae*

In some embodiments of the present invention, a probiotic composition that is suitable for use in the invention, for example topically or orally, and especially orally, comprises, or in some embodiments consists essentially of, a microorganism of the genus *Lachnospiraceae* sp., preferably *Lachnospiraceae* bacterium DJF_VP30.

In some embodiments of the present invention, a probiotic composition comprising a *Lachnospiraceae* sp. does not include a *Lactobacillus* sp. In some embodiments of the present invention, a probiotic composition comprising a *Lachnospiraceae* sp. does not include a *Clostridium* sp. In some embodiments of the present invention, a probiotic composition comprising a *Lachnospiraceae* sp. does not include a *Eubacterium* sp. In some embodiments of the present invention, a probiotic composition comprising a *Lachnospiraceae* sp. does not include a *Barnesiella* sp. In some embodiments of the present invention, a probiotic composition comprising a *Lachnospiraceae* sp. does not include an *Acetanaerobacterium* sp. In some embodiments of the present invention, a probiotic composition comprising a *Lachnospiraceae* sp. does not include a *Porphyromonadaceae* sp. In some embodiments of the present invention, a probiotic composition comprising a *Lachnospiraceae* sp. does not include a *Butyrivibrio* sp. In some embodiments of the present invention, a probiotic composition comprising a *Lachnospiraceae* sp. does not include a *Butyricimonas* sp. In some embodiments of the present invention, a probiotic composition comprising a *Lachnospiraceae* sp. does not include a *Porpyromonas* sp. In some embodiments of the present invention, a probiotic composition comprising a *Lachnospiraceae* sp. does not include a *Prevotella* sp. In some embodiments of the present invention, a probiotic composition comprising a *Lachnospiraceae* sp. does not include a *Rumen bacteriyum* sp. In some embodiments of the present invention, a probiotic composition comprising a *Lachnospiraceae* sp. does not include a *Filifactor* sp. In some embodiments of the present invention, a probiotic composition comprising a *Lachnospiraceae* sp. does not include a *Cyanobacterium* sp. In some embodiments of the present invention, a probiotic composition comprising a *Lachnospiraceae* sp. does not include a *Alistipes* sp. In some embodiments of the present invention, a probiotic composition comprising a *Lachnospiraceae* sp. does not include a microorganism listed in Table 7B.

x. *Porphyromonas*

In some embodiments of the present invention, a probiotic composition that is suitable for use in the invention, for example topically or orally, and especially orally, comprises, or in some embodiments consists essentially of, a microorganism of the genus *Porphyromonas* sp., preferably *Porphyromonas* sp. C1075.

In some embodiments of the present invention, a probiotic composition comprising a *Porphyromonas* sp. does not include a *Lactobacillus* sp. In some embodiments of the present invention, a probiotic composition comprising a *Porphyromonas* sp. does not include a *Clostridium* sp. In some embodiments of the present invention, a probiotic composition comprising a *Porphyromonas* sp. does not include a *Eubacterium* sp. In some embodiments of the present invention, a probiotic composition comprising a

*Porphyromonas* sp. does not include a *Barnesiella* sp. In some embodiments of the present invention, a probiotic composition comprising a *Porphyromonas* sp. does not include an *Acetanaerobacterium* sp. In some embodiments of the present invention, a probiotic composition comprising a *Porphyromonas* sp. does not include a *Porphyromonadaceae* sp. In some embodiments of the present invention, a probiotic composition comprising a *Porphyromonas* sp. does not include a *Butyrivibrio* sp. In some embodiments of the present invention, a probiotic composition comprising a *Porphyromonas* sp. does not include a *Butyricimonas* sp. In some embodiments of the present invention, a probiotic composition comprising a *Porphyromonas* sp. does not include a *Lachnospiraceae* sp. In some embodiments of the present invention, a probiotic composition comprising a *Porphyromonas* sp. does not include a *Prevotella* sp. In some embodiments of the present invention, a probiotic composition comprising a *Porphyromonas* sp. does not include a *Rumen bacteriyum* sp. In some embodiments of the present invention, a probiotic composition comprising a *Porphyromonas* sp. does not include a *Filifactor* sp. In some embodiments of the present invention, a probiotic composition comprising a *Porphyromonas* sp. does not include a *Cyanobacterium* sp. In some embodiments of the present invention, a probiotic composition comprising a *Porphyromonas* sp. does not include a *Alistipes* sp. In some embodiments of the present invention, a probiotic composition comprising a *Porphyromonas* sp. does not include a microorganism listed in Table 7B.

xi. *Prevotella*

In some embodiments of the present invention, a probiotic composition that is suitable for use in the invention, for example topically or orally, and especially orally, comprises, or in some embodiments consists essentially of, a microorganism of the genus *Prevotella* sp., preferably *Prevotella* sp. oral clone CY006.

In some embodiments of the present invention, a probiotic composition comprising a *Prevotella* sp. does not include a *Lactobacillus* sp. In some embodiments of the present invention, a probiotic composition comprising a *Prevotella* sp. does not include a *Clostridium* sp. In some embodiments of the present invention, a probiotic composition comprising a *Prevotella* sp. does not include a *Eubacterium* sp. In some embodiments of the present invention, a probiotic composition comprising a *Prevotella* sp. does not include a *Barnesiella* sp. In some embodiments of the present invention, a probiotic composition comprising a *Prevotella* sp. does not include an *Acetanaerobacterium* sp. In some embodiments of the present invention, a probiotic composition comprising a *Prevotella* sp. does not include a *Porphyromonadaceae* sp. In some embodiments of the present invention, a probiotic composition comprising a *Prevotella* sp. does not include a *Butyrivibrio* sp. In some embodiments of the present invention, a probiotic composition comprising a *Prevotella* sp. does not include a *Butyricimonas* sp. In some embodiments of the present invention, a probiotic composition comprising a *Prevotella* sp. does not include a *Lachnospiraceae* sp. In some embodiments of the present invention, a probiotic composition comprising a *Prevotella* sp. does not include a *Porphyromonas* sp. In some embodiments of the present invention, a probiotic composition comprising a *Prevotella* sp. does not include a *Rumen bacteriyum* sp. In some embodiments of the present invention, a probiotic composition comprising a *Prevotella* sp. does not include a *Filifactor* sp. In some embodiments of the present invention, a probiotic composition comprising a *Prevotella* sp. does not include a *Cyanobacterium* sp. In some embodiments of the present invention, a probiotic composition comprising a *Prevotella* sp. does not include a *Alistipes* sp. In some embodiments of the present invention, a probiotic composition comprising a *Prevotella* sp. does not include a microorganism listed in Table 7B.

xii. *Rumen bacterium*

In some embodiments of the present invention, a probiotic composition that is suitable for use in the invention, for example topically or orally, and especially orally, comprises, or in some embodiments consists essentially of, a microorganism of the genus *Rumen bacterium* sp., preferably *Rumen bacterium* NK4A66.

In some embodiments of the present invention, a probiotic composition comprising a *Rumen bacterium* sp. does not include a *Lactobacillus* sp. In some embodiments of the present invention, a probiotic composition comprising a *Rumen bacterium* sp. does not include a *Clostridium* sp. In some embodiments of the present invention, a probiotic composition comprising a *Rumen bacterium* sp. does not include a *Eubacterium* sp. In some embodiments of the present invention, a probiotic composition comprising a *Rumen bacterium* sp. does not include a *Barnesiella* sp. In some embodiments of the present invention, a probiotic composition comprising a *Rumen bacterium* sp. does not include an *Acetanaerobacterium* sp. In some embodiments of the present invention, a probiotic composition comprising a *Rumen bacterium* sp. does not include a *Porphyromonadaceae* sp. In some embodiments of the present invention, a probiotic composition comprising a *Rumen bacterium* sp. does not include a *Butyrivibrio* sp. In some embodiments of the present invention, a probiotic composition comprising a *Rumen bacterium* sp. does not include a *Butyricimonas* sp. In some embodiments of the present invention, a probiotic composition comprising a *Rumen bacterium* sp. does not include a *Lachnospiraceae* sp. In some embodiments of the present invention, a probiotic composition comprising a *Rumen bacterium* sp. does not include a *Porphyromonas* sp. In some embodiments of the present invention, a probiotic composition comprising a *Rumen bacterium* sp. does not include a *Prevotella* sp. In some embodiments of the present invention, a probiotic composition comprising a *Rumen bacterium* sp. does not include a *Filifactor* sp. In some embodiments of the present invention, a probiotic composition comprising a *Rumen bacterium* sp. does not include a *Cyanobacterium* sp. In some embodiments of the present invention, a probiotic composition comprising a *Rumen bacterium* sp. does not include a *Alistipes* sp. In some embodiments of the present invention, a probiotic composition comprising a *Rumen bacterium* sp. does not include a microorganism listed in Table 7B.

xiii. *Filifactor*

In some embodiments of the present invention, a probiotic composition that is suitable for use in the invention, for example topically or orally, and especially orally, comprises, or in some embodiments consists essentially of, a microorganism of the genus *Filifactor* sp., preferably *Filifactor alocis*.

In some embodiments of the present invention, a probiotic composition comprising a *Filifactor* sp. does not include a *Lactobacillus* sp. In some embodiments of the present invention, a probiotic composition comprising a *Filifactor* sp. does not include a *Clostridium* sp. In some embodiments of the present invention, a probiotic composition comprising a *Filifactor* sp. does not include a *Eubacterium* sp. In some embodiments of the present invention, a probiotic composition comprising a *Filifactor* sp. does not include a *Barne-

*siella* sp. In some embodiments of the present invention, a probiotic composition comprising a *Filifactor* sp. does not include an *Acetanaerobacterium* sp. In some embodiments of the present invention, a probiotic composition comprising a *Filifactor* sp. does not include a *Porphyromonadaceae* sp. In some embodiments of the present invention, a probiotic composition comprising a *Filifactor* sp. does not include a *Butyrivibrio* sp. In some embodiments of the present invention, a probiotic composition comprising a *Filifactor* sp. does not include a *Butyricimonas* sp. In some embodiments of the present invention, a probiotic composition comprising a *Filifactor* sp. does not include a *Lachnospiraceae* sp. In some embodiments of the present invention, a probiotic composition comprising a *Filifactor* sp. does not include a *Porphyromonas* sp. In some embodiments of the present invention, a probiotic composition comprising a *Filifactor* sp. does not include a *Prevotella* sp. In some embodiments of the present invention, a probiotic composition comprising a *Filifactor* sp. does not include a *Rumen bacterium* sp. In some embodiments of the present invention, a probiotic composition comprising a *Filifactor* sp. does not include a *Cyanobacterium* sp. In some embodiments of the present invention, a probiotic composition comprising a *Filifactor* sp. does not include a *Alistipes* sp. In some embodiments of the present invention, a probiotic composition comprising a *Filifactor* sp. does not include a microorganism listed in Table 7B.

xiv. *Cyanobacterium*

In some embodiments of the present invention, a probiotic composition that is suitable for use in the invention, for example topically or orally, and especially orally, comprises, or in some embodiments consists essentially of, a microorganism of the genus *Cyanobacterium* sp., preferably *Cyanobacterium* sp. MS-B-20.

In some embodiments of the present invention, a probiotic composition comprising a *Cyanobacterium* sp. does not include a *Lactobacillus* sp. In some embodiments of the present invention, a probiotic composition comprising a *Cyanobacterium* sp. does not include a *Clostridium* sp. In some embodiments of the present invention, a probiotic composition comprising a *Cyanobacterium* sp. does not include a *Eubacterium* sp. In some embodiments of the present invention, a probiotic composition comprising a *Cyanobacterium* sp. does not include a *Barnesiella* sp. In some embodiments of the present invention, a probiotic composition comprising a *Cyanobacterium* sp. does not include an *Acetanaerobacterium* sp. In some embodiments of the present invention, a probiotic composition comprising a *Cyanobacterium* sp. does not include a *Porphyromonadaceae* sp. In some embodiments of the present invention, a probiotic composition comprising a *Cyanobacterium* sp. does not include a *Butyrivibrio* sp. In some embodiments of the present invention, a probiotic composition comprising a *Cyanobacterium* sp. does not include a *Butyricimonas* sp. In some embodiments of the present invention, a probiotic composition comprising a *Cyanobacterium* sp. does not include a *Lachnospiraceae* sp. In some embodiments of the present invention, a probiotic composition comprising a *Cyanobacterium* sp. does not include a *Porphyromonas* sp. In some embodiments of the present invention, a probiotic composition comprising a *Cyanobacterium* sp. does not include a *Prevotella* sp. In some embodiments of the present invention, a probiotic composition comprising a *Cyanobacterium* sp. does not include a *Rumen bacterium* sp. In some embodiments of the present invention, a probiotic composition comprising a *Cyanobacterium* sp. does not include a *Filifactor* sp. In some embodiments of the present invention, a probiotic composition comprising a *Cyanobacterium* sp. does not include a *Alistipes* sp. In some embodiments of the present invention, a probiotic composition comprising a *Cyanobacterium* sp. does not include a microorganism listed in Table 7B.

xv. *Alistipes*

In some embodiments of the present invention, a probiotic composition that is suitable for use in the invention, for example topically or orally, and especially orally, comprises, or in some embodiments consists essentially of, a microorganism of the genus *Alistipes* sp., preferably *Alistipes onderdonkii*.

In some embodiments of the present invention, a probiotic composition comprising a *Alistipes* sp. does not include a *Lactobacillus* sp. In some embodiments of the present invention, a probiotic composition comprising a *Alistipes* sp. does not include a *Clostridium* sp. In some embodiments of the present invention, a probiotic composition comprising a *Alistipes* sp. does not include a *Eubacterium* sp. In some embodiments of the present invention, a probiotic composition comprising a *Alistipes* sp. does not include a *Barnesiella* sp. In some embodiments of the present invention, a probiotic composition comprising a *Alistipes* sp. does not include an *Acetanaerobacterium* sp. In some embodiments of the present invention, a probiotic composition comprising a *Alistipes* sp. does not include a *Porphyromonadaceae* sp. In some embodiments of the present invention, a probiotic composition comprising a *Alistipes* sp. does not include a *Butyrivibrio* sp. In some embodiments of the present invention, a probiotic composition comprising a *Alistipes* sp. does not include a *Butyricimonas* sp. In some embodiments of the present invention, a probiotic composition comprising a *Alistipes* sp. does not include a *Lachnospiraceae* sp. In some embodiments of the present invention, a probiotic composition comprising a *Alistipes* sp. does not include a *Porphyromonas* sp. In some embodiments of the present invention, a probiotic composition comprising a *Alistipes* sp. does not include a *Prevotella* sp. In some embodiments of the present invention, a probiotic composition comprising a *Alistipes* sp. does not include a *Rumen bacterium* sp. In some embodiments of the present invention, a probiotic composition comprising a *Alistipes* sp. does not include a *Filifactor* sp. In some embodiments of the present invention, a probiotic composition comprising a *Alistipes* sp. does not include a *Cynaobacterium* sp. In some embodiments of the present invention, a probiotic composition comprising a *Alistipes* sp. does not include a microorganism listed in Table 7B.

xvi. Combinations of Beneficial Microorganisms

In some embodiments of the present invention, a probiotic composition that is suitable for use in the invention, for example topically or orally, and especially orally, comprises a combination of beneficial microorganisms. Any beneficial microorganisms described herein, in particular in Table 7A can be used in compositions and methods of the present invention. In addition, beneficial microorganisms are described in Example D. Any beneficial microorganisms described herein, in particular in Example D can be used in compositions and methods of the present invention.

In some embodiments, a probiotic composition that is suitable for use in the invention, for example topically or orally, and especially orally, comprises, or in some embodiments consists essentially of, a combination of at least 2, 3, 4, 5, 6, 7, 8, 9, 10, 11, 12, 13, 14, 15, 16, 17, 18, 19, 20, or 21 microorganisms selected from microorganisms listed in Table 7A.

B. Fungal Microbiota

Abundant and diverse fungal microbiota in the murine intestine useful for composition and methods of the present invention have been described by Scupham et al. (*Appl Environ Microbiol,* 2006, 72:793-801), herewith incorporated by reference in its entirety.

C. Commensal Microbiota

Commensal microbiota altering the abundance and TCR responsiveness of splenic naïve CD4$^+$ T lymphocytes useful for composition and methods of the present invention have been described by Huang et al. (*Clin Immunol,* 2005, 117: 221-230), herewith incorporated by reference in its entirety.

D. Antibiotics

In some embodiments, a method of the present comprises the step of inhibiting the growth of a detrimental microorganism in a subject by administering to the subject an antibiotic inhibiting the growth of the detrimental microorganism.

Antibiotics refer to a group of agents, but are not limited to, aminoglycoside antibiotics, glycopeptide antibiotics, macrolide antibiotics, and combinations thereof. Exemplary antibiotics may be active against gram-negative bacteria, as well as, active against both gram-positive and gram negative bacteria. Non-limiting examples of antibiotics include erythromycin, garamycin, gentamicin, kanamycin, neomycin, netilmicin, paromomycin, tobramycin, vancomycin, and their analogs, and a combination thereof. There are a variety of antibiotics that can be used in a method of the present invention. In some embodiments, an antibiotic or a combination of antibodies is selected from penicillins, cephalosporins, carbapenems, aminoglycosides, sulfonamides, quinolones, macrolides, tetracyclines, lipopeptides and oxazolidinones. Suitable antibiotics can be substituted in cases wherein a subject has a known or suspected hypersensitivity to a class of antibiotics, such as cephalosporins and combinations thereof, In some embodiments, the antibiotic or combination of antibiotics may be specifically selected based on the resistance profile of a subject's bacterial microbiota.

In some embodiments, an antibiotic or an antibiotic cocktail (comprising at least two antibiotics) is selected from amoxicillin, ampicillin, bacampicillin, carbenicillin, cloxacillin, dicloxacillin, flucloxacillin, mezlocillin, nafcillin, oxacillin, penicillin G, penicillin V, Piperacillin, Pivampicillin, Pivmecillinam, Ticarcillin, cefacetrile, cefadroxil, cephalexin, cefaloglycin, cefalonium, cefaloridine, cefalotin, cefamandole, cefapirin, cefatoxin, cefatrizine, cefazaflur, cephalexin, cefazedone, cefazolin, cefepime, cefradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefminox, cefotetan, cefoxitin, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, imipenem, meropenem, ertapenem, doripenem, panipenem, betamipron, biapenem, razupenem, amikacin, arbekacin, gentamicin, kanamycin, neomycin, netilmicin, paromomycin, rhodostreptomycin, streptomycin, tobramycin, apramycin, framycetin, ribostamycin, bekanamycin, dibekacin, tobramycin, spectinomycin, hygromycin B, paromomycin sulfate, sisomicin, isepamicin, verdamicin, astromicin, sulfasalazine, sulfamethoxazole, sulfamethizole, sulfisoxazole, fluoroquinolone, ketolide, ceftobiprole, flumequine, nalidixic acid, oxolinic acid, piromidic acid, pipemidic acid, rosoxacin, ciprofloxacin, enoxacin, lomefloxacin, nadifloxacin, norfloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, azithromycin, erythromycin, clarithromycin, dirithromycin, roxithromycin, telithromycin, demeclocycline, doxycycline, minocycline, oxytetracycline, tetracycline, linezolid, clindamycin, metronidazole, vancomycin, rifabutin, rifampin, nitrofurantoin, chloramphenicol, and combinations thereof.

In some embodiments, a composition comprises an antibiotic having an elimination half-life of less than 20 hours. In some embodiments, a composition comprises an antibiotic having an elimination half-life of about 1 to 12 hours. The following are examples of some antibiotics with half-lives of about 1 to 12 hours from which an antibiotic or a combination of antibiotics can be selected: Cefadroxil, cefazolin, cephalexin, cephalothin, cephapirin, cephacelor, cephprozil, cephadrine, cefamandole, cefonicid, ceforanide, cefuroxime, cefixime, cefoperazone, cefotaxime, cefpodoxime, ceftaxidime, ceftibuten, ceftizoxime, ceftriaxone, cefepime, cefmetazole, cefotetan, cefoxitin, loracarbef, imipenem, erythromycin (and erythromycin salts such as estolate, ethylsuccinate, gluceptate, lactobionate, stearate), azithromycin, clarithromycoin, dirithromycin, troleanomycin, penicillin V, penicillin salts, and complexes, methicillin, nafcillin, oxacillin, cloxacillin, dicloxacillin, amoxicillin, amoxicillin and clavulanate potassium, ampicillin, bacampicillin, carbenicillin indanyl sodium (and other salts of carbenicillin) mezlocillin, piperacillin, piperacillin and taxobactam, ticarcillin, ticarcillin and clavulanate potassium, clindamycin, vancomycin, novobiocin, aminosalicylic acid, capreomycin, cycloserine, ethambutol HCl and other salts, ethionamide, and isoniazid, ciprofloxacin, levofloxacin, lomefloxacin, nalidixic acid, norfloxacin, ofloxacin, sparfloxacin, sulfacytine, sulfamerazine, sulfamethazine, sulfamethixole, sulfasalazine, sulfisoxazole, sulfapyrizine, sulfadiazine, sulfinethoxazole, sulfapyridine, metronidazole, methenamine, fosfomycin, nitrofurantoin, trimethoprim, clofazimine, co-triamoxazole, pentamidine, and trimetrexate.

In some embodiments, the antibiotic is selected from an aminoglycoside antibiotic, a glycopeptide antibiotic, a macrolide antibiotic, and a combination thereof. In some embodiments, the antibiotic is selected from erythromycin, gentamicin, tobramycin, vancomycin, and a combination thereof. In some embodiments, the antibiotic is gentamicin.

The antibiotic or a combination of at least two antibiotics (sometimes referred to as antibiotic cocktail) can be administered to a subject per se, or in a pharmaceutical composition where they are mixed with suitable carriers or excipients.

D. Bacteriophages

In some embodiments, a method of the present comprises inhibiting the growth of a detrimental microorganism in a subject by administering to the subject a bacteriophage, preferably a lytic bacteriophage, e.g., a bacteriophage that targets a detrimental microorganism such as a species of the *Enterobacter, Helicobacter, Pseudomonas, Escherichia, Klebsiella, Staphylococcus, Proteus, Salmonella, Listeria, Clostridium* or *Shigella* genera, such as *Enterobacter cloacae, Helicobacter acinonychis, Helicobacter anseris, Helicobacter aurati, Helicobacter bilis, Helicobacter bizzozeronii, Helicobacter brantae, Helicobacter canadensis, Helicobacter canis, Helicobacter cetorum, Helicobacter cholecystus, Helicobacter cinaedi, Helicobacter cynogastri-* cus, *Helicobacter felis, Helicobacter fennelliae, Helicobacter ganmani, Helicobacter hepaticus, Helicobacter mesocricetorum, Helicobacter marmotae, Helicobacter muridarum, Helicobacter mustelae, Helicobacter pametensis, Helicobacter pullorum, Helicobacter pylori, Helicobacter rappini, Helicobacter rodentium, Helicobacter salomonis, Helicobacter trogontum, Helicobacter typhlonius, Helicobacter winghamensis, Escherichia coli, Escherichia coli* O157:H7, *Salmonella enterica, Salmonella bongori, Salmonella subterranean, Salmonella typhimurium, Listeria fleischmannii, Listeria grayi, Listeria innocua, Listeria ivanovii, Listeria marthii, Listeria monocytogenes, Listeria rocourtiae, Listeria seeligeri, Listeria weihenstephanensis, Listeria welshimeri, Clostridium acetobutylicum, Clostridium argentinense, Clostridium aerotolerans, Clostridium baratii, Clostridium beijerinckii, Clostridium bifermentans, Clostridium botulinum, Clostridium butyricum, Clostridium cadaveric, Clostridium cellulolyticum, Clostridium chauvoei, Clostridium clostridioforme, Clostridium colicanis, Clostridium difficile, Clostridium estertheticum, Clostridium fallax, Clostridium feseri, Clostridium formicaceticum, Clostridium histolyticum, Clostridium innocuum, Clostridium kluyveri, Clostridium ljungdahlii, Clostridium lavalense, Clostridium novyi, Clostridium oedematiens, Clostridium paraputrificum, Clostridium perfringensi, Clostridium phytofermentans, Clostridium piliforme, Clostridium ragsdalei, Clostridium ramosum, Clostridium scatologenes, Clostridium septicum, Clostridium sordellii, Clostridium sporogenes, Clostridium sticklandii, Clostridium tertium, Clostridium tetani, Clostridium thermocellum, Clostridium thermosaccharolyticum, Clostridium tyrobutyricum, Shigella dysenteriae, Shigella flexneri, Shigella boydii,* and *Shigella sonnei*. Optionally, the bacteriophage targets a detrimental microorganism selected from *Enterobacter cloacae, Helicobacter pylori, Helicobacter hepaticus, Salmonella typhimurium,* and *Shigella dysenteriae*, such as *Helicobacter pylori*. In some embodiments, the bacteriophage targets a microorganism listed in Table 7B. Preferably, the bacteriophage targets *Helicobacter pylori, Helicobacter hepaticus, Salmonella typhimurium, Shigella, E. coli* O157:H7, *Listeria monocytogenes* or *Clostridium perfringens*.

Bacteriophages refer to viruses capable of invading bacterial cells. Preferably, the bacteriophage destroys the bacteria by causing it to lyse, i.e. break open.

In some embodiments, the bacteriophages are used in combination with one or more other bacteriophages. The combinations of bacteriophages can target the same detrimental microorganism or different detrimental microorganisms. Preferably, the combination of bacteriophages targets the same detrimental microorganism.

In some embodiments, the bacteriophage or combination of bacteriophages are used in combination with one or more probiotic microorganisms. The probiotic microorganism may be selected from *Lactobacillus* sp., *Clostridium* sp., *Eubacterium* sp., *Barnesiella* sp., *Acetanaerobacterium* sp., *Porphyromonadaceae* sp., *Butyrivibrio* sp., *Butyricimimonas* sp., *Lachnospiraceae* sp., *Porpyromonas* sp., *Prevotella* sp., *Rumen bacterium* sp., *Filifactor* sp., *Cyanobacterium* sp., and *Alistipes* sp. The probiotic microorganism may be at least one of the probiotic microorganisms listed in Table 6 or at least one of the probiotic microorganisms listed in Table 7A. In some embodiments, probiotic microorganism is a *Lactobacillus* sp. A preferred *Lactobacillus* sp is *Lactobacillus johnsonii*. A preferred *Lactobacillus johnsonii* is *Lactobacillus johnsonii* 456.

The bacteriophage or combination of bacteriophages may used in combination with one or more antibiotics. In some embodiments, an antibiotic or a combination of antibodies is selected from penicillins, cephalosporins, carbapenems, aminoglycosides, sulfonamides, quinolones, macrolides, tetracyclines, lipopeptides and oxazolidinones.

III. Formulation, Dosage and Administration

A. Formulation and Dosage

A microorganism of the invention may be formulated in a composition in a proportion of at least 0.0001% expressed as dry weight, in particular in a proportion from 0.0001% to 30%, in particular in a proportion from 0.001% to 20% and more particularly in a proportion from 0.01% to 15% by weight, in particular from 0.1% to 10% by weight and especially from 1% to 5% by weight relative to the total weight of the composition containing it.

In general, a composition according to the invention intended to be administered orally may comprise for the live microorganisms from $10^3$ to $10^{15}$ colony forming units (cfu)/g, in particular from $10^5$ to $10^{15}$ cfu/g and more particularly from $10^7$ to $10^{12}$ cfu/g (colony forming units per gram) of live microorganisms per gram of composition, or equivalent doses calculated for inactivated or dead microorganisms or for microorganism fractions or for produced metabolites. In some embodiments, the composition according to the invention intended to be administered orally may comprise bacteriophages from $10^5$ to $10^{10}$ plaque-forming units (PFU)/g, preferably $10^7$ to $10^8$ PFU/g.

In particular, in a composition administered orally, the corresponding microorganism and/or fraction and/or metabolite concentration may be adjusted so as to correspond to doses, expressed as microorganism equivalent, ranging from $10^5$ to $10^{13}$ cfu/day and in particular from $10^8$ to $10^{11}$ cfu/day. In some embodiments, the bacteriophages are administered at a dose of $10^5$ to $10^{10}$ PFU/day, preferably $10^7$ to $10^8$ PFU/day.

A use of a microorganism according to the invention necessarily takes place in an effective amount, i.e. an amount that allows the probiotic microorganism to display its active properties with regard to the conditions that are to be prevented and/or treated.

A microorganism may also be included in a composition in the form of fractions of cell components or in the form of metabolites, in particular in the form of a lysate. The microorganism(s), metabolite(s) or fraction(s) may also be introduced in the form of a lyophilized powder, a culture supernatant and/or, where appropriate, in a concentrated form.

When a composition comprises metabolites, the contents of metabolites in the compositions correspond substantially to the contents that may be produced by $10^3$ to $10^{15}$ cfu, in particular $10^5$ to $10^{15}$ cfu and more particularly $10^7$ to $10^{12}$ cfu of live microorganisms per gram of composition.

A microorganism of the invention may be formulated in a composition with one or more fungal microbiota, one or more commensal microbiota, one or more antibiotics, one or more bacteriophages or a combination thereof. Preferably, the microorganism of the invention is formulated in a composition with one or more antibiotics, one or more bacteriophages, or a combination thereof. Optionally, the composition comprises $10^5$ to $10^{10}$ PFU of the one or more bacteriophages, preferably $10^7$ to $10^8$ PFU.

A composition according to the invention may comprise a physiologically or pharmaceutically acceptable medium or carrier.

A probiotic microorganism of the invention may be formulated with an excipient and component that is common for such oral compositions or food supplements, e.g., especially fatty and/or aqueous components, humectants, thickeners, preserving agents, texturizers, flavor enhancers and/or coating agents, antioxidants and preserving agents. Formulating agents and excipients for oral compositions, and especially for food supplements, are known in this field and will not be the subject of a detailed description herein.

In the case of a composition in accordance with the invention for oral administration, the use of an ingestible support is preferred. The ingestible support may be of diverse nature according to the type of composition under consideration. Tablets, gel capsules or lozenges, suspensions, oral supplements in dry form and oral supplements in liquid form are especially suitable for use as food supports.

Milk, yoghurt, cheese, fermented milks, milk-based fermented products, ice creams, cereal-based products or fermented cereal-based products, milk-based powders, baby and infant formulas, food products of confectionery type, chocolate, cereals or animal feed, in particular for pets, are also suitable for use as food supports.

Formulation of the oral compositions according to the invention may be performed via any usual process known to those skilled in the art for producing drinkable solutions, sugar-coated tablets, gel capsules, gels, emulsions, tablets to be swallowed or chewed, wafer capsules, especially soft or hard wafer capsules, granules to be dissolved, syrups, solid or liquid foods, and hydrogels allowing controlled release.

In particular, a probiotic microorganism according to the invention may be incorporated into any form of food supplement or enriched food, for example food bars, or compacted or loose powders. The powders may be diluted with water, with soda, with dairy products or soybean derivatives, or may be incorporated into food bars.

In some embodiments, a composition according to the invention administered orally may be formulated in the form of sugar-coated tablets, gel capsules, gels, emulsions, tablets, wafer capsules, hydrogels, food bars, compacted or loose powders, liquid suspensions or solutions, confectioneries, fermented milks, fermented cheeses, chewing gum, toothpaste or spray solutions.

In particular, a composition according to the invention may be a food composition for human consumption. It may in particular be a case of nutritional whole foods, drinks, mineral waters, soups, dietary supplements and replacement foods, nutritional bars, confectioneries, fermented or unfermented milk-based products, yoghurt products, milk-based powders, enteral nutritional products, baby and/or infant compositions, fermented or unfermented cereal-based products, ice creams, chocolate, coffee, or "culinary" products such as mayonnaise, tomato puree or salad dressings.

The composition according to the invention may also be intended for animals, especially pets, such as cats and dogs, and may be formulated in the form of feed or food supplements for animals.

An oral composition of the invention may also comprise other nutritional active agents chosen from (i) anti-aging nutritional active agents, such as food antioxidants, nutrients with radical-scavenging properties and cofactors of antioxidant endogenous enzymes, vitamins A, C and E, carotenoids, xanthophylls, isoflavones, certain minerals such as zinc, copper, magnesium or selenium, lipoic acid, coenzyme Q10, superoxide dismutase (SOD) or taurine, unsaponifiable fractions extracted from fats of plant origin, Aloe vera, native or hydrolyzed marine collagen, and plant or marine oils rich in omega-3 and omega-6 fatty acids (including gamma.-linolenic acid), (ii) photoprotective nutritional active agents such as antioxidants and free-radical scavengers: vitamins A, C and E, carotenoids, xanthophylls, certain minerals such as zinc, copper, magnesium or selenium, coenzyme Q10 and superoxide dismutase (SOD), (iii) nutritional ingredients with moisturizing or immunomodulatory properties such as the extract of *Polypodium leucotomos*, plant or marine oils rich in omega-3 or omega-6 fatty acids, including gamma-linolenic acid.

B. Administration

In some embodiments of the present invention, a probiotic microorganism that is suitable for use in the invention may be administered orally, topically or parenterally, and in particular orally. A microorganism of the invention may be administered in a composition with one or more fungal microbiota, one or more commensal microbiota, one or more antibiotics, one or more bacteriophages or a combination thereof. Preferably, the microorganism of the invention is administered in a composition with one or more antibiotics, one or more bacteriophages, or a combination thereof.

In some embodiments of the present invention, a probiotic microorganism is used orally, parenterally or topically.

An effective amount of microorganism may be administered in a single dose per day or in fractional doses over the day, for example two to three times a day. By way of example, the oral administration of a probiotic microorganism according to the invention may be performed at a rate, for example, of 3 times a day or more, generally over a prolonged period of at least 4 weeks, or even 4 to 15 weeks, optionally comprising one or more periods of stoppage or being repeated after a period of stoppage.

As one of skill in the art will appreciate, compositions of the present invention, not having adverse effects upon administration to a subject, may be administered daily to the subject.

III. Methods

A. Overview

The invention described herein can be used to improve prognosis of a disease, such as a disease related to genome instability, such as ataxia telangiectasia, p53 deficiency, or exposure to radiation. For example, the invention can be used to improve the prognosis of ataxia telangiectasia (AT), by prolonging life expectancy as well as cancer onset and is applicable to a variety of cancer-prone diseases as well as delaying cancer in the general population. Ataxia telangiectasia is a debilitating genetic disease characterized by neurological and cardiovascular disorders, immune deficiency, early-onset of carcinogenesis, as well as a shortened lifespan. So far a cure for AT does not exist: symptoms can be treated, however care is mainly supportive. Preventive care is virtually non-existent, although high vitamin doses are sometimes used. Applicants propose that a specific cocktail of pre-biotics, pro-biotics and/or anti-biotics can be used as a prophylactic to delay carcinogenesis and mortality. The mechanistic interaction between intestinal microbiota and cancer is difficult to understand, however, there is substantial cross-talk between microbiota and the immune system which can lead to inflammation and cytotoxicity. The immune response can both promote and mitigate carcinogenesis. In a similar manner, it is believed that promoting the growth of beneficial bacteria and preventing the growth of detrimental bacteria will improve prognosis of other diseases involving premature carcinogenesis as well as the health of the general population.

Methods altering the intestinal microbiota of patients suffering from genomic instability, such as AT patients, using specific combinations of pre-biotics, pro-biotics, bacteriophages and/or anti-biotics to establish a defined intestinal microbiota can increase their lifespan in a simple, non-invasive manner. In addition, the processes altered by the intestinal microbiota, namely inflammation and oxidative stress are responsible for all major killers, such as almost all cancers, heart disease, neurodegenerative diseases and ageing itself. Without being bound by theory, it is believed that effects of intestinal microbiota are exacerbated in Atm-deficient mice since they are cancer-prone and that changes in the intestinal microbiota may add 20 to 30% in the life expectancy in wildtype mice or humans.

The inventors have observed, surprisingly, that the administration of a food supplement comprising a probiotic microorganism, especially of the genus *Lactobacillus* sp., in particular *Lactobacillus johnsonii* and more particularly *Lactobacillus johnsonii* 456, can substantially affect genetic instability, DNA damage, genotoxicity, immunological markers, longevity and lymphoma latency in an ATM deficient host.

The use of probiotic microorganisms according to the invention advantageously makes it possible to modulate genetic instability, DNA damage, genotoxicity, immunological markers, longevity and lymphoma latency in a subject, such as an ATM deficient host.

As will be appreciated further herein, compositions of the present invention can be used advantageously in methods of treating and preventing symptoms arising in a subject having AT.

As will be appreciated further herein, compositions of the present invention can be used advantageously in methods of treating and preventing symptoms arising in a subject having a p53-deficiency-associated cancer.

As will be appreciated further herein, compositions of the present invention can be used advantageously in methods of treating and preventing symptoms arising in a subject having radiation-induced toxicity to normal tissue during or caused by radiation treatment.

B. Method for Treating, Preventing, or Delaying the Onset of an Ataxia-Telangiectasia (AT)-Associated Condition in a Subject Having AT The present invention provides a method for treating, preventing, or delaying the onset of an ataxia-telangiectasia (AT)-associated condition in a subject having AT. In some embodiments, this method comprises administering to a subject having AT and diagnosed with an AT-associated condition a therapeutically effective amount of a composition comprising a probiotic microorganism. Thereby the AT-associated condition in the subject is treated, prevented or delayed. In some embodiments, this method comprises administering to a subject having AT and at risk of developing an AT-associated condition a therapeutically effective amount of a composition comprising a probiotic microorganism. Thereby the AT-associated condition in the subject is treated, prevented or delayed.

In some embodiments, this method comprises sustaining a beneficial level of a probiotic microorganism in a subject having AT and diagnosed with an AT-associated condition by administering to the subject a therapeutically effective amount of a composition comprising a probiotic microorganism. Thereby the AT-associated condition in the subject is treated, prevented or delayed. In some embodiments, this method comprises sustaining a beneficial level of a probiotic microorganism in a subject having AT and at risk of developing an AT-associated condition by administering to the subject a therapeutically effective amount of a composition comprising a probiotic microorganism. Thereby the AT-associated condition in the subject is treated, prevented or delayed.

In some embodiments, this method comprises restoring the presence of a beneficial level of a probiotic microorganism in a subject having AT and diagnosed with an AT-associated condition by administering to the subject a therapeutically effective amount of a composition comprising a probiotic microorganism. Thereby the AT-associated condition in the subject is treated, prevented or delayed. In some embodiments, this method comprises restoring the presence of a beneficial level of a probiotic microorganism in a subject having AT and at risk of developing an AT-associated condition by administering to the subject a therapeutically effective amount of a composition comprising a probiotic microorganism. Thereby the AT-associated condition in the subject is treated, prevented or delayed.

In some embodiments, this method comprises inhibiting the growth of detrimental microorganisms in a subject having AT and diagnosed with an AT-associated condition by administering to the subject a cocktail comprising a therapeutically effective amount of antibiotics. Thereby the AT-associated condition in the subject is treated, prevented or delayed. In some embodiments, this method comprises inhibiting the growth of detrimental microorganisms in a subject having AT and at risk of developing an AT-associated condition by administering to the subject a cocktail comprising a therapeutically effective amount of antibiotics. Thereby the AT-associated condition in the subject is treated, prevented or delayed.

In some embodiments, this method comprises inhibiting the growth of a detrimental microorganism in a subject having AT and diagnosed with an AT-associated condition by administering to the subject a therapeutically effective amount of an antibiotic inhibiting the growth of the detrimental microorganism. Thereby the AT-associated condition in the subject is treated, prevented or delayed. In some embodiments, this method comprises inhibiting the growth of a detrimental microorganism in a subject having AT and at risk of developing an AT-associated condition by administering to the subject a therapeutically effective amount of an antibiotic inhibiting the growth of the detrimental microorganism. Thereby the AT-associated condition in the subject is treated, prevented or delayed.

In some embodiments, this method comprises inhibiting the growth of detrimental microorganisms in a subject having AT and diagnosed with an AT-associated condition by administering to the subject a therapeutically effective amount of one or more bacteriophages, as described herein. Thereby the AT-associated condition in the subject is treated, prevented or delayed. In some embodiments, this method comprises inhibiting the growth of detrimental microorganisms in a subject having AT and at risk of developing an AT-associated condition by administering to the subject a therapeutically effective amount of one or more bacteriophages, as described herein. Thereby the AT-associated condition or any other condition in the subject is treated, prevented or delayed.

In some embodiments, the AT-associated condition is selected from the group consisting of a cancerous condition, a neurological degeneration, an immunodeficiency, an inflammatory condition, an inflammation-induced genotoxicity, a radiation sensitivity, an abundance of hepatic and/or migratory cells, and a genetic instability.

In some embodiments, the AT-associated condition comprises neurological degeneration. In some embodiments, the neurological degeneration is a condition selected from inability or difficulty of a subject to walk, inability or difficulty of a subject to move, inability or difficulty of a subject to swallow. A subject unable or having difficulty to walk or a subject unable or having difficulty to move may be a subject who is wheelchair bound.

In some embodiments, the AT-associated condition is radiation sensitivity.

In some embodiments, the AT-associated condition is a genetic instability.

While many genetic instabilities can be treated, mitigated or prevented using methods and compositions of the present invention, in some embodiments, the genetic instability is selected from Nijmegen Breakage Syndrome, Fanconi's anemia, Werner Syndrome, Blooms Syndrome, and Li Fraumeni Disease.

In some embodiments, the genetic instability is Nijmegen Breakage Syndrome.

In some embodiments, the genetic instability is Fanconi's anemia.

In some embodiments, the genetic instability is Werner Syndrome.

In some embodiments, the genetic instability is Blooms Syndrome.

In some embodiments, the genetic instability is Li Fraumeni Disease.

C. Method for Treating, Preventing, or Delaying the Onset of a Cancerous Condition in a Subject Having AT In some embodiments, the AT-associated condition is a cancerous condition. Methods of the present invention can be practiced in vitro and in vivo. In one aspect of the present invention, a method for treating or preventing a cancerous condition in a subject suffering from a cancerous condition is provided. This method comprises administering to a subject having been diagnosed with a cancer or at risk of developing a cancer a therapeutically effective amount of a composition of the present invention, wherein the cancerous condition is characterized by unwanted growth or proliferation of a cell expressing one or more cell surface marker, and wherein administering results in the treatment of the subject or in preventing the cancerous condition from occurring in the subject or in delaying the onset of the cancerous condition.

In some embodiments, this method comprises the step of selecting a subject having AT and diagnosed with a cancerous condition. In some embodiments, this method comprises selecting a subject having AT and at risk of developing a cancerous condition.

In some embodiments of the present invention, a composition of the present invention is used to treat a subject suffering from a hematologic cancer expressing one or more cell surface marker. Hematologic cancers include, but are not limited to cancer of blood (myeloid leukemia (acute and chronic), acute lymphoblastic leukemia, chronic lymphocytic leukemia, myeloproliferative diseases, multiple myeloma, myelodysplastic syndrome), Hodgkin's disease, and non-Hodgkin's lymphoma (malignant lymphoma).

A "hematologic cancer" includes any malignancy associated with cells in the bloodstream. Examples thereof include B and T cell lymphomas, leukemias including but not limited to low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia, chronic leukocytic leukemia, acute myelogenous leukemia, acute lymphoblastic leukemia, chronic lymphocytic leukemia, chronic myelogenous leukemia, lymphoblastic leukemia, lymphocytic leukemia, monocytic leukemia, myelogenous leukemia, and promyelocytic leukemia. It should be clear to those of skill in the art that these lymphomas will often have different names due to changing systems of classification, and that patients having lymphomas and leukemias classified under different names may also benefit from the therapeutic regimens of the present invention.

In some embodiments, the cancerous condition is a hematologic cancer.

In some embodiments, the cancerous condition is a lymphoid malignancy.

In some embodiments, the cancerous condition is a neoplasia.

In some embodiments, the cancerous condition is non-Hodgkin's B cell lymphoma.

In some embodiments, the cancerous condition is acute lymphocytic leukemia.

In some embodiments, the cancerous condition is a Hodgkin's lymphoma.

D. Method for Treating, Preventing, or Delaying the Onset of an Inflammatory Condition in a Subject Having AT In some embodiments, the AT-associated condition is an inflammatory condition.

In some embodiments, this method comprises selecting a subject having AT and diagnosed with an inflammatory condition. In some embodiments, this method comprises selecting a subject having AT and at risk of developing an inflammatory condition.

In some embodiments, the inflammatory condition is selected from a substantially increased expression level of transforming growth factor type beta, a substantially increased expression level of interleukin (IL)-10, a substantially increased expression level of IL-4, a substantially decreased expression level of myeloid differentiation primary response 88, a substantially decreased expression level of IL-12, a substantially decreased expression level IL-1β, and a substantially decreased expression level of interferon gamma, wherein the substantially increased and substantially decreased expression levels are in comparison to the respective expression levels in a subject not having AT.

In some embodiments, the inflammatory condition is a substantially increased expression level of TGF-β (Transforming Growth Factor Type Beta) nucleic acid and/or TGF-β polypeptide) in the subject having AT when compared to a subject not having AT.

In some embodiments, the inflammatory condition is a substantially increased expression level of IL-10 (Interleukin-10) nucleic acid and/or IL-10 polypeptide in the subject having AT when compared to a subject not having AT.

In some embodiments, the inflammatory condition is a substantially increased expression level of IL-4 (Interleukin-4) nucleic acid and/or IL-4 polypeptide in the subject having AT when compared to a subject not having AT.

In some embodiments, the inflammatory condition is a substantially decreased expression level of MyD-88 (Myeloid Differentiation Primary Response Gene/Polypeptide (88)) nucleic acid and/or MyD-88 polypeptide in the subject having AT when compared to a subject not having AT.

In some embodiments, the inflammatory condition is a substantially decreased expression level of IL-12 (Interleukin 12) nucleic acid and/or IL-12 polypeptide in the subject having AT when compared to a subject not having AT.

In some embodiments, the inflammatory condition is a substantially decreased expression level of IL-1β (Interleukin-1 Beta) nucleic acid and/or IL-1β polypeptide in the subject having AT when compared to a subject not having AT.

In some embodiments, the inflammatory condition is a substantially decreased expression level of IFN-γ (Interferon Gamma) nucleic acid and/or IFN-γ polypeptide in the subject having AT when compared to a subject not having AT.

E. Method for Treating, Preventing, or Delaying the Onset of Inflammation-Induced Genotoxicity in a Subject Having AT In some embodiments, the AT-associated condition is inflammation-induced genotoxicity.

In some embodiments, this method comprises the step of selecting a subject having AT and being diagnosed with inflammation-induced genotoxicity. In some embodiments, this method comprises the step of selecting a subject having AT and being at risk of developing inflammation-induced genotoxicity.

In some embodiments, the inflammation-induced genotoxicity is accompanied by a substantially increased expression level of TGF-β nucleic acid and/or TGF-β polypeptide in the subject having AT when compared to a subject not having AT.

In some embodiments, the inflammation-induced genotoxicity is accompanied by a substantially increased expression level of IL-10 nucleic acid and/or IL-10 polypeptide in the subject having AT when compared to a subject not having AT.

In some embodiments, the inflammation-induced genotoxicity is accompanied by a substantially increased expression level of IL-4 nucleic acid and/or IL-4 polypeptide in the subject having AT when compared to a subject not having AT.

In some embodiments, the inflammation-induced genotoxicity is accompanied by a substantially decreased expression level of MyD-88 nucleic acid and/or MyD-88 polypeptide in the subject having AT when compared to a subject not having AT.

In some embodiments, the inflammation-induced genotoxicity is accompanied by a substantially decreased expression level of IL-12 nucleic acid and/or IL-12 polypeptide in the subject having AT when compared to a subject not having AT.

In some embodiments, the inflammation-induced genotoxicity is accompanied by a substantially decreased expression level of IL-1β nucleic acid and/or IL-1β polypeptide in the subject having AT when compared to a subject not having AT.

In some embodiments, the inflammation-induced genotoxicity is accompanied by a substantially decreased expression level of IFN-γ nucleic acid and/or IFN-γ polypeptide in the subject having AT when compared to a subject not having AT.

In some embodiments, the inflammation-induced genotoxicity comprises DNA damage, in particular DNA instability and DNA breakage. DNA breakage can include double-strand DNA breakage and single-strand DNA breakage. In some embodiments of the present invention chromosomal breakage is substantially reduced upon administration to a subject of a composition of the present invention, in particular a composition comprising *Lactobacillus johnsonii*.

In some embodiments, the inflammation-induced genotoxicity comprises deletion of DNA.

F. Method for Reducing the Abundance of Hepatic and/or Migratory Cells in a Subject Having AT In some embodiments, the AT-associated condition is abundance of hepatic and/or migratory cells in a subject.

In some embodiments, this method comprises selecting a subject having AT and diagnosed with a substantial increase of hepatic and/or migratory cells. In some embodiments, this method comprises selecting a subject having AT and at risk of developing a substantial increase of hepatic and/or migratory cells.

G. Method for Treating, Preventing, or Delaying the Onset of a Cancer in a Subject Having a p53 Deficiency or Having a p53 Deficiency-Associated Cancer The present invention provides a method for treating, preventing, or delaying the onset of cancer in a subject having a p53 deficiency. In some embodiments, this method comprises administering to a subject having a p53 deficiency and diagnosed with a p53 deficiency a therapeutically effective amount of a composition comprising a probiotic microorganism. Thereby the p53 deficiency-associated cancer in the subject is treated, prevented or delayed. In some embodiments, this method comprises administering to a subject having a p53 deficiency and at risk of developing a p53-deficiency-associated cancer a therapeutically effective amount of a composition comprising a probiotic microorganism. Thereby the p53-deficiency-associated cancer in the subject is treated, prevented or delayed.

In some embodiments, this method comprises selecting a subject having a p53 deficiency and diagnosed with a p53 deficiency-associated cancer. In some embodiments, this method comprises selecting a subject having a p53 deficiency and being at risk of developing a p53 deficiency-associated cancer.

In some embodiments, selecting a subject having or suspected of having a p53 deficiency comprises obtaining a biological sample from that subject and determining in the biological sample obtained from the subject if the subject has a p53 deficiency. Determining a p53 deficiency in a biological sample can be done in a variety of ways. Non-limiting examples, e.g., include, determining a p53 nucleic acid expression level, determining a nucleotide sequence for a gene encoding a p53 polypeptide, determining the level of a p53 polypeptide expression, or determining the amino acid sequence of a p53 polypeptide. Methods for such determination are known in the art and include, but are not limited to, e.g., Northern blot analysis, Southern blot analysis, PCR analysis, RNA sequencing, DNA sequencing, amino acid sequencing, mass spectrometry, etc. A p53 deficiency will be evidenced by (i) a lower than normal expression level of a p53 nucleic acid, (ii), a lower than normal expression level of a p53 polypeptide, (iii), a mutation in a gene encoding a p53 polypeptide that is not present in a wildtype or normal gene encoding a wildtype or normal p53 polypeptide, (iv) a mutation in a gene transcript encoding a p53 polypeptide that is not present in a wildtype or normal gene transcript encoding a wildtype or normal p53 polypeptide, (v) a mutation in an amino acid sequence of a p53 polypeptide that is not present in an amino acid sequence of a wildtype or normal p53 polypeptide. One of skill in the art will appreciate that along with the biological samples being analyzed for a p53 deficiency, appropriate control sample(s) will be analyzed under same conditions and that the results obtained analyzing the biological sample(s) will be compared to the results obtained by analyzing appropriate control sample(s). Thus, a substantially reduced expression of a p53 nucleic acid or a p53 polypeptide and/or a substantially increased expression of a mutated p53 nucleic acid or p53 polypeptide can be determined in a sample obtained from a subject.

In some embodiments, this method comprises sustaining a beneficial level of a probiotic microorganism in a subject having a p53 deficiency and diagnosed with a p53 deficiency-associated cancer by administering to the subject a therapeutically effective amount of a composition comprising a probiotic microorganism. Thereby the p53 deficiency-associated cancer in the subject is treated, prevented or delayed. In some embodiments, this method comprises sustaining a beneficial level of a probiotic microorganism in a subject having a p53 deficiency and at risk of developing p53 deficiency-associated cancer by administering to the subject a therapeutically effective amount of a composition comprising a probiotic microorganism. Thereby the p53 deficiency-associated cancer in the subject is treated, prevented or delayed.

In some embodiments, this method comprises restoring the presence of a beneficial level of a probiotic microorganism in a subject having a p53 deficiency and diagnosed with p53 deficiency-associated cancer by administering to the subject a therapeutically effective amount of a composition comprising a probiotic microorganism. Thereby the p53 deficiency-associated cancer in the subject is treated, prevented or delayed. In some embodiments, this method comprises restoring the presence of a beneficial level of a probiotic microorganism in a subject having a p53 deficiency and at risk of developing p53 deficiency-associated cancer by administering to the subject a therapeutically effective amount of a composition comprising a probiotic microorganism. Thereby the p53 deficiency-associated cancer in the subject is treated, prevented or delayed.

In some embodiments, this method comprises inhibiting the growth of detrimental microorganisms in a subject having a p53 deficiency and diagnosed with p53 deficiency-associated cancer by administering to the subject a therapeutically effective amount of a composition comprising two or more antibiotics. Thereby the p53 deficiency-associated cancer in the subject is treated, prevented or delayed. In some embodiments, this method comprises inhibiting the growth of detrimental microorganisms in a subject having a p53 deficiency and at risk of developing a p53 deficiency-associated cancer by administering to the subject a therapeutically effective amount of a composition comprising two or more antibiotics. Thereby the p53 deficiency-associated cancer in the subject is treated, prevented or delayed.

In some embodiments, this method comprises inhibiting the growth of a detrimental microorganism in a subject having a p53 deficiency and diagnosed with a p53 deficiency-associated cancer by administering to the subject a therapeutically effective amount of an antibiotic inhibiting the growth of the detrimental microorganism. Thereby the p53 deficiency-associated cancer in the subject is treated, prevented or delayed. In some embodiments, this method comprises inhibiting the growth of a detrimental microorganism in a subject having a p53 deficiency and at risk of developing a p53 deficiency-associated cancer by administering to the subject a therapeutically effective amount of an antibiotic inhibiting the growth of the detrimental microorganism. Thereby the p53 deficiency-associated cancer in the subject is treated, prevented or delayed.

In some embodiments, this method comprises inhibiting the growth of detrimental microorganisms in a subject having a p53 deficiency and diagnosed with p53 deficiency-associated cancer by administering to the subject a therapeutically effective amount of one or more bacteriophages, as described herein. Thereby the p53 deficiency-associated cancer in the subject is treated, prevented or delayed. In some embodiments, this method comprises inhibiting the growth of detrimental microorganisms in a subject having a p53 deficiency and at risk of developing a p53 deficiency-associated cancer by administering to the subject a therapeutically effective amount of one or more bacteriophages, as described herein. Thereby the p53 deficiency-associated cancer in the subject is treated, prevented or delayed.

Compositions of the present invention can be used to treat any cancer having a p53 deficiency as described herein and referred to as a "p53 deficiency-associated cancer." In some embodiments of the present invention, a p53 deficiency-associated cancer is selected from a lung cancer, a sarcoma, a gastrointestinal cancer, a cancer of the genitourinary tract, a liver cancer, a skin cancer, a gynecological cancer, a bone cancer, a cancer of the nervous system, a hematologic cancer, a cancer of the adrenal glands, and a cancer associated with Li Fraumeni Disease.

In some embodiment of the present invention, a composition of the present invention is used to treat a subject suffering from a lung cancer having a p53 deficiency. A p53 deficiency-associated lung cancer includes, but is not limited to, bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, SCLC, and NSCLC.

In some embodiments of the present invention, a composition of the present invention is used to treat a subject suffering from a sarcoma having a p53 deficiency. A p53 deficiency-associated sarcoma includes, but is not limited to, cancers such as angiosarcoma, fibrosarcoma, rhabdomyosarcoma, liposarcoma, myxoma, rhabdomyoma, fibroma, lipoma and teratoma.

In some embodiments of the present invention, a composition of the present invention is used to treat a subject suffering from a gastrointestinal cancer having a p53 deficiency. A p53 deficiency-associated gastrointestinal cancer includes, but is not limited to cancers of esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, VIPoma), small bowel (adenocarcinoma, lymphoma, carcinoid tumors, Kaposi's sarcoma, leiomyoma, hemangioma, lipoma, neurofibroma, fibroma), and large bowel (adenocarcinoma, tubular adenoma, villous adenoma, hamartoma, leiomyoma).

In some embodiments of the present invention, a composition of the present invention is used to treat a subject suffering from a cancer of the genitourinary tract having a p53 deficiency. A p53 deficiency-associated cancer of the genitourinary tract includes, but is not limited to cancers of kidney (adenocarcinoma, Wilms tumor (nephroblastoma), lymphoma, leukemia, renal cell carcinoma), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, Leydig cell tumor, fibroma, fibroadenoma, adenomatoid tumors, lipoma).

In some embodiments of the present invention, a composition of the present invention is used to treat a subject suffering from a liver cancer having a p53 deficiency. A p53 deficiency-associated liver cancer includes, but is not limited to, hepatocellular carcinoma, cholangiocarcinoma, hepatoblastoma, angiosarcoma, hepatocellular adenoma, and hemangioma.

In some embodiments of the present invention, a composition of the present invention is used to treat a subject suffering from a skin cancer having a p53 deficiency. A p53 deficiency-associated skin cancer includes, but is not limited to, malignant melanoma, basal cell carcinoma, squamous cell carcinoma, Kaposi's sarcoma, nevi, dysplastic nevi, lipoma, angioma, dermatofibroma, keloids, and psoriasis.

In some embodiments of the present invention, a composition of the present invention is used to treat a subject suffering from a gynecological cancer having a p53 deficiency. A p53 deficiency-associated gynecological cancer includes, but is not limited to, cancer of uterus (endometrial carcinoma), cervix (cervical carcinoma, pre-invasive cervical dysplasia), ovaries (ovarian carcinoma (serous cystadenocarcinoma, mucinous cystadenocarcinoma, endometrioid carcinoma, clear cell adenocarcinoma, unclassified carcinoma), granulosa-theca cell tumors, Sertoli-Leydig cell tumors, dysgerminoma, malignant teratoma and other germ cell tumors), vulva (squamous cell carcinoma, intraepithelial carcinoma, adenocarcinoma, fibrosarcoma, melanoma), vagina (clear cell carcinoma, squamous cell carcinoma, sarcoma botryoides (embryonal rhabdomyosarcoma), and fallopian tubes (carcinoma).

In some embodiments of the present invention, a composition of the present invention is used to treat a subject suffering from a bone cancer having a p53 deficiency. p53 deficiency-associated bone cancer includes, but is not limited to, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxoid fibroma, osteoid osteoma, and giant cell tumors.

In some embodiments of the present invention, a composition of the present invention is used to treat a subject suffering from a cancer of the nervous system having a p53 deficiency. A p53 deficiency-associated cancer of the nervous system includes, but is not limited to cancers of skull (osteoma, hemangioma, granuloma, xanthoma, Paget's disease of bone), meninges (meningioma, meningiosarcoma, gliomatosis), brain (astrocytoma, medulloblastoma, glioma, ependymoma, germinoma (pinealoma), glioblastoma multiforme, oligodendroglioma, schwannoma, retinoblastoma, congenital tumors), and spinal cord (neurofibroma, meningioma, glioma, sarcoma.

In some embodiments of the present invention, a composition of the present invention is used to treat a subject suffering from a hematologic cancer having a p53 deficiency. A p53 deficiency-associated hematologic cancer includes, but is not limited to cancer of blood (myeloid leukemia (acute and chronic), acute lymphoblastic leukemia, chronic lymphocytic leukemia, myeloproliferative diseases, multiple myeloma, myelodysplastic syndrome), Hodgkin's disease, and non-Hodgkin's lymphoma (malignant lymphoma).

In some embodiments of the present invention, a composition of the present invention is used to treat a subject suffering from a cancer of adrenal glands having a p53 deficiency. A p53 deficiency-associated cancer of adrenal glands includes, but is not limited to, neuroblastoma.

Li Fraumeni Disease is a heterozygous p53 deficiency in humans who, when afflicted, in almost 100%, develop cancer. p53 homozygosity in humans, however, has not been described, as it is possibly lethal. Applicants have shown the beneficial effects of administering a composition of the present invention to homozygous p53 deficient mice. Thus, in some embodiments of the present invention, a p53 deficiency associated cancer is Li Fraumeni Disease.

H. Method for Treating, Mitigating, and Preventing Damage to Normal Tissue in a Subject being Exposed to Radiation When a subject is exposed to radiation cells and tissue of that subject become irradiated and, as a consequence thereof damaged or killed. Exposure to radiation includes, but is not limited to radiation oncology for the treatment of cancer, exposure caused by accidental radiation, and exposure caused by environmental radiation. Particularly when treating a subject to radiation, e.g., in oncology treatment when treating a cancer patient, not only are the tumor or cancer cells of the patient exposed to radiation (a desired result), but, as an unwanted result of such treatment, normal tissue is also exposed to radiation and will be damaged when not treated or when such damage is not prevented.

The present invention provides methods for treating, mitigating, and preventing damage to normal tissue in a subject previously exposed, being exposed, or intended to be exposed to radiation. In some embodiments, this method comprises administering to the subject previously exposed, being exposed, or intended to be exposed to radiation a therapeutically effective amount of a composition comprising a probiotic microorganism. Thereby the damage to normal tissue in the subject is treated, mitigated or prevented.

In some embodiments, this method comprises sustaining a beneficial level of a probiotic microorganism in a subject previously exposed, being exposed, or intended to be exposed to radiation comprising administering to the subject a therapeutically effective amount of a probiotic microorganism. Thereby the damage in the subject is treated, mitigated, or prevented.

In some embodiments, this method comprises restoring the presence of a beneficial level of a probiotic microorganism in a subject previously exposed, being exposed, or intended to be exposed to radiation by administering to the subject a therapeutically effective amount of a composition comprising a probiotic microorganism. Thereby the damage in the subject is treated, mitigated, or prevented.

In some embodiments, this method comprises inhibiting the growth of at least one detrimental microorganism in a subject previously exposed, being exposed, or intended to be exposed to radiation by administering to the subject a therapeutically effective amount of a composition comprising two or more antibiotics, sometimes referred to herein as a combination of antibiotics or as a cocktail of antibiotics. Thereby the damage in the subject is treated, mitigated or prevented.

In some embodiments, this method comprises inhibiting the growth of a detrimental microorganism in a subject previously exposed, being exposed, or intended to be exposed to radiation by administering to the subject a therapeutically effective amount of an antibiotic inhibiting the growth of the detrimental microorganism. Thereby the damage in the subject is treated, mitigated or prevented.

In some embodiments, this method comprises inhibiting the growth of at least one detrimental microorganism in a subject previously exposed, being exposed, or intended to be exposed to radiation by administering to the subject a therapeutically effective amount of one or more bacteriophages, as described herein. Thereby the damage in the subject is treated, mitigated or prevented.

In some embodiments, this method comprises selecting a subject being exposed to radiation. In some embodiments, this method comprises selecting a subject having a condition requiring exposure to radiation. In some embodiments, the condition requiring exposure to radiation is a cancer. All cancers described herein can be treated by radiation treatment.

In some embodiments, the exposure to radiation is exposure to natural or environmental radiation. In some embodiments, the exposure to radiation is exposure caused by accidental radiation, such as a nuclear fall-out or a nuclear accident.

I. Method for Reducing or Preventing the Occurrence of a Spontaneous Genetic Instability in a Subject The present invention provides methods for reducing or preventing the occurrence of a spontaneous genetic instability in a subject. In some embodiments, this method comprises administering to a subject in need of having the occurrence of a spontaneous genetic instability reduced or prevented a therapeutically effective amount of a composition comprising a probiotic microorganism. Thereby the occurrence of the spontaneous genetic instability is reduced or prevented. As one of ordinary skill in the art will appreciate, methods and compositions of the present invention can be used in methods for reducing or preventing the occurrence of two or more spontaneous genetic instabilities in a subject or in methods for reducing or preventing the occurrence of a combination of spontaneous genetic instabilities in a subject.

In some embodiments, this method comprises sustaining a beneficial level of a probiotic microorganism in the subject in need of having the occurrence of a spontaneous genetic instability reduced or prevented by administering to the subject a therapeutically effective amount of a probiotic microorganism. Thereby the occurrence of the spontaneous genetic instability is reduced or prevented.

In some embodiments, this method comprises restoring the presence of a beneficial level of a probiotic microorganism in a subject in need of having the occurrence of a spontaneous genetic instability reduced or prevented by administering to the subject a therapeutically effective amount of a composition comprising a probiotic microorganism. Thereby the occurrence of the spontaneous genetic instability is reduced or prevented.

In some embodiments, this method comprises inhibiting the growth of at least one detrimental microorganism in a subject in need of having the occurrence of a spontaneous genetic instability reduced or prevented by administering to the subject a therapeutically effective amount of a composition comprising two or more antibiotics, sometimes referred to herein as a combination of antibiotics or as a cocktail of antibiotics. Thereby the occurrence of the spontaneous genetic instability is reduced or prevented.

In some embodiments, this method comprises inhibiting the growth of a detrimental microorganism in a subject in need of having the occurrence of a spontaneous genetic instability reduced or prevented by administering to the subject a therapeutically effective amount of an antibiotic inhibiting the growth of the detrimental microorganism. Thereby the occurrence of the spontaneous genetic instability is reduced or prevented.

In some embodiments, this method comprises inhibiting the growth of at least one detrimental microorganism in a subject in need of having the occurrence of a spontaneous genetic instability reduced or prevented by administering to the subject a therapeutically effective amount of one or more bacteriophages, as described herein. Thereby the occurrence of the spontaneous genetic instability is reduced or prevented.

In some embodiments, this method comprises selecting a subject in need of having a spontaneous genetic instability reduced or prevented. In some embodiments, the spontaneous genetic instability causes a spontaneous cancer in the subject. In some embodiments, the spontaneous cancer is a lymphoma.

J. Methods for Determining and Monitoring Responsiveness and Non-Responsiveness of a Subject being Treated The invention further provides methods for determining and monitoring whether a subject is responsive to a method of treatment or prevention as described herein. As one of ordinary skill in the art will appreciate those methods depend on the underlying disease being treated, such as AT, a p53 deficiency, a p53 deficiency-associated cancer or radiation-induced toxicity to normal tissue. For example, such methods comprise measuring the level of expression of at least one predictive marker in a subject's cancer, determining expression of p53 in a subject's cell, determining the extent of DNA damage in a subject's cell or tissue or determining the composition of a subject's microbiota as described herein. An informative expression level of a predictive marker in a subject's sample is an indication that the subject is a responsive subject and would benefit from a method of treatment or prevention as described herein.

Preferred embodiments of this invention are described herein. Of course, variations, changes, modifications and substitution of equivalents of those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

For all of the methods described herein, the probiotic microorganism may be administered in a composition such as any of the compositions described herein, e.g., comprising one or more fungal microbiota, one or more commensal microbiota, one or more antibiotics, one or more bacteriophages or a combination thereof. Preferably, the microorganism of the invention is administered in a composition with one or more antibiotics, one or more bacteriophages, or a combination thereof.

In some embodiments, the composition comprising a probiotic microorganism comprises a *Lactobacillus* sp.

In some embodiments, the composition comprising a probiotic microorganism comprises *Lactobacillus johnsonii*.

In some embodiments, the composition comprising a probiotic microorganism comprises *Lactobacillus johnsonii* 456.

The compositions are administered to the subject in a therapeutically effective amount.

IV. Examples

The below examples are meant to illustrate specific embodiments of the methods and compositions described herein and should not be construed as limiting the scope of the invention in any way.

Example A. General Experimental Procedures

1. Animal Housing and Husbandry $Atm^{-/-}$ mice were obtained by intercrossing $Atm^{+/-}$ mice and identified by genotyping as described (Liao et al., 1999, *Mol Cell Biol* 19:3095-3102). Mice were housed under standard conditions in accordance with the Animal Research Committee at UCLA. Mice were housed under two types of specific pathogen free (SPF) conditions, where either sterile (SPF-S) or non-sterile (SPF-N) food, water, and bedding were employed. $Atm^{-/-}$ mice harboring RM and CM microbiota were created by rederivation as described in Fujiwara et al. (2008, *J Immunol* 180:5843-5852) and by antibiotic treatment (Rakoff-Nahoum et al., 2004, *Cell* 118:229-241) followed by orogastric gavage of CM feces, respectively.

2. Mouse Longevity Studies

For the $Atm^{-/-}$ mice longevity studies, animals were kept until they were found dead, developed signs of tumors or became sick, at which time they were euthanized. Mice were sent to a veterinary pathologist for necropsy. Differences in longevity and lymphoma latency were analyzed using the log-rank test.

3. Pun Reversion Assay

Pun reversions were counted in mice that were 10 days old. Pun reversions can be seen as a black spot on the fur and were counted as described previously (Bishop et al., 2000, *Cancer Res* 60:395-399). Statistics were done using the $\chi 2$ test.

4. Oxidative Stress and DNA Damage

Frozen blood was prepared for enzymatic measurement of the oxidized form of glutathione using the Bioxytech® GSH:GSSG-412 kit assay (Oxis, Beverly Hills, Calif., USA). Reduced GSH and GSSG were determined separately by reaction with glutathione reductase. The colorimetric assay was performed in triplicate for each blood sample from all male experimental $Atm^{-/-}$ mice. Data was expressed as the ratio of free GSH to GSSG.

For determination of oxidative DNA damage, enzyme Ogg1-modified Comet assay was used. Samples loaded onto Gelbond film are incubated in the enzyme-containing buffer according to manufacturer's recommendation and then lysed and electrophoresed.

$\gamma$-H2AX is a measure of DNA double-strand breaks (DSBs; Rogakou et al., 1998, *J Biol Chem* 273(10):5858-68). Since ATM deficient cells have problems repairing DSBs this method can be used to detect any difference in genotoxicity conferred by the different intestinal microbiota conditions. Cells with more than four distinct foci are considered positive cells. The number of positive cells is then compared for control groups versus treated groups via a paired Student's t-test.

5. Micronucleus Assay

Micronuclei (MN) formation in peripheral blood erythrocytes to assess chromosomal instability can be determined using an in vivo micronucleus assay. The incidence of micronuclei as measured in the in vivo MN assay has commonly been used as an index of cytogenetic damage, including chromosome breaks, spindle abnormalities, or structurally abnormal chromosomes in many cell types; most frequently in erythroblasts/erythrocytes from peripheral blood or bone marrow (Hayashi et al., 1994, *Mutat Res* 312(3):293-304; Steinheider et al., 1985, *Cell Biol Toxicol* 1(3):197-211). The frequency of MN formation is calculated as a number of micronucleated erythrocytes per 2000 erythrocytes per mouse. Micronuclei were examined in peripheral blood erythrocytes stained with Wright-Giemsa (Sigma-Aldrich, St. Louis, Mo., USA). At least 2,000 erythrocytes were counted at 100× magnification as described previously (Westbrook et al., 2009, *Cancer Res* 69:4827-4834). Statistics were done using Student's t-tests.

6. Alkaline Comet Assay

DNA strand breaks were measured in peripheral blood cells using the alkaline comet assay. The alkaline comet assay detects single and double DNA strand breaks and was performed essentially as described (McNamee et al., 2000, *Mutat Res* 466(1):63-9). Blood was collected from the facial vein of mice approximately 6-months-old and diluted 1:1 with RPMI+20% DMSO for storage at −80° C. until the assay was performed. The comet assay was basically performed as previously described (Westbrook et al., 2009, *Cancer Res* 69:4827-4834). Statistical analyses were done using Student's t-tests.

7. Bacteria Community Analyses of SPF-N and SPF-S Mice

Fecal pellets from $Atm^{+/-}$ mice (SPF-N and SPF-S) were collected and immediately snap-frozen in liquid nitrogen and stored at −80° C. Nucleic acids from fecal pellets were purified using a phenol-chloroform extraction with bead-beating (Griffiths et al., 2000, *Appl Environ Microbiol* 66:5488-5491) and a fragment of the 16S rRNA gene targeting the V6-V9 region of most bacteria was amplified with PCR primers 909F (5'-ACTCAAAKGAATWGACGG-3') and 1492R (5'-NTACCTTGTTACGACT-3'). The template was amplified and tagged with a sample-specific 8-nt barcode sequence via a 2-step, low cycle number barcoded PCR protocol described previously (Berry et al., 2011, *Appl Environ Microbiol* 77:7846-7849). Pyrosequencing was performed on a GS FLX 454 sequencer at the Norwegian Sequencing Centre.

Pyrosequencing data was analyzed as previously described (Berry et al., 2012, *ISME J.* doi:10.1038/ismey.2012.39). Briefly, reads were quality-filtered using LUCY (Chou and Holmes, 2001, *Bioinformatics* 17, 1093-1104) and clustered into phylotypes at 97% identity using UCLUST (Edgar, 2010, *Bioinformatics* 26, 2460-2461). Taxonomic classifications were assigned and alpha and beta diversity metrics were produced using the QIIME software package (Caporaso et al., 2010, *Nat Meth* 7:335-336). The VEGAN package (Dixon, 2003, *J Vegetation Science* 14:927-930) was used for permutational multivariate analysis of variance and the indispecies package (De Cáceres and Legendre, 2009, *Ecology* 90:3566-3574) was used to identify phylotypes that were indicators for a colony type. To focus on abundant indicators, only indicators that had an elevated relative abundance of at least 1% (e.g., 0.5% to 1.5%) were considered.

8. Bacteria Community Analyses of CM and RM Mice

Intestinal mucosa samples of CM and RM mice were obtained as described in Presley et al. (2010, *Appl Environ Microbiol* 76:936-941). DNA was extracted from these samples using the PowerSoil DNA Isolation Kit (MO BIO Laboratories, Carlsbad, Calif., USA), and a 30-second bead-beating step using a Mini-Beadbeater-16 (BioSpec Products, Bartlesville, Okla., USA). One hundred microliter PCR amplification reactions were performed in an MJ Research PTC-200 thermal cycler (Bio-Rad Inc., Hercules, Calif., USA) and contained: 50 mM Tris (pH 8.3), 500 µg/ml bovine serum albumin (BSA), 2.5 mM $MgCl_2$, 250 µM of each deoxynucleotide triphosphate (dNTP), 400 nM of forward PCR primer, 200 nM of each reverse PCR primer, 4 µl of DNA template, and 2.5 units JumpStart Taq DNA polymerase (Sigma-Aldrich, St. Louis, Mo., USA). PCR primers targeted a portion of the 16S and 23S rRNA genes and the hypervariable intergenic region, with the reverse primers including a 12-bp barcode (Tables 1 and 2).

TABLE 1

Reverse PCR Primers used in the Illumina-based high throughput sequence analysis of bacterial rRNA genes (each reverse PCR primer is comprised of the 4 adjoining segments in each row shown below).

| No. | 3' Illumina Adapter | Barcode | Spacer | Reverse 23S Primer (23SR) |
|---|---|---|---|---|
| 1 | CAAGCAGAAGACGGCATACGAGAT | CTAGCGTGCGTT | AGTCAGTCAGCC | GGGTTBCCCCATTCRG |
| 2 | CAAGCAGAAGACGGCATACGAGAT | TCGACATCTCTT | AGTCAGTCAGCC | GGGTTBCCCCATTCRG |
| 3 | CAAGCAGAAGACGGCATACGAGAT | ACGAGACTGATT | AGTCAGTCAGCC | GGGTTBCCCCATTCRG |
| 4 | CAAGCAGAAGACGGCATACGAGAT | CGAGTCACGATT | AGTCAGTCAGCC | GGGTTBCCCCATTCRG |
| 5 | CAAGCAGAAGACGGCATACGAGAT | GCCATAGTGTGT | AGTCAGTCAGCC | GGGTTBCCCCATTCRG |
| 6 | CAAGCAGAAGACGGCATACGAGAT | GTAGACATGTGT | AGTCAGTCAGCC | GGGTTBCCCCATTCRG |
| 7 | CAAGCAGAAGACGGCATACGAGAT | TAGACACCGTGT | AGTCAGTCAGCC | GGGTTBCCCCATTCRG |
| 8 | CAAGCAGAAGACGGCATACGAGAT | CGGATCTAGTGT | AGTCAGTCAGCC | GGGTTBCCCCATTCRG |
| 9 | CAAGCAGAAGACGGCATACGAGAT | GACCACTGCTGT | AGTCAGTCAGCC | GGGTTBCCCCATTCRG |
| 10 | CAAGCAGAAGACGGCATACGAGAT | ATGAAGCACTGT | AGTCAGTCAGCC | GGGTTBCCCCATTCRG |
| 11 | CAAGCAGAAGACGGCATACGAGAT | TCGCGCAACTGT | AGTCAGTCAGCC | GGGTTBCCCCATTCRG |
| 12 | CAAGCAGAAGACGGCATACGAGAT | GCTAAGTGATGT | AGTCAGTCAGCC | GGGTTBCCCCATTCRG |
| 13 | CAAGCAGAAGACGGCATACGAGAT | CACGTGACATGT | AGTCAGTCAGCC | GGGTTBCCCCATTCRG |
| 14 | CAAGCAGAAGACGGCATACGAGAT | TGCGCTGAATGT | AGTCAGTCAGCC | GGGTTBCCCCATTCRG |
| 15 | CAAGCAGAAGACGGCATACGAGAT | GATGTATGTGGT | AGTCAGTCAGCC | GGGTTBCCCCATTCRG |
| 16 | CAAGCAGAAGACGGCATACGAGAT | GCATCGTCTGGT | AGTCAGTCAGCC | GGGTTBCCCCATTCRG |
| 17 | CAAGCAGAAGACGGCATACGAGAT | CTAGTCGCTGGT | AGTCAGTCAGCC | GGGTTBCCCCATTCRG |
| 18 | CAAGCAGAAGACGGCATACGAGAT | TCTGATCGAGGT | AGTCAGTCAGCC | GGGTTBCCCCATTCRG |
| 19 | CAAGCAGAAGACGGCATACGAGAT | GATAGCACTCGT | AGTCAGTCAGCC | GGGTTBCCCCATTCRG |
| 20 | CAAGCAGAAGACGGCATACGAGAT | TGGTCGCATCGT | AGTCAGTCAGCC | GGGTTBCCCCATTCRG |
| 21 | CAAGCAGAAGACGGCATACGAGAT | TAGCAGTTGCGT | AGTCAGTCAGCC | GGGTTBCCCCATTCRG |
| 22 | CAAGCAGAAGACGGCATACGAGAT | GTATCTGCGCGT | AGTCAGTCAGCC | GGGTTBCCCCATTCRG |
| 23 | CAAGCAGAAGACGGCATACGAGAT | TCCAGATAGCGT | AGTCAGTCAGCC | GGGTTBCCCCATTCRG |
| 24 | CAAGCAGAAGACGGCATACGAGAT | GACACTCACCGT | AGTCAGTCAGCC | GGGTTBCCCCATTCRG |
| 25 | CAAGCAGAAGACGGCATACGAGAT | TGCTACAGACGT | AGTCAGTCAGCC | GGGTTBCCCCATTCRG |
| 26 | CAAGCAGAAGACGGCATACGAGAT | TCTACGGCACGT | AGTCAGTCAGCC | GGGTTBCCCCATTCRG |
| 27 | CAAGCAGAAGACGGCATACGAGAT | GTGTGCTAACGT | AGTCAGTCAGCC | GGGTTBCCCCATTCRG |

TABLE 1-continued

Reverse PCR Primers used in the Illumina-based high throughput sequence analysis of bacterial rRNA genes (each reverse PCR primer is comprised of the 4 adjoining segments in each row shown below).

| No. | 3' Illumina Adapter | Barcode | Spacer | Reverse 23S Primer (23SR) |
|---|---|---|---|---|
| 28 | CAAGCAGAAGACGGCATACGAGAT | ATAGGCTGTAGT | AGTCAGTCAGCC | GGGTTBCCCCATTCRG |
| 29 | CAAGCAGAAGACGGCATACGAGAT | ACCACACGTAGT | AGTCAGTCAGCC | GGGTTBCCCCATTCRG |
| 30 | CAAGCAGAAGACGGCATACGAGAT | TATGGAGCTAGT | AGTCAGTCAGCC | GGGTTBCCCCATTCRG |
| 31 | CAAGCAGAAGACGGCATACGAGAT | GAGTATCTGAGT | AGTCAGTCAGCC | GGGTTBCCCCATTCRG |
| 32 | CAAGCAGAAGACGGCATACGAGAT | ATCGAATCGAGT | AGTCAGTCAGCC | GGGTTBCCCCATTCRG |
| 33 | CAAGCAGAAGACGGCATACGAGAT | CTCTAGAAGAGT | AGTCAGTCAGCC | GGGTTBCCCCATTCRG |
| 34 | CAAGCAGAAGACGGCATACGAGAT | ATGGCTGTCAGT | AGTCAGTCAGCC | GGGTTBCCCCATTCRG |
| 35 | CAAGCAGAAGACGGCATACGAGAT | ACTAGGATCAGT | AGTCAGTCAGCC | GGGTTBCCCCATTCRG |
| 36 | CAAGCAGAAGACGGCATACGAGAT | TACGCGTACAGT | AGTCAGTCAGCC | GGGTTBCCCCATTCRG |
| 37 | CAAGCAGAAGACGGCATACGAGAT | AGTACGCAGTCT | AGTCAGTCAGCC | GGGTTBCCCCATTCRG |
| 38 | CAAGCAGAAGACGGCATACGAGAT | CACTTGCTCTCT | AGTCAGTCAGCC | GGGTTBCCCCATTCRG |
| 39 | CAAGCAGAAGACGGCATACGAGAT | TGCTCTTGCTCT | AGTCAGTCAGCC | GGGTTBCCCCATTCRG |
| 40 | CAAGCAGAAGACGGCATACGAGAT | CTTAGCTACTCT | AGTCAGTCAGCC | GGGTTBCCCCATTCRG |
| 41 | CAAGCAGAAGACGGCATACGAGAT | GCTCAGGACTCT | AGTCAGTCAGCC | GGGTTBCCCCATTCRG |
| 42 | CAAGCAGAAGACGGCATACGAGAT | GCGCGTGTATCT | AGTCAGTCAGCC | GGGTTBCCCCATTCRG |
| 43 | CAAGCAGAAGACGGCATACGAGAT | TCGAGCCGATCT | AGTCAGTCAGCC | GGGTTBCCCCATTCRG |
| 44 | CAAGCAGAAGACGGCATACGAGAT | ATGCAGAGATCT | AGTCAGTCAGCC | GGGTTBCCCCATTCRG |
| 45 | CAAGCAGAAGACGGCATACGAGAT | AGCAGAACATCT | AGTCAGTCAGCC | GGGTTBCCCCATTCRG |
| 46 | CAAGCAGAAGACGGCATACGAGAT | TAGGCTCGTGCT | AGTCAGTCAGCC | GGGTTBCCCCATTCRG |
| 47 | CAAGCAGAAGACGGCATACGAGAT | CTCTCATATGCT | AGTCAGTCAGCC | GGGTTBCCCCATTCRG |
| 48 | CAAGCAGAAGACGGCATACGAGAT | TGCACAGTCGCT | AGTCAGTCAGCC | GGGTTBCCCCATTCRG |
| 49 | CAAGCAGAAGACGGCATACGAGAT | AGATAGCTCGCT | AGTCAGTCAGCC | GGGTTBCCCCATTCRG |
| 50 | CAAGCAGAAGACGGCATACGAGAT | TCGTGGATAGCT | AGTCAGTCAGCC | GGGTTBCCCCATTCRG |
| 51 | CAAGCAGAAGACGGCATACGAGAT | CCTCTGAGAGCT | AGTCAGTCAGCC | GGGTTBCCCCATTCRG |
| 52 | CAAGCAGAAGACGGCATACGAGAT | GACTAGTCAGCT | AGTCAGTCAGCC | GGGTTBCCCCATTCRG |
| 53 | CAAGCAGAAGACGGCATACGAGAT | ACAGTGCGTCCT | AGTCAGTCAGCC | GGGTTBCCCCATTCRG |
| 54 | CAAGCAGAAGACGGCATACGAGAT | GTCGTGTAGCCT | AGTCAGTCAGCC | GGGTTBCCCCATTCRG |
| 55 | CAAGCAGAAGACGGCATACGAGAT | GCGATCACACCT | AGTCAGTCAGCC | GGGTTBCCCCATTCRG |
| 56 | CAAGCAGAAGACGGCATACGAGAT | AGTGATGTGACT | AGTCAGTCAGCC | GGGTTBCCCCATTCRG |
| 57 | CAAGCAGAAGACGGCATACGAGAT | CAGCTATGGACT | AGTCAGTCAGCC | GGGTTBCCCCATTCRG |
| 58 | CAAGCAGAAGACGGCATACGAGAT | TCAGAGTAGACT | AGTCAGTCAGCC | GGGTTBCCCCATTCRG |
| 59 | CAAGCAGAAGACGGCATACGAGAT | GCTTCTCTCACT | AGTCAGTCAGCC | GGGTTBCCCCATTCRG |
| 60 | CAAGCAGAAGACGGCATACGAGAT | ACGCATCGCACT | AGTCAGTCAGCC | GGGTTBCCCCATTCRG |
| 61 | CAAGCAGAAGACGGCATACGAGAT | AGAGCATCCACT | AGTCAGTCAGCC | GGGTTBCCCCATTCRG |
| 62 | CAAGCAGAAGACGGCATACGAGAT | CACCGTGACACT | AGTCAGTCAGCC | GGGTTBCCCCATTCRG |
| 63 | CAAGCAGAAGACGGCATACGAGAT | CGATCGAACACT | AGTCAGTCAGCC | GGGTTBCCCCATTCRG |

TABLE 1-continued

Reverse PCR Primers used in the Illumina-based high throughput sequence analysis of bacterial rRNA genes (each reverse PCR primer is comprised of the 4 adjoining segments in each row shown below).

| No. | 3' Illumina Adapter | Barcode | Spacer | Reverse 23S Primer (23SR) |
|---|---|---|---|---|
| 64 | CAAGCAGAAGACGGCATACGAGAT | GACGCACTAACT | AGTCAGTCAGCC | GGGTTBCCCCATTCRG |
| 65 | CAAGCAGAAGACGGCATACGAGAT | CGCCACGTGTAT | AGTCAGTCAGCC | GGGTTBCCCCATTCRG |
| 66 | CAAGCAGAAGACGGCATACGAGAT | TCGAAGACGTAT | AGTCAGTCAGCC | GGGTTBCCCCATTCRG |
| 67 | CAAGCAGAAGACGGCATACGAGAT | GCGCAATAGTAT | AGTCAGTCAGCC | GGGTTBCCCCATTCRG |
| 68 | CAAGCAGAAGACGGCATACGAGAT | CTGAGTGAGTAT | AGTCAGTCAGCC | GGGTTBCCCCATTCRG |
| 69 | CAAGCAGAAGACGGCATACGAGAT | GTATGGAGCTAT | AGTCAGTCAGCC | GGGTTBCCCCATTCRG |
| 70 | CAAGCAGAAGACGGCATACGAGAT | GAGATCGCCTAT | AGTCAGTCAGCC | GGGTTBCCCCATTCRG |
| 71 | CAAGCAGAAGACGGCATACGAGAT | GCACTGGCATAT | AGTCAGTCAGCC | GGGTTBCCCCATTCRG |
| 72 | CAAGCAGAAGACGGCATACGAGAT | GTGACTAGTGAT | AGTCAGTCAGCC | GGGTTBCCCCATTCRG |
| 73 | CAAGCAGAAGACGGCATACGAGAT | CTGTGATCGGAT | AGTCAGTCAGCC | GGGTTBCCCCATTCRG |
| 74 | CAAGCAGAAGACGGCATACGAGAT | ACTACTGAGGAT | AGTCAGTCAGCC | GGGTTBCCCCATTCRG |
| 75 | CAAGCAGAAGACGGCATACGAGAT | ATCGTCCGCGAT | AGTCAGTCAGCC | GGGTTBCCCCATTCRG |
| 76 | CAAGCAGAAGACGGCATACGAGAT | GAGTTGTACGAT | AGTCAGTCAGCC | GGGTTBCCCCATTCRG |
| 77 | CAAGCAGAAGACGGCATACGAGAT | ACCAGCTCAGAT | AGTCAGTCAGCC | GGGTTBCCCCATTCRG |
| 78 | CAAGCAGAAGACGGCATACGAGAT | ATAGCACCAGAT | AGTCAGTCAGCC | GGGTTBCCCCATTCRG |
| 79 | CAAGCAGAAGACGGCATACGAGAT | CACGATGGTCAT | AGTCAGTCAGCC | GGGTTBCCCCATTCRG |
| 80 | CAAGCAGAAGACGGCATACGAGAT | GAGCGTATCCAT | AGTCAGTCAGCC | GGGTTBCCCCATTCRG |
| 81 | CAAGCAGAAGACGGCATACGAGAT | TAGAGCTGCCAT | AGTCAGTCAGCC | GGGTTBCCCCATTCRG |
| 82 | CAAGCAGAAGACGGCATACGAGAT | TGTGCACGCCAT | AGTCAGTCAGCC | GGGTTBCCCCATTCRG |
| 83 | CAAGCAGAAGACGGCATACGAGAT | GTAGTAGACCAT | AGTCAGTCAGCC | GGGTTBCCCCATTCRG |
| 84 | CAAGCAGAAGACGGCATACGAGAT | AGTCGTGCACAT | AGTCAGTCAGCC | GGGTTBCCCCATTCRG |
| 85 | CAAGCAGAAGACGGCATACGAGAT | AAGTCGACACAT | AGTCAGTCAGCC | GGGTTBCCCCATTCRG |
| 86 | CAAGCAGAAGACGGCATACGAGAT | GTGCACGATAAT | AGTCAGTCAGCC | GGGTTBCCCCATTCRG |
| 87 | CAAGCAGAAGACGGCATACGAGAT | CGCTCACAGAAT | AGTCAGTCAGCC | GGGTTBCCCCATTCRG |
| 88 | CAAGCAGAAGACGGCATACGAGAT | TCGTGCGTGTTG | AGTCAGTCAGCC | GGGTTBCCCCATTCRG |
| 89 | CAAGCAGAAGACGGCATACGAGAT | TGCTCACGTGTG | AGTCAGTCAGCC | GGGTTBCCCCATTCRG |
| 90 | CAAGCAGAAGACGGCATACGAGAT | ACGTCCACTGTG | AGTCAGTCAGCC | GGGTTBCCCCATTCRG |
| 91 | CAAGCAGAAGACGGCATACGAGAT | GTGTTAGATGTG | AGTCAGTCAGCC | GGGTTBCCCCATTCRG |
| 92 | CAAGCAGAAGACGGCATACGAGAT | GCTCACAATGTG | AGTCAGTCAGCC | GGGTTBCCCCATTCRG |
| 93 | CAAGCAGAAGACGGCATACGAGAT | TAGCCTGTCGTG | AGTCAGTCAGCC | GGGTTBCCCCATTCRG |
| 94 | CAAGCAGAAGACGGCATACGAGAT | ACATGTCACGTG | AGTCAGTCAGCC | GGGTTBCCCCATTCRG |
| 95 | CAAGCAGAAGACGGCATACGAGAT | TCAACAGTAGTG | AGTCAGTCAGCC | GGGTTBCCCCATTCRG |
| 96 | CAAGCAGAAGACGGCATACGAGAT | CTAATCAGAGTG | AGTCAGTCAGCC | GGGTTBCCCCATTCRG |

TABLE 2

Forward PCR primer used in the Illumina-based high throughput sequence analysis of bacterial rRNA genes (The forward PCR primer is comprised of the 3 adjoining segments shown below).

| Name | 5' Illumina Adapter | Spacer | Forward 16S Primer (1507F) |
|---|---|---|---|
| IL-ITS-PCR-F | AATGATACGG CGACCACCGA GATCTACAC | TATCGCC GTTGT | GGTGAAGTCG TAACAAGGTA |

Thermal cycling parameters were 94° C. for 5 min; 35 cycles of 94° C. for 20 sec, 56° C. for 20 sec, and 72° C. for 40 sec, and followed by 72° C. for 5 min. PCR products were purified using a MinElute 96 UF PCR Purification Kit (Qiagen, Valencia, Calif., USA). DNA sequencing was performed using an Illumina HiSeq 2000 (Illumina, Inc., San Diego, Calif.). Clusters were created using a template concentration of 2.5 pM. One hundred base sequencing reads of the 5' end of the amplicons and seven base barcode reads were obtained using the sequencing primers listed in Table 3. De-multiplexing, quality control, and OTU binning were performed using QIIME (Caporaso et al. 2010). OTUs were binned at 97% identity.

TABLE 3

Sequencing primers used in the Illumina-based high throughput sequence analysis of bacterial rRNA genes

| Name | Purpose | Sequence |
|---|---|---|
| IL-ITS-Read-1 | 5' sequencing primer | CACTATCGCCGTTGTGGTGAAGT CGTAACAAGGTA |
| IL-ITS-Index | Barcode sequencing primer | YGAATGGGGVAACCCGGCTGACT GACT |

9. *Lactobacillus johnsonii* Isolation and Koch's Postulates Experimentation

*Lactobacillus johnsonii* (strain RM 6-1) was isolated from RM wildtype mouse feces using *Lactobacillus* Selection Agar (BD, Franklin Lakes, N.J., USA). For the Koch's postulates experiments, this bacterium was grown on LB agar supplemented with 2% glucose and 0.05% (wt/vol) cysteine at 37° C. under anaerobic conditions. The strain was grown overnight and suspended in phosphate-buffered saline (PBS). Prior to inoculation with *L. johnsonii*, CM Atm$^{-/-}$ mice were treated with 1 g/L ampicillin (Sigma-Aldrich), neomycin (Thermo Fisher Scientific, Waltham, Mass., USA), and metronidazole (Baxter, Deerfield, Ill., USA) and 500 mg/L vancomycin (Hospira, Lake Forest, Ill.) in their drinking water for 1 week as described previously (Rakoff-Nahoum et al., 2004, *Cell* 118:229-241). Then, 109 CFU of *L. johnsonii* was administrated every other day by orogastric gavage to a group of eight animals for four successive weeks; in addition, the drinking water for same group of animals contained 109 CFU/ml of *L. johnsonii*. Fecal population densities of *L. johnsonii* were measured before, during, and after *L. johnsonii* administration, using a previously described sequence-selective qPCR assay (Presley et al., 2010, *Appl Environ Microbiol* 76:936-941). After four weeks, mice were euthanized using 3% isoflurane and analyzed as described herein.

10. Gene Expression by RT-PCR

RNA from peripheral blood mononuclear cells (PBMC) or tissue was collected using phenol-chloroform extraction followed by ethanol precipitation. Pellets were resuspended in nucleotide-free water, and RNA was treated with 200 units of DNase I (Ambion, Huntingdon, United Kingdom) for 2 hours at 37° C. RNA levels of transforming growth factor β (TGF-β), interleukin-1β (IL-1β), interleukin-4 (IL-4), interleukin-10 (IL-10), interleukin-10 (IL-10), interferon gamma (IFN-γ), and myeloid differentiation primary response gene 88 (MYD88) were determined from cDNA and compared as relative expression changes in *L. johnsonii*-treated animals compared to PBS-treated animals. Taqman real-time PCR validation of gene expression was performed using the TaqMan® Gene Expression Assays system (Applied Biosystems, Carlsbad, Calif., USA). The level of gene transcription was normalized to GAPDH (glyceraldehyde-3-phosphate dehydrogenase).

11. Flow Cytometry

PBMC or tissue cell pellets were resuspended in staining buffer. Lymphocytes were stained with CD3, CD4, CD19, and CD335 antibodies (Biolegend, San Diego, Calif., USA). Cells were fixed in 4% paraformaldehyde-phosphate-buffered saline (PBS) and scanned on a Becton Dickinson FACS Calibur flow cytometer. A minimum of 25,000 events were collected. Flow cytometry data were analyzed using Tree Star FlowJo software. Statistical analyses (Student's t test) were used to determine if mean values were different ($P<0.05$).

12. Sequence Data

DNA sequence data has been deposited at the NCBI Short Read Archive under accession number (to be determined).

Example B. Housing Affects Genetic Instability, Lifespan, Glutathione Levels, and Lymphoma Latency of Atm$^{-/-}$ Mice When Applicants moved mice from Harvard University to the University of California Los Angeles (UCLA) in the year 2000, the median lifespan of their Atm$^{-/-}$ mice began to increase over a seven-year period from approximately 4 to 12 months (unpublished observations). At Harvard, mice were housed in non-sterile conditions (SPF-N; Table 4) compared to a sterile condition at UCLA (SPF-S):

TABLE 4

Four isogenic mouse colonies harboring different bacterial communities

| Name | Description | Sterile Housing* |
|---|---|---|
| Sterile (SPF-S) | Harvard colony moved to sterile housing at UCLA. | Yes |
| Semi-Conventional (SPF-N) | Harvard colony exposed to conventional mice for 24-hours, and then bred in conventional housing at UCLA. | No |
| Conventional Microbiota (CM) | Harvard colony treated with antibiotics, inoculated with conventional mouse feces, and then bred in conventional housing at UCLA. | No |
| Restricted Microbiota (RM) | Atm-/- rederived with restricted microbiota | Yes |

*Autoclaved Bedding, Cages, Food, Water

To examine the influence of housing conditions on traits associated with ATM deficiency, Atm$^{-/-}$ and wildtype mice from three housing conditions were compared: (i) Harvard housing and (ii and iii) UCLA housing in specific pathogen free (SPF) conditions with either sterile (SPF-S) or non-sterile (SPF-N) food, water and bedding Genetic instability was assessed using the pun reversion assay, which measures DNA deletion events repaired by homologous recombination (Bishop et al., 2000, Cancer Res 60:395-399). While lifespan increased in the Atm$^{-/-}$ mice over seven years under SPF-S conditions, DNA deletion frequency decreased to 10%. These levels are comparable to the wildtype mice (FIG. 1A), indicating loss of the abnormally high genetic instability that is a hallmark of Atm$^{-/-}$ mice and human cells from A-T subjects (Bishop et al., 2000, Cancer Res 60:395-399; Guo et al., 2010, Science 330:517-521). Conversely, DNA deletion frequencies of Atm$^{-/-}$ mice housed under SPF-N conditions were 43%, a level even higher than those observed in the Harvard colony (FIG. 1A).

Figure 8:
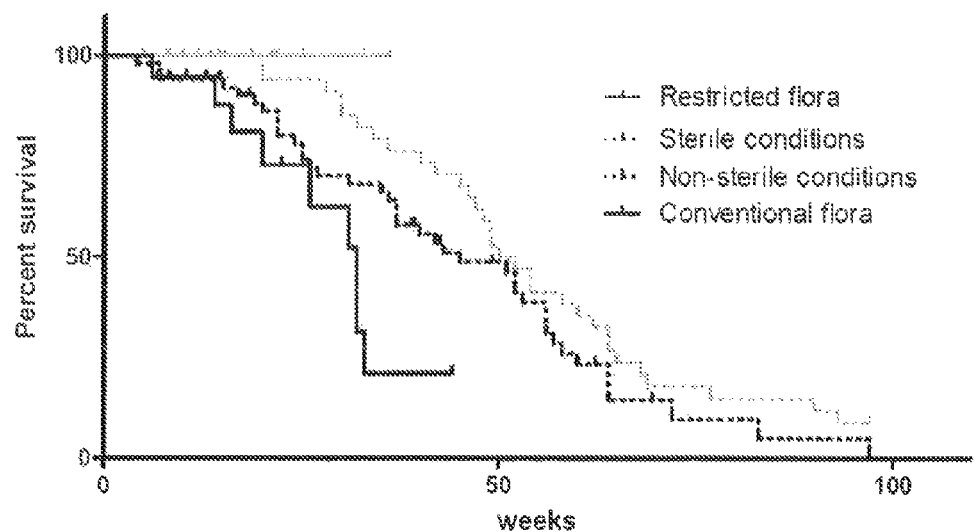
FIG. 8 depicts that survival curves of Atm-deficient mice are different depending on housing conditions and microbiota they are exposed to. Semi-conventionalized (SPF-N) mice in a non-sterile (SPF-N) facility have a decreased median lifespan compared to mice housed in a sterile (SPF-S) facility. The grey lines represent mice, which were housed in sterile (SPF-S) conditions and the black lines represent mice that were housed in non-sterile (SPF-N) conditions. The survival curve of the mice with conventional microbiota is significantly different than all of the other curves (p<0.05). Details are described herein, e.g., in Example B.
Figure 9:
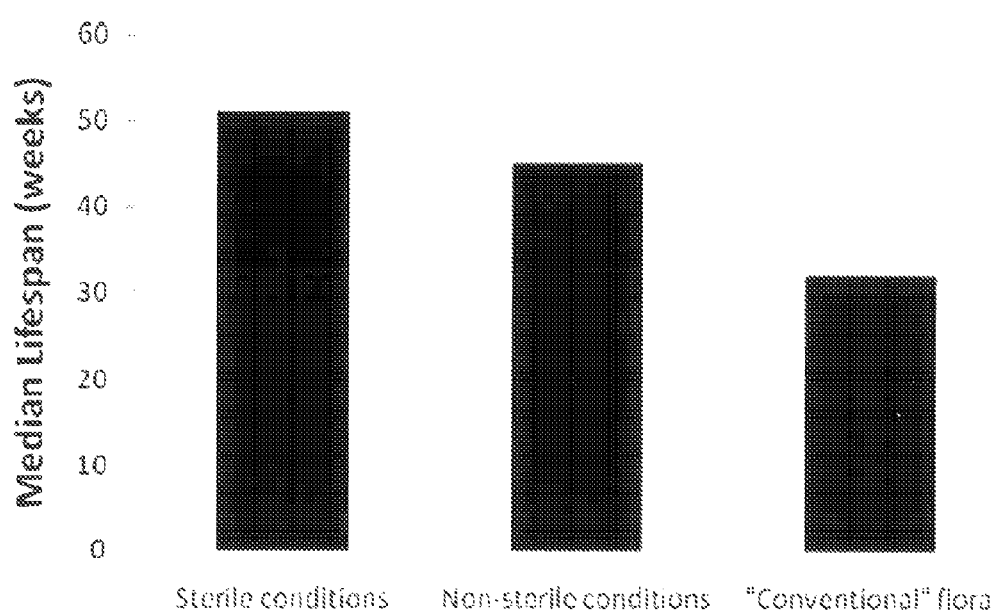
FIG. 9 depicts that the median lifespan of Atm-deficient mice decreases as their microbiota became less restricted. The median lifespan of the restricted microbiota mice is not yet defined because no mice have died. The RM mice have a median life expectancy of 80 weeks.
Figure 10:
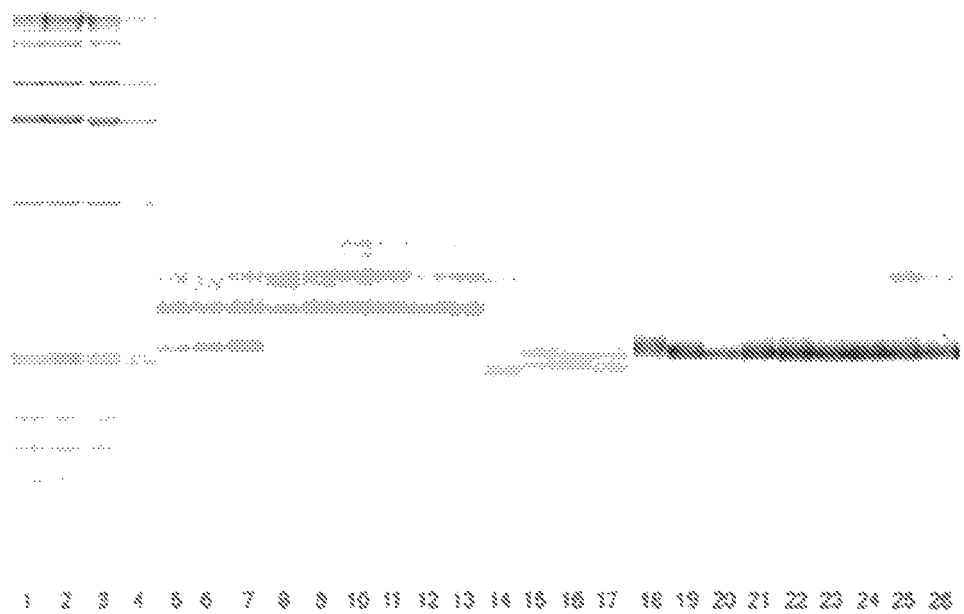
FIG. 10 depicts a ribosomal intergenic spacer analysis (RISA) results showing mice in different facilities have different banding patterns of 18S rRNA. Marker lanes (1-4; 1 kb ladder; Invitrogen, Inc. USA) as well as samples from mice in a non-sterile (SPF-N) facility (lanes 5-13), conventional mice (CM) (lanes 14-17), and mice in a sterile (SPF-S) environment (lanes 18-26).

Focusing on the two UCLA Atm$^{-/-}$ mouse colonies, lifespan and lymphoma latency were compared. SPF-N mice exhibited significantly shorter lifespan than SPF-S mice (FIG. 1B, see also FIGS. 8 and 9). Since Atm$^{-/-}$ mice primarily die from lymphomas (Barlow et al., 1996, Cell 86:159-171), we examined the cause of mortality or morbidity. Although the incidence of lymphomas was similar between mice housed in SPF-N (74%) and SPF-S (76.5%) conditions, time of onset was significantly shorter in the SPF-N mice (FIG. 1C). The median age at which SPF-N mice died of lymphoma was 25 weeks compared to 60 weeks for SPF-S mice. These results are consistent with the observed increase in SPF-N genetic instability (FIG. 1A), likely the primary driver of accelerated carcinogenesis.

The roles of diet and microbiota to test possible causes of the increased lifespan and decreased genetic instability observed in the mice was examined. Since N-acetyl cysteine, an anti-oxidant, can decrease genetic instability (Reliene et al., 2004, Cancer Res 64:5148-5153) and increase longevity (Ito et al., 2007, J Immunol 178:103-110; Reliene and Schiestl, 2006a, DNA Repair (Amst) 5:852-859), it was reasoned that the excess vitamin E, also an anti-oxidant, in the normal diet (Harlan Teklad 8650) may also be protective. Therefore, mice were put on a customized diet (Harlan Teklad TD.05171) decreasing the excess level of vitamin E to levels that mice require (134 IU/kg compared to <50 IU/kg). The diet that animals were given at Harvard University (PicoLab 5LJ5) was also used. Neither diet had an effect on genetic instability or lifespan (data not shown).

After observing the striking effects of housing on ATM-deficient traits, the intestinal bacteria inhabiting the two UCLA Atm$^{-/-}$ mouse colonies were examined High throughput sequence analysis of rRNA genes revealed that these two colonies harbor distinct microbial communities (FIG. 1D). An indicator analysis identified several bacterial phylotypes whose populations correlated with genetic instability, suggesting a possible role. One correlate is a member of the Helicobacteriaceae, which are bacteria known to promote cancer (FIG. 2).

To test the role of microbiota, in some experiments, mice from the sterile (SPF-S) facility were exposed to mice with a conventional microbiota for 24 hours. Mice can incorporate microbiota from the bedding and fur of the mice they are co-housed with and they have a habit of coprophagia. The bacterial populations were examined using two types of rRNA gene analyses. High throughput sequencing provided an extensive analysis at relatively low taxonomic resolution while ribosomal intergenic spacer analysis (RISA) provided an examination at relatively high taxonomic resolution, but only for the most abundant phylotypes. Co-housing sterile mice (SPF-S) with conventional mice (CM) was enough to stably (over at least 2 generations) change the spectrum of bacterial rRNA genes in fecal samples (FIG. 1D and data not shown). Because these mice were only passively exposed to conventional microbiota, these mice are referred to herein as semi-conventionalized (SPF-N, Table 4). These mice are isogenic to mice housed in the sterile (SPF-S) facility, decreasing the chance that genetics is a factor in the experiments described herein.

To determine if genetic instability was affected by exposing mice to conventional microbiota, in some experiments the pink-eyed unstable mutation reversion assay was used. This assay measures DNA deletions of one 70 kb tandem repeat in the p allele leading to reversion back to the functional protein. These reversions can be seen as black spots in the fur and represent a DNA deletion event repaired by homologous recombination (Bishop et al., 2000, Cancer Res 60:395-399). Increases in fur-spots have been seen in cancer prone mouse models as well as in response to carcinogens (Reliene et al., 2007, Adv Genet 58:67-87). Bishop et al. found that 30.3% of Atm$^{-/-}$ mice had fur-spots while only 17.7% of wildtype littermates had fur-spots (P<0.05) (as previously described (Bishop et al., 2000, Cancer Res 60:395-399) and FIG. 1A). After the mice were housed in sterile (SPF-S) conditions for seven years, DNA deletion frequency decreased in Atm$^{-/-}$ mice to 10%, even slightly lower than the wildtype mice (FIG. 1A, sterile (SPF-S) conditions), indicating a complete disappearance of genetic instability, which is a hallmark of Atm-deficient mice and human cells (Bishop et al., 2000, Cancer Res 60:395-399; Lavin et al., 2007, Br Med Bull 81-82:129-147). After mice were exposed to conventional microbiota however, the frequency of DNA deletions was again elevated in Atm$^{-/-}$ mice to about 43% (P<0.01) (FIG. 1A, semi-conventional mice). As a comparison, exposure of mice to conventional microbiota on DNA deletions had a similar effect as almost lethal doses of the potent carcinogen benzo(a)pyrene to wildtype mice (Schiestl et al., 1997, Proc Natl Acad Sci USA 94:4576-4581).

Since oxidative stress can be produced by intestinal microbiota both directly and indirectly (Federico et al., 2007, Int J Cancer 121:2381-2386; Kullisaar et al., 2003, Br J Nutr 90:449-456; Kullisaar et al., 2002, Int J Food Microbiol 72:215-224), and oxidative stress is associated with both DNA damage and carcinogenesis (Evans et al., 2004, Mutat Res 567:1-61; Klaunig et al., Toxicol Pathol 38:96-109), the antioxidant state of Atm$^{-/-}$ mice in sterile (SPF-S) conditions and semi-conventional Atm$^{-/-}$ mice was assessed. Glutathione (GSH) is a major antioxidant in the cell and decreased levels of GSH are associated with several diseases including cancer (Ballatori et al., 2009, Biol Chem 390:191-214). It was found that GSH levels in the peripheral blood of semi-conventional Atm$^{-/-}$ mice are significantly lower than in Atm$^{-/-}$ mice housed in sterile (SPF-S) conditions (data not shown, p<0.01). Therefore oxidative stress may play a role in the increased genetic instability and decreased lymphoma latency in semi-conventional Atm$^{-/-}$ mice.

Example C. Atm$^{-/-}$ Mice with Restricted Microbiota (RM) have Increased Lifespan and Decreased Systemic Genotoxicity and Oxidative Stress To further the investigation into the role of intestinal microbiota in lymphoma penetrance, Atm$^{-/-}$ mice harboring intestinal microbiota from the conventional microbiota (CM) and restricted microbiota (RM) mouse models were created. These models were chosen because CM and RM harbor distinct intestinal microbiota (Fujiwara et al., 2008, *J Immunol* 180:5843-5852; Presley et al., 2010, *Appl Environ Microbiol* 76:936-941; Wei et al., 2010, *J Immunol;* 184: 1218-1226), and RM mice possess immunologic traits that can potentially influence lymphoma penetrance, including unusually high levels of cytolytic central memory CD8$^+$ T cells that target neoplastic cells. Moreover, RM mice are carefully maintained in an isolated facility and these immunologic traits have persisted for many years, thus providing a stable platform for Applicants' investigations.

Lifespan in the two mouse colonies was significantly different, with median survival of CM mice (32 weeks) being shorter than RM mice (80 weeks) (FIG. 3A). Examination of systemic genotoxicity using three different metrics showed that Atm$^{-/-}$ mice with CM microbiota exhibited higher DNA damage than those with RM microbiota. Clastogenic DNA damage, determined by the presence of micronuclei in peripheral blood erythrocytes, was nearly 85% higher in CM versus RM mice (FIG. 3B). DNA strand breaks, measured by the alkaline comet assay, were also higher in CM than RM mice (FIG. 3C). A third indicator of DNA damage in cells, percent tail DNA at the 80th percentile using the alkaline comet assay, was likewise higher in CM over RM mice (data not shown).

Since oxidative stress can be produced by intestinal microbiota both directly and indirectly (Kullisaar et al., 2002, *Int J Food Microbiol* 72:215-224; Kullisaar et al., 2003, *Br J Nutr* 90:449-456; Federico et al., 2007, *Int J Cancer* 121:2381-2386), and oxidative stress is associated with both genotoxicity and carcinogenesis (Evans et al., 2004, *Mutat Res* 567:1-61; Klaunig et al., 2010, *Toxicol Pathol* 38:96-109), the antioxidant state of Atm$^{-/-}$ mice harboring CM and RM microbiota was also assessed. Glutathione (GSH) is a major cellular antioxidant and decreased levels of GSH are associated with several diseases including cancer (Ballatori et al., 2009, *Biol Chem* 390:191-214). A metric of oxidative stress can be expressed as the ratio of GSH and the dimeric oxidized form GSSG in peripheral blood. It was found that Atm$^{-/-}$ mice harboring CM microbiota had higher ratios of oxidative stress compared to RM mice (FIG. 3D), suggesting it may also play a role in lymphoma penetrance in this model system.

Figure 2:
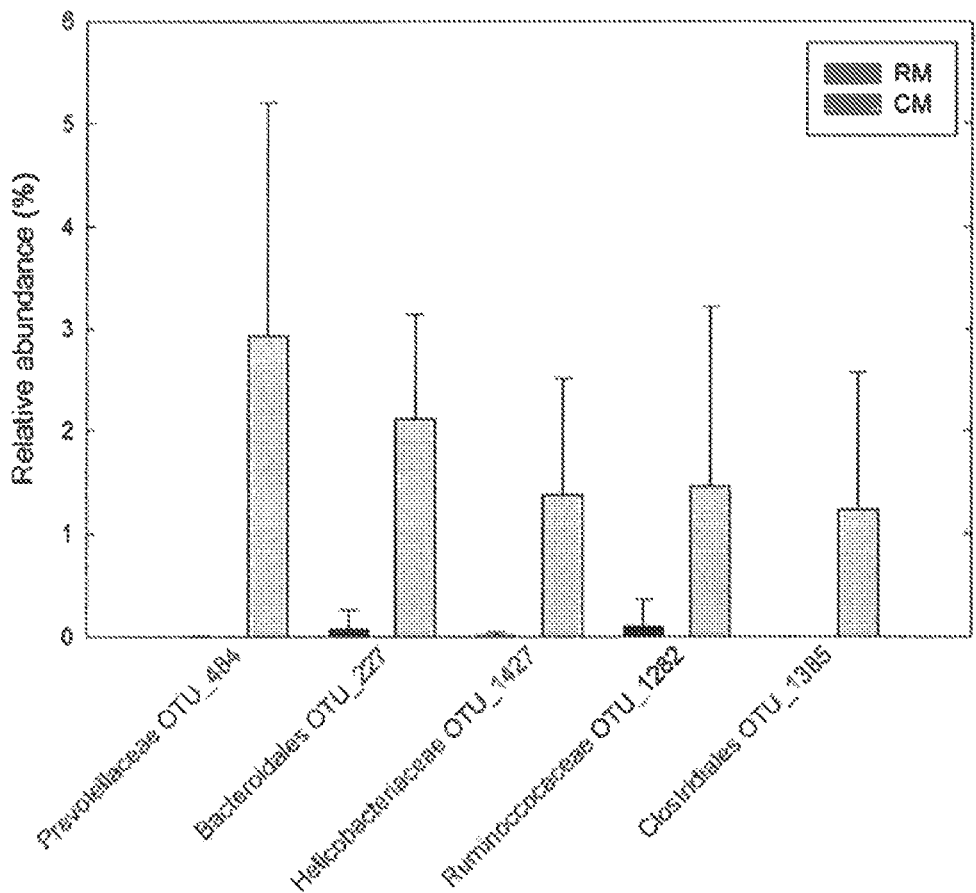
FIG. 2 depicts the relative abundance of indicator bacterial phylotypes in mice. Fecal bacteria of age- and litter-matched CM and RM mice (n=4-5 for each type) were subjected to an indicator analysis. All identified abundant bacterial indicators were for CM mice. Error bars indicate standard deviation. Details are described herein, e.g., in Example B.
Figure 3:
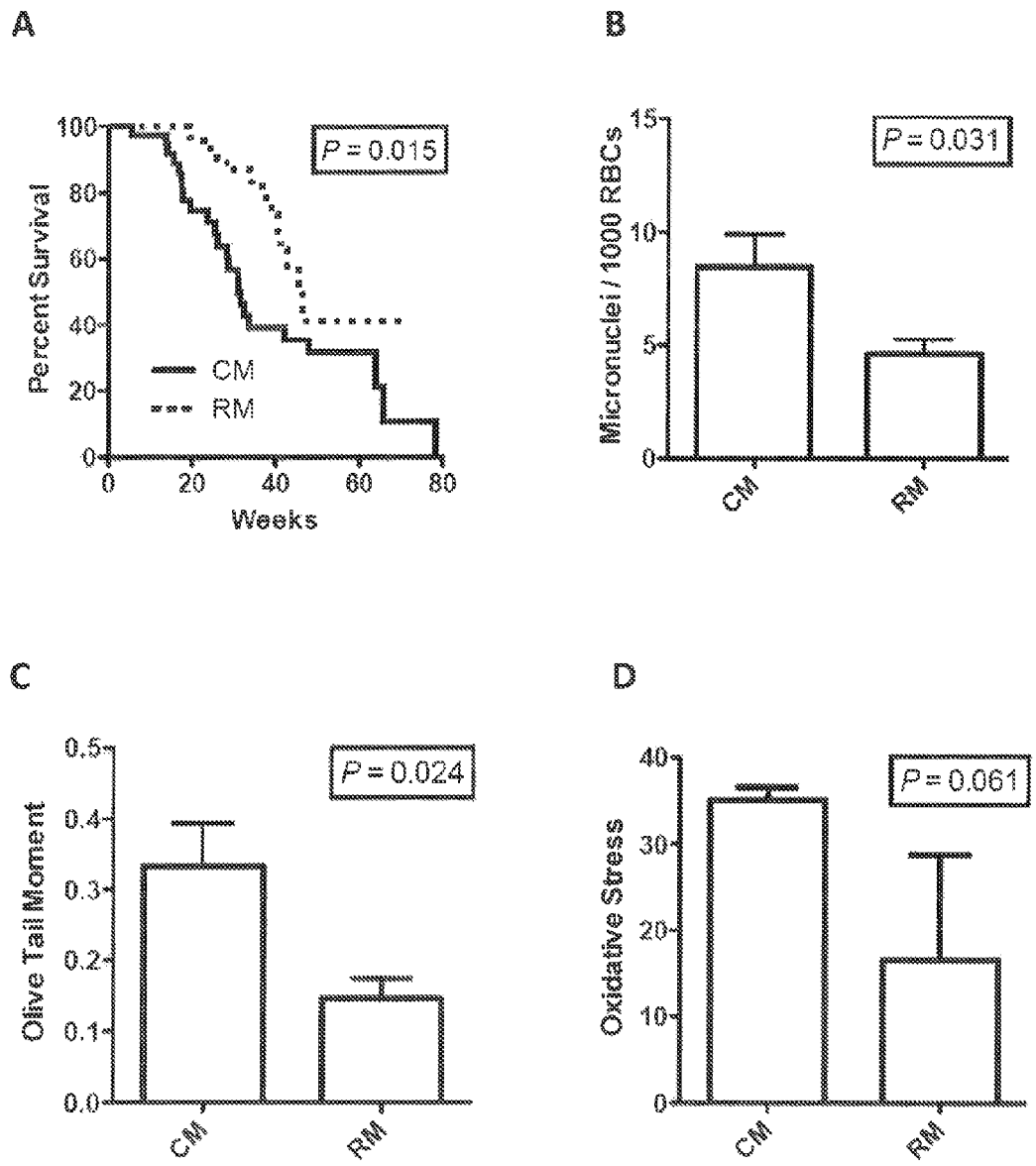
FIG. 3 depicts lifespan, genotoxicity, and oxidative stress of Atm$^{-/-}$ mice bearing CM and RM microbiota. (A) Kaplan-Meier survival of CM and RM Atm$^{-/-}$ mice (n=38 and 31 for CM and RM mice, respectively). (B) Bone marrow erythrocyte micronuclei levels (n=5 and 6 for CM and RM mice, respectively). (C) Olive tail moments in blood leucocytes (n=5 for both groups). (D) Oxidative stress measured by GSH/GSSG ratios (n=2 and 3 for CM and RM mice, respectively). All measurements were in mice aged 4-6 months. Error bars indicate SE. Details are described herein, e.g., in Example C.

The results presented in FIGS. 1 to 3 suggest that the intestinal microbiota is a major contributor to the phenotypic differences observed within and among Atm$^{-/-}$ mouse colonies (Reliene and Schiestl, 2006b, *DNA Repair (Amst)* 5:651-653).

Example D. Microbiota in CM and RM Mice are Distinct

Figure 4:
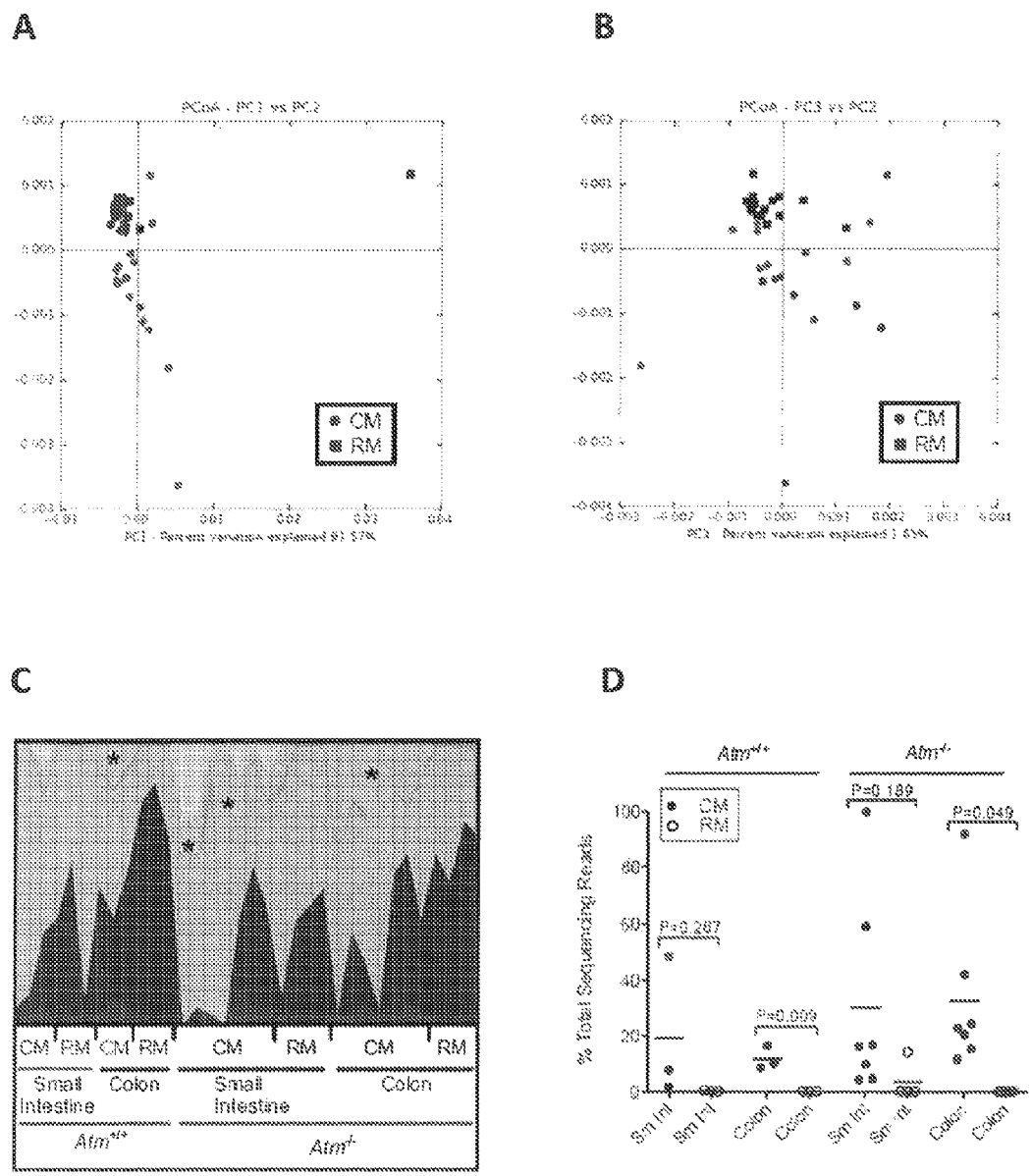
FIG. 4 depicts that intestinal microbiota in CM and RM mice are distinct at the community and phyla levels. (A, B) A weighted UniFrac analysis of bacteria in mice in CM (circles) and RM (squares) conditions. (C) Area plot of phyla in CM and RM mice by genotype and intestinal region. (D) Distribution and abundance of proteobacteria by genotype and intestinal region. For CM, n=3, 7, 3, 7 for small intestine (SI)-Atm$^{+/+}$, SI-Atm–/–, colon (CLN)-Atm$^{+/+}$, and CLN-Atm$^{-/-}$, respectively. For RM, n=3, 4, 3, 4 for SI-Atm$^{+/+}$, SI-Atm$^{-/-}$, CLN-Atm$^{+/+}$, and CLN-Atm$^{-/-}$, respectively. Details are described herein, e.g., in Example D.

A high throughput sequence analysis revealed broad taxonomic differences in bacterial rRNA gene composition from the intestinal mucosa of CM and RM mice. This analysis was performed because all prior investigations of CM and RM microbiota were relatively shallow in depth (Fujiwara et al., 2008, *J Immunol* 180:5843-5852; Presley et al., 2010, *Appl Environ Microbiol* 76:936-941; Wei et al., 2010, *J Immunol* 184:1218-1226). A weighted UniFrac analysis showed distinct grouping and tighter clustering in RM than CM mice (FIGS. 4A and 4B). These results are consistent with the manner in which RM mice were created and maintained, including isolated housing conditions and initial oral inoculum containing relatively few bacterial taxa (Fujiwara et al., 2008, *J Immunol* 180:5843-5852). The majority of rRNA gene sequences were classified into the phyla Bacteroidetes (dark shaded) and Firmicutes (light shaded) (FIG. 4C). However, the most consistent phyla-level difference between CM and RM was in the Proteobacteria (see asterisks in FIG. 4C), with the most statistically significant difference occurring in the colon (FIG. 4D). Although compositional differences were detected between mouse genotypes (Atm$^{-/-}$ versus Atm$^{+/+}$) and intestinal regions (small intestine versus colon), CM versus RM provided the most distinct groupings (FIGS. 4A and 4B). A more comprehensive taxonomic analysis is provided in Table 5.

TABLE 5

Taxonomic Analysis. Data was generated by an Illumina-based high throughput sequence analysis of rRNA genes. Values in the table indicate number of sequencing reads.

| Taxon ID | Taxon | CM Atm+/+ Small Intestine | | | RM Atm+/+ Small Intestine | | |
|---|---|---|---|---|---|---|---|
| 1 | No blast hit; Other | 5.2E−03 | 2.2E−03 | 8.9E−03 | 2.6E−03 | 5.0E−03 | 1.0E−03 |
| 2 | Actinobacteria | 1.1E−04 | 3.4E−04 | 8.9E−04 | 2.7E−04 | 2.9E−04 | 5.2E−05 |
| 3 | Aquificae | 0.0E+00 | 0.0E+00 | 0.0E+00 | 4.6E−07 | 5.1E−07 | 0.0E+00 |
| 4 | Bacteroidetes | 6.7E−03 | 2.4E−02 | 6.2E−02 | 9.7E−04 | 2.4E−02 | 1.9E−03 |
| 5 | Bacteroidetes/Chlorobi group | 5.0E−02 | 8.1E−02 | 2.5E−01 | 3.8E−01 | 5.5E−01 | 9.8E−02 |
| 6 | Chlamydiae/Verrucomicrobia group | 1.9E−06 | 7.1E−06 | 7.3E−05 | 0.0E+00 | 0.0E+00 | 0.0E+00 |
| 7 | Chloroflexi | 1.9E−06 | 0.0E+00 | 1.1E−06 | 4.8E−05 | 6.2E−05 | 2.6E−06 |
| 8 | Chrysiogenetes | 0.0E+00 | 2.1E−05 | 0.0E+00 | 0.0E+00 | 0.0E+00 | 0.0E+00 |
| 9 | Cyanobacteria | 1.9E−05 | 4.4E−05 | 1.1E−03 | 7.4E−06 | 1.9E−05 | 2.6E−06 |
| 10 | Deferribacteres | 9.4E−05 | 2.6E−07 | 1.9E−04 | 0.0E+00 | 0.0E+00 | 0.0E+00 |
| 11 | Fibrobacteres/Acidobacteria group | 4.7E−07 | 5.3E−07 | 0.0E+00 | 1.8E−06 | 0.0E+00 | 0.0E+00 |
| 12 | Firmicutes | 4.3E−01 | 8.6E−01 | 4.7E−01 | 6.1E−01 | 3.9E−01 | 8.9E−01 |
| 13 | Gemmatimonadetes | 4.7E−07 | 4.5E−06 | 1.5E−05 | 4.3E−05 | 1.6E−05 | 1.4E−05 |
| 14 | NOT_LABELED | 2.5E−03 | 1.6E−03 | 3.5E−02 | 2.5E−03 | 2.3E−02 | 5.5E−03 |
| 15 | Planctomycetes | 1.1E−05 | 5.8E−06 | 3.5E−05 | 0.0E+00 | 2.0E−06 | 0.0E+00 |
| 16 | Proteobacteria | 4.8E−01 | 1.6E−02 | 7.5E−02 | 1.1E−03 | 4.2E−03 | 1.3E−03 |
| 17 | Spirochaetes | 0.0E+00 | 0.0E+00 | 0.0E+00 | 7.8E−06 | 3.8E−04 | 8.8E−07 |
| 18 | Synergistetes | 0.0E+00 | 5.3E−07 | 0.0E+00 | 0.0E+00 | 0.0E+00 | 0.0E+00 |
| 19 | Tenericutes | 2.4E−02 | 1.2E−02 | 9.8E−02 | 2.4E−05 | 6.1E−04 | 3.6E−05 |
| 20 | Thermodesulfobacteria | 1.4E−06 | 2.4E−06 | 5.4E−07 | 5.1E−06 | 1.0E−06 | 2.6E−06 |
| 21 | Thermotogae | 1.4E−06 | 5.3E−07 | 0.0E+00 | 9.2E−07 | 5.1E−07 | 1.5E−06 |
| 22 | Verrucomicrobia | 2.3E−04 | 1.3E−04 | 1.0E−03 | 2.4E−05 | 1.8E−04 | 3.0E−05 |

TABLE 5-continued

Taxonomic Analysis. Data was generated by an Illumina-based high throughput sequence analysis of rRNA genes. Values in the table indicate number of sequencing reads.

| Taxon ID | CM Atm+/+ Colon | | | RM Atm+/+ Colon | | |
|---|---|---|---|---|---|---|
| 1 | 1.5E−03 | 1.2E−03 | 1.3E−03 | 2.4E−03 | 1.8E−03 | 1.3E−03 |
| 2 | 4.0E−04 | 5.3E−04 | 5.7E−04 | 3.3E−04 | 1.3E−04 | 2.4E−04 |
| 3 | 0.0E+00 | 0.0E+00 | 0.0E+00 | 1.7E−06 | 8.1E−07 | 9.9E−07 |
| 4 | 4.6E−02 | 9.2E−02 | 7.8E−02 | 9.8E−03 | 1.5E−02 | 6.8E−03 |
| 5 | 4.5E−01 | 2.9E−01 | 4.6E−01 | 7.8E−01 | 8.4E−01 | 6.4E−01 |
| 6 | 2.0E−04 | 1.6E−04 | 1.2E−04 | 0.0E+00 | 0.0E+00 | 0.0E+00 |
| 7 | 3.7E−06 | 1.8E−05 | 7.6E−07 | 1.0E−04 | 2.8E−05 | 2.1E−04 |
| 8 | 0.0E+00 | 0.0E+00 | 0.0E+00 | 0.0E+00 | 0.0E+00 | 0.0E+00 |
| 9 | 2.2E−04 | 3.0E−03 | 9.9E−04 | 2.7E−05 | 2.4E−05 | 9.9E−06 |
| 10 | 7.8E−05 | 6.3E−05 | 6.6E−05 | 0.0E+00 | 0.0E+00 | 0.0E+00 |
| 11 | 0.0E+00 | 0.0E+00 | 0.0E+00 | 0.0E+00 | 0.0E+00 | 0.0E+00 |
| 12 | 4.0E−01 | 4.3E−01 | 3.5E−01 | 1.9E−01 | 1.3E−01 | 3.3E−01 |
| 13 | 0.0E+00 | 3.4E−05 | 1.6E−05 | 2.4E−05 | 1.3E−05 | 0.0E+00 |
| 14 | 9.9E−03 | 1.5E−02 | 2.5E−02 | 1.7E−02 | 1.3E−02 | 2.4E−02 |
| 15 | 2.8E−05 | 2.8E−05 | 2.1E−05 | 0.0E+00 | 8.1E−07 | 5.0E−07 |
| 16 | 9.9E−02 | 1.6E−01 | 8.4E−02 | 1.0E−03 | 4.3E−04 | 1.2E−03 |
| 17 | 9.2E−07 | 0.0E+00 | 0.0E+00 | 2.9E−04 | 5.2E−05 | 2.5E−04 |
| 18 | 0.0E+00 | 3.3E−06 | 0.0E+00 | 3.3E−06 | 8.1E−07 | 4.0E−06 |
| 19 | 4.6E−04 | 1.8E−03 | 7.6E−04 | 5.7E−05 | 2.0E−04 | 1.8E−05 |
| 20 | 9.2E−07 | 0.0E+00 | 0.0E+00 | 2.2E−06 | 0.0E+00 | 0.0E+00 |
| 21 | 4.6E−07 | 0.0E+00 | 0.0E+00 | 0.0E+00 | 0.0E+00 | 0.0E+00 |
| 22 | 1.2E−05 | 2.4E−05 | 3.7E−05 | 7.2E−06 | 1.1E−05 | 4.8E−05 |
| CM Atm−/− Small Intestine | | | | | | |
| 1 | 1.0E−03 | 9.4E−03 | 9.2E−04 | 9.1E−05 | 5.8E−03 | 6.3E−03 | 4.9E−03 |
| 2 | 8.5E−05 | 6.0E−04 | 1.1E−04 | 1.8E−06 | 8.8E−04 | 5.2E−04 | 3.4E−04 |
| 3 | 0.0E+00 | 0.0E+00 | 0.0E+00 | 0.0E+00 | 0.0E+00 | 0.0E+00 | 0.0E+00 |
| 4 | 3.6E−04 | 6.5E−03 | 6.5E−03 | 3.9E−05 | 1.1E−01 | 6.1E−02 | 7.5E−02 |
| 5 | 2.2E−04 | 4.5E−02 | 2.9E−02 | 9.1E−05 | 2.7E−01 | 4.9E−01 | 3.3E−01 |
| 6 | 5.3E−06 | 4.7E−05 | 2.1E−05 | 0.0E+00 | 2.9E−05 | 1.5E−05 | 3.8E−05 |
| 7 | 0.0E+00 | 9.4E−05 | 7.7E−07 | 0.0E+00 | 5.5E−05 | 1.2E−05 | 7.7E−05 |
| 8 | 0.0E+00 | 0.0E+00 | 0.0E+00 | 0.0E+00 | 0.0E+00 | 0.0E+00 | 0.0E+00 |
| 9 | 4.8E−05 | 9.4E−04 | 3.4E−05 | 7.8E−07 | 3.8E−04 | 6.6E−05 | 3.0E−04 |
| 10 | 0.0E+00 | 2.7E−06 | 5.8E−06 | 0.0E+00 | 2.9E−05 | 0.0E+00 | 1.7E−06 |
| 11 | 1.3E−06 | 1.8E−06 | 0.0E+00 | 0.0E+00 | 0.0E+00 | 0.0E+00 | 4.3E−07 |
| 12 | 1.1E−01 | 5.1E−01 | 7.5E−01 | 1.7E−03 | 3.1E−01 | 3.7E−01 | 3.6E−01 |
| 13 | 6.3E−07 | 4.4E−06 | 8.6E−05 | 0.0E+00 | 1.1E−05 | 2.9E−05 | 3.0E−06 |
| 14 | 6.9E−03 | 3.8E−03 | 1.7E−01 | 2.5E−05 | 9.6E−03 | 1.4E−02 | 1.1E−02 |
| 15 | 1.3E−06 | 2.8E−05 | 4.6E−06 | 0.0E+00 | 1.8E−05 | 4.4E−05 | 1.7E−05 |
| 16 | 5.9E−01 | 1.6E−01 | 4.7E−02 | 1.0E+00 | 1.7E−01 | 4.2E−02 | 9.8E−02 |
| 17 | 0.0E+00 | 2.5E−05 | 3.8E−07 | 0.0E+00 | 0.0E+00 | 0.0E+00 | 2.1E−05 |
| 18 | 0.0E+00 | 1.9E−04 | 0.0E+00 | 0.0E+00 | 0.0E+00 | 0.0E+00 | 0.0E+00 |
| 19 | 2.9E−01 | 2.6E−01 | 6.2E−04 | 5.3E−05 | 1.2E−01 | 1.8E−02 | 1.1E−01 |
| 20 | 0.0E+00 | 4.4E−07 | 8.8E−06 | 0.0E+00 | 1.2E−04 | 0.0E+00 | 8.5E−07 |
| 21 | 0.0E+00 | 4.4E−06 | 0.0E+00 | 0.0E+00 | 0.0E+00 | 0.0E+00 | 4.3E−07 |
| 22 | 2.3E−05 | 7.3E−04 | 1.3E−05 | 3.1E−06 | 2.4E−04 | 3.2E−04 | 2.6E−04 |
| RM Atm−/− Small Intestine | | | | | | | |
| 1 | 4.2E−02 | 2.5E−03 | 6.3E−04 | 8.7E−04 |
| 2 | 8.0E−03 | 5.8E−04 | 1.7E−04 | 8.0E−05 |
| 3 | 1.9E−06 | 6.8E−07 | 9.4E−07 | 0.0E+00 |
| 4 | 3.8E−04 | 5.5E−03 | 6.4E−03 | 1.3E−02 |
| 5 | 5.9E−02 | 3.6E−01 | 4.2E−01 | 4.7E−01 |
| 6 | 0.0E+00 | 0.0E+00 | 0.0E+00 | 0.0E+00 |
| 7 | 1.8E−03 | 9.2E−05 | 3.0E−05 | 2.1E−05 |
| 8 | 0.0E+00 | 0.0E+00 | 0.0E+00 | 0.0E+00 |
| 9 | 5.6E−06 | 1.2E−05 | 6.6E−06 | 1.1E−05 |
| 10 | 0.0E+00 | 0.0E+00 | 0.0E+00 | 0.0E+00 |
| 11 | 0.0E+00 | 1.4E−05 | 0.0E+00 | 0.0E+00 |
| 12 | 7.1E−01 | 6.1E−01 | 5.6E−01 | 4.8E−01 |
| 13 | 7.7E−05 | 9.7E−05 | 3.0E−04 | 3.3E−05 |
| 14 | 3.3E−02 | 1.7E−02 | 1.5E−02 | 3.0E−02 |
| 15 | 1.2E−05 | 0.0E+00 | 0.0E+00 | 0.0E+00 |
| 16 | 1.4E−01 | 2.1E−03 | 5.1E−04 | 3.3E−04 |
| 17 | 9.0E−04 | 1.1E−05 | 2.2E−06 | 0.0E+00 |
| 18 | 8.6E−06 | 6.8E−07 | 0.0E+00 | 0.0E+00 |

TABLE 5-continued

Taxonomic Analysis. Data was generated by an Illumina-based high throughput sequence analysis of rRNA genes. Values in the table indicate number of sequencing reads.

| | | | | | | |
|---|---|---|---|---|---|---|
| 19 | 1.5E−04 | 2.0E−05 | 3.0E−05 | 1.6E−05 | | |
| 20 | 2.5E−06 | 6.8E−07 | 6.3E−07 | 1.3E−06 | | |
| 21 | 0.0E+00 | 6.8E−07 | 0.0E+00 | 3.2E−07 | | |
| 22 | 6.3E−03 | 3.6E−05 | 6.0E−06 | 4.5E−06 | | |

CM Atm−/− Colon

| | | | | | | | |
|---|---|---|---|---|---|---|---|
| 1 | 3.9E−03 | 2.5E−03 | 2.7E−03 | 9.4E−04 | 3.9E−03 | 3.6E−03 | 1.3E−03 |
| 2 | 1.1E−03 | 4.6E−04 | 9.4E−04 | 1.3E−04 | 8.3E−04 | 4.0E−04 | 5.2E−04 |
| 3 | 0.0E+00 | 0.0E+00 | 0.0E+00 | 1.5E−06 | 7.7E−07 | 0.0E+00 | 0.0E+00 |
| 4 | 2.7E−02 | 2.0E−02 | 8.2E−02 | 1.9E−02 | 1.1E−01 | 6.3E−02 | 5.1E−02 |
| 5 | 1.1E−02 | 3.1E−01 | 1.4E−01 | 3.6E−02 | 4.2E−01 | 5.3E−01 | 3.2E−01 |
| 6 | 1.4E−04 | 1.8E−04 | 1.5E−04 | 3.3E−06 | 1.0E−04 | 3.7E−05 | 2.3E−04 |
| 7 | 9.3E−05 | 2.4E−05 | 4.2E−05 | 1.7E−05 | 2.6E−05 | 8.6E−06 | 1.8E−05 |
| 8 | 0.0E+00 | 0.0E+00 | 0.0E+00 | 0.0E+00 | 0.0E+00 | 0.0E+00 | 0.0E+00 |
| 9 | 3.7E−03 | 1.5E−03 | 5.0E−03 | 6.5E−05 | 1.0E−03 | 3.7E−04 | 5.6E−04 |
| 10 | 1.3E−04 | 9.5E−05 | 1.6E−04 | 9.9E−05 | 6.8E−05 | 2.9E−05 | 1.0E−04 |
| 11 | 0.0E+00 | 0.0E+00 | 0.0E+00 | 0.0E+00 | 0.0E+00 | 0.0E+00 | 0.0E+00 |
| 12 | 5.1E−01 | 4.5E−01 | 4.9E−01 | 2.0E−02 | 2.9E−01 | 1.6E−01 | 5.0E−01 |
| 13 | 6.1E−06 | 1.1E−05 | 2.0E−05 | 3.0E−07 | 9.2E−06 | 2.3E−05 | 1.9E−06 |
| 14 | 2.0E−02 | 8.4E−03 | 4.3E−02 | 3.7E−03 | 1.6E−02 | 1.5E−02 | 9.1E−03 |
| 15 | 2.4E−05 | 2.3E−05 | 4.7E−05 | 9.1E−07 | 2.2E−05 | 5.4E−06 | 3.5E−05 |
| 16 | 4.2E−01 | 2.0E−01 | 2.4E−01 | 9.2E−01 | 1.5E−01 | 2.3E−01 | 1.2E−01 |
| 17 | 1.8E−05 | 3.6E−05 | 0.0E+00 | 0.0E+00 | 6.9E−06 | 0.0E+00 | 2.6E−05 |
| 18 | 0.0E+00 | 0.0E+00 | 0.0E+00 | 0.0E+00 | 0.0E+00 | 0.0E+00 | 0.0E+00 |
| 19 | 1.3E−03 | 1.1E−03 | 8.2E−05 | 8.0E−04 | 2.1E−03 | 5.6E−04 | 3.3E−04 |
| 20 | 0.0E+00 | 0.0E+00 | 1.8E−04 | 3.1E−05 | 1.5E−04 | 1.1E−05 | 0.0E+00 |
| 21 | 0.0E+00 | 1.0E−06 | 0.0E+00 | 0.0E+00 | 0.0E+00 | 0.0E+00 | 0.0E+00 |
| 22 | 1.0E−04 | 4.9E−05 | 4.3E−05 | 9.4E−06 | 6.9E−05 | 4.2E−04 | 1.7E−05 |

RM Atm−/− Colon

| | | | | |
|---|---|---|---|---|
| 1 | 2.3E−03 | 3.1E−03 | 2.6E−03 | 1.7E−03 |
| 2 | 7.0E−04 | 5.4E−04 | 3.2E−04 | 2.0E−04 |
| 3 | 4.9E−06 | 1.9E−06 | 1.1E−06 | 2.1E−06 |
| 4 | 1.9E−02 | 1.7E−02 | 2.6E−02 | 1.0E−02 |
| 5 | 5.8E−01 | 4.9E−01 | 6.9E−01 | 6.5E−01 |
| 6 | 0.0E+00 | 0.0E+00 | 0.0E+00 | 0.0E+00 |
| 7 | 1.2E−04 | 6.2E−05 | 1.4E−04 | 1.2E−04 |
| 8 | 0.0E+00 | 0.0E+00 | 0.0E+00 | 0.0E+00 |
| 9 | 1.5E−05 | 1.4E−05 | 2.5E−05 | 9.4E−06 |
| 10 | 0.0E+00 | 0.0E+00 | 0.0E+00 | 0.0E+00 |
| 11 | 0.0E+00 | 0.0E+00 | 0.0E+00 | 0.0E+00 |
| 12 | 3.7E−01 | 4.7E−01 | 2.5E−01 | 3.1E−01 |
| 13 | 4.5E−05 | 1.4E−05 | 5.7E−06 | 1.1E−05 |
| 14 | 2.5E−02 | 2.1E−02 | 3.0E−02 | 2.9E−02 |
| 15 | 3.8E−06 | 4.7E−06 | 2.9E−06 | 1.3E−06 |
| 16 | 1.8E−03 | 1.2E−03 | 1.1E−03 | 4.0E−04 |
| 17 | 1.5E−04 | 1.7E−04 | 5.1E−05 | 1.2E−04 |
| 18 | 7.5E−07 | 4.7E−07 | 0.0E+00 | 0.0E+00 |
| 19 | 6.9E−04 | 2.7E−04 | 1.0E−04 | 3.3E−05 |
| 20 | 1.5E−06 | 0.0E+00 | 5.7E−07 | 0.0E+00 |
| 21 | 7.5E−07 | 0.0E+00 | 1.1E−06 | 0.0E+00 |
| 22 | 4.7E−05 | 2.7E−05 | 1.7E−05 | 1.7E−05 |

Figure 5:
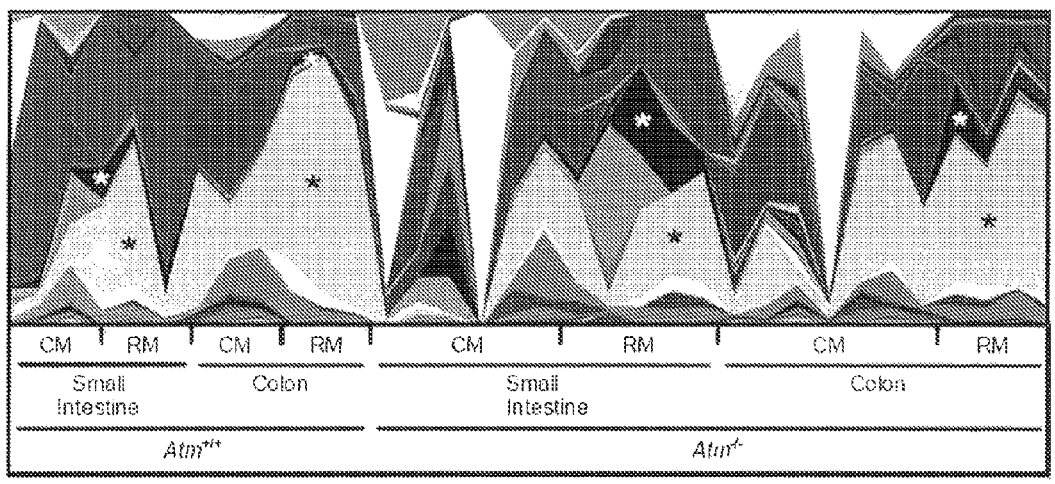
FIG. 5 depicts that intestinal microbiota in CM and RM mice are distinct at the OTU level. (A) Area plot of the most abundant OTUs in CM and RM mice by genotype and intestinal region. (B) Distribution and abundance of *Porphyromonas asaccharolytica* by genotype and intestinal region. (C) Distribution and abundance of *Lactobacillus johnsonii* by genotype and intestinal region. See FIG. 4 legend for mouse numbers per genotype and intestinal region. Details are described herein, e.g., in Example D.
Figure 5:
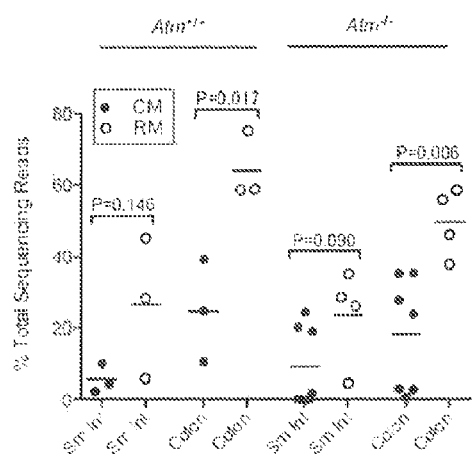
Figure 5:
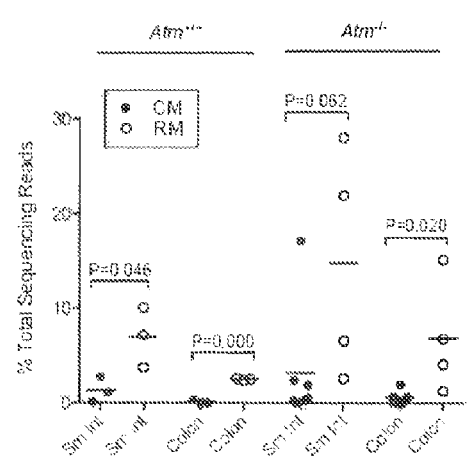

An analysis of the rRNA gene sequences at a finer taxonomic level revealed several large operational taxonomic units (OTUs) from the intestinal mucosa that were differentially abundant in CM and RM mice (FIG. 5A). Differentially abundant OTUs were considered worthy of further study because they might represent individual bacterial species participating in the enhancement or inhibition of systemic genotoxicity or other pertinent CM-RM metrics. The closest BLAST hit of one of the most abundant OTUs in many RM habitats was *Porphyromonas asaccharolytica* (98% identity to CP002689, 43% coverage) (see black asterisks in FIG. 5A). This phylotype was significantly more abundant in the colon of RM than CM in both $Atm^{-/-}$ and $Atm^{+/+}$ mice, and comprised at least 50% of the total sequencing reads from these habitats (FIG. 5B), warranting further investigation as a potential inhibitor of systemic genotoxicity. Similarly, another OTU exhibiting higher populations in most of the RM habitats (FIG. 5C, and see white asterisks in FIG. 5A) had high sequence identity to *Lactobacillus johnsonii* (100% identity to CP002464, 100% coverage). A phylotype that was more abundant in CM than RM mice, and therefore a candidate for causing the observed genotoxicity, included a member of the Helicobacteriaceae (FIG. 2). A more comprehensive taxonomic analysis is provided in the Table 6:

TABLE 6

| | Taxonomic Analysis |
|---|---|
| Taxon ID | Taxon |
| 1 | No blast hit; Other; Other; Other; Other; Other; Other |
| 2 | Actinobacteria; c_Actinobacteria; o_Acidimicrobiales; f_Acidimicrobiaceae; g_*Acidimicrobium*; s_NOT_LABELED |
| 3 | Actinobacteria; c_Actinobacteria; o_Acidimicrobiales; f_Acidimicrobiaceae; g_NOT_LABELED; s_NOT_LABELED |
| 4 | Actinobacteria; c_Actinobacteria; o_Acidimicrobiales; f_NOT_LABELED; g_NOT_LABELED; s_NOT_LABELED |
| 5 | Actinobacteria; c_Actinobacteria; o_Actinomycetales; f_Actinomycetaceae; g_*Trueperella*; s_NOT_LABELED |
| 6 | Actinobacteria; c_Actinobacteria; o_Actinomycetales; f_Corynebacteriaceae; g_*Corynebacterium*; s_*Corynebacterium amycolatum* |
| 7 | Actinobacteria; c_Actinobacteria; o_Actinomycetales; f_Corynebacteriaceae; g_*Corynebacterium*; s_*Corynebacterium aurimucosum* |
| 8 | Actinobacteria; c_Actinobacteria; o_Actinomycetales; f_Corynebacteriaceae; g_*Corynebacterium*; s_*Corynebacterium diphtheriae* |
| 9 | Actinobacteria; c_Actinobacteria; o_Actinomycetales; f_Corynebacteriaceae; g_*Corynebacterium*; s_*Corynebacterium glutamicum* |
| 10 | Actinobacteria; c_Actinobacteria; o_Actinomycetales; f_Corynebacteriaceae; g_*Corynebacterium*; s_*Corynebacterium jeikeium* |
| 11 | Actinobacteria; c_Actinobacteria; o_Actinomycetales; f_Corynebacteriaceae; g_*Corynebacterium*; s_*Corynebacterium kroppenstedtii* |
| 12 | Actinobacteria; c_Actinobacteria; o_Actinomycetales; f_Corynebacteriaceae; g_*Corynebacterium*; s_*Corynebacterium resistens* |
| 13 | Actinobacteria; c_Actinobacteria; o_Actinomycetales; f_Corynebacteriaceae; g_*Corynebacterium*; s_*Corynebacterium ulcerans* |
| 14 | Actinobacteria; c_Actinobacteria; o_Actinomycetales; f_Corynebacteriaceae; g_*Corynebacterium*; s_*Corynebacterium variabile* |
| 15 | Actinobacteria; c_Actinobacteria; o_Actinomycetales; f_Corynebacteriaceae; g_*Corynebacterium*; s_NOT_LABELED |
| 16 | Actinobacteria; c_Actinobacteria; o_Actinomycetales; f_Dermabacteraceae; g_*Dermabacter*; s_NOT_LABELED |
| 17 | Actinobacteria; c_Actinobacteria; o_Actinomycetales; f_Frankiaceae; g_*Frankia*; s_NOT_LABELED |
| 18 | Actinobacteria; c_Actinobacteria; o_Actinomycetales; f_Frankiaceae; g_NOT_LABELED; s_NOT_LABELED |
| 19 | Actinobacteria; c_Actinobacteria; o_Actinomycetales; f_Geodermatophilaceae; g_*Geodermatophilus*; s_*Geodermatophilus obscurus* |
| 20 | Actinobacteria; c_Actinobacteria; o_Actinomycetales; f_Gordoniaceae; g_*Gordonia*; s_*Gordonia polyisoprenivorans* |
| 21 | Actinobacteria; c_Actinobacteria; o_Actinomycetales; f_Intrasporangiaceae; g_NOT_LABELED; s_NOT_LABELED |
| 22 | Actinobacteria; c_Actinobacteria; o_Actinomycetales; f_Kineosporiaceae; g_*Kineococcus*; s_NOT_LABELED |
| 23 | Actinobacteria; c_Actinobacteria; o_Actinomycetales; f_Kineosporiaceae; g_NOT_LABELED; s_NOT_LABELED |
| 24 | Actinobacteria; c_Actinobacteria; o_Actinomycetales; f_Microbacteriaceae; g_*Clavibacter*; s_*Clavibacter michiganensis* |
| 25 | Actinobacteria; c_Actinobacteria; o_Actinomycetales; f_Microbacteriaceae; g_*Microbacterium*; s_NOT_LABELED |
| 26 | Actinobacteria; c_Actinobacteria; o_Actinomycetales; f_Microbacteriaceae; g_*Rathayibacter*; s_NOT_LABELED |
| 27 | Actinobacteria; c_Actinobacteria; o_Actinomycetales; f_Micrococcaceae; g_*Renibacterium*; s_*Renibacterium salmoninarum* |
| 28 | Actinobacteria; c_Actinobacteria; o_Actinomycetales; f_Micromonosporaceae; g_*Actinoplanes*; s_NOT_LABELED |
| 29 | Actinobacteria; c_Actinobacteria; o_Actinomycetales; f_Micromonosporaceae; g_*Asanoa*; s_NOT_LABELED |
| 30 | Actinobacteria; c_Actinobacteria; o_Actinomycetales; f_Micromonosporaceae; g_*Micromonospora*; s_NOT_LABELED |

TABLE 6-continued

Taxonomic Analysis

| Taxon ID | Taxon |
|---|---|
| 31 | Actinobacteria; c_Actinobacteria; o_Actinomycetales; f_Mycobacteriaceae; g_*Mycobacterium*; s_*Mycobacterium parascrofulaceum* |
| 32 | Actinobacteria; c_Actinobacteria; o_Actinomycetales; f_Mycobacteriaceae; g_*Mycobacterium*; s_NOT_LABELED |
| 33 | Actinobacteria; c_Actinobacteria; o_Actinomycetales; f_NOT_LABELED; g_NOT_LABELED; s_NOT_LABELED |
| 34 | Actinobacteria; c_Actinobacteria; o_Actinomycetales; f_Nakamurellaceae; g_Humicoccus; s_NOT_LABELED |
| 35 | Actinobacteria; c_Actinobacteria; o_Actinomycetales; f_Nocardiaceae; g_*Nocardia*; s_NOT_LABELED |
| 36 | Actinobacteria; c_Actinobacteria; o_Actinomycetales; f_Nocardiaceae; g_*Rhodococcus*; s_*Rhodococcus erythropolis* |
| 37 | Actinobacteria; c_Actinobacteria; o_Actinomycetales; f_Nocardioidaceae; g_*Nocardioides*; s_NOT_LABELED |
| 38 | Actinobacteria; c_Actinobacteria; o_Actinomycetales; f_Promicromonosporaceae; g_*Xylanimonas*; s_*Xylanimonas cellulosilytica* |
| 39 | Actinobacteria; c_Actinobacteria; o_Actinomycetales; f_Propionibacteriaceae; g_*Microlunatus*; s_*Microlunatus phosphovorus* |
| 40 | Actinobacteria; c_Actinobacteria; o_Actinomycetales; f_Propionibacteriaceae; g_*Propionibacterium*; s_*Propionibacterium granulosum* |
| 41 | Actinobacteria; c_Actinobacteria; o_Actinomycetales; f_Pseudonocardiaceae; g_*Saccharomonospora*; s_*Saccharomonospora viridis* |
| 42 | Actinobacteria; c_Actinobacteria; o_Actinomycetales; f_Pseudonocardiaceae; g_*Saccharopolyspora*; s_*Saccharopolyspora erythraea* |
| 43 | Actinobacteria; c_Actinobacteria; o_Actinomycetales; f_Streptomycetaceae; g_*Kitasatospora*; s_*Kitasatospora setae* |
| 44 | Actinobacteria; c_Actinobacteria; o_Actinomycetales; f_Streptomycetaceae; g_*Streptomyces*; s_NOT_LABELED |
| 45 | Actinobacteria; c_Actinobacteria; o_Actinomycetales; f_Streptomycetaceae; g_*Streptomyces*; s_*Streptomyces avermitilis* |
| 46 | Actinobacteria; c_Actinobacteria; o_Actinomycetales; f_Streptomycetaceae; g_*Streptomyces*; s_*Streptomyces scabiei* |
| 47 | Actinobacteria; c_Actinobacteria; o_Actinomycetales; f_Streptomycetaceae; g_*Streptomyces*; s_*Streptomyces turgidiscabies* |
| 48 | Actinobacteria; c_Actinobacteria; o_Bifidobacteriales; f_Bifidobacteriaceae; g_*Bifidobacterium*; s_*Bifidobacterium pseudolongum* |
| 49 | Actinobacteria; c_Actinobacteria; o_Bifidobacteriales; f_Bifidobacteriaceae; g_*Gardnerella*; s_*Gardnerella vaginalis* |
| 50 | Actinobacteria; c_Actinobacteria; o_Coriobacteriales; f_Coriobacteriaceae; g_*Atopobium*; s_*Atopobium parvulum* |
| 51 | Actinobacteria; c_Actinobacteria; o_Coriobacteriales; f_Coriobacteriaceae; g_*Coriobacterium*; s_*Coriobacterium glomerans* |
| 52 | Actinobacteria; c_Actinobacteria; o_Coriobacteriales; f_Coriobacteriaceae; g_*Eggerthella*; s_NOT_LABELED |
| 53 | Actinobacteria; c_Actinobacteria; o_Coriobacteriales; f_Coriobacteriaceae; g_*Olsenella*; s_*Olsenella uli* |
| 54 | Actinobacteria; c_Actinobacteria; o_NOT_LABELED; f_NOT_LABELED; g_NOT_LABELED; s_NOT_LABELED |
| 55 | Actinobacteria; c_Actinobacteria; o_Solirubrobacterales; f_Conexibacteraceae; g_*Conexibacter*; s_NOT_LABELED |
| 56 | Actinobacteria; c_Actinobacteria; o_environmental samples; f_NOT_LABELED; g_NOT_LABELED; s_NOT_LABELED |
| 57 | Aquificae; c_Aquificae; o_Aquificales; f_Desulfurobacteriaceae; g_*Desulfurobacterium*; s_*Desulfurobacterium thermolithotrophum* |
| 58 | Bacteroidetes; c_Bacteroidia; o_Bacteroidales; f_Bacteroidaceae; g_*Bacteroides*; s_*Bacteroides fragilis* |
| 59 | Bacteroidetes; c_Bacteroidia; o_Bacteroidales; f_Bacteroidaceae; g_*Bacteroides*; s_*Bacteroides helcogenes* |
| 60 | Bacteroidetes; c_Bacteroidia; o_Bacteroidales; f_Bacteroidaceae; g_*Bacteroides*; s_*Bacteroides salanitronis* |
| 61 | Bacteroidetes; c_Bacteroidia; o_Bacteroidales; f_Bacteroidaceae; g_*Bacteroides*; s_*Bacteroides thetaiotaomicron* |
| 62 | Bacteroidetes; c_Bacteroidia; o_Bacteroidales; f_Bacteroidaceae; g_*Bacteroides*; s_*Bacteroides vulgatus* |
| 63 | Bacteroidetes; c_Bacteroidia; o_Bacteroidales; f_Porphyromonadaceae; g_*Odoribacter*; s_*Odoribacter splanchnicus* |
| 64 | Bacteroidetes; c_Bacteroidia; o_Bacteroidales; f_Porphyromonadaceae; g_*Parabacteroides*; s_*Parabacteroides distasonis* |
| 65 | Bacteroidetes; c_Bacteroidia; o_Bacteroidales; f_Porphyromonadaceae; g_*Porphyromonas*; s_*Porphyromonas gingivalis* |
| 66 | Bacteroidetes; c_Bacteroidia; o_Bacteroidales; f_Porphyromonadaceae; g_*Tannerella*; s_*Tannerella forsythia* |
| 67 | Bacteroidetes; c_Bacteroidia; o_Bacteroidales; f_Prevotellaceae; g_*Prevotella*; s_*Prevotella ruminicola* |
| 68 | Bacteroidetes; c_Cytophagia; o_Cytophagales; f_Cyclobacteriaceae; g_*Cyclobacterium*; s_*Cyclobacterium marinum* |

TABLE 6-continued

Taxonomic Analysis

| Taxon ID | Taxon |
|---|---|
| 69 | Bacteroidetes; c_Cytophagia; o_Cytophagales; f_Cytophagaceae; g_*Dyadobacter*; s_*Dyadobacter fermentans* |
| 70 | Bacteroidetes; c_Cytophagia; o_Cytophagales; f_Cytophagaceae; g_*Spirosoma*; s_*Spirosoma linguale* |
| 71 | Bacteroidetes; c_Cytophagia; o_Cytophagales; f_Flammeovirgaceae; g_*Marivirga*; s_*Marivirga tractuosa* |
| 72 | Bacteroidetes; c_Flavobacteriia; o_Flavobacteriales; f_Blattabacteriaceae; g_*Blattabacterium*; s_*Blattabacterium punctulatus* |
| 73 | Bacteroidetes; c_Flavobacteriia; o_Flavobacteriales; f_Blattabacteriaceae; g_*Blattabacterium*; s_*Blattabacterium* sp. (Periplaneta americana) |
| 74 | Bacteroidetes; c_Flavobacteriia; o_Flavobacteriales; f_Cryomorphaceae; g_NOT_LABELED; s_*Owenweeksia hongkongensis* |
| 75 | Bacteroidetes; c_Flavobacteriia; o_Flavobacteriales; f_Flavobacteriaceae; g_*Capnocytophaga*; s_*Capnocytophaga canimorsus* |
| 76 | Bacteroidetes; c_Flavobacteriia; o_Flavobacteriales; f_Flavobacteriaceae; g_*Croceibacter*; s_*Croceibacter atlanticus* |
| 77 | Bacteroidetes; c_Flavobacteriia; o_Flavobacteriales; f_Flavobacteriaceae; g_*Gramella*; s_*Gramella forsetii* |
| 78 | Bacteroidetes; c_Sphingobacteriia; o_Sphingobacteriales; f_Sphingobacteriaceae; g_*Pedobacter*; s_*Pedobacter saltans* |
| 79 | Bacteroidetes/Chlorobi group; c_Bacteroidia; o_Bacteroidales; f_Bacteroidaceae; g_*Bacteroides*; s_*Bacteroides caccae* |
| 80 | Bacteroidetes/Chlorobi group; c_Bacteroidia; o_Bacteroidales; f_Bacteroidaceae; g_*Bacteroides*; s_*Bacteroides fragilis* |
| 81 | Bacteroidetes/Chlorobi group; c_Bacteroidia; o_Bacteroidales; f_Bacteroidaceae; g_*Bacteroides*; s_*Bacteroides uniformis* |
| 82 | Bacteroidetes/Chlorobi group; c_Bacteroidia; o_Bacteroidales; f_Bacteroidaceae; g_*Bacteroides*; s_NOT_LABELED |
| 83 | Bacteroidetes/Chlorobi group; c_Bacteroidia; o_Bacteroidales; f_NOT_LABELED; g_NOT_LABELED; s_NOT_LABELED |
| 84 | Bacteroidetes/Chlorobi group; c_Bacteroidia; o_Bacteroidales; f_Porphyromonadaceae; g_*Dysgonomonas*; s_NOT_LABELED |
| 85 | Bacteroidetes/Chlorobi group; c_Bacteroidia; o_Bacteroidales; f_Porphyromonadaceae; g_*Porphyromonas*; s_NOT_LABELED |
| 86 | Bacteroidetes/Chlorobi group; c_Bacteroidia; o_Bacteroidales; f_Porphyromonadaceae; g_*Porphyromonas*; s_*Porphyromonas asaccharolytica* |
| 87 | Bacteroidetes/Chlorobi group; c_Bacteroidia; o_Bacteroidales; f_Porphyromonadaceae; g_*Porphyromonas*; s_*Porphyromonas endodontalis* |
| 88 | Bacteroidetes/Chlorobi group; c_Bacteroidia; o_Bacteroidales; f_Porphyromonadaceae; g_*Porphyromonas*; s_*Porphyromonas levii* |
| 89 | Bacteroidetes/Chlorobi group; c_Bacteroidia; o_Bacteroidales; f_Prevotellaceae; g_*Prevotella*; s_*Prevotella intermedia* |
| 90 | Bacteroidetes/Chlorobi group; c_Bacteroidia; o_Bacteroidales; f_Prevotellaceae; g_*Prevotella*; s_*Prevotella melaninogenica* |
| 91 | Bacteroidetes/Chlorobi group; c_Flavobacteriia; o_Flavobacteriales; f_Flavobacteriaceae; g_*Bergeyella*; s_NOT_LABELED |
| 92 | Bacteroidetes/Chlorobi group; c_Flavobacteriia; o_Flavobacteriales; f_Flavobacteriaceae; g_*Chryseobacterium*; s_NOT_LABELED |
| 93 | Bacteroidetes/Chlorobi group; c_Flavobacteriia; o_Flavobacteriales; f_Flavobacteriaceae; g_*Elizabethkingia*; s_NOT_LABELED |
| 94 | Bacteroidetes/Chlorobi group; c_Flavobacteriia; o_Flavobacteriales; f_Flavobacteriaceae; g_*Flavobacterium*; s_*Flavobacterium columnare* |
| 95 | Bacteroidetes/Chlorobi group; c_Flavobacteriia; o_Flavobacteriales; f_Flavobacteriaceae; g_*Riemerella*; s_*Riemerella anatipestifer* |
| 96 | Bacteroidetes/Chlorobi group; c_NOT_LABELED; o_NOT_LABELED; f_NOT_LABELED; g_NOT_LABELED; s_NOT_LABELED |
| 97 | Bacteroidetes/Chlorobi group; c_Sphingobacteriia; o_Sphingobacteriales; f_NOT_LABELED; g_NOT_LABELED; s_NOT_LABELED |
| 98 | Chlamydiae/Verrucomicrobia group; c_Opitutae; o_NOT_LABELED; f_Opitutaceae; g_*Opitutus*; s_NOT_LABELED |

TABLE 6-continued

Taxonomic Analysis

| Taxon ID | Taxon |
|---|---|
| 99 | Chlamydiae/Verrucomicrobia group; c_Verrucomicrobiae; o_Verrucomicrobiales; f_NOT_LABELED; g_NOT_LABELED; s_NOT_LABELED |
| 100 | Chloroflexi; c_Caldilineae; o_Caldilineales; f_Caldilineaceae; g_*Caldilinea*; s_*Caldilinea aerophila* |
| 101 | Chloroflexi; c_Chloroflexi; o_Chloroflexales; f_Chloroflexaceae; g_*Chloroflexus*; s_NOT_LABELED |
| 102 | Chloroflexi; c_Chloroflexi; o_Chloroflexales; f_Chloroflexaceae; g_*Roseiflexus*; s_*Roseiflexus castenholzii* |
| 103 | Chloroflexi; c_Chloroflexi; o_Herpetosiphonales; f_Herpetosiphonaceae; g_*Herpetosiphon*; s_*Herpetosiphon aurantiacus* |
| 104 | Chrysiogenetes; c_Chrysiogenetes; o_Chrysiogenales; f_Chrysiogenaceae; g_*Desulfurispirillum*; s_*Desulfurispirillum indicum* |
| 105 | Cyanobacteria; c_NOT_LABELED; o_Chroococcales; f_NOT_LABELED; g_Acaryochloris; s_NOT_LABELED |
| 106 | Cyanobacteria; c_NOT_LABELED; o_NOT_LABELED; f_NOT_LABELED; g_NOT_LABELED; s_NOT_LABELED |
| 107 | Cyanobacteria; c_NOT_LABELED; o_Oscillatoriales; f_NOT_LABELED; g_Lyngbya; s_NOT_LABELED |
| 108 | Cyanobacteria; c_NOT_LABELED; o_Oscillatoriales; f_NOT_LABELED; g_*Microcoleus*; s_*Microcoleus steenstrupii* |
| 109 | Deferribacteres; c_Deferribacteres; o_Deferribacterales; f_Deferribacteraceae; g_*Denitrovibrio*; s_*Denitrovibrio acetiphilus* |
| 110 | Deferribacteres; c_Deferribacteres; o_Deferribacterales; f_Deferribacteraceae; g_*Flexistipes*; s_*Flexistipes sinusarabici* |
| 111 | Fibrobacteres/Acidobacteria group; c_Acidobacteriia; o_Acidobacteriales; f_Acidobacteriaceae; g_NOT_LABELED; s_NOT_LABELED |
| 112 | Fibrobacteres/Acidobacteria group; c_NOT_LABELED; o_NOT_LABELED; f_NOT_LABELED; g_NOT_LABELED; s_NOT_LABELED |
| 113 | Fibrobacteres/Acidobacteria group; c_Solibacteres; o_Solibacterales; f_Solibacteraceae; g_*Candidatus* Solibacter; s_NOT_LABELED |
| 114 | Firmicutes; c_Bacilli; o_Bacillales; f_Alicyclobacillaceae; g_*Alicyclobacillus*; s_*Alicyclobacillus acidocaldarius* |
| 115 | Firmicutes; c_Bacilli; o_Bacillales; f_Alicyclobacillaceae; g_*Alicyclobacillus*; s_NOT_LABELED |
| 116 | Firmicutes; c_Bacilli; o_Bacillales; f_Alicyclobacillaceae; g_*Kyrpidia*; s_*Kyrpidia tusciae* |
| 117 | Firmicutes; c_Bacilli; o_Bacillales; f_Bacillaceae; g_*Amphibacillus*; s_NOT_LABELED |
| 118 | Firmicutes; c_Bacilli; o_Bacillales; f_Bacillaceae; g_*Anoxybacillus*; s_*Anoxybacillus flavithermus* |
| 119 | Firmicutes; c_Bacilli; o_Bacillales; f_Bacillaceae; g_*Bacillus*; s_*Bacillus cellulosilyticus* |
| 120 | Firmicutes; c_Bacilli; o_Bacillales; f_Bacillaceae; g_*Bacillus*; s_*Bacillus cereus* |
| 121 | Firmicutes; c_Bacilli; o_Bacillales; f_Bacillaceae; g_*Bacillus*; s_*Bacillus circulans* |
| 122 | Firmicutes; c_Bacilli; o_Bacillales; f_Bacillaceae; g_*Bacillus*; s_*Bacillus coagulans* |
| 123 | Firmicutes; c_Bacilli; o_Bacillales; f_Bacillaceae; g_*Bacillus*; s_*Bacillus halodurans* |
| 124 | Firmicutes; c_Bacilli; o_Bacillales; f_Bacillaceae; g_*Bacillus*; s_*Bacillus megaterium* |
| 125 | Firmicutes; c_Bacilli; o_Bacillales; f_Bacillaceae; g_*Bacillus*; s_*Bacillus pseudofirmus* |
| 126 | Firmicutes; c_Bacilli; o_Bacillales; f_Bacillaceae; g_*Bacillus*; s_*Bacillus pumilus* |
| 127 | Firmicutes; c_Bacilli; o_Bacillales; f_Bacillaceae; g_*Bacillus*; s_*Bacillus subtilis* group |
| 128 | Firmicutes; c_Bacilli; o_Bacillales; f_Bacillaceae; g_*Bacillus*; s_NOT_LABELED |
| 129 | Firmicutes; c_Bacilli; o_Bacillales; f_Bacillaceae; g_*Geobacillus*; s_*Geobacillus stearothermophilus* |
| 130 | Firmicutes; c_Bacilli; o_Bacillales; f_Bacillaceae; g_*Geobacillus*; s_*Geobacillus thermoglucosidasius* |
| 131 | Firmicutes; c_Bacilli; o_Bacillales; f_Bacillaceae; g_*Geobacillus*; s_NOT_LABELED |
| 132 | Firmicutes; c_Bacilli; o_Bacillales; f_Bacillaceae; g_*Gracilibacillus*; s_NOT_LABELED |
| 133 | Firmicutes; c_Bacilli; o_Bacillales; f_Bacillaceae; g_*Halobacillus*; s_*Halobacillus halophilus* |
| 134 | Firmicutes; c_Bacilli; o_Bacillales; f_Bacillaceae; g_*Halobacillus*; s_NOT_LABELED |
| 135 | Firmicutes; c_Bacilli; o_Bacillales; f_Bacillaceae; g_*Lysinibacillus*; s_*Lysinibacillus sphaericus* |
| 136 | Firmicutes; c_Bacilli; o_Bacillales; f_Bacillaceae; g_*Lysinibacillus*; s_NOT_LABELED |
| 137 | Firmicutes; c_Bacilli; o_Bacillales; f_Bacillaceae; g_NOT_LABELED; s_NOT_LABELED |
| 138 | Firmicutes; c_Bacilli; o_Bacillales; f_Bacillaceae; g_*Oceanobacillus*; s_*Oceanobacillus iheyensis* |
| 139 | Firmicutes; c_Bacilli; o_Bacillales; f_Bacillaceae; g_*Virgibacillus*; s_NOT_LABELED |
| 140 | Firmicutes; c_Bacilli; o_Bacillales; f_Listeriaceae; g_*Listeria*; s_*Listeria ivanovii* |
| 141 | Firmicutes; c_Bacilli; o_Bacillales; f_NOT_LABELED; g_*Exiguobacterium*; s_NOT_LABELED |
| 142 | Firmicutes; c_Bacilli; o_Bacillales; f_NOT_LABELED; g_*Gemella*; s_*Gemella haemolysans* |
| 143 | Firmicutes; c_Bacilli; o_Bacillales; f_NOT_LABELED; g_*Gemella*; s_*Gemella morbillorum* |
| 144 | Firmicutes; c_Bacilli; o_Bacillales; f_NOT_LABELED; g_*Gemella*; s_*Gemella sanguinis* |

TABLE 6-continued

Taxonomic Analysis

| Taxon ID | Taxon |
|---|---|
| 145 | Firmicutes; c_Bacilli; o_Bacillales; f_NOT_LABELED; g_*Gemella*; s_NOT_LABELED |
| 146 | Firmicutes; c_Bacilli; o_Bacillales; f_Paenibacillaceae; g_*Brevibacillus*; s_*Brevibacillus brevis* |
| 147 | Firmicutes; c_Bacilli; o_Bacillales; f_Paenibacillaceae; g_*Brevibacillus*; s_NOT_LABELED |
| 148 | Firmicutes; c_Bacilli; o_Bacillales; f_Paenibacillaceae; g_*Paenibacillus*; s_NOT_LABELED |
| 149 | Firmicutes; c_Bacilli; o_Bacillales; f_Paenibacillaceae; g_*Paenibacillus*; s_*Paenibacillus larvae* |
| 150 | Firmicutes; c_Bacilli; o_Bacillales; f_Pasteuriaceae; g_*Pasteuria*; s_NOT_LABELED |
| 151 | Firmicutes; c_Bacilli; o_Bacillales; f_Planococcaceae; g_*Ureibacillus*; s_NOT_LABELED |
| 152 | Firmicutes; c_Bacilli; o_Bacillales; f_Planococcaceae; g_*Ureibacillus*; s_*Ureibacillus thermosphaericus* |
| 153 | Firmicutes; c_Bacilli; o_Bacillales; f_Sporolactobacillaceae; g_Sporolactobacillus; s_NOT_LABELED |
| 154 | Firmicutes; c_Bacilli; o_Bacillales; f_Staphylococcaceae; g_*Staphylococcus*; s_NOT_LABELED |
| 155 | Firmicutes; c_Bacilli; o_Bacillales; f_Staphylococcaceae; g_*Staphylococcus*; s_*Staphylococcus aureus* |
| 156 | Firmicutes; c_Bacilli; o_Bacillales; f_Staphylococcaceae; g_*Staphylococcus*; s_*Staphylococcus epidermidis* |
| 157 | Firmicutes; c_Bacilli; o_Bacillales; f_Staphylococcaceae; g_*Staphylococcus*; s_*Staphylococcus saprophyticus* |
| 158 | Firmicutes; c_Bacilli; o_Bacillales; f_Staphylococcaceae; g_*Staphylococcus*; s_*Staphylococcus simulans* |
| 159 | Firmicutes; c_Bacilli; o_Lactobacillales; f_Aerococcaceae; g_*Abiotrophia*; s_*Abiotrophia defectiva* |
| 160 | Firmicutes; c_Bacilli; o_Lactobacillales; f_Carnobacteriaceae; g_*Atopostipes*; s_NOT_LABELED |
| 161 | Firmicutes; c_Bacilli; o_Lactobacillales; f_Carnobacteriaceae; g_*Granulicatella*; s_*Granulicatella adiacens* |
| 162 | Firmicutes; c_Bacilli; o_Lactobacillales; f_Carnobacteriaceae; g_*Granulicatella*; s_*Granulicatella elegans* |
| 163 | Firmicutes; c_Bacilli; o_Lactobacillales; f_Enterococcaceae; g_*Enterococcus*; s_*Enterococcus faecalis* |
| 164 | Firmicutes; c_Bacilli; o_Lactobacillales; f_Enterococcaceae; g_*Enterococcus*; s_NOT_LABELED |
| 165 | Firmicutes; c_Bacilli; o_Lactobacillales; f_Enterococcaceae; g_*Melissococcus*; s_*Melissococcus plutonius* |
| 166 | Firmicutes; c_Bacilli; o_Lactobacillales; f_Lactobacillaceae; g_*Lactobacillus*; s_*Lactobacillus acidophilus* |
| 167 | Firmicutes; c_Bacilli; o_Lactobacillales; f_Lactobacillaceae; g_*Lactobacillus*; s_*Lactobacillus animalis* |
| 168 | Firmicutes; c_Bacilli; o_Lactobacillales; f_Lactobacillaceae; g_*Lactobacillus*; s_*Lactobacillus delbrueckii* |
| 169 | Firmicutes; c_Bacilli; o_Lactobacillales; f_Lactobacillaceae; g_*Lactobacillus*; s_*Lactobacillus gasseri* |
| 170 | Firmicutes; c_Bacilli; o_Lactobacillales; f_Lactobacillaceae; g_*Lactobacillus*; s_*Lactobacillus hilgardii* |
| 171 | Firmicutes; c_Bacilli; o_Lactobacillales; f_Lactobacillaceae; g_*Lactobacillus*; s_*Lactobacillus jensenii* |
| 172 | Firmicutes; c_Bacilli; o_Lactobacillales; f_Lactobacillaceae; g_*Lactobacillus*; s_*Lactobacillus johnsonii* |
| 173 | Firmicutes; c_Bacilli; o_Lactobacillales; f_Lactobacillaceae; g_*Lactobacillus*; s_*Lactobacillus kefiranofaciens* |
| 174 | Firmicutes; c_Bacilli; o_Lactobacillales; f_Lactobacillaceae; g_*Lactobacillus*; s_*Lactobacillus reuteri* |
| 175 | Firmicutes; c_Bacilli; o_Lactobacillales; f_Lactobacillaceae; g_*Lactobacillus*; s_NOT_LABELED |
| 176 | Firmicutes; c_Bacilli; o_Lactobacillales; f_Lactobacillaceae; g_*Pediococcus*; s_*Pediococcus acidilactici* |
| 177 | Firmicutes; c_Bacilli; o_Lactobacillales; f_Leuconostocaceae; g_*Leuconostoc*; s_*Leuconostoc mesenteroides* |
| 178 | Firmicutes; c_Bacilli; o_Lactobacillales; f_Leuconostocaceae; g_*Weissella*; s_NOT_LABELED |
| 179 | Firmicutes; c_Bacilli; o_Lactobacillales; f_Streptococcaceae; g_*Lactococcus*; s_*Lactococcus lactis* |
| 180 | Firmicutes; c_Bacilli; o_Lactobacillales; f_Streptococcaceae; g_*Streptococcus*; s_*Streptococcus agalactiae* |
| 181 | Firmicutes; c_Bacilli; o_Lactobacillales; f_Streptococcaceae; g_*Streptococcus*; s_*Streptococcus anginosus* |
| 182 | Firmicutes; c_Bacilli; o_Lactobacillales; f_Streptococcaceae; g_*Streptococcus*; s_*Streptococcus australis* |
| 183 | Firmicutes; c_Bacilli; o_Lactobacillales; f_Streptococcaceae; g_*Streptococcus*; s_*Streptococcus criceti* |
| 184 | Firmicutes; c_Bacilli; o_Lactobacillales; f_Streptococcaceae; g_*Streptococcus*; s_*Streptococcus cristatus* |
| 185 | Firmicutes; c_Bacilli; o_Lactobacillales; f_Streptococcaceae; g_*Streptococcus*; s_*Streptococcus dysgalactiae* group |
| 186 | Firmicutes; c_Bacilli; o_Lactobacillales; f_Streptococcaceae; g_*Streptococcus*; s_*Streptococcus gordonii* |
| 187 | Firmicutes; c_Bacilli; o_Lactobacillales; f_Streptococcaceae; g_*Streptococcus*; s_*Streptococcus infantarius* |

TABLE 6-continued

Taxonomic Analysis

| Taxon ID | Taxon |
|---|---|
| 188 | Firmicutes; c_Bacilli; o_Lactobacillales; f_Streptococcaceae; g_*Streptococcus*; s_*Streptococcus infantis* |
| 189 | Firmicutes; c_Bacilli; o_Lactobacillales; f_Streptococcaceae; g_*Streptococcus*; s_*Streptococcus intermedius* |
| 190 | Firmicutes; c_Bacilli; o_Lactobacillales; f_Streptococcaceae; g_*Streptococcus*; s_*Streptococcus pneumoniae* |
| 191 | Firmicutes; c_Bacilli; o_Lactobacillales; f_Streptococcaceae; g_*Streptococcus*; s_*Streptococcus pyogenes* |
| 192 | Firmicutes; c_Bacilli; o_Lactobacillales; f_Streptococcaceae; g_*Streptococcus*; s_*Streptococcus sanguinis* |
| 193 | Firmicutes; c_Bacilli; o_Lactobacillales; f_Streptococcaceae; g_*Streptococcus*; s_*Streptococcus sobrinus* |
| 194 | Firmicutes; c_Bacilli; o_Lactobacillales; f_Streptococcaceae; g_*Streptococcus*; s_*Streptococcus thermophilus* |
| 195 | Firmicutes; c_Bacilli; o_Lactobacillales; f_Streptococcaceae; g_*Streptococcus*; s_*Streptococcus uberis* |
| 196 | Firmicutes; c_Clostridia; o_Clostridiales; f_Clostridiaceae; g_*Alkaliphilus*; s_*Alkaliphilus metalliredigens* |
| 197 | Firmicutes; c_Clostridia; o_Clostridiales; f_Clostridiaceae; g_*Alkaliphilus*; s_*Alkaliphilus oremlandii* |
| 198 | Firmicutes; c_Clostridia; o_Clostridiales; f_Clostridiaceae; g_*Alkaliphilus*; s_NOT_LABELED |
| 199 | Firmicutes; c_Clostridia; o_Clostridiales; f_Clostridiaceae; g_*Candidatus Arthromitus*; s_James_SFB |
| 200 | Firmicutes; c_Clostridia; o_Clostridiales; f_Clostridiaceae; g_*Candidatus Arthromitus*; s_NOT_LABELED |
| 201 | Firmicutes; c_Clostridia; o_Clostridiales; f_Clostridiaceae; g_*Clostridium*; s_*Clostridium botulinum* |
| 202 | Firmicutes; c_Clostridia; o_Clostridiales; f_Clostridiaceae; g_*Clostridium*; s_*Clostridium cellulolyticum* |
| 203 | Firmicutes; c_Clostridia; o_Clostridiales; f_Clostridiaceae; g_*Clostridium*; s_*Clostridium innocuum* |
| 204 | Firmicutes; c_Clostridia; o_Clostridiales; f_Clostridiaceae; g_*Clostridium*; s_*Clostridium kluyveri* |
| 205 | Firmicutes; c_Clostridia; o_Clostridiales; f_Clostridiaceae; g_*Clostridium*; s_*Clostridium ljungdahlii* |
| 206 | Firmicutes; c_Clostridia; o_Clostridiales; f_Clostridiaceae; g_*Clostridium*; s_*Clostridium novyi* |
| 207 | Firmicutes; c_Clostridia; o_Clostridiales; f_Clostridiaceae; g_*Clostridium*; s_*Clostridium phytofermentans* |
| 208 | Firmicutes; c_Clostridia; o_Clostridiales; f_Clostridiaceae; g_*Clostridium*; s_*Clostridium saccharolyticum* |
| 209 | Firmicutes; c_Clostridia; o_Clostridiales; f_Clostridiaceae; g_*Clostridium*; s_*Clostridium thermocellum* |
| 210 | Firmicutes; c_Clostridia; o_Clostridiales; f_Clostridiaceae; g_*Clostridium*; s_NOT_LABELED |
| 211 | Firmicutes; c_Clostridia; o_Clostridiales; f_Clostridiaceae; g_NOT_LABELED; s_NOT_LABELED |
| 212 | Firmicutes; c_Clostridia; o_Clostridiales; f_Clostridiales Family XI. Incertae Sedis; g_*Anaerococcus*; s_*Anaerococcus prevotii* |
| 213 | Firmicutes; c_Clostridia; o_Clostridiales; f_Clostridiales Family XI. Incertae Sedis; g_*Finegoldia*; s_*Finegoldia magna* |
| 214 | Firmicutes; c_Clostridia; o_Clostridiales; f_Clostridiales Family XI. Incertae Sedis; g_NOT_LABELED; s_*Parvimonas micra* |
| 215 | Firmicutes; c_Clostridia; o_Clostridiales; f_Clostridiales Family XI. Incertae Sedis; g_*Peptoniphilus*; s_*Peptoniphilus asaccharolyticus* |
| 216 | Firmicutes; c_Clostridia; o_Clostridiales; f_Eubacteriaceae; g_*Eubacterium*; s_*Eubacterium eligens* |
| 217 | Firmicutes; c_Clostridia; o_Clostridiales; f_Eubacteriaceae; g_*Eubacterium*; s_*Eubacterium limosum* |
| 218 | Firmicutes; c_Clostridia; o_Clostridiales; f_Eubacteriaceae; g_*Eubacterium*; s_*Eubacterium rectale* |
| 219 | Firmicutes; c_Clostridia; o_Clostridiales; f_Eubacteriaceae; g_*Eubacterium*; s_NOT_LABELED |
| 220 | Firmicutes; c_Clostridia; o_Clostridiales; f_Heliobacteriaceae; g_*Heliobacterium*; s_*Heliobacterium modesticaldum* |
| 221 | Firmicutes; c_Clostridia; o_Clostridiales; f_Lachnospiraceae; g_*Butyrivibrio*; s_*Clostridium proteoclasticum* |
| 222 | Firmicutes; c_Clostridia; o_Clostridiales; f_Lachnospiraceae; g_*Roseburia*; s_*Roseburia hominis* |
| 223 | Firmicutes; c_Clostridia; o_Clostridiales; f_NOT_LABELED; g_NOT_LABELED; s_Clostridiales genomosp. BVAB3 |
| 224 | Firmicutes; c_Clostridia; o_Clostridiales; f_NOT_LABELED; g_NOT_LABELED; s_NOT_LABELED |
| 225 | Firmicutes; c_Clostridia; o_Clostridiales; f_Oscillospiraceae; g_*Oscillibacter*; s_*Oscillibacter valericigenes* |
| 226 | Firmicutes; c_Clostridia; o_Clostridiales; f_Peptococcaceae; g_*Cryptanaerobacter*; s_NOT_LABELED |
| 227 | Firmicutes; c_Clostridia; o_Clostridiales; f_Peptococcaceae; g_*Dehalobacter*; s_*Dehalobacter restrictus* |

TABLE 6-continued

Taxonomic Analysis

| Taxon ID | Taxon |
|---|---|
| 228 | Firmicutes; c_Clostridia; o_Clostridiales; f_Peptococcaceae; g_*Desulfitobacterium*; s_*Desulfitobacterium hafniense* |
| 229 | Firmicutes; c_Clostridia; o_Clostridiales; f_Peptococcaceae; g_*Desulfosporosinus*; s_*Desulfosporosinus orientis* |
| 230 | Firmicutes; c_Clostridia; o_Clostridiales; f_Peptococcaceae; g_*Desulfotomaculum*; s_*Desulfotomaculum carboxydivorans* |
| 231 | Firmicutes; c_Clostridia; o_Clostridiales; f_Peptococcaceae; g_*Desulfotomaculum*; s_*Desulfotomaculum reducens* |
| 232 | Firmicutes; c_Clostridia; o_Clostridiales; f_Peptococcaceae; g_*Desulfotomaculum*; s_*Desulfotomaculum ruminis* |
| 233 | Firmicutes; c_Clostridia; o_Clostridiales; f_Peptococcaceae; g_*Syntrophobotulus*; s_*Syntrophobotulus glycolicus* |
| 234 | Firmicutes; c_Clostridia; o_Clostridiales; f_Peptostreptococcaceae; g_*Filifactor*; s_*Filifactor alocis* |
| 235 | Firmicutes; c_Clostridia; o_Clostridiales; f_Peptostreptococcaceae; g_NOT_LABELED; s_(*Clostridium*) *difficile* |
| 236 | Firmicutes; c_Clostridia; o_Clostridiales; f_Ruminococcaceae; g_*Ethanoligenens*; s_*Ethanoligenens harbinense* |
| 237 | Firmicutes; c_Clostridia; o_Clostridiales; f_Ruminococcaceae; g_*Ruminococcus*; s_*Ruminococcus albus* |
| 238 | Firmicutes; c_Clostridia; o_Halanaerobiales; f_Halobacteroidaceae; g_*Acetohalobium*; s_*Acetohalobium arabaticum* |
| 239 | Firmicutes; c_Clostridia; o_NOT_LABELED; f_NOT_LABELED; g_NOT_LABELED; s_NOT_LABELED |
| 240 | Firmicutes; c_Clostridia; o_Thermoanaerobacterales; f_Thermoanaerobacteraceae; g_*Ammonifex*; s_*Ammonifex degensii* |
| 241 | Firmicutes; c_Clostridia; o_Thermoanaerobacterales; f_Thermoanaerobacteraceae; g_*Carboxydothermus*; s_*Carboxydothermus hydrogenoformans* |
| 242 | Firmicutes; c_Clostridia; o_Thermoanaerobacterales; f_Thermoanaerobacteraceae; g_*Moorella*; s_*Moorella thermoacetica* |
| 243 | Firmicutes; c_Clostridia; o_Thermoanaerobacterales; f_Thermoanaerobacteraceae; g_*Thermoanaerobacter*; s_*Thermoanaerobacter brockii* |
| 244 | Firmicutes; c_Clostridia; o_Thermoanaerobacterales; f_Thermoanaerobacterales Family III. Incertae Sedis; g_*Thermoanaerobacterium*; s_*Thermoanaerobacterium xylanolyticum* |
| 245 | Firmicutes; c_Clostridia; o_Thermoanaerobacterales; f_Thermoanaerobacterales Family III. Incertae Sedis; g_*Thermosediminibacter*; s_*Thermosediminibacter oceani* |
| 246 | Firmicutes; c_Clostridia; o_Thermoanaerobacterales; f_Thermoanaerobacterales Family IV. Incertae Sedis; g_*Mahella*; s_*Mahella australiensis* |
| 247 | Firmicutes; c_Clostridia; o_Thermoanaerobacterales; f_Thermodesulfobiaceae; g_*Coprothermobacter*; s_*Coprothermobacter proteolyticus* |
| 248 | Firmicutes; c_Erysipelotrichi; o_Erysipelotrichales; f_Erysipelotrichaceae; g_*Bulleidia*; s_NOT_LABELED |
| 249 | Firmicutes; c_Erysipelotrichi; o_Erysipelotrichales; f_Erysipelotrichaceae; g_*Erysipelothrix*; s_*Erysipelotlwix rhusiopathiae* |
| 250 | Firmicutes; c_Erysipelotrichi; o_Erysipelotrichales; f_Erysipelotrichaceae; g_*Erysipelothrix*; s_*Erysipelothrix tonsillarum* |
| 251 | Firmicutes; c_Erysipelotrichi; o_Erysipelotrichales; f_Erysipelotrichaceae; g_*Turicibacter*; s_NOT_LABELED |
| 252 | Firmicutes; c_Erysipelotrichi; o_Erysipelotrichales; f_Erysipelotrichaceae; g_*Turicibacter*; s_*Turicibacter sanguinis* |
| 253 | Firmicutes; c_Erysipelotrichi; o_Erysipelotrichales; f_Erysipelotrichaceae; g_unclassified Erysipelotrichaceae; s_C10-JB-F |
| 254 | Firmicutes; c_Erysipelotrichi; o_Erysipelotrichales; f_Erysipelotrichaceae; g_unclassified Erysipelotrichaceae; s_D05-JB-F |
| 255 | Firmicutes; c_Erysipelotrichi; o_Erysipelotrichales; f_Erysipelotrichaceae; g_unclassified Erysipelotrichaceae; s_D07-JB-F |
| 256 | Firmicutes; c_Erysipelotrichi; o_Erysipelotrichales; f_Erysipelotrichaceae; g_unclassified Erysipelotrichaceae; s_E10-SI-F |
| 257 | Firmicutes; c_Erysipelotrichi; o_Erysipelotrichales; f_Erysipelotrichaceae; g_unclassified Erysipelotrichaceae; s_H04-C3H-DTT |
| 258 | Firmicutes; c_Erysipelotrichi; o_Erysipelotrichales; f_Erysipelotrichaceae; g_unclassified Erysipelotrichaceae; s_H07-A-CM-Large-DTT |
| 259 | Firmicutes; c_Erysipelotrichi; o_Erysipelotrichales; f_Erysipelotrichaceae; g_unclassified Erysipelotrichaceae; s_H08-A-CM-Large-DTT |
| 260 | Firmicutes; c_Erysipelotrichi; o_Erysipelotrichales; f_Erysipelotrichaceae; g_unclassified Erysipelotrichaceae; s_H08-C3H-DTT |
| 261 | Firmicutes; c_Erysipelotrichi; o_Erysipelotrichales; f_Erysipelotrichaceae; g_unclassified Erysipelotrichaceae; s_H09-A-RM-Sm-DTT |
| 262 | Firmicutes; c_Erysipelotrichi; o_Erysipelotrichales; f_Erysipelotrichaceae; g_unclassified Erysipelotrichaceae; s_H11-A-RM-Large-DTT |
| 263 | Firmicutes; c_NOT_LABELED; o_NOT_LABELED; f_NOT_LABELED; g_NOT_LABELED; s_NOT_LABELED |
| 264 | Firmicutes; c_Negativicutes; o_Selenomonadales; f_Acidaminococcaceae; g_*Acidaminococcus*; s_*Acidaminococcus fermentans* |
| 265 | Firmicutes; c_Negativicutes; o_Selenomonadales; f_Veillonellaceae; g_*Megasphaera*; s_NOT_LABELED |

TABLE 6-continued

Taxonomic Analysis

| Taxon ID | Taxon |
|---|---|
| 266 | Firmicutes; c_Negativicutes; o_Selenomonadales; f_Veillonellaceae; g_*Pectinatus*; s_NOT_LABELED |
| 267 | Firmicutes; c_Negativicutes; o_Selenomonadales; f_Veillonellaceae; g_*Veillonella*; s_*Veillonella parvula* |
| 268 | Firmicutes; c_Negativicutes; o_Selenomonadales; f_Veillonellaceae; g_*Zymophilus*; s_NOT_LABELED |
| 269 | Gemmatimonadetes; c_Gemmatimonadetes; o_Gemmatimonadales; f_Gemmatimonadaceae; g_*Gemmatimonas*; s_NOT_LABELED |
| 270 | Gemmatimonadetes; c_Gemmatimonadetes; o_Gemmatimonadales; f_Gemmatimonadaceae; g_NOT_LABELED; s_NOT_LABELED |
| 271 | NOT_LABELED; c_NOT_LABELED; o_NOT_LABELED; f_NOT_LABELED; g_NOT_LABELED; s_NOT_LABELED |
| 272 | Planctomycetes; c_Planctomycetia; o_Planctomycetales; f_NOT_LABELED; g_NOT_LABELED; s_NOT_LABELED |
| 273 | Proteobacteria; c_Alphaproteobacteria; o_Caulobacterales; f_Caulobacteraceae; g_*Caulobacter*; s_*Caulobacter segnis* |
| 274 | Proteobacteria; c_Alphaproteobacteria; o_NOT_LABELED; f_NOT_LABELED; g_NOT_LABELED; s_NOT_LABELED |
| 275 | Proteobacteria; c_Alphaproteobacteria; o_Rhizobiales; f_Bradyrhizobiaceae; g_*Bradyrhizobium*; s_*Bradyrhizobium japonicum* |
| 276 | Proteobacteria; c_Alphaproteobacteria; o_Rhizobiales; f_Bradyrhizobiaceae; g_*Bradyrhizobium*; s_NOT_LABELED |
| 277 | Proteobacteria; c_Alphaproteobacteria; o_Rhizobiales; f_Bradyrhizobiaceae; g_NOT_LABELED; s_NOT_LABELED |
| 278 | Proteobacteria; c_Alphaproteobacteria; o_Rhizobiales; f_Bradyrhizobiaceae; g_*Rhodopseudomonas*; s_*Rhodopseudomonas palustris* |
| 279 | Proteobacteria; c_Alphaproteobacteria; o_Rhizobiales; f_NOT_LABELED; g_NOT_LABELED; s_NOT_LABELED |
| 280 | Proteobacteria; c_Alphaproteobacteria; o_Rhizobiales; f_Rhizobiaceae; g_*Candidatus Liberibacter*; s_*Candidatus Liberibacter asiaticus* |
| 281 | Proteobacteria; c_Alphaproteobacteria; o_Rhizobiales; f_Rhizobiaceae; g_*Candidatus Liberibacter*; s_NOT_LABELED |
| 282 | Proteobacteria; c_Alphaproteobacteria; o_Rhizobiales; f_Rhizobiaceae; g_*Rhizobium*; s_*Rhizobium etli* |
| 283 | Proteobacteria; c_Alphaproteobacteria; o_Rhizobiales; f_Xanthobacteraceae; g_NOT_LABELED; s_NOT_LABELED |
| 284 | Proteobacteria; c_Alphaproteobacteria; o_Rhodobacterales; f_Rhodobacteraceae; g_*Paracoccus*; s_*Paracoccus denitrificans* |
| 285 | Proteobacteria; c_Alphaproteobacteria; o_Rhodobacterales; f_Rhodobacteraceae; g_*Rhodobacter*; s_*Rhodobacter sphaeroides* |
| 286 | Proteobacteria; c_Alphaproteobacteria; o_Sphingomonadales; f_Sphingomonadaceae; g_NOT_LABELED; s_NOT_LABELED |
| 287 | Proteobacteria; c_Alphaproteobacteria; o_Sphingomonadales; f_Sphingomonadaceae; g_*Sphingobium*; s_*Sphingobium chlorophenolicum* |
| 288 | Proteobacteria; c_Alphaproteobacteria; o_Sphingomonadales; f_Sphingomonadaceae; g_*Sphingomonas*; s_NOT_LABELED |
| 289 | Proteobacteria; c_Alphaproteobacteria; o_Sphingomonadales; f_Sphingomonadaceae; g_*Sphingopyxis*; s_*Sphingopyxis alaskensis* |
| 290 | Proteobacteria; c_Betaproteobacteria; o_Burkholderiales; f_Alcaligenaceae; g_*Achromobacter*; s_*Achromobacter xylosoxidans* |
| 291 | Proteobacteria; c_Betaproteobacteria; o_Burkholderiales; f_Alcaligenaceae; g_*Bordetella*; s_*Bordetella pertussis* |
| 292 | Proteobacteria; c_Betaproteobacteria; o_Burkholderiales; f_Burkholderiaceae; g_*Burkholderia*; s_*Burkholderia cepacia* complex |
| 293 | Proteobacteria; c_Betaproteobacteria; o_Burkholderiales; f_Burkholderiaceae; g_*Burkholderia*; s_*Burkholderia rhizoxinica* |
| 294 | Proteobacteria; c_Betaproteobacteria; o_Burkholderiales; f_Burkholderiaceae; g_*Cupriavidus*; s_*Cupriavidus metallidurans* |
| 295 | Proteobacteria; c_Betaproteobacteria; o_Burkholderiales; f_Burkholderiaceae; g_*Ralstonia*; s_*Ralstonia pickettii* |
| 296 | Proteobacteria; c_Betaproteobacteria; o_Burkholderiales; f_Comamonadaceae; g_*Delftia*; s_*Delftia acidovorans* |
| 297 | Proteobacteria; c_Betaproteobacteria; o_Burkholderiales; f_Comamonadaceae; g_NOT_LABELED; s_NOT_LABELED |
| 298 | Proteobacteria; c_Betaproteobacteria; o_Burkholderiales; f_Comamonadaceae; g_*Variovorax*; s_NOT_LABELED |
| 299 | Proteobacteria; c_Betaproteobacteria; o_Burkholderiales; f_Comamonadaceae; g_*Variovorax*; s_*Variovorax paradoxus* |
| 300 | Proteobacteria; c_Betaproteobacteria; o_Burkholderiales; f_NOT_LABELED; g_*Methylibium*; s_*Methylibium petroleiphilum* |
| 301 | Proteobacteria; c_Betaproteobacteria; o_Burkholderiales; f_NOT_LABELED; g_*Thiomonas*; s_NOT_LABELED |
| 302 | Proteobacteria; c_Betaproteobacteria; o_Burkholderiales; f_Oxalobacteraceae; g_*Collimonas*; s_*Collimonas fungivorans* |
| 303 | Proteobacteria; c_Betaproteobacteria; o_Burkholderiales; f_Oxalobacteraceae; g_*Herbaspirillum*; s_NOT_LABELED |
| 304 | Proteobacteria; c_Betaproteobacteria; o_Burkholderiales; f_Oxalobacteraceae; g_Herminiimonas; s_NOT_LABELED |

TABLE 6-continued

Taxonomic Analysis

| Taxon ID | Taxon |
|---|---|
| 305 | Proteobacteria; c_Betaproteobacteria; o_Burkholderiales; f_Oxalobacteraceae; g_*Janthinobacterium*; s_NOT_LABELED |
| 306 | Proteobacteria; c_Betaproteobacteria; o_Hydrogenophilales; f_Hydrogenophilaceae; g_*Thiobacillus*; s_NOT_LABELED |
| 307 | Proteobacteria; c_Betaproteobacteria; o_NOT_LABELED; f_NOT_LABELED; g_Kinetoplastibacterium; s_NOT_LABELED |
| 308 | Proteobacteria; c_Betaproteobacteria; o_NOT_LABELED; f_NOT_LABELED; g_NOT_LABELED; s_NOT_LABELED |
| 309 | Proteobacteria; c_Betaproteobacteria; o_Neisseriales; f_Neisseriaceae; g_*Neisseria*; s_*Neisseria gonorrhoeae* |
| 310 | Proteobacteria; c_Betaproteobacteria; o_Neisseriales; f_Neisseriaceae; g_*Neisseria*; s_*Neisseria meningitidis* |
| 311 | Proteobacteria; c_Betaproteobacteria; o_Nitrosomonadales; f_Nitrosomonadaceae; g_NOT_LABELED; s_NOT_LABELED |
| 312 | Proteobacteria; c_Betaproteobacteria; o_Rhodocyclales; f_Rhodocyclaceae; g_*Azoarcus*; s_NOT_LABELED |
| 313 | Proteobacteria; c_Deltaproteobacteria; o_Desulfovibrionales; f_Desulfovibrionaceae; g_*Bilophila*; s_*Bilophila wadsworthia* |
| 314 | Proteobacteria; c_Deltaproteobacteria; o_Desulfovibrionales; f_Desulfovibrionaceae; g_*Desulfovibrio*; s_*Desulfovibrio desulfuricans* |
| 315 | Proteobacteria; c_Deltaproteobacteria; o_Desulfovibrionales; f_Desulfovibrionaceae; g_*Desulfovibrio*; s_*Desulfovibrio vulgaris* |
| 316 | Proteobacteria; c_Deltaproteobacteria; o_Desulfovibrionales; f_Desulfovibrionaceae; g_*Lawsonia*; s_*Lawsonia intracellularis* |
| 317 | Proteobacteria; c_Deltaproteobacteria; o_Desulfuromonadales; f_Geobacteraceae; g_*Geobacter*; s_*Geobacter uraniireducens* |
| 318 | Proteobacteria; c_Deltaproteobacteria; o_Desulfuromonadales; f_NOT_LABELED; g_NOT_LABELED; s_NOT_LABELED |
| 319 | Proteobacteria; c_Deltaproteobacteria; o_Myxococcales; f_Kofleriaceae; g_*Haliangium*; s_NOT_LABELED |
| 320 | Proteobacteria; c_Deltaproteobacteria; o_Myxococcales; f_Myxococcaceae; g_*Anaeromyxobacter*; s_NOT_LABELED |
| 321 | Proteobacteria; c_Deltaproteobacteria; o_Myxococcales; f_Myxococcaceae; g_*Corallococcus*; s_*Corallococcus coralloides* |
| 322 | Proteobacteria; c_Deltaproteobacteria; o_Myxococcales; f_NOT_LABELED; g_NOT_LABELED; s_NOT_LABELED |
| 323 | Proteobacteria; c_Deltaproteobacteria; o_Myxococcales; f_Polyangiaceae; g_Sorangium; s_NOT_LABELED |
| 324 | Proteobacteria; c_Deltaproteobacteria; o_NOT_LABELED; f_NOT_LABELED; g_NOT_LABELED; s_NOT_LABELED |
| 325 | Proteobacteria; c_Epsilonproteobacteria; o_Campylobacterales; f_Helicobacteraceae; g_*Helicobacter*; s_*Helicobacter hepaticus* |
| 326 | Proteobacteria; c_Epsilonproteobacteria; o_Campylobacterales; f_Helicobacteraceae; g_*Helicobacter*; s_NOT_LABELED |
| 327 | Proteobacteria; c_Epsilonproteobacteria; o_Campylobacterales; f_Helicobacteraceae; g_*Wolinella*; s_*Wolinella succinogenes* |
| 328 | Proteobacteria; c_Gammaproteobacteria; o_Acidithiobacillales; f_Acidithiobacillaceae; g_*Acidithiobacillus*; s_*Acidithiobacillus caldus* |
| 329 | Proteobacteria; c_Gammaproteobacteria; o_Acidithiobacillales; f_Acidithiobacillaceae; g_*Acidithiobacillus*; s_*Acidithiobacillus ferrooxidans* |
| 330 | Proteobacteria; c_Gammaproteobacteria; o_Cardiobacteriales; f_Cardiobacteriaceae; g_*Dichelobacter*; s_*Dichelobacter nodosus* |
| 331 | Proteobacteria; c_Gammaproteobacteria; o_Enterobacteriales; f_Enterobacteriaceae; g_*Citrobacter*; s_*Citrobacter koseri* |
| 332 | Proteobacteria; c_Gammaproteobacteria; o_Enterobacteriales; f_Enterobacteriaceae; g_*Enterobacter*; s_*Enterobacter aerogenes* |
| 333 | Proteobacteria; c_Gammaproteobacteria; o_Enterobacteriales; f_Enterobacteriaceae; g_*Enterobacter*; s_*Enterobacter cancerogenus* |
| 334 | Proteobacteria; c_Gammaproteobacteria; o_Enterobacteriales; f_Enterobacteriaceae; g_*Enterobacter*; s_*Enterobacter cloacae* complex |
| 335 | Proteobacteria; c_Gammaproteobacteria; o_Enterobacteriales; f_Enterobacteriaceae; g_*Enterobacter*; s_NOT_LABELED |
| 336 | Proteobacteria; c_Gammaproteobacteria; o_Enterobacteriales; f_Enterobacteriaceae; g_*Erwinia*; s_*Erwinia amylovora* |
| 337 | Proteobacteria; c_Gammaproteobacteria; o_Enterobacteriales; f_Enterobacteriaceae; g_*Escherichia*; s_*Escherichia coli* |
| 338 | Proteobacteria; c_Gammaproteobacteria; o_Enterobacteriales; f_Enterobacteriaceae; g_*Klebsiella*; s_*Klebsiella pneumoniae* |
| 339 | Proteobacteria; c_Gammaproteobacteria; o_Enterobacteriales; f_Enterobacteriaceae; g_*Klebsiella*; s_*Klebsiella variicola* |
| 340 | Proteobacteria; c_Gammaproteobacteria; o_Enterobacteriales; f_Enterobacteriaceae; g_*Klebsiella*; s_NOT_LABELED |
| 341 | Proteobacteria; c_Gammaproteobacteria; o_Enterobacteriales; f_Enterobacteriaceae; g_NOT_LABELED; s_NOT_LABELED |

TABLE 6-continued

Taxonomic Analysis

| Taxon ID | Taxon |
|---|---|
| 342 | Proteobacteria; c_Gammaproteobacteria; o_Enterobacteriales; f_Enterobacteriaceae; g_*Pantoea*; s_*Pantoea vagans* |
| 343 | Proteobacteria; c_Gammaproteobacteria; o_Enterobacteriales; f_Enterobacteriaceae; g_*Salmonella*; s_*Salmonella enterica* |
| 344 | Proteobacteria; c_Gammaproteobacteria; o_Enterobacteriales; f_Enterobacteriaceae; g_*Serratia*; s_*Serratia marcescens* |
| 345 | Proteobacteria; c_Gammaproteobacteria; o_Enterobacteriales; f_Enterobacteriaceae; g_*Shigella*; s_*Shigella flexneri* |
| 346 | Proteobacteria; c_Gammaproteobacteria; o_NOT_LABELED; f_NOT_LABELED; g_NOT_LABELED; s_NOT_LABELED |
| 347 | roteobacteria; c_Gammaproteobacteria; o_Oceanospirillales; f_Halomonadaceae; g_*Halomonas*; s_NOT_LABELED |
| 348 | Proteobacteria; c_Gammaproteobacteria; o_Pasteurellales; f_Pasteurellaceae; g_*Actinobacillus*; s_*Actinobacillus pleuropneumoniae* |
| 349 | Proteobacteria; c_Gammaproteobacteria; o_Pasteurellales; f_Pasteurellaceae; g_*Aggregatibacter*; s_*Aggregatibacter aphrophilus* |
| 350 | Proteobacteria; c_Gammaproteobacteria; o_Pasteurellales; f_Pasteurellaceae; g_*Gallibacterium*; s_*Gallibacterium anatis* |
| 351 | Proteobacteria; c_Gammaproteobacteria; o_Pasteurellales; f_Pasteurellaceae; g_*Haemophilus*; s_*Haemophilus influenzae* |
| 352 | Proteobacteria; c_Gammaproteobacteria; o_Pasteurellales; f_Pasteurellaceae; g_*Haemophilus*; s_*Haemophilus parainfluenzae* |
| 353 | Proteobacteria; c_Gammaproteobacteria; o_Pasteurellales; f_Pasteurellaceae; g_*Haemophilus*; s_*Haemophilus parasuis* |
| 354 | Proteobacteria; c_Gammaproteobacteria; o_Pasteurellales; f_Pasteurellaceae; g_*Pasteurella*; s_*Pasteurella multocida* |
| 355 | Proteobacteria; c_Gammaproteobacteria; o_Pseudomonadales; f_Moraxellaceae; g_*Acinetobacter*; s_*Acinetobacter bereziniae* |
| 356 | Proteobacteria; c_Gammaproteobacteria; o_Pseudomonadales; f_Pseudomonadaceae; g_*Pseudomonas*; s_NOT_LABELED |
| 357 | Proteobacteria; c_Gammaproteobacteria; o_Pseudomonadales; f_Pseudomonadaceae; g_*Pseudomonas*; s_*Pseudomonas aeruginosa* |
| 358 | Proteobacteria; c_Gammaproteobacteria; o_Pseudomonadales; f_Pseudomonadaceae; g_*Pseudomonas*; s_*Pseudomonas aeruginosa* group |
| 359 | Proteobacteria; c_Gammaproteobacteria; o_Pseudomonadales; f_Pseudomonadaceae; g_*Pseudomonas*; s_*Pseudomonas fluorescens* group |
| 360 | Proteobacteria; c_Gammaproteobacteria; o_Pseudomonadales; f_Pseudomonadaceae; g_*Pseudomonas*; s_*Pseudomonas mendocina* |
| 361 | Proteobacteria; c_Gammaproteobacteria; o_Thiotrichales; f_Thiotrichaceae; g_*Thiotlwix*; s_NOT_LABELED |
| 362 | Proteobacteria; c_Gammaproteobacteria; o_Xanthomonadales; f_Xanthomonadaceae; g_*Stenotrophomonas*; s_*Stenotrophomonas maltophilia* |
| 363 | Proteobacteria; c_NOT_LABELED; o_NOT_LABELED; f_NOT_LABELED; g_NOT_LABELED; s_NOT_LABELED |
| 364 | Spirochaetes; c_Spirochaetia; o_Spirochaetales; f_Spirochaetaceae; g_*Spirochaeta*; s_*Spirochaeta thermophila* |
| 365 | Spirochaetes; c_Spirochaetia; o_Spirochaetales; f_Spirochaetaceae; g_*Treponema*; s_NOT_LABELED |
| 366 | Synergistetes; c_Synergistia; o_Synergistales; f_Synergistaceae; g_*Aminobacterium*; s_*Aminobacterium colombiense* |
| 367 | Synergistetes; c_Synergistia; o_Synergistales; f_Synergistaceae; g_*Thermanaerovibrio*; s_*Thermanaerovibrio acidaminovorans* |
| 368 | Tenericutes; c_Mollicutes; o_Acholeplasmatales; f_Acholeplasmataceae; g_*Acholeplasma*; s_NOT_LABELED |
| 369 | Tenericutes; c_Mollicutes; o_Acholeplasmatales; f_Acholeplasmataceae; g_*Candidatus* Phytoplasma; s_NOT_LABELED |
| 370 | Tenericutes; c_Mollicutes; o_Entomoplasmatales; f_Entomoplasmataceae; g_*Entomoplasma*; s_NOT_LABELED |
| 371 | Tenericutes; c_Mollicutes; o_Entomoplasmatales; f_Spiroplasmataceae; g_*Spiroplasma*; s_NOT_LABELED |
| 372 | Tenericutes; c_Mollicutes; o_Mycoplasmatales; f_Mycoplasmataceae; g_*Mycoplasma*; s_NOT_LABELED |
| 373 | Tenericutes; c_Mollicutes; o_Mycoplasmatales; f_Mycoplasmataceae; g_*Ureaplasma*; s_*Ureaplasma urealyticum* |
| 374 | Thermodesulfobacteria; c_Thermodesulfobacteria; o_Thermodesulfobacteriales; f_Thermodesulfobacteriaceae; g_*Thermodesulfatator*; s_*Thermodesulfatator indicus* |
| 375 | Thermodesulfobacteria; c_Thermodesulfobacteria; o_Thermodesulfobacteriales; f_Thermodesulfobacteriaceae; g_*Thermodesulfobacterium*; s_NOT_LABELED |
| 376 | Thermotogae; c_Thermotogae; o_Thermotogales; f_Thermotogaceae; g_*Kosmotoga*; s_*Kosmotoga olearia* |
| 377 | Verrucomicrobia; c_Opitutae; o_Puniceicoccales; f_Puniceicoccaceae; g_*Coraliomargarita*; s_*Coraliomargarita akajimensis* |
| 378 | Verrucomicrobia; c_Verrucomicrobiae; o_Verrucomicrobiales; f_Verrucomicrobiaceae; g_*Akkermansia*; s_*Akkermansia muciniphila* |

| Taxon ID | CM Atm+/+ Small Intestine | | | RM Atm+/+ Small Intestine | | |
|---|---|---|---|---|---|---|
| 1 | 5.2E−03 | 2.2E−03 | 8.9E−03 | 2.6E−03 | 5.0E−03 | 1.0E−03 |
| 2 | 0.0E+00 | 2.6E−07 | 0.0E+00 | 4.6E−07 | 1.0E−06 | 0.0E+00 |
| 3 | 0.0E+00 | 0.0E+00 | 0.0E+00 | 0.0E+00 | 0.0E+00 | 0.0E+00 |
| 4 | 0.0E+00 | 9.3E−06 | 0.0E+00 | 1.1E−04 | 2.0E−05 | 6.2E−06 |
| 5 | 0.0E+00 | 0.0E+00 | 0.0E+00 | 0.0E+00 | 0.0E+00 | 0.0E+00 |
| 6 | 0.0E+00 | 0.0E+00 | 0.0E+00 | 0.0E+00 | 0.0E+00 | 0.0E+00 |
| 7 | 2.9E−05 | 2.0E−05 | 0.0E+00 | 4.2E−06 | 1.0E−05 | 2.1E−06 |
| 8 | 3.8E−06 | 2.4E−06 | 5.3E−05 | 0.0E+00 | 0.0E+00 | 0.0E+00 |
| 9 | 0.0E+00 | 2.6E−07 | 0.0E+00 | 0.0E+00 | 0.0E+00 | 2.9E−07 |
| 10 | 0.0E+00 | 0.0E+00 | 0.0E+00 | 0.0E+00 | 0.0E+00 | 1.5E−06 |
| 11 | 0.0E+00 | 0.0E+00 | 0.0E+00 | 0.0E+00 | 0.0E+00 | 0.0E+00 |
| 12 | 0.0E+00 | 8.5E−06 | 0.0E+00 | 0.0E+00 | 0.0E+00 | 0.0E+00 |
| 13 | 0.0E+00 | 0.0E+00 | 0.0E+00 | 0.0E+00 | 0.0E+00 | 0.0E+00 |
| 14 | 0.0E+00 | 0.0E+00 | 0.0E+00 | 4.6E−07 | 0.0E+00 | 0.0E+00 |
| 15 | 0.0E+00 | 0.0E+00 | 0.0E+00 | 0.0E+00 | 0.0E+00 | 0.0E+00 |
| 16 | 1.9E−06 | 0.0E+00 | 8.7E−06 | 0.0E+00 | 0.0E+00 | 0.0E+00 |
| 17 | 0.0E+00 | 2.6E−07 | 6.0E−06 | 0.0E+00 | 2.0E−06 | 0.0E+00 |
| 18 | 0.0E+00 | 0.0E+00 | 0.0E+00 | 0.0E+00 | 0.0E+00 | 0.0E+00 |
| 19 | 0.0E+00 | 0.0E+00 | 0.0E+00 | 0.0E+00 | 0.0E+00 | 0.0E+00 |
| 20 | 0.0E+00 | 2.6E−07 | 2.2E−06 | 0.0E+00 | 0.0E+00 | 0.0E+00 |
| 21 | 4.7E−06 | 1.8E−05 | 2.4E−04 | 0.0E+00 | 0.0E+00 | 0.0E+00 |
| 22 | 0.0E+00 | 0.0E+00 | 0.0E+00 | 0.0E+00 | 0.0E+00 | 5.9E−07 |
| 23 | 3.3E−06 | 0.0E+00 | 0.0E+00 | 1.4E−06 | 0.0E+00 | 0.0E+00 |
| 24 | 0.0E+00 | 9.5E−06 | 2.2E−06 | 0.0E+00 | 2.5E−06 | 0.0E+00 |
| 25 | 0.0E+00 | 0.0E+00 | 0.0E+00 | 0.0E+00 | 0.0E+00 | 0.0E+00 |
| 26 | 0.0E+00 | 0.0E+00 | 0.0E+00 | 0.0E+00 | 0.0E+00 | 0.0E+00 |
| 27 | 0.0E+00 | 0.0E+00 | 5.4E−07 | 0.0E+00 | 0.0E+00 | 0.0E+00 |
| 28 | 0.0E+00 | 0.0E+00 | 0.0E+00 | 0.0E+00 | 0.0E+00 | 0.0E+00 |
| 29 | 0.0E+00 | 0.0E+00 | 2.2E−06 | 0.0E+00 | 0.0E+00 | 0.0E+00 |
| 30 | 0.0E+00 | 0.0E+00 | 0.0E+00 | 0.0E+00 | 5.1E−07 | 0.0E+00 |
| 31 | 0.0E+00 | 5.3E−07 | 5.4E−07 | 0.0E+00 | 2.0E−06 | 0.0E+00 |
| 32 | 1.9E−05 | 2.1E−05 | 0.0E+00 | 1.5E−05 | 1.4E−04 | 0.0E+00 |
| 33 | 3.8E−06 | 4.2E−06 | 1.3E−04 | 1.2E−05 | 3.1E−06 | 2.9E−07 |
| 34 | 0.0E+00 | 0.0E+00 | 0.0E+00 | 0.0E+00 | 0.0E+00 | 0.0E+00 |
| 35 | 0.0E+00 | 0.0E+00 | 2.7E−06 | 0.0E+00 | 0.0E+00 | 0.0E+00 |
| 36 | 0.0E+00 | 0.0E+00 | 0.0E+00 | 0.0E+00 | 7.6E−06 | 0.0E+00 |
| 37 | 0.0E+00 | 0.0E+00 | 0.0E+00 | 0.0E+00 | 0.0E+00 | 0.0E+00 |
| 38 | 0.0E+00 | 0.0E+00 | 0.0E+00 | 0.0E+00 | 0.0E+00 | 0.0E+00 |
| 39 | 0.0E+00 | 0.0E+00 | 0.0E+00 | 0.0E+00 | 0.0E+00 | 0.0E+00 |
| 40 | 0.0E+00 | 0.0E+00 | 0.0E+00 | 0.0E+00 | 1.0E−06 | 0.0E+00 |
| 41 | 0.0E+00 | 0.0E+00 | 1.1E−04 | 0.0E+00 | 0.0E+00 | 2.3E−05 |
| 42 | 0.0E+00 | 0.0E+00 | 2.5E−05 | 0.0E+00 | 0.0E+00 | 0.0E+00 |
| 43 | 0.0E+00 | 0.0E+00 | 6.2E−05 | 9.2E−07 | 0.0E+00 | 8.5E−06 |
| 44 | 1.9E−06 | 0.0E+00 | 1.2E−05 | 0.0E+00 | 0.0E+00 | 0.0E+00 |
| 45 | 0.0E+00 | 4.2E−05 | 0.0E+00 | 1.8E−05 | 2.0E−06 | 0.0E+00 |
| 46 | 0.0E+00 | 0.0E+00 | 0.0E+00 | 0.0E+00 | 0.0E+00 | 0.0E+00 |
| 47 | 0.0E+00 | 2.6E−07 | 1.6E−06 | 0.0E+00 | 0.0E+00 | 0.0E+00 |
| 48 | 0.0E+00 | 1.7E−04 | 0.0E+00 | 0.0E+00 | 0.0E+00 | 0.0E+00 |
| 49 | 0.0E+00 | 0.0E+00 | 0.0E+00 | 0.0E+00 | 0.0E+00 | 4.1E−06 |
| 50 | 0.0E+00 | 1.9E−05 | 2.1E−04 | 3.7E−05 | 2.4E−05 | 5.9E−06 |
| 51 | 0.0E+00 | 0.0E+00 | 0.0E+00 | 6.3E−05 | 6.8E−05 | 0.0E+00 |
| 52 | 0.0E+00 | 2.6E−06 | 0.0E+00 | 4.6E−07 | 0.0E+00 | 0.0E+00 |
| 53 | 0.0E+00 | 4.2E−06 | 0.0E+00 | 5.5E−06 | 7.6E−06 | 0.0E+00 |
| 54 | 0.0E+00 | 1.3E−06 | 1.0E−05 | 0.0E+00 | 4.1E−06 | 0.0E+00 |
| 55 | 4.7E−05 | 1.9E−06 | 1.7E−05 | 0.0E+00 | 0.0E+00 | 0.0E+00 |
| 56 | 0.0E+00 | 0.0E+00 | 0.0E+00 | 0.0E+00 | 0.0E+00 | 0.0E+00 |
| 57 | 0.0E+00 | 0.0E+00 | 0.0E+00 | 4.6E−07 | 5.1E−07 | 0.0E+00 |
| 58 | 6.7E−04 | 8.0E−04 | 1.5E−02 | 9.6E−05 | 1.3E−03 | 8.7E−05 |
| 59 | 1.1E−03 | 3.1E−03 | 5.1E−03 | 9.2E−07 | 1.0E−02 | 2.1E−06 |
| 60 | 4.5E−04 | 9.3E−03 | 1.3E−02 | 1.8E−05 | 7.7E−03 | 6.7E−06 |
| 61 | 1.9E−05 | 3.3E−05 | 2.8E−04 | 0.0E+00 | 0.0E+00 | 0.0E+00 |
| 62 | 1.1E−04 | 2.2E−03 | 2.1E−03 | 1.3E−05 | 4.4E−04 | 1.2E−05 |
| 63 | 1.5E−05 | 1.5E−05 | 5.5E−05 | 7.9E−05 | 1.2E−04 | 1.9E−05 |
| 64 | 5.9E−05 | 1.6E−04 | 3.5E−03 | 9.2E−07 | 1.4E−04 | 2.9E−07 |
| 65 | 2.7E−03 | 6.3E−03 | 4.8E−04 | 4.6E−06 | 4.6E−06 | 2.3E−06 |
| 66 | 5.8E−04 | 5.1E−04 | 2.8E−03 | 0.0E+00 | 2.7E−04 | 0.0E+00 |
| 67 | 3.0E−04 | 7.4E−04 | 1.6E−02 | 9.2E−07 | 3.1E−06 | 8.8E−07 |
| 68 | 0.0E+00 | 0.0E+00 | 0.0E+00 | 0.0E+00 | 3.1E−06 | 0.0E+00 |
| 69 | 2.7E−04 | 4.8E−06 | 2.5E−03 | 7.0E−04 | 3.3E−03 | 1.6E−03 |
| 70 | 9.4E−07 | 5.3E−07 | 5.4E−06 | 7.8E−06 | 1.8E−05 | 2.1E−06 |
| 71 | 1.4E−05 | 6.6E−06 | 1.9E−05 | 4.6E−05 | 8.4E−05 | 5.0E−06 |
| 72 | 0.0E+00 | 0.0E+00 | 5.4E−07 | 0.0E+00 | 2.0E−06 | 2.9E−07 |
| 73 | 0.0E+00 | 0.0E+00 | 0.0E+00 | 4.6E−07 | 5.1E−07 | 2.9E−07 |
| 74 | 4.7E−07 | 2.6E−07 | 7.0E−06 | 2.3E−06 | 3.1E−06 | 1.2E−06 |
| 75 | 0.0E+00 | 8.2E−06 | 3.3E−05 | 0.0E+00 | 0.0E+00 | 0.0E+00 |
| 76 | 4.0E−04 | 4.6E−04 | 1.6E−03 | 4.6E−07 | 2.3E−05 | 1.4E−04 |
| 77 | 1.7E−05 | 2.9E−06 | 2.7E−05 | 3.7E−06 | 4.2E−05 | 1.5E−06 |
| 78 | 0.0E+00 | 0.0E+00 | 4.9E−06 | 1.8E−06 | 2.0E−06 | 0.0E+00 |

-continued

| | | | | | | |
|---|---|---|---|---|---|---|
| 79 | 1.7E−05 | 4.3E−03 | 5.5E−03 | 3.2E−06 | 6.6E−06 | 2.9E−06 |
| 80 | 2.4E−05 | 1.0E−05 | 0.0E+00 | 4.6E−07 | 1.5E−05 | 5.6E−06 |
| 81 | 0.0E+00 | 0.0E+00 | 7.6E−06 | 0.0E+00 | 0.0E+00 | 0.0E+00 |
| 82 | 1.9E−03 | 4.0E−02 | 1.2E−01 | 4.7E−02 | 4.1E−02 | 1.9E−02 |
| 83 | 2.6E−04 | 2.9E−04 | 1.8E−03 | 1.0E−03 | 1.5E−03 | 4.7E−03 |
| 84 | 0.0E+00 | 0.0E+00 | 0.0E+00 | 0.0E+00 | 1.5E−06 | 0.0E+00 |
| 85 | 3.7E−04 | 3.1E−03 | 5.4E−03 | 5.1E−02 | 4.3E−02 | 1.7E−02 |
| 86 | 4.3E−02 | 2.2E−02 | 9.9E−02 | 2.8E−01 | 4.5E−01 | 5.8E−02 |
| 87 | 1.4E−06 | 2.6E−07 | 2.7E−06 | 1.0E−05 | 1.4E−05 | 8.8E−07 |
| 88 | 0.0E+00 | 5.3E−07 | 5.4E−07 | 0.0E+00 | 0.0E+00 | 5.9E−07 |
| 89 | 4.2E−05 | 0.0E+00 | 1.3E−04 | 1.3E−05 | 0.0E+00 | 2.1E−06 |
| 90 | 4.7E−07 | 0.0E+00 | 3.8E−06 | 0.0E+00 | 0.0E+00 | 0.0E+00 |
| 91 | 1.5E−05 | 0.0E+00 | 5.4E−07 | 0.0E+00 | 5.1E−07 | 0.0E+00 |
| 92 | 0.0E+00 | 2.6E−07 | 0.0E+00 | 1.5E−05 | 0.0E+00 | 0.0E+00 |
| 93 | 0.0E+00 | 0.0E+00 | 0.0E+00 | 0.0E+00 | 0.0E+00 | 0.0E+00 |
| 94 | 4.2E−03 | 1.0E−02 | 2.2E−02 | 2.5E−04 | 4.4E−04 | 6.1E−05 |
| 95 | 0.0E+00 | 0.0E+00 | 5.4E−07 | 0.0E+00 | 0.0E+00 | 0.0E+00 |
| 96 | 1.3E−04 | 2.9E−04 | 2.1E−03 | 3.2E−06 | 9.0E−05 | 2.9E−04 |
| 97 | 4.2E−06 | 5.3E−07 | 0.0E+00 | 9.2E−07 | 0.0E+00 | 5.9E−07 |
| 98 | 1.9E−06 | 7.1E−06 | 2.3E−05 | 0.0E+00 | 0.0E+00 | 0.0E+00 |
| 99 | 0.0E+00 | 0.0E+00 | 5.0E−05 | 0.0E+00 | 0.0E+00 | 0.0E+00 |
| 100 | 0.0E+00 | 0.0E+00 | 0.0E+00 | 0.0E+00 | 2.4E−05 | 0.0E+00 |
| 101 | 9.4E−07 | 0.0E+00 | 5.4E−07 | 4.8E−05 | 3.8E−05 | 2.3E−06 |
| 102 | 9.4E−07 | 0.0E+00 | 0.0E+00 | 0.0E+00 | 0.0E+00 | 2.9E−07 |
| 103 | 0.0E+00 | 0.0E+00 | 5.4E−07 | 0.0E+00 | 0.0E+00 | 0.0E+00 |
| 104 | 0.0E+00 | 2.1E−05 | 0.0E+00 | 0.0E+00 | 0.0E+00 | 0.0E+00 |
| 105 | 0.0E+00 | 2.1E−05 | 1.1E−03 | 4.6E−07 | 1.5E−06 | 2.9E−07 |
| 106 | 0.0E+00 | 2.6E−07 | 2.2E−06 | 0.0E+00 | 2.0E−06 | 2.9E−07 |
| 107 | 1.9E−05 | 2.3E−05 | 8.1E−06 | 6.9E−06 | 1.5E−05 | 2.1E−06 |
| 108 | 0.0E+00 | 0.0E+00 | 0.0E+00 | 0.0E+00 | 0.0E+00 | 0.0E+00 |
| 109 | 0.0E+00 | 2.6E−07 | 5.4E−07 | 0.0E+00 | 0.0E+00 | 0.0E+00 |
| 110 | 9.4E−05 | 0.0E+00 | 1.9E−04 | 0.0E+00 | 0.0E+00 | 0.0E+00 |
| 111 | 0.0E+00 | 5.3E−07 | 0.0E+00 | 1.8E−06 | 0.0E+00 | 0.0E+00 |
| 112 | 0.0E+00 | 0.0E+00 | 0.0E+00 | 0.0E+00 | 0.0E+00 | 0.0E+00 |
| 113 | 4.7E−07 | 0.0E+00 | 0.0E+00 | 0.0E+00 | 0.0E+00 | 0.0E+00 |
| 114 | 2.9E−05 | 4.5E−06 | 1.9E−05 | 0.0E+00 | 3.6E−06 | 0.0E+00 |
| 115 | 7.3E−04 | 5.8E−05 | 1.0E−04 | 7.6E−05 | 1.2E−03 | 5.1E−05 |
| 116 | 0.0E+00 | 0.0E+00 | 0.0E+00 | 0.0E+00 | 0.0E+00 | 0.0E+00 |
| 117 | 0.0E+00 | 0.0E+00 | 0.0E+00 | 0.0E+00 | 0.0E+00 | 0.0E+00 |
| 118 | 0.0E+00 | 0.0E+00 | 0.0E+00 | 0.0E+00 | 0.0E+00 | 0.0E+00 |
| 119 | 0.0E+00 | 0.0E+00 | 0.0E+00 | 0.0E+00 | 0.0E+00 | 0.0E+00 |
| 120 | 3.8E−06 | 3.9E−05 | 1.1E−04 | 1.4E−06 | 0.0E+00 | 0.0E+00 |
| 121 | 0.0E+00 | 0.0E+00 | 1.1E−05 | 0.0E+00 | 1.0E−06 | 0.0E+00 |
| 122 | 0.0E+00 | 1.6E−06 | 1.6E−06 | 0.0E+00 | 4.1E−06 | 0.0E+00 |
| 123 | 1.4E−06 | 2.6E−07 | 1.1E−05 | 0.0E+00 | 0.0E+00 | 0.0E+00 |
| 124 | 1.4E−06 | 2.6E−06 | 1.1E−06 | 0.0E+00 | 0.0E+00 | 3.8E−06 |
| 125 | 3.3E−06 | 7.9E−07 | 4.3E−06 | 0.0E+00 | 1.3E−04 | 5.3E−06 |
| 126 | 1.9E−06 | 0.0E+00 | 1.1E−06 | 0.0E+00 | 0.0E+00 | 0.0E+00 |
| 127 | 0.0E+00 | 0.0E+00 | 0.0E+00 | 0.0E+00 | 0.0E+00 | 0.0E+00 |
| 128 | 3.8E−06 | 8.9E−05 | 1.7E−03 | 6.0E−05 | 2.4E−03 | 3.4E−05 |
| 129 | 4.3E−05 | 0.0E+00 | 0.0E+00 | 0.0E+00 | 5.1E−07 | 0.0E+00 |
| 130 | 0.0E+00 | 0.0E+00 | 0.0E+00 | 0.0E+00 | 0.0E+00 | 0.0E+00 |
| 131 | 0.0E+00 | 0.0E+00 | 0.0E+00 | 0.0E+00 | 2.5E−06 | 9.7E−06 |
| 132 | 0.0E+00 | 0.0E+00 | 0.0E+00 | 0.0E+00 | 0.0E+00 | 0.0E+00 |
| 133 | 0.0E+00 | 0.0E+00 | 0.0E+00 | 0.0E+00 | 0.0E+00 | 0.0E+00 |
| 134 | 1.0E−04 | 1.0E−05 | 1.3E−03 | 4.6E−07 | 4.5E−04 | 2.9E−07 |
| 135 | 0.0E+00 | 0.0E+00 | 0.0E+00 | 0.0E+00 | 0.0E+00 | 0.0E+00 |
| 136 | 0.0E+00 | 0.0E+00 | 0.0E+00 | 0.0E+00 | 8.1E−05 | 2.6E−06 |
| 137 | 0.0E+00 | 0.0E+00 | 0.0E+00 | 0.0E+00 | 0.0E+00 | 0.0E+00 |
| 138 | 0.0E+00 | 0.0E+00 | 0.0E+00 | 0.0E+00 | 0.0E+00 | 0.0E+00 |
| 139 | 0.0E+00 | 2.9E−06 | 9.8E−05 | 6.0E−06 | 4.8E−05 | 5.0E−06 |
| 140 | 3.6E−05 | 8.5E−06 | 6.7E−04 | 2.9E−05 | 1.2E−03 | 2.8E−05 |
| 141 | 0.0E+00 | 0.0E+00 | 0.0E+00 | 0.0E+00 | 0.0E+00 | 0.0E+00 |
| 142 | 0.0E+00 | 0.0E+00 | 0.0E+00 | 0.0E+00 | 0.0E+00 | 2.9E−07 |
| 143 | 0.0E+00 | 0.0E+00 | 0.0E+00 | 0.0E+00 | 0.0E+00 | 2.9E−07 |
| 144 | 0.0E+00 | 0.0E+00 | 0.0E+00 | 0.0E+00 | 0.0E+00 | 0.0E+00 |
| 145 | 0.0E+00 | 0.0E+00 | 0.0E+00 | 0.0E+00 | 0.0E+00 | 0.0E+00 |
| 146 | 0.0E+00 | 0.0E+00 | 0.0E+00 | 0.0E+00 | 0.0E+00 | 2.9E−07 |
| 147 | 0.0E+00 | 0.0E+00 | 0.0E+00 | 0.0E+00 | 0.0E+00 | 0.0E+00 |
| 148 | 1.6E−04 | 3.4E−06 | 7.1E−04 | 2.2E−05 | 6.7E−04 | 3.0E−05 |
| 149 | 0.0E+00 | 0.0E+00 | 0.0E+00 | 0.0E+00 | 0.0E+00 | 0.0E+00 |
| 150 | 1.4E−05 | 9.9E−05 | 3.2E−06 | 4.0E−04 | 4.5E−05 | 2.7E−04 |
| 151 | 0.0E+00 | 0.0E+00 | 0.0E+00 | 0.0E+00 | 0.0E+00 | 0.0E+00 |
| 152 | 0.0E+00 | 0.0E+00 | 0.0E+00 | 0.0E+00 | 0.0E+00 | 0.0E+00 |
| 153 | 0.0E+00 | 0.0E+00 | 0.0E+00 | 0.0E+00 | 0.0E+00 | 0.0E+00 |
| 154 | 3.1E−02 | 3.4E−06 | 9.0E−02 | 2.0E−05 | 1.0E−04 | 1.3E−05 |
| 155 | 6.1E−06 | 1.1E−06 | 4.0E−05 | 2.8E−06 | 0.0E+00 | 8.8E−07 |
| 156 | 0.0E+00 | 3.3E−05 | 0.0E+00 | 1.4E−05 | 9.2E−06 | 0.0E+00 |
| 157 | 2.9E−05 | 0.0E+00 | 8.9E−05 | 0.0E+00 | 0.0E+00 | 0.0E+00 |

-continued

| | | | | | | |
|---|---|---|---|---|---|---|
| 158 | 0.0E+00 | 0.0E+00 | 0.0E+00 | 0.0E+00 | 0.0E+00 | 0.0E+00 |
| 159 | 5.2E−04 | 8.9E−05 | 4.6E−04 | 0.0E+00 | 2.1E−04 | 1.6E−05 |
| 160 | 0.0E+00 | 0.0E+00 | 0.0E+00 | 0.0E+00 | 1.1E−05 | 0.0E+00 |
| 161 | 0.0E+00 | 0.0E+00 | 0.0E+00 | 0.0E+00 | 0.0E+00 | 1.5E−06 |
| 162 | 0.0E+00 | 0.0E+00 | 0.0E+00 | 0.0E+00 | 0.0E+00 | 2.3E−06 |
| 163 | 1.3E−03 | 7.9E−07 | 0.0E+00 | 0.0E+00 | 0.0E+00 | 0.0E+00 |
| 164 | 0.0E+00 | 5.0E−06 | 7.0E−05 | 1.2E−05 | 2.4E−04 | 4.7E−06 |
| 165 | 0.0E+00 | 3.4E−05 | 0.0E+00 | 0.0E+00 | 0.0E+00 | 0.0E+00 |
| 166 | 0.0E+00 | 0.0E+00 | 1.6E−06 | 0.0E+00 | 0.0E+00 | 0.0E+00 |
| 167 | 2.2E−02 | 1.6E−02 | 7.3E−02 | 1.5E−02 | 1.7E−02 | 6.9E−03 |
| 168 | 0.0E+00 | 0.0E+00 | 6.5E−06 | 0.0E+00 | 0.0E+00 | 2.9E−07 |
| 169 | 0.0E+00 | 2.6E−07 | 5.4E−07 | 4.6E−07 | 0.0E+00 | 8.8E−07 |
| 170 | 0.0E+00 | 0.0E+00 | 0.0E+00 | 0.0E+00 | 0.0E+00 | 0.0E+00 |
| 171 | 0.0E+00 | 0.0E+00 | 0.0E+00 | 0.0E+00 | 0.0E+00 | 0.0E+00 |
| 172 | 6.2E−04 | 2.7E−02 | 1.0E−02 | 1.0E−01 | 3.7E−02 | 7.1E−02 |
| 173 | 0.0E+00 | 0.0E+00 | 0.0E+00 | 0.0E+00 | 0.0E+00 | 0.0E+00 |
| 174 | 2.5E−02 | 9.7E−03 | 1.1E−02 | 4.6E−06 | 1.1E−05 | 3.8E−06 |
| 175 | 9.4E−07 | 0.0E+00 | 0.0E+00 | 0.0E+00 | 0.0E+00 | 0.0E+00 |
| 176 | 0.0E+00 | 0.0E+00 | 0.0E+00 | 0.0E+00 | 0.0E+00 | 0.0E+00 |
| 177 | 0.0E+00 | 0.0E+00 | 5.4E−07 | 0.0E+00 | 0.0E+00 | 0.0E+00 |
| 178 | 0.0E+00 | 2.6E−07 | 0.0E+00 | 4.6E−06 | 4.1E−05 | 5.9E−07 |
| 179 | 6.6E−06 | 0.0E+00 | 0.0E+00 | 0.0E+00 | 0.0E+00 | 0.0E+00 |
| 180 | 1.0E−05 | 0.0E+00 | 2.8E−05 | 0.0E+00 | 0.0E+00 | 2.9E−07 |
| 181 | 0.0E+00 | 7.9E−07 | 5.4E−06 | 0.0E+00 | 0.0E+00 | 0.0E+00 |
| 182 | 0.0E+00 | 0.0E+00 | 0.0E+00 | 0.0E+00 | 2.4E−05 | 2.9E−06 |
| 183 | 0.0E+00 | 0.0E+00 | 4.3E−06 | 0.0E+00 | 0.0E+00 | 0.0E+00 |
| 184 | 0.0E+00 | 0.0E+00 | 0.0E+00 | 0.0E+00 | 1.2E−05 | 1.3E−05 |
| 185 | 2.8E−04 | 0.0E+00 | 4.2E−04 | 3.2E−06 | 3.8E−04 | 6.2E−06 |
| 186 | 0.0E+00 | 0.0E+00 | 1.7E−04 | 0.0E+00 | 3.1E−06 | 2.1E−06 |
| 187 | 6.9E−05 | 0.0E+00 | 0.0E+00 | 0.0E+00 | 0.0E+00 | 0.0E+00 |
| 188 | 4.7E−07 | 0.0E+00 | 0.0E+00 | 0.0E+00 | 0.0E+00 | 2.9E−07 |
| 189 | 0.0E+00 | 0.0E+00 | 0.0E+00 | 0.0E+00 | 0.0E+00 | 0.0E+00 |
| 190 | 5.1E−04 | 2.2E−04 | 2.8E−03 | 5.5E−06 | 1.5E−05 | 9.9E−05 |
| 191 | 4.7E−07 | 0.0E+00 | 4.2E−04 | 3.3E−05 | 6.5E−04 | 8.5E−06 |
| 192 | 0.0E+00 | 0.0E+00 | 8.7E−06 | 0.0E+00 | 1.0E−06 | 2.3E−06 |
| 193 | 5.0E−05 | 0.0E+00 | 1.5E−04 | 0.0E+00 | 5.1E−07 | 0.0E+00 |
| 194 | 3.3E−04 | 0.0E+00 | 6.0E−05 | 2.8E−06 | 3.0E−05 | 5.7E−05 |
| 195 | 0.0E+00 | 0.0E+00 | 0.0E+00 | 0.0E+00 | 0.0E+00 | 0.0E+00 |
| 196 | 0.0E+00 | 0.0E+00 | 0.0E+00 | 4.6E−07 | 0.0E+00 | 0.0E+00 |
| 197 | 0.0E+00 | 7.9E−07 | 0.0E+00 | 0.0E+00 | 0.0E+00 | 0.0E+00 |
| 198 | 0.0E+00 | 0.0E+00 | 0.0E+00 | 0.0E+00 | 0.0E+00 | 0.0E+00 |
| 199 | 1.7E−03 | 4.7E−04 | 1.2E−05 | 1.1E−04 | 4.9E−02 | 5.1E−05 |
| 200 | 0.0E+00 | 0.0E+00 | 0.0E+00 | 0.0E+00 | 3.1E−06 | 0.0E+00 |
| 201 | 0.0E+00 | 4.0E−06 | 1.7E−05 | 0.0E+00 | 0.0E+00 | 0.0E+00 |
| 202 | 0.0E+00 | 0.0E+00 | 0.0E+00 | 0.0E+00 | 0.0E+00 | 0.0E+00 |
| 203 | 0.0E+00 | 5.3E−07 | 0.0E+00 | 4.1E−05 | 4.4E−04 | 8.8E−07 |
| 204 | 0.0E+00 | 0.0E+00 | 1.6E−06 | 0.0E+00 | 0.0E+00 | 0.0E+00 |
| 205 | 0.0E+00 | 0.0E+00 | 0.0E+00 | 4.6E−07 | 0.0E+00 | 0.0E+00 |
| 206 | 0.0E+00 | 0.0E+00 | 0.0E+00 | 0.0E+00 | 0.0E+00 | 0.0E+00 |
| 207 | 2.8E−06 | 6.9E−05 | 2.1E−04 | 7.2E−05 | 5.8E−04 | 1.3E−05 |
| 208 | 1.3E−03 | 1.5E−04 | 6.5E−03 | 3.5E−04 | 1.0E−02 | 3.0E−04 |
| 209 | 0.0E+00 | 0.0E+00 | 0.0E+00 | 0.0E+00 | 0.0E+00 | 0.0E+00 |
| 210 | 2.2E−04 | 1.9E−04 | 1.0E−03 | 1.2E−05 | 3.6E−04 | 1.3E−05 |
| 211 | 0.0E+00 | 0.0E+00 | 0.0E+00 | 9.2E−07 | 0.0E+00 | 3.5E−06 |
| 212 | 4.7E−07 | 0.0E+00 | 0.0E+00 | 0.0E+00 | 0.0E+00 | 1.5E−05 |
| 213 | 0.0E+00 | 1.3E−06 | 0.0E+00 | 0.0E+00 | 0.0E+00 | 0.0E+00 |
| 214 | 0.0E+00 | 0.0E+00 | 0.0E+00 | 0.0E+00 | 0.0E+00 | 0.0E+00 |
| 215 | 1.9E−06 | 0.0E+00 | 3.2E−06 | 0.0E+00 | 0.0E+00 | 0.0E+00 |
| 216 | 8.0E−05 | 5.2E−05 | 3.8E−05 | 1.5E−05 | 6.7E−04 | 2.2E−05 |
| 217 | 0.0E+00 | 0.0E+00 | 0.0E+00 | 0.0E+00 | 0.0E+00 | 0.0E+00 |
| 218 | 1.0E−04 | 5.0E−05 | 2.0E−04 | 6.5E−06 | 3.7E−04 | 1.5E−05 |
| 219 | 0.0E+00 | 0.0E+00 | 0.0E+00 | 0.0E+00 | 0.0E+00 | 0.0E+00 |
| 220 | 3.1E−04 | 3.0E−04 | 2.3E−04 | 1.1E−05 | 3.6E−04 | 2.1E−06 |
| 221 | 0.0E+00 | 0.0E+00 | 5.4E−07 | 0.0E+00 | 0.0E+00 | 0.0E+00 |
| 222 | 0.0E+00 | 2.6E−07 | 3.2E−06 | 0.0E+00 | 0.0E+00 | 0.0E+00 |
| 223 | 0.0E+00 | 0.0E+00 | 0.0E+00 | 3.7E−05 | 0.0E+00 | 0.0E+00 |
| 224 | 0.0E+00 | 5.3E−07 | 0.0E+00 | 0.0E+00 | 0.0E+00 | 0.0E+00 |
| 225 | 3.5E−05 | 0.0E+00 | 4.7E−04 | 6.0E−06 | 3.9E−04 | 2.9E−05 |
| 226 | 0.0E+00 | 5.3E−07 | 0.0E+00 | 0.0E+00 | 0.0E+00 | 0.0E+00 |
| 227 | 0.0E+00 | 5.3E−07 | 0.0E+00 | 0.0E+00 | 3.6E−06 | 0.0E+00 |
| 228 | 0.0E+00 | 0.0E+00 | 0.0E+00 | 0.0E+00 | 0.0E+00 | 0.0E+00 |
| 229 | 0.0E+00 | 0.0E+00 | 0.0E+00 | 0.0E+00 | 0.0E+00 | 0.0E+00 |
| 230 | 0.0E+00 | 0.0E+00 | 0.0E+00 | 8.1E−06 | 1.1E−05 | 0.0E+00 |
| 231 | 1.4E−06 | 0.0E+00 | 6.5E−06 | 0.0E+00 | 5.4E−05 | 0.0E+00 |
| 232 | 8.5E−03 | 3.7E−02 | 1.3E−01 | 3.6E−05 | 2.3E−04 | 2.1E−05 |
| 233 | 9.4E−07 | 2.6E−07 | 1.2E−05 | 0.0E+00 | 3.1E−06 | 0.0E+00 |
| 234 | 0.0E+00 | 0.0E+00 | 0.0E+00 | 0.0E+00 | 0.0E+00 | 0.0E+00 |
| 235 | 4.5E−05 | 1.9E−05 | 5.3E−05 | 6.5E−06 | 2.9E−04 | 9.7E−06 |
| 236 | 1.3E−04 | 3.2E−05 | 1.1E−03 | 2.4E−05 | 5.1E−04 | 1.7E−05 |

-continued

| | | | | | | |
|---|---|---|---|---|---|---|
| 237 | 0.0E+00 | 0.0E+00 | 6.4E−05 | 1.4E−06 | 2.0E−05 | 2.3E−06 |
| 238 | 0.0E+00 | 0.0E+00 | 9.5E−04 | 0.0E+00 | 1.0E−06 | 0.0E+00 |
| 239 | 0.0E+00 | 0.0E+00 | 3.6E−05 | 0.0E+00 | 0.0E+00 | 0.0E+00 |
| 240 | 0.0E+00 | 0.0E+00 | 0.0E+00 | 0.0E+00 | 0.0E+00 | 0.0E+00 |
| 241 | 0.0E+00 | 2.9E−06 | 1.5E−05 | 0.0E+00 | 0.0E+00 | 0.0E+00 |
| 242 | 0.0E+00 | 7.9E−07 | 2.2E−06 | 0.0E+00 | 0.0E+00 | 0.0E+00 |
| 243 | 6.5E−05 | 8.7E−06 | 5.4E−04 | 1.1E−05 | 4.3E−04 | 9.7E−06 |
| 244 | 0.0E+00 | 0.0E+00 | 0.0E+00 | 0.0E+00 | 0.0E+00 | 2.9E−07 |
| 245 | 0.0E+00 | 0.0E+00 | 0.0E+00 | 0.0E+00 | 0.0E+00 | 0.0E+00 |
| 246 | 0.0E+00 | 0.0E+00 | 0.0E+00 | 0.0E+00 | 0.0E+00 | 0.0E+00 |
| 247 | 0.0E+00 | 0.0E+00 | 1.1E−06 | 0.0E+00 | 0.0E+00 | 0.0E+00 |
| 248 | 0.0E+00 | 0.0E+00 | 0.0E+00 | 0.0E+00 | 0.0E+00 | 0.0E+00 |
| 249 | 0.0E+00 | 0.0E+00 | 0.0E+00 | 0.0E+00 | 0.0E+00 | 0.0E+00 |
| 250 | 0.0E+00 | 0.0E+00 | 0.0E+00 | 0.0E+00 | 0.0E+00 | 0.0E+00 |
| 251 | 9.9E−04 | 9.6E−05 | 2.1E−03 | 7.1E−05 | 3.5E−03 | 5.1E−05 |
| 252 | 3.3E−01 | 7.4E−01 | 1.0E−01 | 4.9E−01 | 1.4E−01 | 8.0E−01 |
| 253 | 0.0E+00 | 0.0E+00 | 0.0E+00 | 0.0E+00 | 0.0E+00 | 2.9E−07 |
| 254 | 2.0E−04 | 9.8E−05 | 3.9E−04 | 6.9E−05 | 1.1E−04 | 5.2E−05 |
| 255 | 0.0E+00 | 0.0E+00 | 0.0E+00 | 0.0E+00 | 0.0E+00 | 0.0E+00 |
| 256 | 0.0E+00 | 7.9E−07 | 4.2E−03 | 9.2E−07 | 1.5E−06 | 0.0E+00 |
| 257 | 0.0E+00 | 0.0E+00 | 0.0E+00 | 0.0E+00 | 5.4E−05 | 0.0E+00 |
| 258 | 2.4E−04 | 2.2E−02 | 5.2E−03 | 1.4E−06 | 8.9E−05 | 2.6E−06 |
| 259 | 2.1E−05 | 0.0E+00 | 4.0E−04 | 0.0E+00 | 5.1E−07 | 7.3E−06 |
| 260 | 9.9E−06 | 4.5E−05 | 9.7E−04 | 9.1E−05 | 2.0E−02 | 3.6E−04 |
| 261 | 5.7E−05 | 7.8E−03 | 7.0E−04 | 1.8E−05 | 9.7E−02 | 1.2E−02 |
| 262 | 3.3E−05 | 2.4E−06 | 5.4E−07 | 1.1E−05 | 1.7E−06 | 2.8E−05 |
| 263 | 0.0E+00 | 1.0E−04 | 1.2E−04 | 0.0E+00 | 5.1E−07 | 0.0E+00 |
| 264 | 7.3E−04 | 2.8E−04 | 1.1E−02 | 1.2E−04 | 3.2E−03 | 1.5E−04 |
| 265 | 2.1E−05 | 1.8E−05 | 6.1E−05 | 2.8E−06 | 5.1E−07 | 0.0E+00 |
| 266 | 0.0E+00 | 0.0E+00 | 0.0E+00 | 0.0E+00 | 0.0E+00 | 0.0E+00 |
| 267 | 0.0E+00 | 0.0E+00 | 0.0E+00 | 0.0E+00 | 0.0E+00 | 1.1E−05 |
| 268 | 9.4E−06 | 7.1E−06 | 6.8E−05 | 1.8E−06 | 5.4E−05 | 2.1E−06 |
| 269 | 4.7E−07 | 4.5E−06 | 1.5E−05 | 4.3E−05 | 1.6E−05 | 1.4E−05 |
| 270 | 0.0E+00 | 0.0E+00 | 0.0E+00 | 0.0E+00 | 0.0E+00 | 0.0E+00 |
| 271 | 2.5E−03 | 1.6E−03 | 3.5E−02 | 2.5E−03 | 2.3E−02 | 5.5E−03 |
| 272 | 1.1E−05 | 5.8E−06 | 3.5E−05 | 0.0E+00 | 2.0E−06 | 0.0E+00 |
| 273 | 0.0E+00 | 0.0E+00 | 0.0E+00 | 8.9E−05 | 0.0E+00 | 0.0E+00 |
| 274 | 0.0E+00 | 0.0E+00 | 0.0E+00 | 0.0E+00 | 0.0E+00 | 0.0E+00 |
| 275 | 0.0E+00 | 0.0E+00 | 0.0E+00 | 0.0E+00 | 0.0E+00 | 0.0E+00 |
| 276 | 0.0E+00 | 0.0E+00 | 0.0E+00 | 0.0E+00 | 0.0E+00 | 0.0E+00 |
| 277 | 1.9E−05 | 0.0E+00 | 2.2E−06 | 9.2E−07 | 1.5E−06 | 2.9E−07 |
| 278 | 9.4E−07 | 1.1E−06 | 5.4E−07 | 9.2E−07 | 2.0E−06 | 0.0E+00 |
| 279 | 0.0E+00 | 2.6E−07 | 0.0E+00 | 0.0E+00 | 1.0E−06 | 5.9E−07 |
| 280 | 0.0E+00 | 0.0E+00 | 0.0E+00 | 0.0E+00 | 0.0E+00 | 0.0E+00 |
| 281 | 0.0E+00 | 0.0E+00 | 5.4E−07 | 1.4E−06 | 0.0E+00 | 5.9E−07 |
| 282 | 0.0E+00 | 5.3E−07 | 5.4E−07 | 0.0E+00 | 0.0E+00 | 0.0E+00 |
| 283 | 0.0E+00 | 0.0E+00 | 0.0E+00 | 6.9E−06 | 0.0E+00 | 0.0E+00 |
| 284 | 0.0E+00 | 0.0E+00 | 0.0E+00 | 0.0E+00 | 0.0E+00 | 0.0E+00 |
| 285 | 0.0E+00 | 0.0E+00 | 0.0E+00 | 0.0E+00 | 0.0E+00 | 0.0E+00 |
| 286 | 0.0E+00 | 0.0E+00 | 0.0E+00 | 0.0E+00 | 0.0E+00 | 0.0E+00 |
| 287 | 0.0E+00 | 0.0E+00 | 0.0E+00 | 1.3E−05 | 0.0E+00 | 0.0E+00 |
| 288 | 0.0E+00 | 0.0E+00 | 0.0E+00 | 0.0E+00 | 5.1E−07 | 0.0E+00 |
| 289 | 0.0E+00 | 0.0E+00 | 0.0E+00 | 0.0E+00 | 0.0E+00 | 0.0E+00 |
| 290 | 1.8E−05 | 0.0E+00 | 2.0E−05 | 0.0E+00 | 4.1E−06 | 4.7E−06 |
| 291 | 0.0E+00 | 0.0E+00 | 2.2E−06 | 0.0E+00 | 0.0E+00 | 0.0E+00 |
| 292 | 0.0E+00 | 0.0E+00 | 0.0E+00 | 0.0E+00 | 0.0E+00 | 0.0E+00 |
| 293 | 2.4E−06 | 9.8E−06 | 2.6E−05 | 9.2E−07 | 1.0E−05 | 2.9E−07 |
| 294 | 0.0E+00 | 0.0E+00 | 0.0E+00 | 9.7E−06 | 0.0E+00 | 0.0E+00 |
| 295 | 6.4E−03 | 4.6E−03 | 2.0E−02 | 5.6E−04 | 3.2E−03 | 9.6E−04 |
| 296 | 1.5E−05 | 5.6E−06 | 3.6E−05 | 8.8E−06 | 9.2E−06 | 2.9E−07 |
| 297 | 0.0E+00 | 0.0E+00 | 2.7E−06 | 0.0E+00 | 0.0E+00 | 0.0E+00 |
| 298 | 0.0E+00 | 0.0E+00 | 0.0E+00 | 0.0E+00 | 0.0E+00 | 0.0E+00 |
| 299 | 0.0E+00 | 0.0E+00 | 0.0E+00 | 0.0E+00 | 1.0E−06 | 0.0E+00 |
| 300 | 0.0E+00 | 0.0E+00 | 0.0E+00 | 0.0E+00 | 0.0E+00 | 0.0E+00 |
| 301 | 0.0E+00 | 2.6E−07 | 1.6E−06 | 4.6E−07 | 3.6E−06 | 0.0E+00 |
| 302 | 0.0E+00 | 0.0E+00 | 0.0E+00 | 0.0E+00 | 0.0E+00 | 0.0E+00 |
| 303 | 3.4E−05 | 0.0E+00 | 0.0E+00 | 0.0E+00 | 1.2E−05 | 0.0E+00 |
| 304 | 0.0E+00 | 0.0E+00 | 0.0E+00 | 0.0E+00 | 0.0E+00 | 0.0E+00 |
| 305 | 0.0E+00 | 0.0E+00 | 0.0E+00 | 0.0E+00 | 0.0E+00 | 0.0E+00 |
| 306 | 4.2E−06 | 0.0E+00 | 0.0E+00 | 0.0E+00 | 0.0E+00 | 0.0E+00 |
| 307 | 0.0E+00 | 0.0E+00 | 5.4E−07 | 0.0E+00 | 0.0E+00 | 0.0E+00 |
| 308 | 0.0E+00 | 0.0E+00 | 1.6E−06 | 0.0E+00 | 0.0E+00 | 0.0E+00 |
| 309 | 2.8E−06 | 0.0E+00 | 0.0E+00 | 0.0E+00 | 6.1E−06 | 5.9E−07 |
| 310 | 9.4E−07 | 0.0E+00 | 1.5E−05 | 0.0E+00 | 0.0E+00 | 0.0E+00 |
| 311 | 0.0E+00 | 2.6E−07 | 0.0E+00 | 0.0E+00 | 5.1E−07 | 0.0E+00 |
| 312 | 3.2E−04 | 6.7E−04 | 2.2E−04 | 4.6E−07 | 1.0E−06 | 0.0E+00 |
| 313 | 3.2E−05 | 3.9E−05 | 0.0E+00 | 0.0E+00 | 0.0E+00 | 0.0E+00 |
| 314 | 4.0E−04 | 9.0E−05 | 5.0E−03 | 2.3E−06 | 0.0E+00 | 0.0E+00 |
| 315 | 1.8E−03 | 9.7E−03 | 1.1E−02 | 8.8E−06 | 1.5E−05 | 2.9E−06 |

-continued

| | | | | | | |
|---|---|---|---|---|---|---|
| 316 | 3.8E−05 | 6.8E−05 | 1.4E−04 | 0.0E+00 | 0.0E+00 | 0.0E+00 |
| 317 | 3.3E−06 | 0.0E+00 | 9.2E−06 | 0.0E+00 | 0.0E+00 | 0.0E+00 |
| 318 | 0.0E+00 | 2.6E−07 | 5.4E−07 | 0.0E+00 | 0.0E+00 | 0.0E+00 |
| 319 | 0.0E+00 | 0.0E+00 | 0.0E+00 | 0.0E+00 | 0.0E+00 | 0.0E+00 |
| 320 | 1.9E−06 | 5.3E−07 | 8.1E−06 | 6.9E−05 | 2.5E−05 | 1.0E−05 |
| 321 | 0.0E+00 | 0.0E+00 | 0.0E+00 | 0.0E+00 | 0.0E+00 | 0.0E+00 |
| 322 | 0.0E+00 | 0.0E+00 | 5.4E−07 | 9.2E−07 | 0.0E+00 | 0.0E+00 |
| 323 | 2.8E−06 | 1.1E−06 | 5.1E−05 | 0.0E+00 | 0.0E+00 | 0.0E+00 |
| 324 | 0.0E+00 | 0.0E+00 | 4.3E−06 | 0.0E+00 | 0.0E+00 | 0.0E+00 |
| 325 | 4.4E−04 | 2.4E−04 | 7.3E−03 | 1.2E−05 | 6.1E−06 | 1.4E−05 |
| 326 | 2.5E−04 | 2.3E−04 | 1.2E−02 | 9.2E−07 | 2.5E−06 | 8.8E−07 |
| 327 | 0.0E+00 | 0.0E+00 | 0.0E+00 | 0.0E+00 | 0.0E+00 | 0.0E+00 |
| 328 | 0.0E+00 | 0.0E+00 | 0.0E+00 | 0.0E+00 | 0.0E+00 | 0.0E+00 |
| 329 | 0.0E+00 | 0.0E+00 | 0.0E+00 | 0.0E+00 | 0.0E+00 | 0.0E+00 |
| 330 | 0.0E+00 | 0.0E+00 | 1.6E−06 | 0.0E+00 | 0.0E+00 | 0.0E+00 |
| 331 | 5.6E−06 | 7.0E−05 | 4.1E−04 | 4.2E−06 | 5.5E−05 | 1.9E−05 |
| 332 | 2.1E−04 | 6.6E−06 | 2.7E−04 | 1.0E−04 | 6.8E−05 | 7.2E−05 |
| 333 | 0.0E+00 | 0.0E+00 | 3.8E−06 | 0.0E+00 | 0.0E+00 | 0.0E+00 |
| 334 | 2.7E−04 | 1.5E−04 | 8.5E−04 | 3.5E−05 | 2.2E−04 | 5.9E−05 |
| 335 | 3.2E−05 | 5.8E−06 | 1.9E−04 | 2.3E−06 | 2.2E−05 | 9.7E−06 |
| 336 | 0.0E+00 | 0.0E+00 | 0.0E+00 | 0.0E+00 | 1.0E−06 | 0.0E+00 |
| 337 | 4.3E−01 | 2.4E−04 | 9.7E−04 | 9.7E−05 | 3.6E−04 | 8.1E−05 |
| 338 | 1.4E−04 | 1.4E−04 | 6.6E−04 | 1.2E−05 | 6.7E−05 | 2.5E−05 |
| 339 | 1.4E−06 | 5.3E−07 | 0.0E+00 | 0.0E+00 | 0.0E+00 | 0.0E+00 |
| 340 | 9.0E−05 | 1.2E−05 | 7.7E−05 | 2.3E−06 | 1.3E−05 | 4.7E−06 |
| 341 | 0.0E+00 | 0.0E+00 | 0.0E+00 | 0.0E+00 | 0.0E+00 | 0.0E+00 |
| 342 | 0.0E+00 | 0.0E+00 | 0.0E+00 | 0.0E+00 | 0.0E+00 | 0.0E+00 |
| 343 | 1.4E−06 | 0.0E+00 | 0.0E+00 | 0.0E+00 | 0.0E+00 | 0.0E+00 |
| 344 | 2.4E−06 | 0.0E+00 | 0.0E+00 | 0.0E+00 | 4.6E−06 | 0.0E+00 |
| 345 | 2.8E−06 | 0.0E+00 | 0.0E+00 | 0.0E+00 | 0.0E+00 | 0.0E+00 |
| 346 | 0.0E+00 | 0.0E+00 | 5.4E−07 | 0.0E+00 | 0.0E+00 | 0.0E+00 |
| 347 | 1.4E−04 | 7.9E−06 | 1.0E−04 | 1.2E−05 | 3.1E−06 | 6.2E−06 |
| 348 | 0.0E+00 | 0.0E+00 | 0.0E+00 | 0.0E+00 | 0.0E+00 | 0.0E+00 |
| 349 | 6.4E−04 | 1.1E−06 | 8.9E−04 | 9.2E−07 | 5.1E−07 | 5.9E−07 |
| 350 | 0.0E+00 | 0.0E+00 | 0.0E+00 | 0.0E+00 | 0.0E+00 | 0.0E+00 |
| 351 | 2.5E−03 | 7.7E−06 | 7.4E−03 | 0.0E+00 | 5.1E−07 | 5.9E−07 |
| 352 | 0.0E+00 | 0.0E+00 | 0.0E+00 | 9.2E−06 | 0.0E+00 | 4.7E−06 |
| 353 | 9.4E−07 | 0.0E+00 | 3.2E−05 | 0.0E+00 | 0.0E+00 | 0.0E+00 |
| 354 | 1.6E−02 | 2.6E−07 | 6.6E−03 | 1.4E−06 | 0.0E+00 | 0.0E+00 |
| 355 | 0.0E+00 | 0.0E+00 | 0.0E+00 | 4.8E−05 | 0.0E+00 | 0.0E+00 |
| 356 | 0.0E+00 | 0.0E+00 | 0.0E+00 | 0.0E+00 | 0.0E+00 | 0.0E+00 |
| 357 | 2.1E−02 | 5.3E−07 | 2.7E−06 | 4.6E−07 | 2.5E−06 | 8.8E−07 |
| 358 | 4.1E−05 | 0.0E+00 | 0.0E+00 | 0.0E+00 | 0.0E+00 | 0.0E+00 |
| 359 | 8.9E−06 | 0.0E+00 | 2.7E−06 | 1.8E−06 | 0.0E+00 | 2.9E−07 |
| 360 | 0.0E+00 | 0.0E+00 | 0.0E+00 | 0.0E+00 | 0.0E+00 | 0.0E+00 |
| 361 | 1.5E−04 | 8.7E−06 | 8.4E−04 | 0.0E+00 | 0.0E+00 | 0.0E+00 |
| 362 | 9.8E−05 | 3.1E−05 | 8.1E−05 | 2.3E−06 | 3.2E−05 | 1.8E−06 |
| 363 | 0.0E+00 | 0.0E+00 | 0.0E+00 | 0.0E+00 | 0.0E+00 | 0.0E+00 |
| 364 | 0.0E+00 | 0.0E+00 | 0.0E+00 | 0.0E+00 | 2.5E−06 | 0.0E+00 |
| 365 | 0.0E+00 | 0.0E+00 | 0.0E+00 | 7.8E−06 | 3.7E−04 | 8.8E−07 |
| 366 | 0.0E+00 | 0.0E+00 | 0.0E+00 | 0.0E+00 | 0.0E+00 | 0.0E+00 |
| 367 | 0.0E+00 | 5.3E−07 | 0.0E+00 | 0.0E+00 | 0.0E+00 | 0.0E+00 |
| 368 | 2.8E−06 | 9.1E−05 | 4.3E−06 | 0.0E+00 | 1.5E−06 | 0.0E+00 |
| 369 | 3.3E−06 | 4.5E−06 | 1.1E−06 | 5.5E−06 | 2.0E−06 | 1.6E−05 |
| 370 | 0.0E+00 | 2.4E−05 | 0.0E+00 | 0.0E+00 | 0.0E+00 | 0.0E+00 |
| 371 | 5.2E−06 | 8.5E−06 | 1.6E−06 | 0.0E+00 | 5.9E−04 | 0.0E+00 |
| 372 | 1.9E−06 | 5.6E−06 | 3.2E−06 | 0.0E+00 | 0.0E+00 | 0.0E+00 |
| 373 | 2.4E−02 | 1.2E−02 | 9.8E−02 | 1.8E−05 | 1.5E−05 | 2.0E−05 |
| 374 | 0.0E+00 | 0.0E+00 | 0.0E+00 | 0.0E+00 | 0.0E+00 | 0.0E+00 |
| 375 | 1.4E−06 | 2.4E−06 | 5.4E−07 | 5.1E−06 | 1.0E−06 | 2.6E−06 |
| 376 | 1.4E−06 | 5.3E−07 | 0.0E+00 | 9.2E−07 | 5.1E−07 | 1.5E−06 |
| 377 | 0.0E+00 | 0.0E+00 | 0.0E+00 | 0.0E+00 | 1.0E−06 | 0.0E+00 |
| 378 | 2.3E−04 | 1.3E−04 | 1.0E−03 | 2.4E−05 | 1.8E−04 | 3.0E−05 |

| Taxon ID | CM Atm+/+ Colon | | | RM Atm+/+ Colon | | |
|---|---|---|---|---|---|---|
| 1 | 1.5E−03 | 1.2E−03 | 1.3E−03 | 2.4E−03 | 1.8E−03 | 1.3E−03 |
| 2 | 0.0E+00 | 0.0E+00 | 7.6E−07 | 2.2E−06 | 1.2E−06 | 0.0E+00 |
| 3 | 9.2E−07 | 1.3E−06 | 7.6E−07 | 0.0E+00 | 0.0E+00 | 0.0E+00 |
| 4 | 4.0E−05 | 5.0E−05 | 8.4E−06 | 7.1E−05 | 2.1E−05 | 1.5E−05 |
| 5 | 0.0E+00 | 0.0E+00 | 0.0E+00 | 0.0E+00 | 0.0E+00 | 0.0E+00 |
| 6 | 0.0E+00 | 0.0E+00 | 0.0E+00 | 0.0E+00 | 0.0E+00 | 0.0E+00 |
| 7 | 0.0E+00 | 0.0E+00 | 8.4E−06 | 1.7E−06 | 0.0E+00 | 0.0E+00 |
| 8 | 1.5E−05 | 4.6E−06 | 1.5E−05 | 5.6E−07 | 4.1E−07 | 0.0E+00 |
| 9 | 0.0E+00 | 6.6E−07 | 3.1E−06 | 0.0E+00 | 0.0E+00 | 0.0E+00 |
| 10 | 0.0E+00 | 1.3E−06 | 0.0E+00 | 1.1E−05 | 0.0E+00 | 0.0E+00 |
| 11 | 0.0E+00 | 0.0E+00 | 0.0E+00 | 0.0E+00 | 0.0E+00 | 0.0E+00 |
| 12 | 0.0E+00 | 0.0E+00 | 0.0E+00 | 0.0E+00 | 0.0E+00 | 0.0E+00 |

-continued

| | | | | | | |
|---|---|---|---|---|---|---|
| 13 | 0.0E+00 | 0.0E+00 | 0.0E+00 | 0.0E+00 | 0.0E+00 | 0.0E+00 |
| 14 | 4.6E−07 | 5.3E−06 | 2.3E−06 | 2.2E−06 | 0.0E+00 | 0.0E+00 |
| 15 | 0.0E+00 | 0.0E+00 | 0.0E+00 | 0.0E+00 | 0.0E+00 | 0.0E+00 |
| 16 | 0.0E+00 | 0.0E+00 | 0.0E+00 | 0.0E+00 | 0.0E+00 | 0.0E+00 |
| 17 | 1.8E−06 | 1.3E−06 | 0.0E+00 | 5.6E−06 | 1.2E−06 | 5.5E−06 |
| 18 | 0.0E+00 | 0.0E+00 | 0.0E+00 | 0.0E+00 | 0.0E+00 | 0.0E+00 |
| 19 | 0.0E+00 | 0.0E+00 | 0.0E+00 | 0.0E+00 | 0.0E+00 | 0.0E+00 |
| 20 | 6.9E−06 | 5.3E−06 | 5.3E−06 | 0.0E+00 | 0.0E+00 | 0.0E+00 |
| 21 | 1.8E−04 | 2.8E−04 | 2.2E−04 | 5.6E−07 | 0.0E+00 | 0.0E+00 |
| 22 | 0.0E+00 | 0.0E+00 | 0.0E+00 | 0.0E+00 | 0.0E+00 | 0.0E+00 |
| 23 | 0.0E+00 | 6.6E−07 | 0.0E+00 | 3.3E−06 | 0.0E+00 | 0.0E+00 |
| 24 | 1.4E−06 | 4.6E−06 | 3.8E−06 | 1.7E−06 | 2.4E−06 | 1.5E−06 |
| 25 | 0.0E+00 | 0.0E+00 | 0.0E+00 | 0.0E+00 | 0.0E+00 | 0.0E+00 |
| 26 | 0.0E+00 | 0.0E+00 | 0.0E+00 | 0.0E+00 | 0.0E+00 | 0.0E+00 |
| 27 | 4.6E−07 | 1.3E−06 | 1.5E−06 | 0.0E+00 | 0.0E+00 | 0.0E+00 |
| 28 | 0.0E+00 | 0.0E+00 | 0.0E+00 | 0.0E+00 | 0.0E+00 | 0.0E+00 |
| 29 | 0.0E+00 | 0.0E+00 | 1.5E−06 | 0.0E+00 | 0.0E+00 | 0.0E+00 |
| 30 | 9.2E−07 | 0.0E+00 | 0.0E+00 | 0.0E+00 | 0.0E+00 | 5.0E−07 |
| 31 | 0.0E+00 | 0.0E+00 | 0.0E+00 | 0.0E+00 | 0.0E+00 | 0.0E+00 |
| 32 | 3.7E−06 | 1.3E−05 | 7.6E−07 | 8.2E−05 | 3.1E−05 | 6.5E−05 |
| 33 | 5.5E−06 | 1.2E−05 | 2.2E−05 | 5.1E−05 | 9.7E−06 | 9.9E−07 |
| 34 | 0.0E+00 | 0.0E+00 | 0.0E+00 | 0.0E+00 | 0.0E+00 | 0.0E+00 |
| 35 | 5.1E−06 | 2.0E−06 | 4.6E−06 | 0.0E+00 | 0.0E+00 | 0.0E+00 |
| 36 | 0.0E+00 | 0.0E+00 | 0.0E+00 | 0.0E+00 | 0.0E+00 | 0.0E+00 |
| 37 | 0.0E+00 | 0.0E+00 | 0.0E+00 | 0.0E+00 | 0.0E+00 | 0.0E+00 |
| 38 | 0.0E+00 | 0.0E+00 | 0.0E+00 | 0.0E+00 | 0.0E+00 | 0.0E+00 |
| 39 | 0.0E+00 | 0.0E+00 | 0.0E+00 | 0.0E+00 | 0.0E+00 | 0.0E+00 |
| 40 | 0.0E+00 | 1.3E−06 | 3.8E−06 | 0.0E+00 | 0.0E+00 | 0.0E+00 |
| 41 | 0.0E+00 | 0.0E+00 | 0.0E+00 | 0.0E+00 | 0.0E+00 | 0.0E+00 |
| 42 | 0.0E+00 | 0.0E+00 | 0.0E+00 | 0.0E+00 | 0.0E+00 | 0.0E+00 |
| 43 | 0.0E+00 | 6.6E−07 | 0.0E+00 | 0.0E+00 | 0.0E+00 | 0.0E+00 |
| 44 | 1.4E−06 | 0.0E+00 | 7.6E−07 | 0.0E+00 | 0.0E+00 | 0.0E+00 |
| 45 | 0.0E+00 | 0.0E+00 | 0.0E+00 | 0.0E+00 | 0.0E+00 | 3.5E−06 |
| 46 | 0.0E+00 | 0.0E+00 | 0.0E+00 | 0.0E+00 | 0.0E+00 | 0.0E+00 |
| 47 | 4.6E−07 | 2.0E−06 | 3.1E−06 | 0.0E+00 | 0.0E+00 | 0.0E+00 |
| 48 | 4.6E−07 | 8.6E−06 | 7.6E−07 | 0.0E+00 | 0.0E+00 | 0.0E+00 |
| 49 | 0.0E+00 | 0.0E+00 | 1.9E−05 | 0.0E+00 | 0.0E+00 | 0.0E+00 |
| 50 | 2.1E−05 | 3.9E−05 | 1.4E−04 | 3.7E−05 | 2.6E−05 | 7.4E−05 |
| 51 | 2.8E−06 | 0.0E+00 | 0.0E+00 | 5.1E−05 | 2.6E−05 | 6.5E−05 |
| 52 | 0.0E+00 | 0.0E+00 | 0.0E+00 | 3.9E−06 | 0.0E+00 | 0.0E+00 |
| 53 | 0.0E+00 | 0.0E+00 | 0.0E+00 | 9.5E−06 | 5.3E−06 | 2.5E−06 |
| 54 | 1.2E−05 | 8.6E−06 | 2.3E−06 | 0.0E+00 | 8.1E−07 | 2.5E−06 |
| 55 | 1.0E−04 | 8.4E−05 | 1.0E−04 | 0.0E+00 | 0.0E+00 | 0.0E+00 |
| 56 | 0.0E+00 | 0.0E+00 | 0.0E+00 | 0.0E+00 | 0.0E+00 | 0.0E+00 |
| 57 | 0.0E+00 | 0.0E+00 | 0.0E+00 | 1.7E−06 | 8.1E−07 | 9.9E−07 |
| 58 | 6.5E−03 | 1.6E−02 | 2.1E−02 | 4.4E−03 | 8.2E−04 | 9.6E−04 |
| 59 | 3.4E−03 | 6.1E−03 | 6.4E−03 | 1.7E−05 | 5.7E−03 | 2.0E−06 |
| 60 | 2.2E−03 | 2.1E−02 | 1.6E−02 | 9.5E−05 | 4.4E−03 | 1.1E−05 |
| 61 | 1.2E−04 | 4.3E−04 | 3.0E−04 | 0.0E+00 | 0.0E+00 | 0.0E+00 |
| 62 | 1.3E−03 | 6.9E−03 | 2.3E−03 | 1.0E−03 | 1.4E−04 | 2.8E−04 |
| 63 | 8.0E−05 | 3.7E−05 | 6.7E−05 | 1.5E−04 | 1.7E−04 | 7.8E−05 |
| 64 | 4.4E−04 | 6.0E−03 | 4.9E−03 | 1.5E−04 | 8.6E−05 | 3.7E−05 |
| 65 | 2.0E−02 | 1.8E−02 | 6.0E−04 | 6.1E−06 | 6.5E−06 | 5.0E−06 |
| 66 | 3.3E−03 | 1.6E−03 | 2.5E−03 | 5.6E−07 | 1.2E−04 | 5.0E−07 |
| 67 | 3.7E−03 | 1.4E−02 | 2.0E−02 | 2.8E−06 | 1.2E−06 | 9.9E−07 |
| 68 | 0.0E+00 | 0.0E+00 | 0.0E+00 | 0.0E+00 | 4.1E−07 | 0.0E+00 |
| 69 | 1.4E−03 | 1.1E−05 | 2.2E−03 | 3.8E−03 | 3.6E−03 | 5.2E−03 |
| 70 | 6.5E−06 | 1.3E−06 | 9.2E−06 | 1.3E−05 | 1.8E−05 | 5.5E−06 |
| 71 | 1.0E−04 | 1.4E−05 | 4.5E−05 | 1.1E−04 | 1.2E−04 | 6.2E−05 |
| 72 | 0.0E+00 | 0.0E+00 | 0.0E+00 | 5.6E−07 | 8.1E−07 | 9.9E−07 |
| 73 | 4.6E−07 | 0.0E+00 | 7.6E−07 | 2.2E−06 | 8.1E−07 | 5.0E−07 |
| 74 | 7.8E−06 | 6.6E−07 | 6.1E−06 | 1.0E−05 | 5.7E−06 | 5.5E−06 |
| 75 | 4.6E−06 | 1.2E−04 | 1.7E−05 | 0.0E+00 | 0.0E+00 | 0.0E+00 |
| 76 | 2.6E−03 | 1.2E−03 | 1.6E−03 | 1.1E−06 | 2.3E−05 | 9.9E−05 |
| 77 | 2.1E−04 | 5.0E−05 | 5.3E−05 | 5.0E−05 | 6.3E−05 | 7.4E−05 |
| 78 | 1.4E−06 | 2.0E−06 | 4.6E−06 | 0.0E+00 | 8.1E−07 | 0.0E+00 |
| 79 | 2.8E−06 | 8.8E−03 | 6.6E−03 | 3.3E−06 | 3.6E−06 | 6.5E−06 |
| 80 | 0.0E+00 | 0.0E+00 | 0.0E+00 | 0.0E+00 | 0.0E+00 | 2.5E−05 |
| 81 | 9.7E−06 | 2.8E−05 | 3.1E−05 | 0.0E+00 | 0.0E+00 | 0.0E+00 |
| 82 | 9.2E−03 | 1.1E−01 | 1.6E−01 | 9.3E−02 | 3.2E−02 | 2.4E−02 |
| 83 | 1.4E−03 | 2.8E−03 | 2.2E−03 | 1.6E−03 | 1.2E−02 | 9.0E−03 |
| 84 | 0.0E+00 | 0.0E+00 | 0.0E+00 | 0.0E+00 | 4.9E−06 | 5.0E−07 |
| 85 | 2.1E−03 | 1.1E−02 | 5.5E−03 | 9.5E−02 | 3.9E−02 | 1.8E−02 |
| 86 | 3.9E−01 | 1.0E−01 | 2.5E−01 | 5.9E−01 | 7.5E−01 | 5.9E−01 |
| 87 | 1.8E−05 | 3.3E−06 | 9.9E−06 | 1.4E−05 | 1.5E−05 | 8.9E−06 |
| 88 | 0.0E+00 | 1.3E−05 | 0.0E+00 | 0.0E+00 | 0.0E+00 | 5.0E−07 |
| 89 | 0.0E+00 | 0.0E+00 | 3.1E−06 | 1.1E−06 | 0.0E+00 | 9.9E−07 |
| 90 | 4.0E−05 | 1.1E−04 | 3.4E−05 | 0.0E+00 | 0.0E+00 | 0.0E+00 |
| 91 | 9.2E−07 | 0.0E+00 | 0.0E+00 | 1.1E−06 | 8.1E−07 | 9.9E−07 |

-continued

| | | | | | | |
|---|---|---|---|---|---|---|
| 92 | 0.0E+00 | 0.0E+00 | 0.0E+00 | 3.1E−05 | 4.1E−07 | 0.0E+00 |
| 93 | 0.0E+00 | 0.0E+00 | 0.0E+00 | 1.9E−04 | 0.0E+00 | 0.0E+00 |
| 94 | 3.8E−02 | 4.8E−02 | 3.7E−02 | 5.0E−04 | 6.5E−04 | 4.2E−04 |
| 95 | 0.0E+00 | 0.0E+00 | 0.0E+00 | 0.0E+00 | 0.0E+00 | 0.0E+00 |
| 96 | 1.6E−03 | 4.5E−03 | 3.2E−03 | 8.9E−06 | 5.5E−05 | 2.5E−04 |
| 97 | 1.4E−06 | 4.0E−05 | 7.6E−07 | 1.7E−06 | 4.1E−07 | 0.0E+00 |
| 98 | 2.0E−04 | 1.6E−04 | 1.1E−04 | 0.0E+00 | 0.0E+00 | 0.0E+00 |
| 99 | 0.0E+00 | 6.6E−06 | 1.5E−06 | 0.0E+00 | 0.0E+00 | 0.0E+00 |
| 100 | 0.0E+00 | 0.0E+00 | 0.0E+00 | 1.9E−05 | 4.9E−06 | 3.0E−05 |
| 101 | 3.2E−06 | 1.6E−05 | 7.6E−07 | 4.4E−05 | 2.4E−05 | 4.1E−05 |
| 102 | 4.6E−07 | 0.0E+00 | 0.0E+00 | 4.0E−05 | 0.0E+00 | 1.4E−04 |
| 103 | 0.0E+00 | 2.0E−06 | 0.0E+00 | 0.0E+00 | 0.0E+00 | 0.0E+00 |
| 104 | 0.0E+00 | 0.0E+00 | 0.0E+00 | 0.0E+00 | 0.0E+00 | 0.0E+00 |
| 105 | 1.8E−04 | 3.0E−03 | 9.9E−04 | 1.7E−06 | 1.6E−06 | 9.9E−07 |
| 106 | 1.4E−06 | 4.0E−06 | 7.6E−07 | 0.0E+00 | 0.0E+00 | 9.9E−07 |
| 107 | 4.0E−05 | 3.2E−05 | 6.9E−06 | 2.6E−05 | 2.3E−05 | 8.0E−06 |
| 108 | 0.0E+00 | 0.0E+00 | 0.0E+00 | 0.0E+00 | 0.0E+00 | 0.0E+00 |
| 109 | 4.6E−06 | 2.6E−06 | 3.1E−06 | 0.0E+00 | 0.0E+00 | 0.0E+00 |
| 110 | 7.4E−05 | 6.1E−05 | 6.3E−05 | 0.0E+00 | 0.0E+00 | 0.0E+00 |
| 111 | 0.0E+00 | 0.0E+00 | 0.0E+00 | 0.0E+00 | 0.0E+00 | 0.0E+00 |
| 112 | 0.0E+00 | 0.0E+00 | 0.0E+00 | 0.0E+00 | 0.0E+00 | 0.0E+00 |
| 113 | 0.0E+00 | 0.0E+00 | 0.0E+00 | 0.0E+00 | 0.0E+00 | 0.0E+00 |
| 114 | 0.0E+00 | 0.0E+00 | 6.1E−06 | 0.0E+00 | 1.2E−06 | 0.0E+00 |
| 115 | 1.5E−03 | 6.9E−04 | 8.1E−05 | 5.7E−03 | 1.2E−03 | 8.5E−03 |
| 116 | 0.0E+00 | 0.0E+00 | 0.0E+00 | 0.0E+00 | 0.0E+00 | 0.0E+00 |
| 117 | 0.0E+00 | 0.0E+00 | 0.0E+00 | 0.0E+00 | 0.0E+00 | 0.0E+00 |
| 118 | 0.0E+00 | 0.0E+00 | 0.0E+00 | 0.0E+00 | 0.0E+00 | 0.0E+00 |
| 119 | 0.0E+00 | 0.0E+00 | 0.0E+00 | 0.0E+00 | 0.0E+00 | 0.0E+00 |
| 120 | 1.2E−04 | 9.4E−05 | 2.3E−04 | 2.2E−06 | 3.2E−06 | 4.0E−06 |
| 121 | 6.5E−06 | 2.6E−06 | 7.6E−06 | 1.6E−05 | 5.3E−05 | 0.0E+00 |
| 122 | 3.7E−06 | 3.6E−05 | 3.8E−06 | 0.0E+00 | 0.0E+00 | 5.0E−07 |
| 123 | 0.0E+00 | 0.0E+00 | 0.0E+00 | 0.0E+00 | 0.0E+00 | 0.0E+00 |
| 124 | 0.0E+00 | 0.0E+00 | 0.0E+00 | 0.0E+00 | 0.0E+00 | 1.5E−06 |
| 125 | 1.3E−04 | 1.1E−05 | 8.6E−05 | 1.2E−04 | 2.2E−04 | 3.0E−04 |
| 126 | 0.0E+00 | 0.0E+00 | 0.0E+00 | 0.0E+00 | 0.0E+00 | 0.0E+00 |
| 127 | 0.0E+00 | 0.0E+00 | 0.0E+00 | 0.0E+00 | 0.0E+00 | 0.0E+00 |
| 128 | 1.1E−04 | 2.6E−03 | 1.5E−03 | 2.8E−03 | 9.5E−04 | 3.2E−03 |
| 129 | 4.6E−07 | 3.3E−06 | 7.6E−07 | 0.0E+00 | 8.1E−07 | 9.9E−07 |
| 130 | 0.0E+00 | 6.6E−07 | 0.0E+00 | 0.0E+00 | 0.0E+00 | 0.0E+00 |
| 131 | 0.0E+00 | 0.0E+00 | 0.0E+00 | 5.6E−07 | 4.1E−07 | 1.5E−06 |
| 132 | 0.0E+00 | 0.0E+00 | 7.6E−07 | 0.0E+00 | 0.0E+00 | 0.0E+00 |
| 133 | 0.0E+00 | 0.0E+00 | 0.0E+00 | 0.0E+00 | 0.0E+00 | 0.0E+00 |
| 134 | 1.8E−05 | 3.1E−04 | 1.2E−03 | 5.6E−06 | 1.7E−04 | 0.0E+00 |
| 135 | 0.0E+00 | 0.0E+00 | 0.0E+00 | 0.0E+00 | 0.0E+00 | 0.0E+00 |
| 136 | 2.8E−05 | 1.1E−04 | 9.2E−06 | 4.7E−05 | 7.5E−05 | 8.5E−05 |
| 137 | 0.0E+00 | 0.0E+00 | 0.0E+00 | 0.0E+00 | 0.0E+00 | 0.0E+00 |
| 138 | 0.0E+00 | 0.0E+00 | 0.0E+00 | 0.0E+00 | 0.0E+00 | 0.0E+00 |
| 139 | 2.3E−05 | 8.8E−05 | 3.6E−04 | 4.5E−04 | 1.6E−04 | 1.1E−03 |
| 140 | 3.2E−04 | 8.0E−05 | 6.0E−04 | 1.9E−03 | 5.2E−04 | 2.1E−03 |
| 141 | 9.2E−07 | 0.0E+00 | 0.0E+00 | 0.0E+00 | 0.0E+00 | 0.0E+00 |
| 142 | 0.0E+00 | 0.0E+00 | 0.0E+00 | 0.0E+00 | 0.0E+00 | 0.0E+00 |
| 143 | 0.0E+00 | 0.0E+00 | 0.0E+00 | 1.1E−06 | 0.0E+00 | 0.0E+00 |
| 144 | 0.0E+00 | 0.0E+00 | 0.0E+00 | 0.0E+00 | 0.0E+00 | 0.0E+00 |
| 145 | 0.0E+00 | 0.0E+00 | 0.0E+00 | 0.0E+00 | 0.0E+00 | 0.0E+00 |
| 146 | 4.6E−07 | 0.0E+00 | 0.0E+00 | 0.0E+00 | 0.0E+00 | 0.0E+00 |
| 147 | 0.0E+00 | 0.0E+00 | 0.0E+00 | 0.0E+00 | 0.0E+00 | 0.0E+00 |
| 148 | 1.4E−04 | 3.1E−05 | 3.7E−04 | 1.0E−03 | 5.0E−04 | 1.6E−03 |
| 149 | 0.0E+00 | 0.0E+00 | 0.0E+00 | 0.0E+00 | 0.0E+00 | 0.0E+00 |
| 150 | 1.1E−05 | 3.2E−05 | 5.3E−06 | 1.0E−04 | 5.6E−05 | 3.4E−05 |
| 151 | 0.0E+00 | 0.0E+00 | 0.0E+00 | 0.0E+00 | 0.0E+00 | 0.0E+00 |
| 152 | 0.0E+00 | 1.1E−05 | 0.0E+00 | 0.0E+00 | 0.0E+00 | 0.0E+00 |
| 153 | 0.0E+00 | 0.0E+00 | 0.0E+00 | 0.0E+00 | 0.0E+00 | 0.0E+00 |
| 154 | 1.6E−04 | 2.6E−06 | 3.9E−04 | 2.8E−06 | 0.0E+00 | 2.5E−06 |
| 155 | 5.1E−06 | 0.0E+00 | 6.1E−06 | 3.3E−06 | 1.6E−06 | 1.5E−05 |
| 156 | 5.5E−06 | 2.0E−05 | 3.8E−05 | 1.6E−05 | 0.0E+00 | 2.9E−05 |
| 157 | 4.6E−07 | 0.0E+00 | 0.0E+00 | 0.0E+00 | 0.0E+00 | 0.0E+00 |
| 158 | 0.0E+00 | 0.0E+00 | 0.0E+00 | 0.0E+00 | 0.0E+00 | 0.0E+00 |
| 159 | 0.0E+00 | 9.9E−06 | 2.7E−05 | 3.4E−05 | 7.7E−06 | 4.0E−05 |
| 160 | 0.0E+00 | 0.0E+00 | 0.0E+00 | 0.0E+00 | 0.0E+00 | 1.7E−05 |
| 161 | 0.0E+00 | 0.0E+00 | 0.0E+00 | 0.0E+00 | 0.0E+00 | 0.0E+00 |
| 162 | 0.0E+00 | 0.0E+00 | 0.0E+00 | 0.0E+00 | 0.0E+00 | 0.0E+00 |
| 163 | 6.5E−05 | 6.6E−07 | 6.9E−06 | 2.8E−06 | 4.1E−07 | 5.0E−07 |
| 164 | 6.0E−06 | 1.0E−04 | 4.6E−05 | 1.1E−03 | 3.4E−04 | 1.5E−03 |
| 165 | 0.0E+00 | 0.0E+00 | 0.0E+00 | 0.0E+00 | 0.0E+00 | 0.0E+00 |
| 166 | 0.0E+00 | 0.0E+00 | 0.0E+00 | 5.6E−06 | 0.0E+00 | 1.5E−06 |
| 167 | 3.3E−03 | 3.8E−03 | 1.2E−02 | 1.9E−02 | 1.4E−03 | 6.0E−03 |
| 168 | 0.0E+00 | 0.0E+00 | 7.6E−07 | 0.0E+00 | 0.0E+00 | 0.0E+00 |
| 169 | 0.0E+00 | 0.0E+00 | 0.0E+00 | 0.0E+00 | 0.0E+00 | 0.0E+00 |
| 170 | 0.0E+00 | 0.0E+00 | 0.0E+00 | 0.0E+00 | 0.0E+00 | 0.0E+00 |

-continued

| | | | | | | |
|---|---|---|---|---|---|---|
| 171 | 0.0E+00 | 0.0E+00 | 0.0E+00 | 0.0E+00 | 0.0E+00 | 0.0E+00 |
| 172 | 7.4E−05 | 2.7E−03 | 3.7E−04 | 2.5E−02 | 2.4E−02 | 2.3E−02 |
| 173 | 0.0E+00 | 0.0E+00 | 0.0E+00 | 0.0E+00 | 8.1E−07 | 5.0E−07 |
| 174 | 1.6E−04 | 1.9E−03 | 3.4E−04 | 2.7E−04 | 7.7E−06 | 1.4E−05 |
| 175 | 0.0E+00 | 0.0E+00 | 0.0E+00 | 0.0E+00 | 0.0E+00 | 0.0E+00 |
| 176 | 0.0E+00 | 0.0E+00 | 0.0E+00 | 0.0E+00 | 0.0E+00 | 0.0E+00 |
| 177 | 0.0E+00 | 2.0E−06 | 0.0E+00 | 0.0E+00 | 0.0E+00 | 0.0E+00 |
| 178 | 0.0E+00 | 0.0E+00 | 0.0E+00 | 5.0E−06 | 7.3E−06 | 5.0E−07 |
| 179 | 0.0E+00 | 0.0E+00 | 0.0E+00 | 0.0E+00 | 0.0E+00 | 0.0E+00 |
| 180 | 0.0E+00 | 6.6E−07 | 1.5E−06 | 0.0E+00 | 0.0E+00 | 0.0E+00 |
| 181 | 3.7E−06 | 3.3E−06 | 6.9E−06 | 0.0E+00 | 0.0E+00 | 0.0E+00 |
| 182 | 9.2E−07 | 0.0E+00 | 5.3E−06 | 0.0E+00 | 0.0E+00 | 2.0E−05 |
| 183 | 0.0E+00 | 0.0E+00 | 2.3E−06 | 0.0E+00 | 0.0E+00 | 0.0E+00 |
| 184 | 0.0E+00 | 4.6E−06 | 3.1E−06 | 0.0E+00 | 0.0E+00 | 0.0E+00 |
| 185 | 2.1E−03 | 2.8E−05 | 3.3E−04 | 4.5E−04 | 3.8E−04 | 6.7E−04 |
| 186 | 0.0E+00 | 0.0E+00 | 0.0E+00 | 0.0E+00 | 1.1E−05 | 1.0E−04 |
| 187 | 0.0E+00 | 0.0E+00 | 0.0E+00 | 0.0E+00 | 0.0E+00 | 0.0E+00 |
| 188 | 0.0E+00 | 6.6E−07 | 0.0E+00 | 5.6E−07 | 0.0E+00 | 9.9E−07 |
| 189 | 0.0E+00 | 0.0E+00 | 0.0E+00 | 0.0E+00 | 8.1E−07 | 1.4E−05 |
| 190 | 2.8E−06 | 4.3E−05 | 8.1E−05 | 8.4E−06 | 4.5E−06 | 4.3E−05 |
| 191 | 2.8E−06 | 9.2E−06 | 6.3E−04 | 4.2E−04 | 2.9E−04 | 4.4E−04 |
| 192 | 2.3E−05 | 2.7E−05 | 2.1E−05 | 1.0E−05 | 2.4E−06 | 5.5E−06 |
| 193 | 0.0E+00 | 2.6E−06 | 0.0E+00 | 5.6E−07 | 0.0E+00 | 0.0E+00 |
| 194 | 0.0E+00 | 1.3E−06 | 3.8E−06 | 0.0E+00 | 5.7E−06 | 2.0E−06 |
| 195 | 0.0E+00 | 0.0E+00 | 0.0E+00 | 6.1E−06 | 0.0E+00 | 0.0E+00 |
| 196 | 0.0E+00 | 0.0E+00 | 0.0E+00 | 0.0E+00 | 0.0E+00 | 0.0E+00 |
| 197 | 0.0E+00 | 2.1E−05 | 0.0E+00 | 0.0E+00 | 0.0E+00 | 0.0E+00 |
| 198 | 0.0E+00 | 0.0E+00 | 0.0E+00 | 0.0E+00 | 0.0E+00 | 0.0E+00 |
| 199 | 7.4E−06 | 3.6E−05 | 6.2E−05 | 4.7E−04 | 7.1E−05 | 1.1E−04 |
| 200 | 0.0E+00 | 0.0E+00 | 0.0E+00 | 0.0E+00 | 0.0E+00 | 1.5E−06 |
| 201 | 3.7E−06 | 3.0E−05 | 2.3E−05 | 2.2E−06 | 0.0E+00 | 1.5E−06 |
| 202 | 0.0E+00 | 0.0E+00 | 0.0E+00 | 0.0E+00 | 0.0E+00 | 0.0E+00 |
| 203 | 0.0E+00 | 0.0E+00 | 9.0E−05 | 1.4E−03 | 1.5E−04 | 3.1E−05 |
| 204 | 0.0E+00 | 2.6E−06 | 7.6E−07 | 0.0E+00 | 4.1E−07 | 5.0E−07 |
| 205 | 0.0E+00 | 0.0E+00 | 0.0E+00 | 0.0E+00 | 0.0E+00 | 0.0E+00 |
| 206 | 0.0E+00 | 0.0E+00 | 0.0E+00 | 0.0E+00 | 0.0E+00 | 0.0E+00 |
| 207 | 4.6E−07 | 2.2E−03 | 5.3E−05 | 4.2E−04 | 1.7E−04 | 6.5E−04 |
| 208 | 1.0E−02 | 3.2E−03 | 6.5E−03 | 2.2E−02 | 6.9E−03 | 2.8E−02 |
| 209 | 0.0E+00 | 0.0E+00 | 0.0E+00 | 0.0E+00 | 0.0E+00 | 0.0E+00 |
| 210 | 1.6E−03 | 5.5E−03 | 1.6E−03 | 7.2E−04 | 3.3E−04 | 1.2E−03 |
| 211 | 0.0E+00 | 0.0E+00 | 0.0E+00 | 1.1E−06 | 8.1E−07 | 0.0E+00 |
| 212 | 0.0E+00 | 1.1E−05 | 2.3E−05 | 1.1E−06 | 8.1E−07 | 0.0E+00 |
| 213 | 0.0E+00 | 0.0E+00 | 0.0E+00 | 7.2E−06 | 0.0E+00 | 0.0E+00 |
| 214 | 0.0E+00 | 0.0E+00 | 0.0E+00 | 0.0E+00 | 0.0E+00 | 0.0E+00 |
| 215 | 0.0E+00 | 1.3E−06 | 3.8E−06 | 0.0E+00 | 0.0E+00 | 0.0E+00 |
| 216 | 2.0E−04 | 3.9E−04 | 1.7E−05 | 4.4E−04 | 3.4E−04 | 1.2E−03 |
| 217 | 0.0E+00 | 1.9E−05 | 0.0E+00 | 0.0E+00 | 0.0E+00 | 0.0E+00 |
| 218 | 2.5E−04 | 4.3E−04 | 8.9E−05 | 6.3E−04 | 2.4E−04 | 1.3E−03 |
| 219 | 0.0E+00 | 0.0E+00 | 0.0E+00 | 0.0E+00 | 0.0E+00 | 0.0E+00 |
| 220 | 2.6E−05 | 3.8E−04 | 3.5E−04 | 2.5E−04 | 1.9E−04 | 4.1E−05 |
| 221 | 0.0E+00 | 0.0E+00 | 0.0E+00 | 0.0E+00 | 0.0E+00 | 0.0E+00 |
| 222 | 0.0E+00 | 3.7E−05 | 9.9E−06 | 0.0E+00 | 0.0E+00 | 0.0E+00 |
| 223 | 0.0E+00 | 1.8E−05 | 0.0E+00 | 1.6E−05 | 0.0E+00 | 4.5E−05 |
| 224 | 3.7E−06 | 3.3E−06 | 7.6E−07 | 0.0E+00 | 0.0E+00 | 0.0E+00 |
| 225 | 1.3E−03 | 1.1E−03 | 1.1E−03 | 6.9E−04 | 4.5E−04 | 2.6E−03 |
| 226 | 0.0E+00 | 0.0E+00 | 0.0E+00 | 0.0E+00 | 0.0E+00 | 0.0E+00 |
| 227 | 2.3E−06 | 2.0E−05 | 4.6E−06 | 0.0E+00 | 4.1E−07 | 0.0E+00 |
| 228 | 0.0E+00 | 0.0E+00 | 0.0E+00 | 0.0E+00 | 0.0E+00 | 0.0E+00 |
| 229 | 4.2E−06 | 2.6E−06 | 7.6E−07 | 0.0E+00 | 4.1E−07 | 0.0E+00 |
| 230 | 0.0E+00 | 1.3E−06 | 1.5E−06 | 1.7E−05 | 7.3E−06 | 2.0E−05 |
| 231 | 1.4E−06 | 2.9E−05 | 2.3E−06 | 0.0E+00 | 2.2E−05 | 3.9E−05 |
| 232 | 3.4E−01 | 2.9E−01 | 2.9E−01 | 4.7E−05 | 1.2E−04 | 3.3E−05 |
| 233 | 6.0E−06 | 7.2E−06 | 7.6E−07 | 3.7E−05 | 4.9E−06 | 8.4E−06 |
| 234 | 0.0E+00 | 0.0E+00 | 3.5E−05 | 0.0E+00 | 0.0E+00 | 0.0E+00 |
| 235 | 3.5E−04 | 9.6E−04 | 9.7E−05 | 5.7E−04 | 2.8E−04 | 1.4E−03 |
| 236 | 8.5E−04 | 1.0E−03 | 1.9E−03 | 1.2E−03 | 5.6E−04 | 2.0E−03 |
| 237 | 1.8E−06 | 1.3E−06 | 3.1E−05 | 3.8E−05 | 2.3E−05 | 6.8E−05 |
| 238 | 0.0E+00 | 0.0E+00 | 3.0E−05 | 0.0E+00 | 0.0E+00 | 5.0E−07 |
| 239 | 4.4E−05 | 1.3E−04 | 6.5E−05 | 0.0E+00 | 0.0E+00 | 0.0E+00 |
| 240 | 9.2E−07 | 2.0E−06 | 2.3E−06 | 0.0E+00 | 0.0E+00 | 0.0E+00 |
| 241 | 2.8E−06 | 1.1E−05 | 1.5E−06 | 0.0E+00 | 0.0E+00 | 0.0E+00 |
| 242 | 1.8E−06 | 2.6E−06 | 1.5E−06 | 0.0E+00 | 0.0E+00 | 0.0E+00 |
| 243 | 3.4E−04 | 3.4E−04 | 4.1E−04 | 5.9E−04 | 2.9E−04 | 1.0E−03 |
| 244 | 0.0E+00 | 0.0E+00 | 0.0E+00 | 1.3E−05 | 0.0E+00 | 0.0E+00 |
| 245 | 0.0E+00 | 0.0E+00 | 0.0E+00 | 0.0E+00 | 0.0E+00 | 0.0E+00 |
| 246 | 0.0E+00 | 0.0E+00 | 0.0E+00 | 0.0E+00 | 0.0E+00 | 0.0E+00 |
| 247 | 1.4E−06 | 4.0E−06 | 2.3E−06 | 0.0E+00 | 0.0E+00 | 0.0E+00 |
| 248 | 4.6E−07 | 6.6E−07 | 2.0E−04 | 0.0E+00 | 0.0E+00 | 0.0E+00 |
| 249 | 0.0E+00 | 0.0E+00 | 0.0E+00 | 0.0E+00 | 0.0E+00 | 0.0E+00 |

-continued

| | | | | | | |
|---|---|---|---|---|---|---|
| 250 | 0.0E+00 | 0.0E+00 | 0.0E+00 | 0.0E+00 | 0.0E+00 | 0.0E+00 |
| 251 | 1.7E−03 | 1.0E−03 | 1.6E−03 | 4.3E−03 | 1.7E−03 | 4.3E−03 |
| 252 | 2.2E−02 | 7.2E−02 | 4.5E−03 | 8.6E−02 | 3.0E−02 | 1.8E−01 |
| 253 | 0.0E+00 | 0.0E+00 | 0.0E+00 | 0.0E+00 | 4.1E−07 | 0.0E+00 |
| 254 | 8.9E−05 | 2.9E−04 | 2.1E−04 | 8.0E−04 | 4.5E−05 | 7.4E−04 |
| 255 | 0.0E+00 | 0.0E+00 | 0.0E+00 | 0.0E+00 | 0.0E+00 | 0.0E+00 |
| 256 | 0.0E+00 | 1.5E−05 | 3.7E−03 | 5.6E−07 | 0.0E+00 | 0.0E+00 |
| 257 | 0.0E+00 | 0.0E+00 | 0.0E+00 | 3.0E−05 | 0.0E+00 | 0.0E+00 |
| 258 | 3.0E−04 | 2.1E−02 | 5.5E−03 | 2.2E−03 | 2.6E−05 | 1.5E−04 |
| 259 | 7.3E−05 | 2.9E−04 | 1.7E−04 | 5.6E−07 | 9.7E−06 | 4.2E−05 |
| 260 | 2.1E−04 | 2.4E−05 | 5.4E−04 | 5.3E−03 | 2.5E−03 | 6.6E−03 |
| 261 | 3.5E−04 | 6.9E−03 | 2.2E−05 | 1.5E−04 | 5.6E−02 | 2.9E−02 |
| 262 | 7.0E−05 | 4.0E−06 | 3.1E−06 | 5.2E−05 | 2.8E−05 | 1.1E−04 |
| 263 | 1.9E−04 | 1.5E−03 | 1.7E−04 | 0.0E+00 | 0.0E+00 | 0.0E+00 |
| 264 | 5.6E−03 | 1.0E−02 | 7.4E−03 | 7.8E−03 | 3.1E−03 | 1.3E−02 |
| 265 | 4.4E−05 | 4.3E−04 | 6.9E−06 | 5.2E−05 | 0.0E+00 | 8.5E−05 |
| 266 | 0.0E+00 | 0.0E+00 | 0.0E+00 | 0.0E+00 | 0.0E+00 | 0.0E+00 |
| 267 | 0.0E+00 | 0.0E+00 | 0.0E+00 | 0.0E+00 | 0.0E+00 | 0.0E+00 |
| 268 | 9.2E−05 | 1.6E−04 | 6.5E−05 | 4.1E−05 | 4.2E−05 | 1.0E−04 |
| 269 | 0.0E+00 | 3.4E−05 | 1.6E−05 | 2.4E−05 | 1.3E−05 | 0.0E+00 |
| 270 | 0.0E+00 | 0.0E+00 | 0.0E+00 | 0.0E+00 | 0.0E+00 | 0.0E+00 |
| 271 | 9.9E−03 | 1.5E−02 | 2.5E−02 | 1.7E−02 | 1.3E−02 | 2.4E−02 |
| 272 | 2.8E−05 | 2.8E−05 | 2.1E−05 | 0.0E+00 | 8.1E−07 | 5.0E−07 |
| 273 | 0.0E+00 | 0.0E+00 | 0.0E+00 | 5.3E−05 | 0.0E+00 | 0.0E+00 |
| 274 | 0.0E+00 | 0.0E+00 | 0.0E+00 | 0.0E+00 | 0.0E+00 | 0.0E+00 |
| 275 | 0.0E+00 | 0.0E+00 | 0.0E+00 | 0.0E+00 | 0.0E+00 | 0.0E+00 |
| 276 | 0.0E+00 | 0.0E+00 | 0.0E+00 | 0.0E+00 | 0.0E+00 | 0.0E+00 |
| 277 | 6.3E−05 | 4.6E−06 | 4.0E−05 | 8.6E−05 | 3.8E−05 | 0.0E+00 |
| 278 | 0.0E+00 | 0.0E+00 | 0.0E+00 | 0.0E+00 | 0.0E+00 | 0.0E+00 |
| 279 | 0.0E+00 | 0.0E+00 | 0.0E+00 | 0.0E+00 | 0.0E+00 | 0.0E+00 |
| 280 | 0.0E+00 | 0.0E+00 | 0.0E+00 | 0.0E+00 | 0.0E+00 | 0.0E+00 |
| 281 | 0.0E+00 | 0.0E+00 | 0.0E+00 | 0.0E+00 | 0.0E+00 | 2.0E−06 |
| 282 | 0.0E+00 | 6.6E−07 | 0.0E+00 | 0.0E+00 | 0.0E+00 | 0.0E+00 |
| 283 | 0.0E+00 | 0.0E+00 | 0.0E+00 | 4.5E−06 | 0.0E+00 | 0.0E+00 |
| 284 | 0.0E+00 | 0.0E+00 | 0.0E+00 | 0.0E+00 | 0.0E+00 | 0.0E+00 |
| 285 | 0.0E+00 | 0.0E+00 | 0.0E+00 | 0.0E+00 | 0.0E+00 | 0.0E+00 |
| 286 | 0.0E+00 | 0.0E+00 | 0.0E+00 | 0.0E+00 | 0.0E+00 | 0.0E+00 |
| 287 | 0.0E+00 | 0.0E+00 | 0.0E+00 | 5.6E−06 | 0.0E+00 | 0.0E+00 |
| 288 | 0.0E+00 | 0.0E+00 | 0.0E+00 | 0.0E+00 | 4.1E−07 | 0.0E+00 |
| 289 | 0.0E+00 | 0.0E+00 | 0.0E+00 | 0.0E+00 | 0.0E+00 | 0.0E+00 |
| 290 | 0.0E+00 | 2.0E−06 | 0.0E+00 | 0.0E+00 | 0.0E+00 | 0.0E+00 |
| 291 | 3.7E−06 | 5.9E−06 | 1.5E−05 | 0.0E+00 | 0.0E+00 | 0.0E+00 |
| 292 | 0.0E+00 | 0.0E+00 | 0.0E+00 | 0.0E+00 | 0.0E+00 | 0.0E+00 |
| 293 | 2.2E−05 | 8.3E−05 | 6.9E−05 | 1.6E−05 | 5.3E−06 | 2.0E−06 |
| 294 | 0.0E+00 | 0.0E+00 | 0.0E+00 | 1.0E−05 | 0.0E+00 | 0.0E+00 |
| 295 | 2.8E−04 | 4.4E−04 | 4.7E−04 | 3.1E−04 | 1.9E−04 | 9.4E−04 |
| 296 | 1.4E−06 | 1.3E−06 | 7.6E−07 | 1.7E−05 | 2.4E−06 | 0.0E+00 |
| 297 | 0.0E+00 | 0.0E+00 | 0.0E+00 | 0.0E+00 | 0.0E+00 | 0.0E+00 |
| 298 | 0.0E+00 | 0.0E+00 | 0.0E+00 | 0.0E+00 | 0.0E+00 | 0.0E+00 |
| 299 | 1.4E−06 | 6.6E−07 | 0.0E+00 | 0.0E+00 | 4.1E−07 | 5.0E−07 |
| 300 | 0.0E+00 | 0.0E+00 | 0.0E+00 | 0.0E+00 | 0.0E+00 | 0.0E+00 |
| 301 | 4.6E−06 | 7.9E−06 | 3.1E−06 | 1.7E−06 | 4.1E−07 | 2.5E−06 |
| 302 | 0.0E+00 | 0.0E+00 | 0.0E+00 | 0.0E+00 | 0.0E+00 | 0.0E+00 |
| 303 | 0.0E+00 | 6.6E−07 | 0.0E+00 | 0.0E+00 | 0.0E+00 | 0.0E+00 |
| 304 | 0.0E+00 | 0.0E+00 | 0.0E+00 | 0.0E+00 | 0.0E+00 | 0.0E+00 |
| 305 | 0.0E+00 | 0.0E+00 | 0.0E+00 | 0.0E+00 | 0.0E+00 | 0.0E+00 |
| 306 | 0.0E+00 | 0.0E+00 | 0.0E+00 | 0.0E+00 | 0.0E+00 | 5.0E−07 |
| 307 | 0.0E+00 | 6.6E−07 | 0.0E+00 | 0.0E+00 | 0.0E+00 | 0.0E+00 |
| 308 | 2.6E−05 | 2.4E−05 | 1.2E−05 | 5.6E−07 | 4.1E−07 | 0.0E+00 |
| 309 | 0.0E+00 | 0.0E+00 | 0.0E+00 | 3.9E−06 | 0.0E+00 | 0.0E+00 |
| 310 | 0.0E+00 | 0.0E+00 | 0.0E+00 | 0.0E+00 | 0.0E+00 | 5.0E−07 |
| 311 | 2.8E−06 | 3.3E−06 | 7.6E−07 | 1.1E−06 | 4.1E−07 | 5.0E−07 |
| 312 | 1.7E−03 | 9.3E−04 | 1.4E−04 | 2.8E−06 | 0.0E+00 | 0.0E+00 |
| 313 | 0.0E+00 | 7.9E−06 | 0.0E+00 | 0.0E+00 | 0.0E+00 | 0.0E+00 |
| 314 | 1.9E−03 | 2.8E−03 | 3.8E−03 | 1.7E−06 | 4.1E−07 | 5.0E−07 |
| 315 | 3.4E−03 | 6.5E−02 | 1.4E−02 | 2.3E−05 | 1.9E−05 | 9.9E−06 |
| 316 | 5.6E−05 | 6.1E−04 | 5.2E−04 | 0.0E+00 | 4.1E−07 | 0.0E+00 |
| 317 | 2.7E−05 | 6.6E−07 | 1.1E−05 | 0.0E+00 | 0.0E+00 | 0.0E+00 |
| 318 | 1.4E−06 | 0.0E+00 | 0.0E+00 | 0.0E+00 | 0.0E+00 | 0.0E+00 |
| 319 | 9.2E−07 | 2.0E−06 | 3.1E−06 | 0.0E+00 | 0.0E+00 | 0.0E+00 |
| 320 | 8.4E−05 | 3.4E−05 | 3.4E−05 | 4.6E−05 | 3.3E−05 | 6.0E−06 |
| 321 | 0.0E+00 | 0.0E+00 | 7.6E−07 | 0.0E+00 | 0.0E+00 | 0.0E+00 |
| 322 | 2.8E−06 | 1.3E−06 | 3.8E−06 | 5.6E−07 | 0.0E+00 | 0.0E+00 |
| 323 | 6.4E−05 | 3.8E−05 | 4.9E−05 | 5.6E−07 | 0.0E+00 | 0.0E+00 |
| 324 | 9.2E−07 | 0.0E+00 | 7.6E−07 | 0.0E+00 | 0.0E+00 | 0.0E+00 |
| 325 | 6.5E−02 | 7.4E−02 | 3.9E−02 | 7.2E−06 | 7.7E−06 | 9.4E−06 |
| 326 | 4.9E−03 | 2.0E−02 | 2.5E−02 | 2.2E−06 | 2.0E−06 | 2.0E−06 |
| 327 | 2.8E−06 | 1.1E−05 | 1.5E−06 | 0.0E+00 | 0.0E+00 | 5.0E−07 |
| 328 | 1.8E−06 | 2.0E−06 | 1.5E−06 | 0.0E+00 | 0.0E+00 | 0.0E+00 |

-continued

| | | | | | | |
|---|---|---|---|---|---|---|
| 329 | 0.0E+00 | 0.0E+00 | 0.0E+00 | 0.0E+00 | 0.0E+00 | 0.0E+00 |
| 330 | 0.0E+00 | 6.6E−07 | 0.0E+00 | 0.0E+00 | 0.0E+00 | 0.0E+00 |
| 331 | 1.4E−06 | 6.6E−06 | 1.5E−06 | 3.9E−06 | 4.9E−06 | 7.0E−06 |
| 332 | 5.0E−05 | 6.6E−07 | 0.0E+00 | 3.6E−05 | 1.7E−05 | 2.4E−05 |
| 333 | 0.0E+00 | 0.0E+00 | 0.0E+00 | 0.0E+00 | 0.0E+00 | 0.0E+00 |
| 334 | 2.8E−05 | 3.9E−05 | 1.5E−05 | 1.4E−05 | 1.9E−05 | 9.2E−05 |
| 335 | 2.3E−06 | 7.2E−06 | 3.1E−06 | 5.6E−07 | 8.1E−07 | 3.0E−06 |
| 336 | 0.0E+00 | 0.0E+00 | 0.0E+00 | 0.0E+00 | 0.0E+00 | 0.0E+00 |
| 337 | 2.1E−02 | 1.1E−04 | 1.3E−04 | 1.0E−04 | 6.9E−05 | 7.2E−05 |
| 338 | 2.8E−06 | 7.2E−06 | 1.6E−05 | 9.5E−06 | 7.7E−06 | 2.5E−05 |
| 339 | 0.0E+00 | 0.0E+00 | 0.0E+00 | 0.0E+00 | 1.2E−06 | 0.0E+00 |
| 340 | 9.2E−07 | 3.3E−06 | 3.1E−06 | 0.0E+00 | 5.3E−06 | 0.0E+00 |
| 341 | 0.0E+00 | 0.0E+00 | 0.0E+00 | 0.0E+00 | 0.0E+00 | 0.0E+00 |
| 342 | 0.0E+00 | 0.0E+00 | 0.0E+00 | 0.0E+00 | 4.1E−07 | 0.0E+00 |
| 343 | 0.0E+00 | 0.0E+00 | 0.0E+00 | 0.0E+00 | 0.0E+00 | 0.0E+00 |
| 344 | 0.0E+00 | 6.6E−07 | 0.0E+00 | 0.0E+00 | 0.0E+00 | 1.5E−06 |
| 345 | 0.0E+00 | 0.0E+00 | 0.0E+00 | 0.0E+00 | 0.0E+00 | 0.0E+00 |
| 346 | 0.0E+00 | 0.0E+00 | 0.0E+00 | 0.0E+00 | 0.0E+00 | 0.0E+00 |
| 347 | 4.2E−06 | 5.9E−06 | 1.2E−05 | 5.6E−07 | 3.6E−06 | 2.5E−06 |
| 348 | 0.0E+00 | 0.0E+00 | 0.0E+00 | 0.0E+00 | 0.0E+00 | 0.0E+00 |
| 349 | 3.2E−06 | 0.0E+00 | 0.0E+00 | 3.3E−05 | 4.1E−07 | 5.0E−07 |
| 350 | 0.0E+00 | 0.0E+00 | 0.0E+00 | 0.0E+00 | 0.0E+00 | 0.0E+00 |
| 351 | 6.9E−06 | 4.6E−06 | 4.6E−06 | 1.2E−05 | 4.1E−07 | 2.0E−06 |
| 352 | 0.0E+00 | 0.0E+00 | 4.6E−06 | 0.0E+00 | 0.0E+00 | 5.0E−07 |
| 353 | 0.0E+00 | 0.0E+00 | 0.0E+00 | 0.0E+00 | 0.0E+00 | 0.0E+00 |
| 354 | 9.2E−07 | 0.0E+00 | 7.6E−07 | 3.3E−06 | 8.1E−07 | 1.5E−06 |
| 355 | 0.0E+00 | 0.0E+00 | 0.0E+00 | 3.0E−05 | 0.0E+00 | 0.0E+00 |
| 356 | 0.0E+00 | 0.0E+00 | 0.0E+00 | 0.0E+00 | 0.0E+00 | 0.0E+00 |
| 357 | 1.8E−04 | 2.0E−06 | 0.0E+00 | 5.6E−07 | 8.1E−07 | 5.0E−07 |
| 358 | 1.4E−06 | 0.0E+00 | 0.0E+00 | 0.0E+00 | 0.0E+00 | 0.0E+00 |
| 359 | 0.0E+00 | 1.3E−06 | 0.0E+00 | 1.4E−04 | 0.0E+00 | 0.0E+00 |
| 360 | 0.0E+00 | 0.0E+00 | 0.0E+00 | 0.0E+00 | 0.0E+00 | 0.0E+00 |
| 361 | 3.2E−04 | 1.7E−04 | 5.4E−04 | 0.0E+00 | 0.0E+00 | 0.0E+00 |
| 362 | 0.0E+00 | 3.3E−06 | 0.0E+00 | 7.0E−05 | 0.0E+00 | 2.0E−06 |
| 363 | 0.0E+00 | 0.0E+00 | 0.0E+00 | 0.0E+00 | 0.0E+00 | 0.0E+00 |
| 364 | 0.0E+00 | 0.0E+00 | 0.0E+00 | 1.1E−06 | 4.1E−07 | 1.5E−06 |
| 365 | 9.2E−07 | 0.0E+00 | 0.0E+00 | 2.9E−04 | 5.2E−05 | 2.5E−04 |
| 366 | 0.0E+00 | 0.0E+00 | 0.0E+00 | 1.1E−06 | 8.1E−07 | 3.5E−06 |
| 367 | 0.0E+00 | 3.3E−06 | 0.0E+00 | 2.2E−06 | 0.0E+00 | 5.0E−07 |
| 368 | 1.8E−05 | 6.0E−05 | 1.2E−05 | 3.3E−06 | 0.0E+00 | 3.5E−06 |
| 369 | 0.0E+00 | 6.6E−07 | 0.0E+00 | 5.0E−06 | 8.1E−07 | 2.5E−06 |
| 370 | 0.0E+00 | 7.8E−04 | 0.0E+00 | 0.0E+00 | 0.0E+00 | 0.0E+00 |
| 371 | 0.0E+00 | 1.3E−06 | 7.6E−06 | 4.0E−05 | 1.9E−04 | 0.0E+00 |
| 372 | 5.1E−05 | 1.5E−04 | 1.8E−05 | 0.0E+00 | 0.0E+00 | 0.0E+00 |
| 373 | 3.9E−04 | 8.1E−04 | 7.2E−04 | 8.9E−06 | 1.0E−05 | 1.2E−05 |
| 374 | 0.0E+00 | 0.0E+00 | 0.0E+00 | 0.0E+00 | 0.0E+00 | 0.0E+00 |
| 375 | 9.2E−07 | 0.0E+00 | 0.0E+00 | 2.2E−06 | 0.0E+00 | 0.0E+00 |
| 376 | 4.6E−07 | 0.0E+00 | 0.0E+00 | 0.0E+00 | 0.0E+00 | 0.0E+00 |
| 377 | 0.0E+00 | 6.6E−07 | 0.0E+00 | 5.6E−07 | 8.1E−07 | 9.9E−07 |
| 378 | 1.2E−05 | 2.4E−05 | 3.7E−05 | 6.7E−06 | 1.1E−05 | 4.7E−05 |

| Taxon ID | CM Atm−/− Small Intestine | | | | | |
|---|---|---|---|---|---|---|
| 1 | 1.0E−03 | 9.4E−03 | 9.2E−04 | 9.1E−05 | 5.8E−03 | 6.3E−03 | 4.9E−03 |
| 2 | 0.0E+00 | 0.0E+00 | 0.0E+00 | 0.0E+00 | 0.0E+00 | 0.0E+00 | 0.0E+00 |
| 3 | 3.1E−07 | 2.2E−06 | 0.0E+00 | 0.0E+00 | 6.8E−07 | 0.0E+00 | 4.3E−07 |
| 4 | 0.0E+00 | 0.0E+00 | 1.9E−05 | 2.6E−07 | 3.5E−05 | 4.0E−05 | 1.3E−06 |
| 5 | 0.0E+00 | 0.0E+00 | 0.0E+00 | 0.0E+00 | 0.0E+00 | 0.0E+00 | 0.0E+00 |
| 6 | 0.0E+00 | 0.0E+00 | 9.6E−06 | 0.0E+00 | 0.0E+00 | 0.0E+00 | 0.0E+00 |
| 7 | 2.8E−06 | 9.0E−05 | 7.3E−06 | 5.2E−07 | 1.6E−04 | 2.8E−05 | 0.0E+00 |
| 8 | 1.6E−06 | 3.5E−05 | 1.9E−06 | 0.0E+00 | 6.8E−07 | 1.6E−05 | 0.0E+00 |
| 9 | 6.3E−07 | 0.0E+00 | 0.0E+00 | 0.0E+00 | 3.1E−05 | 3.4E−05 | 0.0E+00 |
| 10 | 1.9E−06 | 0.0E+00 | 3.8E−06 | 0.0E+00 | 2.3E−05 | 4.1E−05 | 3.8E−06 |
| 11 | 0.0E+00 | 0.0E+00 | 0.0E+00 | 0.0E+00 | 0.0E+00 | 2.4E−05 | 0.0E+00 |
| 12 | 0.0E+00 | 0.0E+00 | 0.0E+00 | 0.0E+00 | 0.0E+00 | 0.0E+00 | 0.0E+00 |
| 13 | 0.0E+00 | 0.0E+00 | 0.0E+00 | 0.0E+00 | 0.0E+00 | 0.0E+00 | 0.0E+00 |
| 14 | 0.0E+00 | 2.3E−05 | 3.8E−07 | 2.6E−07 | 0.0E+00 | 1.2E−05 | 0.0E+00 |
| 15 | 0.0E+00 | 0.0E+00 | 0.0E+00 | 0.0E+00 | 0.0E+00 | 8.2E−06 | 0.0E+00 |
| 16 | 4.8E−05 | 0.0E+00 | 3.8E−07 | 0.0E+00 | 6.1E−06 | 0.0E+00 | 3.8E−06 |
| 17 | 0.0E+00 | 0.0E+00 | 1.5E−06 | 0.0E+00 | 3.4E−06 | 1.9E−06 | 8.1E−06 |
| 18 | 0.0E+00 | 0.0E+00 | 0.0E+00 | 0.0E+00 | 0.0E+00 | 0.0E+00 | 0.0E+00 |
| 19 | 0.0E+00 | 0.0E+00 | 0.0E+00 | 0.0E+00 | 0.0E+00 | 0.0E+00 | 0.0E+00 |
| 20 | 0.0E+00 | 1.3E−06 | 0.0E+00 | 0.0E+00 | 6.1E−06 | 1.3E−06 | 2.1E−06 |
| 21 | 6.3E−06 | 2.4E−05 | 1.5E−05 | 0.0E+00 | 6.5E−05 | 3.2E−05 | 1.7E−04 |
| 22 | 0.0E+00 | 0.0E+00 | 0.0E+00 | 0.0E+00 | 0.0E+00 | 0.0E+00 | 0.0E+00 |
| 23 | 0.0E+00 | 2.8E−05 | 7.7E−07 | 0.0E+00 | 0.0E+00 | 0.0E+00 | 0.0E+00 |
| 24 | 0.0E+00 | 3.1E−06 | 0.0E+00 | 0.0E+00 | 3.4E−06 | 0.0E+00 | 2.6E−06 |
| 25 | 0.0E+00 | 0.0E+00 | 0.0E+00 | 0.0E+00 | 0.0E+00 | 1.8E−05 | 0.0E+00 |

-continued

| | | | | | | | |
|---|---|---|---|---|---|---|---|
| 26 | 0.0E+00 | 0.0E+00 | 5.8E−06 | 0.0E+00 | 0.0E+00 | 0.0E+00 | 0.0E+00 |
| 27 | 0.0E+00 | 0.0E+00 | 3.8E−07 | 0.0E+00 | 0.0E+00 | 6.3E−07 | 8.5E−07 |
| 28 | 0.0E+00 | 0.0E+00 | 0.0E+00 | 0.0E+00 | 0.0E+00 | 0.0E+00 | 0.0E+00 |
| 29 | 0.0E+00 | 4.0E−06 | 0.0E+00 | 0.0E+00 | 0.0E+00 | 0.0E+00 | 0.0E+00 |
| 30 | 0.0E+00 | 0.0E+00 | 0.0E+00 | 0.0E+00 | 2.7E−06 | 1.9E−06 | 0.0E+00 |
| 31 | 0.0E+00 | 0.0E+00 | 3.8E−07 | 0.0E+00 | 1.4E−06 | 0.0E+00 | 9.0E−06 |
| 32 | 0.0E+00 | 0.0E+00 | 0.0E+00 | 0.0E+00 | 0.0E+00 | 0.0E+00 | 0.0E+00 |
| 33 | 6.3E−06 | 1.2E−05 | 4.6E−06 | 5.2E−07 | 1.8E−05 | 5.0E−05 | 6.8E−06 |
| 34 | 0.0E+00 | 0.0E+00 | 0.0E+00 | 0.0E+00 | 0.0E+00 | 0.0E+00 | 0.0E+00 |
| 35 | 0.0E+00 | 8.9E−06 | 3.1E−06 | 0.0E+00 | 4.8E−06 | 1.8E−05 | 1.3E−06 |
| 36 | 0.0E+00 | 0.0E+00 | 0.0E+00 | 0.0E+00 | 0.0E+00 | 0.0E+00 | 0.0E+00 |
| 37 | 0.0E+00 | 0.0E+00 | 0.0E+00 | 0.0E+00 | 0.0E+00 | 0.0E+00 | 0.0E+00 |
| 38 | 0.0E+00 | 0.0E+00 | 0.0E+00 | 0.0E+00 | 0.0E+00 | 0.0E+00 | 0.0E+00 |
| 39 | 0.0E+00 | 0.0E+00 | 0.0E+00 | 0.0E+00 | 0.0E+00 | 0.0E+00 | 0.0E+00 |
| 40 | 0.0E+00 | 0.0E+00 | 0.0E+00 | 2.6E−07 | 8.5E−05 | 8.2E−06 | 0.0E+00 |
| 41 | 0.0E+00 | 0.0E+00 | 0.0E+00 | 0.0E+00 | 0.0E+00 | 0.0E+00 | 0.0E+00 |
| 42 | 0.0E+00 | 0.0E+00 | 0.0E+00 | 0.0E+00 | 0.0E+00 | 0.0E+00 | 0.0E+00 |
| 43 | 0.0E+00 | 0.0E+00 | 7.7E−07 | 0.0E+00 | 0.0E+00 | 0.0E+00 | 0.0E+00 |
| 44 | 0.0E+00 | 0.0E+00 | 2.3E−06 | 0.0E+00 | 2.7E−06 | 2.5E−06 | 0.0E+00 |
| 45 | 9.1E−06 | 0.0E+00 | 0.0E+00 | 0.0E+00 | 3.4E−06 | 0.0E+00 | 3.0E−06 |
| 46 | 0.0E+00 | 0.0E+00 | 0.0E+00 | 0.0E+00 | 0.0E+00 | 0.0E+00 | 0.0E+00 |
| 47 | 0.0E+00 | 1.3E−06 | 0.0E+00 | 0.0E+00 | 6.8E−07 | 0.0E+00 | 2.6E−06 |
| 48 | 3.1E−07 | 4.4E−07 | 3.8E−07 | 0.0E+00 | 0.0E+00 | 6.3E−07 | 1.7E−06 |
| 49 | 0.0E+00 | 0.0E+00 | 0.0E+00 | 0.0E+00 | 0.0E+00 | 0.0E+00 | 0.0E+00 |
| 50 | 6.9E−06 | 1.9E−04 | 1.5E−05 | 0.0E+00 | 5.7E−05 | 8.3E−05 | 6.7E−05 |
| 51 | 0.0E+00 | 0.0E+00 | 5.0E−06 | 0.0E+00 | 0.0E+00 | 0.0E+00 | 2.1E−06 |
| 52 | 0.0E+00 | 0.0E+00 | 3.1E−06 | 0.0E+00 | 3.1E−04 | 3.8E−06 | 4.3E−06 |
| 53 | 0.0E+00 | 0.0E+00 | 0.0E+00 | 0.0E+00 | 0.0E+00 | 8.3E−05 | 0.0E+00 |
| 54 | 0.0E+00 | 4.7E−05 | 0.0E+00 | 0.0E+00 | 6.8E−06 | 3.1E−06 | 3.4E−06 |
| 55 | 9.4E−07 | 1.3E−04 | 6.5E−06 | 0.0E+00 | 5.6E−05 | 3.1E−06 | 4.8E−05 |
| 56 | 0.0E+00 | 0.0E+00 | 0.0E+00 | 0.0E+00 | 0.0E+00 | 9.4E−06 | 0.0E+00 |
| 57 | 0.0E+00 | 0.0E+00 | 0.0E+00 | 0.0E+00 | 0.0E+00 | 0.0E+00 | 0.0E+00 |
| 58 | 1.7E−04 | 2.6E−03 | 6.7E−04 | 1.2E−05 | 3.3E−03 | 2.4E−03 | 9.4E−03 |
| 59 | 1.3E−06 | 4.7E−04 | 1.4E−03 | 0.0E+00 | 1.1E−02 | 1.3E−02 | 1.2E−02 |
| 60 | 9.7E−06 | 1.6E−04 | 2.1E−03 | 5.2E−06 | 1.3E−02 | 4.0E−02 | 5.1E−03 |
| 61 | 9.4E−07 | 2.4E−05 | 5.0E−06 | 0.0E+00 | 2.3E−04 | 3.4E−05 | 1.1E−04 |
| 62 | 5.7E−05 | 1.2E−03 | 5.3E−04 | 3.1E−06 | 5.4E−04 | 1.3E−04 | 6.6E−04 |
| 63 | 0.0E+00 | 8.9E−06 | 1.5E−06 | 0.0E+00 | 6.6E−05 | 9.2E−05 | 1.1E−04 |
| 64 | 5.3E−05 | 5.5E−05 | 1.6E−04 | 1.0E−05 | 5.0E−03 | 3.0E−04 | 1.9E−03 |
| 65 | 6.3E−06 | 7.1E−04 | 1.4E−04 | 7.8E−07 | 6.7E−02 | 2.4E−05 | 3.9E−02 |
| 66 | 1.6E−06 | 4.4E−04 | 2.3E−04 | 0.0E+00 | 2.2E−03 | 2.7E−03 | 2.0E−03 |
| 67 | 6.2E−05 | 5.8E−04 | 2.4E−04 | 6.5E−06 | 4.4E−03 | 8.5E−04 | 3.0E−03 |
| 68 | 0.0E+00 | 0.0E+00 | 1.2E−06 | 0.0E+00 | 1.4E−06 | 6.3E−07 | 0.0E+00 |
| 69 | 0.0E+00 | 3.6E−06 | 7.7E−04 | 2.6E−07 | 9.6E−06 | 1.1E−05 | 8.5E−06 |
| 70 | 0.0E+00 | 4.4E−07 | 7.7E−07 | 0.0E+00 | 2.2E−05 | 7.5E−06 | 3.4E−06 |
| 71 | 3.1E−07 | 2.2E−06 | 3.8E−07 | 0.0E+00 | 4.5E−05 | 2.9E−05 | 6.0E−05 |
| 72 | 0.0E+00 | 0.0E+00 | 0.0E+00 | 0.0E+00 | 0.0E+00 | 6.3E−07 | 8.5E−07 |
| 73 | 0.0E+00 | 0.0E+00 | 0.0E+00 | 0.0E+00 | 1.4E−06 | 6.3E−07 | 0.0E+00 |
| 74 | 0.0E+00 | 4.4E−07 | 1.9E−06 | 0.0E+00 | 2.0E−06 | 6.3E−07 | 4.3E−06 |
| 75 | 1.3E−06 | 0.0E+00 | 1.2E−06 | 0.0E+00 | 6.4E−05 | 4.4E−06 | 6.8E−06 |
| 76 | 1.6E−06 | 2.8E−04 | 1.9E−04 | 7.8E−07 | 2.1E−03 | 1.1E−03 | 1.2E−03 |
| 77 | 0.0E+00 | 6.2E−06 | 1.2E−06 | 0.0E+00 | 2.3E−05 | 1.9E−05 | 3.1E−05 |
| 78 | 0.0E+00 | 4.4E−07 | 3.8E−07 | 0.0E+00 | 4.8E−06 | 9.4E−06 | 8.5E−07 |
| 79 | 1.3E−06 | 3.6E−06 | 7.5E−04 | 2.3E−06 | 3.5E−03 | 2.1E−02 | 4.4E−04 |
| 80 | 1.6E−05 | 5.1E−05 | 0.0E+00 | 0.0E+00 | 0.0E+00 | 3.1E−06 | 0.0E+00 |
| 81 | 0.0E+00 | 0.0E+00 | 0.0E+00 | 0.0E+00 | 1.4E−06 | 1.3E−06 | 9.4E−06 |
| 82 | 1.3E−05 | 2.0E−02 | 2.1E−02 | 6.7E−06 | 2.5E−02 | 2.2E−01 | 5.5E−02 |
| 83 | 1.7E−05 | 1.9E−04 | 2.3E−04 | 6.0E−06 | 4.6E−03 | 4.0E−04 | 1.0E−03 |
| 84 | 0.0E+00 | 0.0E+00 | 0.0E+00 | 0.0E+00 | 0.0E+00 | 0.0E+00 | 0.0E+00 |
| 85 | 1.5E−05 | 1.2E−04 | 1.9E−03 | 3.4E−06 | 8.2E−03 | 3.4E−02 | 2.9E−03 |
| 86 | 1.4E−04 | 1.8E−02 | 1.9E−03 | 6.6E−05 | 2.0E−01 | 1.9E−01 | 2.4E−01 |
| 87 | 0.0E+00 | 8.9E−07 | 0.0E+00 | 0.0E+00 | 9.6E−06 | 6.9E−06 | 1.5E−05 |
| 88 | 3.1E−07 | 7.0E−04 | 7.0E−05 | 0.0E+00 | 6.8E−07 | 6.3E−07 | 4.3E−07 |
| 89 | 1.9E−06 | 5.3E−06 | 1.2E−05 | 0.0E+00 | 5.0E−05 | 7.5E−05 | 4.3E−07 |
| 90 | 5.6E−06 | 0.0E+00 | 3.8E−07 | 0.0E+00 | 9.8E−05 | 6.3E−07 | 2.3E−05 |
| 91 | 7.5E−06 | 2.7E−04 | 3.8E−07 | 0.0E+00 | 6.0E−05 | 0.0E+00 | 9.8E−06 |
| 92 | 0.0E+00 | 0.0E+00 | 0.0E+00 | 0.0E+00 | 0.0E+00 | 6.3E−07 | 0.0E+00 |
| 93 | 0.0E+00 | 0.0E+00 | 0.0E+00 | 2.6E−07 | 0.0E+00 | 0.0E+00 | 0.0E+00 |
| 94 | 9.1E−06 | 1.3E−03 | 2.0E−03 | 5.7E−06 | 2.7E−02 | 3.0E−02 | 2.2E−02 |
| 95 | 0.0E+00 | 0.0E+00 | 0.0E+00 | 0.0E+00 | 1.4E−06 | 0.0E+00 | 8.5E−07 |
| 96 | 6.3E−07 | 1.3E−05 | 1.4E−04 | 1.0E−06 | 1.0E−03 | 5.6E−04 | 1.5E−03 |
| 97 | 1.6E−06 | 4.3E−03 | 8.4E−04 | 2.6E−07 | 0.0E+00 | 2.4E−05 | 6.5E−03 |
| 98 | 5.3E−06 | 4.7E−05 | 2.0E−05 | 0.0E+00 | 2.9E−05 | 1.0E−03 | 3.5E−05 |
| 99 | 0.0E+00 | 0.0E+00 | 7.7E−07 | 0.0E+00 | 0.0E+00 | 5.0E−06 | 3.4E−06 |
| 100 | 0.0E+00 | 0.0E+00 | 0.0E+00 | 0.0E+00 | 0.0E+00 | 0.0E+00 | 0.0E+00 |
| 101 | 0.0E+00 | 9.3E−05 | 0.0E+00 | 0.0E+00 | 5.5E−05 | 1.2E−05 | 7.7E−05 |
| 102 | 0.0E+00 | 0.0E+00 | 7.7E−07 | 0.0E+00 | 0.0E+00 | 0.0E+00 | 0.0E+00 |
| 103 | 0.0E+00 | 1.3E−06 | 0.0E+00 | 0.0E+00 | 0.0E+00 | 0.0E+00 | 0.0E+00 |
| 104 | 0.0E+00 | 0.0E+00 | 0.0E+00 | 0.0E+00 | 0.0E+00 | 0.0E+00 | 0.0E+00 |

-continued

| | | | | | | | |
|---|---|---|---|---|---|---|---|
| 105 | 4.8E−05 | 9.4E−04 | 3.0E−05 | 7.8E−07 | 3.6E−04 | 5.7E−05 | 2.9E−04 |
| 106 | 0.0E+00 | 8.9E−07 | 0.0E+00 | 0.0E+00 | 3.4E−06 | 0.0E+00 | 0.0E+00 |
| 107 | 0.0E+00 | 0.0E+00 | 4.2E−06 | 0.0E+00 | 1.3E−05 | 8.8E−06 | 1.1E−05 |
| 108 | 0.0E+00 | 0.0E+00 | 0.0E+00 | 0.0E+00 | 0.0E+00 | 0.0E+00 | 0.0E+00 |
| 109 | 0.0E+00 | 2.7E−06 | 0.0E+00 | 0.0E+00 | 2.0E−06 | 0.0E+00 | 1.7E−06 |
| 110 | 0.0E+00 | 0.0E+00 | 5.8E−06 | 0.0E+00 | 2.7E−05 | 0.0E+00 | 0.0E+00 |
| 111 | 0.0E+00 | 0.0E+00 | 0.0E+00 | 0.0E+00 | 0.0E+00 | 0.0E+00 | 0.0E+00 |
| 112 | 0.0E+00 | 0.0E+00 | 0.0E+00 | 0.0E+00 | 0.0E+00 | 0.0E+00 | 0.0E+00 |
| 113 | 1.3E−06 | 1.8E−06 | 0.0E+00 | 0.0E+00 | 0.0E+00 | 0.0E+00 | 4.3E−07 |
| 114 | 2.8E−06 | 0.0E+00 | 6.5E−06 | 0.0E+00 | 9.6E−06 | 5.0E−06 | 0.0E+00 |
| 115 | 9.1E−06 | 3.0E−05 | 1.1E−04 | 0.0E+00 | 4.8E−06 | 1.1E−04 | 7.4E−04 |
| 116 | 0.0E+00 | 0.0E+00 | 0.0E+00 | 0.0E+00 | 0.0E+00 | 0.0E+00 | 0.0E+00 |
| 117 | 0.0E+00 | 0.0E+00 | 6.1E−06 | 0.0E+00 | 0.0E+00 | 0.0E+00 | 0.0E+00 |
| 118 | 0.0E+00 | 0.0E+00 | 0.0E+00 | 0.0E+00 | 0.0E+00 | 0.0E+00 | 0.0E+00 |
| 119 | 0.0E+00 | 0.0E+00 | 5.0E−06 | 0.0E+00 | 0.0E+00 | 0.0E+00 | 0.0E+00 |
| 120 | 4.7E−06 | 1.0E−04 | 4.6E−06 | 0.0E+00 | 5.3E−04 | 1.3E−05 | 6.4E−06 |
| 121 | 0.0E+00 | 8.9E−07 | 3.8E−06 | 0.0E+00 | 0.0E+00 | 0.0E+00 | 8.5E−07 |
| 122 | 0.0E+00 | 5.8E−06 | 0.0E+00 | 0.0E+00 | 5.5E−06 | 6.9E−05 | 4.3E−04 |
| 123 | 1.7E−05 | 3.6E−05 | 0.0E+00 | 0.0E+00 | 3.1E−05 | 6.3E−07 | 2.1E−05 |
| 124 | 0.0E+00 | 0.0E+00 | 0.0E+00 | 0.0E+00 | 0.0E+00 | 0.0E+00 | 0.0E+00 |
| 125 | 0.0E+00 | 9.8E−06 | 3.8E−07 | 0.0E+00 | 0.0E+00 | 0.0E+00 | 1.5E−04 |
| 126 | 3.4E−06 | 0.0E+00 | 1.2E−05 | 0.0E+00 | 0.0E+00 | 0.0E+00 | 0.0E+00 |
| 127 | 0.0E+00 | 0.0E+00 | 1.0E−05 | 0.0E+00 | 0.0E+00 | 4.5E−05 | 0.0E+00 |
| 128 | 1.2E−04 | 2.0E−04 | 1.6E−04 | 7.8E−07 | 2.9E−05 | 9.4E−05 | 5.8E−05 |
| 129 | 3.1E−07 | 1.8E−06 | 0.0E+00 | 0.0E+00 | 6.8E−07 | 0.0E+00 | 1.7E−06 |
| 130 | 0.0E+00 | 0.0E+00 | 0.0E+00 | 0.0E+00 | 0.0E+00 | 0.0E+00 | 0.0E+00 |
| 131 | 0.0E+00 | 0.0E+00 | 0.0E+00 | 0.0E+00 | 0.0E+00 | 0.0E+00 | 0.0E+00 |
| 132 | 0.0E+00 | 0.0E+00 | 0.0E+00 | 0.0E+00 | 1.9E−05 | 0.0E+00 | 0.0E+00 |
| 133 | 0.0E+00 | 0.0E+00 | 0.0E+00 | 0.0E+00 | 0.0E+00 | 0.0E+00 | 0.0E+00 |
| 134 | 6.1E−03 | 1.6E−02 | 2.9E−03 | 2.6E−07 | 4.1E−03 | 1.1E−04 | 6.0E−03 |
| 135 | 0.0E+00 | 0.0E+00 | 0.0E+00 | 0.0E+00 | 0.0E+00 | 0.0E+00 | 0.0E+00 |
| 136 | 0.0E+00 | 0.0E+00 | 0.0E+00 | 0.0E+00 | 0.0E+00 | 4.4E−06 | 0.0E+00 |
| 137 | 0.0E+00 | 0.0E+00 | 0.0E+00 | 0.0E+00 | 0.0E+00 | 0.0E+00 | 0.0E+00 |
| 138 | 0.0E+00 | 0.0E+00 | 0.0E+00 | 0.0E+00 | 0.0E+00 | 0.0E+00 | 0.0E+00 |
| 139 | 0.0E+00 | 2.7E−06 | 1.4E−05 | 2.6E−07 | 6.8E−06 | 0.0E+00 | 3.1E−05 |
| 140 | 2.4E−05 | 3.5E−04 | 5.0E−06 | 0.0E+00 | 1.5E−05 | 1.6E−04 | 3.1E−04 |
| 141 | 0.0E+00 | 0.0E+00 | 0.0E+00 | 0.0E+00 | 0.0E+00 | 0.0E+00 | 0.0E+00 |
| 142 | 0.0E+00 | 0.0E+00 | 0.0E+00 | 0.0E+00 | 2.5E−04 | 0.0E+00 | 0.0E+00 |
| 143 | 0.0E+00 | 0.0E+00 | 0.0E+00 | 0.0E+00 | 1.5E−05 | 0.0E+00 | 0.0E+00 |
| 144 | 0.0E+00 | 0.0E+00 | 0.0E+00 | 0.0E+00 | 0.0E+00 | 0.0E+00 | 0.0E+00 |
| 145 | 0.0E+00 | 2.2E−06 | 0.0E+00 | 0.0E+00 | 0.0E+00 | 0.0E+00 | 0.0E+00 |
| 146 | 0.0E+00 | 0.0E+00 | 3.8E−07 | 5.2E−07 | 0.0E+00 | 0.0E+00 | 0.0E+00 |
| 147 | 0.0E+00 | 0.0E+00 | 0.0E+00 | 0.0E+00 | 0.0E+00 | 0.0E+00 | 0.0E+00 |
| 148 | 5.6E−06 | 4.2E−04 | 3.4E−05 | 4.4E−06 | 1.8E−04 | 2.3E−04 | 9.9E−04 |
| 149 | 0.0E+00 | 0.0E+00 | 0.0E+00 | 0.0E+00 | 0.0E+00 | 0.0E+00 | 0.0E+00 |
| 150 | 0.0E+00 | 8.9E−07 | 7.7E−07 | 2.6E−07 | 1.4E−06 | 3.1E−05 | 1.4E−05 |
| 151 | 0.0E+00 | 0.0E+00 | 0.0E+00 | 0.0E+00 | 0.0E+00 | 0.0E+00 | 6.6E−05 |
| 152 | 0.0E+00 | 0.0E+00 | 0.0E+00 | 0.0E+00 | 0.0E+00 | 0.0E+00 | 0.0E+00 |
| 153 | 3.1E−07 | 0.0E+00 | 0.0E+00 | 0.0E+00 | 0.0E+00 | 0.0E+00 | 0.0E+00 |
| 154 | 1.3E−06 | 4.4E−07 | 2.1E−05 | 5.2E−07 | 6.8E−07 | 4.9E−03 | 1.6E−04 |
| 155 | 4.4E−06 | 0.0E+00 | 6.1E−06 | 0.0E+00 | 5.6E−05 | 1.6E−05 | 1.2E−05 |
| 156 | 2.2E−06 | 2.2E−05 | 1.8E−05 | 5.2E−07 | 6.1E−04 | 9.7E−05 | 0.0E+00 |
| 157 | 0.0E+00 | 0.0E+00 | 0.0E+00 | 0.0E+00 | 0.0E+00 | 6.9E−06 | 4.3E−07 |
| 158 | 0.0E+00 | 0.0E+00 | 0.0E+00 | 0.0E+00 | 0.0E+00 | 0.0E+00 | 0.0E+00 |
| 159 | 3.6E−05 | 4.5E−04 | 3.7E−05 | 5.2E−07 | 1.4E−03 | 7.0E−04 | 0.0E+00 |
| 160 | 6.3E−06 | 0.0E+00 | 0.0E+00 | 0.0E+00 | 4.1E−05 | 0.0E+00 | 0.0E+00 |
| 161 | 2.2E−06 | 0.0E+00 | 0.0E+00 | 0.0E+00 | 0.0E+00 | 1.3E−06 | 0.0E+00 |
| 162 | 0.0E+00 | 0.0E+00 | 0.0E+00 | 0.0E+00 | 1.6E−05 | 6.3E−07 | 0.0E+00 |
| 163 | 1.0E−02 | 3.6E−06 | 5.1E−04 | 1.4E−03 | 8.2E−06 | 5.5E−05 | 2.5E−04 |
| 164 | 0.0E+00 | 4.4E−05 | 1.5E−06 | 0.0E+00 | 1.6E−04 | 8.2E−05 | 7.7E−06 |
| 165 | 0.0E+00 | 0.0E+00 | 0.0E+00 | 0.0E+00 | 0.0E+00 | 0.0E+00 | 0.0E+00 |
| 166 | 0.0E+00 | 0.0E+00 | 8.4E−06 | 0.0E+00 | 0.0E+00 | 0.0E+00 | 4.3E−07 |
| 167 | 1.3E−02 | 7.5E−02 | 1.2E−01 | 2.2E−04 | 3.0E−02 | 3.0E−02 | 3.4E−02 |
| 168 | 2.5E−06 | 0.0E+00 | 8.9E−05 | 0.0E+00 | 0.0E+00 | 1.3E−06 | 2.6E−06 |
| 169 | 0.0E+00 | 4.4E−07 | 3.8E−07 | 0.0E+00 | 0.0E+00 | 0.0E+00 | 0.0E+00 |
| 170 | 3.1E−06 | 0.0E+00 | 0.0E+00 | 0.0E+00 | 0.0E+00 | 0.0E+00 | 0.0E+00 |
| 171 | 4.1E−06 | 0.0E+00 | 0.0E+00 | 0.0E+00 | 0.0E+00 | 0.0E+00 | 0.0E+00 |
| 172 | 4.6E−03 | 1.5E−03 | 1.7E−01 | 1.1E−05 | 2.3E−03 | 1.8E−02 | 2.3E−02 |
| 173 | 0.0E+00 | 0.0E+00 | 0.0E+00 | 0.0E+00 | 0.0E+00 | 0.0E+00 | 0.0E+00 |
| 174 | 5.7E−02 | 8.0E−02 | 1.9E−01 | 2.5E−05 | 4.8E−03 | 4.9E−02 | 1.9E−02 |
| 175 | 0.0E+00 | 5.8E−06 | 3.8E−07 | 0.0E+00 | 0.0E+00 | 6.3E−07 | 2.1E−06 |
| 176 | 0.0E+00 | 7.5E−05 | 0.0E+00 | 0.0E+00 | 0.0E+00 | 0.0E+00 | 0.0E+00 |
| 177 | 0.0E+00 | 0.0E+00 | 0.0E+00 | 0.0E+00 | 0.0E+00 | 6.3E−07 | 0.0E+00 |
| 178 | 0.0E+00 | 2.7E−06 | 7.7E−07 | 0.0E+00 | 2.7E−06 | 0.0E+00 | 0.0E+00 |
| 179 | 0.0E+00 | 0.0E+00 | 0.0E+00 | 0.0E+00 | 0.0E+00 | 0.0E+00 | 0.0E+00 |
| 180 | 2.7E−04 | 5.6E−05 | 1.0E−05 | 0.0E+00 | 6.8E−06 | 1.9E−06 | 2.1E−05 |
| 181 | 0.0E+00 | 6.7E−06 | 0.0E+00 | 0.0E+00 | 2.7E−06 | 0.0E+00 | 3.4E−06 |
| 182 | 0.0E+00 | 0.0E+00 | 1.2E−06 | 0.0E+00 | 0.0E+00 | 0.0E+00 | 0.0E+00 |
| 183 | 0.0E+00 | 2.7E−06 | 0.0E+00 | 0.0E+00 | 0.0E+00 | 6.3E−07 | 0.0E+00 |

-continued

| | | | | | | | |
|---|---|---|---|---|---|---|---|
| 184 | 0.0E+00 | 0.0E+00 | 6.9E−06 | 0.0E+00 | 7.5E−06 | 0.0E+00 | 0.0E+00 |
| 185 | 2.8E−06 | 1.3E−03 | 4.1E−05 | 0.0E+00 | 5.9E−05 | 2.2E−04 | 2.1E−04 |
| 186 | 8.4E−06 | 0.0E+00 | 3.5E−06 | 0.0E+00 | 9.8E−05 | 6.3E−06 | 3.5E−05 |
| 187 | 0.0E+00 | 0.0E+00 | 0.0E+00 | 0.0E+00 | 0.0E+00 | 0.0E+00 | 0.0E+00 |
| 188 | 6.3E−07 | 4.4E−07 | 0.0E+00 | 0.0E+00 | 4.8E−06 | 0.0E+00 | 0.0E+00 |
| 189 | 0.0E+00 | 0.0E+00 | 1.9E−06 | 0.0E+00 | 0.0E+00 | 0.0E+00 | 0.0E+00 |
| 190 | 1.4E−02 | 6.1E−03 | 6.6E−04 | 2.6E−07 | 1.8E−03 | 6.5E−04 | 5.8E−04 |
| 191 | 1.6E−06 | 9.3E−06 | 1.9E−06 | 0.0E+00 | 4.8E−06 | 5.0E−05 | 1.5E−04 |
| 192 | 5.3E−06 | 4.9E−06 | 2.7E−06 | 0.0E+00 | 0.0E+00 | 1.9E−06 | 8.5E−07 |
| 193 | 1.4E−03 | 3.8E−04 | 9.4E−05 | 0.0E+00 | 4.0E−05 | 0.0E+00 | 1.1E−04 |
| 194 | 2.0E−05 | 2.3E−05 | 3.1E−06 | 0.0E+00 | 2.8E−05 | 2.4E−04 | 1.3E−05 |
| 195 | 2.2E−06 | 5.4E−05 | 1.5E−06 | 0.0E+00 | 3.7E−05 | 0.0E+00 | 0.0E+00 |
| 196 | 0.0E+00 | 0.0E+00 | 0.0E+00 | 0.0E+00 | 0.0E+00 | 0.0E+00 | 5.6E−06 |
| 197 | 0.0E+00 | 0.0E+00 | 7.7E−07 | 5.2E−07 | 0.0E+00 | 0.0E+00 | 0.0E+00 |
| 198 | 0.0E+00 | 0.0E+00 | 0.0E+00 | 0.0E+00 | 0.0E+00 | 3.5E−05 | 0.0E+00 |
| 199 | 2.1E−03 | 1.7E−04 | 2.6E−01 | 3.6E−06 | 2.6E−05 | 2.5E−04 | 6.1E−04 |
| 200 | 0.0E+00 | 0.0E+00 | 0.0E+00 | 0.0E+00 | 0.0E+00 | 0.0E+00 | 0.0E+00 |
| 201 | 3.1E−07 | 1.4E−05 | 6.5E−06 | 0.0E+00 | 1.8E−05 | 0.0E+00 | 2.6E−06 |
| 202 | 0.0E+00 | 0.0E+00 | 0.0E+00 | 0.0E+00 | 0.0E+00 | 0.0E+00 | 0.0E+00 |
| 203 | 3.1E−07 | 8.9E−07 | 2.4E−05 | 0.0E+00 | 0.0E+00 | 0.0E+00 | 4.3E−07 |
| 204 | 0.0E+00 | 1.3E−06 | 8.8E−06 | 0.0E+00 | 6.8E−07 | 0.0E+00 | 0.0E+00 |
| 205 | 0.0E+00 | 0.0E+00 | 0.0E+00 | 0.0E+00 | 0.0E+00 | 0.0E+00 | 0.0E+00 |
| 206 | 0.0E+00 | 0.0E+00 | 0.0E+00 | 0.0E+00 | 0.0E+00 | 0.0E+00 | 0.0E+00 |
| 207 | 0.0E+00 | 5.8E−05 | 1.2E−05 | 0.0E+00 | 1.3E−04 | 2.8E−04 | 3.3E−04 |
| 208 | 1.2E−04 | 5.2E−03 | 4.7E−04 | 1.4E−05 | 9.4E−04 | 2.1E−04 | 3.7E−03 |
| 209 | 0.0E+00 | 0.0E+00 | 0.0E+00 | 0.0E+00 | 0.0E+00 | 0.0E+00 | 0.0E+00 |
| 210 | 3.6E−05 | 8.5E−04 | 2.4E−04 | 0.0E+00 | 7.6E−05 | 1.6E−04 | 6.0E−04 |
| 211 | 0.0E+00 | 0.0E+00 | 0.0E+00 | 0.0E+00 | 0.0E+00 | 0.0E+00 | 2.6E−04 |
| 212 | 0.0E+00 | 0.0E+00 | 1.5E−06 | 0.0E+00 | 2.9E−05 | 4.8E−05 | 0.0E+00 |
| 213 | 0.0E+00 | 0.0E+00 | 0.0E+00 | 0.0E+00 | 3.1E−05 | 0.0E+00 | 3.8E−06 |
| 214 | 0.0E+00 | 0.0E+00 | 1.6E−05 | 0.0E+00 | 0.0E+00 | 0.0E+00 | 0.0E+00 |
| 215 | 0.0E+00 | 0.0E+00 | 0.0E+00 | 0.0E+00 | 3.3E−05 | 0.0E+00 | 6.0E−06 |
| 216 | 2.3E−05 | 3.6E−04 | 1.3E−05 | 7.8E−07 | 8.0E−04 | 2.1E−05 | 2.2E−04 |
| 217 | 0.0E+00 | 0.0E+00 | 0.0E+00 | 0.0E+00 | 0.0E+00 | 0.0E+00 | 0.0E+00 |
| 218 | 2.1E−05 | 4.3E−04 | 1.9E−05 | 0.0E+00 | 8.4E−05 | 9.7E−05 | 3.2E−04 |
| 219 | 0.0E+00 | 0.0E+00 | 1.5E−05 | 0.0E+00 | 0.0E+00 | 0.0E+00 | 2.5E−04 |
| 220 | 1.2E−04 | 9.6E−04 | 1.9E−04 | 2.6E−07 | 1.1E−04 | 1.6E−04 | 7.8E−05 |
| 221 | 2.5E−06 | 0.0E+00 | 3.8E−07 | 0.0E+00 | 0.0E+00 | 0.0E+00 | 0.0E+00 |
| 222 | 0.0E+00 | 8.0E−06 | 0.0E+00 | 0.0E+00 | 1.4E−06 | 0.0E+00 | 0.0E+00 |
| 223 | 0.0E+00 | 0.0E+00 | 0.0E+00 | 0.0E+00 | 3.0E−05 | 0.0E+00 | 0.0E+00 |
| 224 | 0.0E+00 | 2.2E−06 | 0.0E+00 | 0.0E+00 | 6.8E−07 | 0.0E+00 | 1.7E−06 |
| 225 | 4.3E−05 | 2.1E−04 | 6.2E−05 | 0.0E+00 | 5.0E−05 | 2.1E−05 | 6.7E−05 |
| 226 | 0.0E+00 | 0.0E+00 | 0.0E+00 | 0.0E+00 | 1.0E−05 | 0.0E+00 | 0.0E+00 |
| 227 | 0.0E+00 | 0.0E+00 | 0.0E+00 | 0.0E+00 | 0.0E+00 | 6.3E−07 | 1.2E−05 |
| 228 | 0.0E+00 | 0.0E+00 | 0.0E+00 | 0.0E+00 | 0.0E+00 | 0.0E+00 | 0.0E+00 |
| 229 | 0.0E+00 | 0.0E+00 | 0.0E+00 | 0.0E+00 | 1.4E−06 | 0.0E+00 | 0.0E+00 |
| 230 | 0.0E+00 | 2.7E−06 | 0.0E+00 | 0.0E+00 | 0.0E+00 | 0.0E+00 | 0.0E+00 |
| 231 | 0.0E+00 | 0.0E+00 | 0.0E+00 | 0.0E+00 | 3.4E−06 | 2.5E−06 | 5.6E−06 |
| 232 | 3.3E−03 | 2.8E−01 | 3.4E−03 | 8.6E−06 | 2.5E−01 | 3.5E−02 | 1.7E−01 |
| 233 | 0.0E+00 | 6.3E−05 | 0.0E+00 | 0.0E+00 | 4.8E−06 | 6.3E−07 | 4.7E−06 |
| 234 | 0.0E+00 | 0.0E+00 | 0.0E+00 | 0.0E+00 | 0.0E+00 | 5.2E−05 | 0.0E+00 |
| 235 | 5.3E−06 | 2.7E−05 | 1.6E−05 | 0.0E+00 | 9.9E−05 | 2.4E−05 | 7.9E−05 |
| 236 | 4.6E−05 | 2.0E−04 | 4.0E−05 | 5.2E−07 | 8.1E−05 | 9.3E−05 | 2.8E−04 |
| 237 | 3.1E−07 | 0.0E+00 | 7.7E−07 | 0.0E+00 | 0.0E+00 | 0.0E+00 | 0.0E+00 |
| 238 | 0.0E+00 | 0.0E+00 | 0.0E+00 | 0.0E+00 | 0.0E+00 | 0.0E+00 | 1.9E−04 |
| 239 | 1.3E−05 | 0.0E+00 | 4.2E−06 | 0.0E+00 | 0.0E+00 | 4.4E−05 | 1.7E−04 |
| 240 | 0.0E+00 | 0.0E+00 | 3.8E−07 | 0.0E+00 | 0.0E+00 | 6.3E−07 | 4.3E−07 |
| 241 | 3.1E−07 | 5.8E−06 | 7.7E−07 | 0.0E+00 | 0.0E+00 | 3.6E−05 | 0.0E+00 |
| 242 | 0.0E+00 | 2.7E−06 | 0.0E+00 | 0.0E+00 | 2.7E−06 | 0.0E+00 | 1.7E−06 |
| 243 | 1.4E−04 | 5.7E−04 | 5.3E−05 | 5.2E−07 | 1.1E−04 | 7.1E−05 | 1.4E−04 |
| 244 | 0.0E+00 | 0.0E+00 | 0.0E+00 | 0.0E+00 | 0.0E+00 | 2.5E−06 | 0.0E+00 |
| 245 | 0.0E+00 | 0.0E+00 | 0.0E+00 | 0.0E+00 | 0.0E+00 | 8.2E−06 | 0.0E+00 |
| 246 | 0.0E+00 | 0.0E+00 | 1.2E−05 | 0.0E+00 | 0.0E+00 | 0.0E+00 | 0.0E+00 |
| 247 | 0.0E+00 | 1.8E−06 | 0.0E+00 | 0.0E+00 | 0.0E+00 | 0.0E+00 | 8.5E−07 |
| 248 | 3.1E−07 | 3.1E−06 | 0.0E+00 | 0.0E+00 | 0.0E+00 | 2.5E−06 | 2.1E−06 |
| 249 | 0.0E+00 | 0.0E+00 | 1.5E−06 | 0.0E+00 | 0.0E+00 | 0.0E+00 | 4.3E−07 |
| 250 | 1.8E−05 | 0.0E+00 | 0.0E+00 | 0.0E+00 | 0.0E+00 | 0.0E+00 | 0.0E+00 |
| 251 | 6.3E−05 | 3.2E−03 | 3.1E−05 | 2.6E−07 | 2.2E−04 | 7.8E−04 | 2.4E−03 |
| 252 | 1.5E−04 | 2.8E−02 | 3.8E−05 | 2.2E−05 | 2.2E−04 | 1.6E−01 | 8.2E−02 |
| 253 | 0.0E+00 | 0.0E+00 | 0.0E+00 | 0.0E+00 | 0.0E+00 | 0.0E+00 | 0.0E+00 |
| 254 | 2.1E−05 | 8.6E−05 | 5.8E−06 | 2.1E−06 | 4.3E−04 | 6.8E−05 | 8.5E−05 |
| 255 | 0.0E+00 | 0.0E+00 | 5.0E−06 | 0.0E+00 | 0.0E+00 | 0.0E+00 | 0.0E+00 |
| 256 | 0.0E+00 | 5.5E−03 | 2.3E−05 | 2.6E−07 | 3.7E−04 | 2.8E−04 | 3.2E−05 |
| 257 | 0.0E+00 | 0.0E+00 | 0.0E+00 | 0.0E+00 | 0.0E+00 | 0.0E+00 | 0.0E+00 |
| 258 | 0.0E+00 | 7.2E−04 | 8.3E−04 | 2.6E−07 | 1.1E−02 | 2.3E−02 | 6.3E−03 |
| 259 | 1.3E−06 | 4.2E−04 | 0.0E+00 | 0.0E+00 | 9.7E−04 | 2.5E−06 | 8.5E−07 |
| 260 | 1.3E−05 | 9.9E−05 | 1.7E−05 | 4.4E−06 | 1.8E−05 | 9.8E−05 | 1.9E−03 |
| 261 | 1.0E−05 | 1.6E−05 | 9.4E−05 | 7.0E−06 | 1.8E−05 | 4.0E−02 | 1.7E−05 |
| 262 | 4.7E−06 | 4.4E−06 | 7.7E−07 | 7.8E−07 | 3.4E−06 | 1.9E−05 | 8.5E−07 |

-continued

| | | | | | | | |
|---|---|---|---|---|---|---|---|
| 263 | 3.0E−05 | 6.9E−04 | 7.3E−05 | 0.0E+00 | 2.0E−04 | 2.4E−05 | 3.0E−06 |
| 264 | 2.1E−04 | 4.2E−03 | 5.7E−04 | 1.8E−06 | 9.5E−04 | 1.2E−03 | 3.2E−03 |
| 265 | 8.8E−06 | 1.8E−06 | 3.5E−05 | 0.0E+00 | 8.6E−05 | 6.3E−07 | 8.9E−05 |
| 266 | 0.0E+00 | 1.9E−04 | 0.0E+00 | 0.0E+00 | 0.0E+00 | 0.0E+00 | 0.0E+00 |
| 267 | 0.0E+00 | 0.0E+00 | 0.0E+00 | 0.0E+00 | 0.0E+00 | 0.0E+00 | 0.0E+00 |
| 268 | 6.3E−07 | 4.4E−06 | 0.0E+00 | 0.0E+00 | 1.8E−05 | 2.3E−05 | 4.9E−05 |
| 269 | 6.3E−07 | 4.4E−06 | 8.6E−05 | 0.0E+00 | 1.1E−05 | 2.9E−05 | 3.0E−06 |
| 270 | 0.0E+00 | 0.0E+00 | 0.0E+00 | 0.0E+00 | 0.0E+00 | 0.0E+00 | 0.0E+00 |
| 271 | 6.9E−03 | 3.8E−03 | 1.7E−01 | 2.5E−05 | 9.6E−03 | 1.4E−02 | 1.1E−02 |
| 272 | 1.3E−06 | 2.8E−05 | 4.6E−06 | 0.0E+00 | 1.8E−05 | 4.4E−06 | 1.7E−05 |
| 273 | 0.0E+00 | 0.0E+00 | 0.0E+00 | 0.0E+00 | 0.0E+00 | 0.0E+00 | 0.0E+00 |
| 274 | 0.0E+00 | 0.0E+00 | 0.0E+00 | 0.0E+00 | 0.0E+00 | 1.3E−06 | 0.0E+00 |
| 275 | 0.0E+00 | 0.0E+00 | 0.0E+00 | 0.0E+00 | 0.0E+00 | 0.0E+00 | 0.0E+00 |
| 276 | 0.0E+00 | 0.0E+00 | 0.0E+00 | 0.0E+00 | 0.0E+00 | 0.0E+00 | 0.0E+00 |
| 277 | 9.4E−07 | 2.1E−05 | 1.2E−06 | 0.0E+00 | 4.1E−06 | 6.3E−06 | 3.0E−05 |
| 278 | 6.3E−07 | 0.0E+00 | 0.0E+00 | 0.0E+00 | 6.8E−07 | 0.0E+00 | 0.0E+00 |
| 279 | 1.6E−06 | 0.0E+00 | 0.0E+00 | 0.0E+00 | 0.0E+00 | 0.0E+00 | 0.0E+00 |
| 280 | 0.0E+00 | 0.0E+00 | 0.0E+00 | 0.0E+00 | 0.0E+00 | 0.0E+00 | 0.0E+00 |
| 281 | 3.1E−07 | 0.0E+00 | 7.7E−07 | 0.0E+00 | 0.0E+00 | 0.0E+00 | 0.0E+00 |
| 282 | 3.1E−07 | 0.0E+00 | 3.8E−07 | 0.0E+00 | 2.0E−06 | 0.0E+00 | 4.3E−07 |
| 283 | 0.0E+00 | 0.0E+00 | 0.0E+00 | 0.0E+00 | 0.0E+00 | 0.0E+00 | 0.0E+00 |
| 284 | 0.0E+00 | 0.0E+00 | 0.0E+00 | 0.0E+00 | 0.0E+00 | 1.7E−05 | 0.0E+00 |
| 285 | 0.0E+00 | 0.0E+00 | 0.0E+00 | 0.0E+00 | 7.5E−06 | 0.0E+00 | 0.0E+00 |
| 286 | 2.1E−05 | 0.0E+00 | 0.0E+00 | 0.0E+00 | 0.0E+00 | 0.0E+00 | 0.0E+00 |
| 287 | 0.0E+00 | 0.0E+00 | 0.0E+00 | 0.0E+00 | 0.0E+00 | 0.0E+00 | 0.0E+00 |
| 288 | 0.0E+00 | 0.0E+00 | 0.0E+00 | 0.0E+00 | 0.0E+00 | 0.0E+00 | 0.0E+00 |
| 289 | 0.0E+00 | 1.4E−05 | 0.0E+00 | 0.0E+00 | 0.0E+00 | 0.0E+00 | 0.0E+00 |
| 290 | 6.3E−07 | 1.1E−05 | 0.0E+00 | 0.0E+00 | 1.6E−05 | 4.4E−06 | 2.1E−06 |
| 291 | 3.1E−07 | 0.0E+00 | 0.0E+00 | 0.0E+00 | 1.4E−06 | 0.0E+00 | 2.1E−06 |
| 292 | 0.0E+00 | 0.0E+00 | 0.0E+00 | 0.0E+00 | 1.6E−05 | 0.0E+00 | 0.0E+00 |
| 293 | 0.0E+00 | 1.6E−05 | 6.1E−06 | 0.0E+00 | 4.2E−05 | 8.3E−05 | 3.5E−05 |
| 294 | 0.0E+00 | 0.0E+00 | 0.0E+00 | 0.0E+00 | 0.0E+00 | 0.0E+00 | 0.0E+00 |
| 295 | 8.7E−04 | 1.6E−02 | 4.6E−04 | 2.4E−05 | 4.7E−03 | 5.3E−03 | 6.3E−03 |
| 296 | 2.2E−06 | 5.6E−05 | 1.9E−06 | 0.0E+00 | 2.1E−05 | 1.1E−05 | 1.5E−05 |
| 297 | 0.0E+00 | 0.0E+00 | 0.0E+00 | 0.0E+00 | 3.4E−06 | 6.3E−06 | 8.5E−07 |
| 298 | 0.0E+00 | 2.5E−05 | 0.0E+00 | 0.0E+00 | 0.0E+00 | 0.0E+00 | 0.0E+00 |
| 299 | 0.0E+00 | 0.0E+00 | 0.0E+00 | 0.0E+00 | 0.0E+00 | 0.0E+00 | 0.0E+00 |
| 300 | 0.0E+00 | 0.0E+00 | 0.0E+00 | 0.0E+00 | 0.0E+00 | 0.0E+00 | 0.0E+00 |
| 301 | 0.0E+00 | 4.0E−06 | 3.8E−07 | 0.0E+00 | 2.0E−06 | 6.3E−07 | 6.0E−06 |
| 302 | 0.0E+00 | 4.4E−07 | 0.0E+00 | 0.0E+00 | 0.0E+00 | 0.0E+00 | 0.0E+00 |
| 303 | 0.0E+00 | 0.0E+00 | 1.2E−06 | 0.0E+00 | 2.7E−05 | 1.7E−05 | 0.0E+00 |
| 304 | 0.0E+00 | 0.0E+00 | 0.0E+00 | 0.0E+00 | 0.0E+00 | 0.0E+00 | 0.0E+00 |
| 305 | 0.0E+00 | 0.0E+00 | 0.0E+00 | 0.0E+00 | 0.0E+00 | 0.0E+00 | 0.0E+00 |
| 306 | 0.0E+00 | 0.0E+00 | 0.0E+00 | 0.0E+00 | 3.4E−06 | 2.3E−05 | 0.0E+00 |
| 307 | 0.0E+00 | 0.0E+00 | 0.0E+00 | 0.0E+00 | 0.0E+00 | 0.0E+00 | 1.7E−06 |
| 308 | 0.0E+00 | 8.9E−07 | 0.0E+00 | 0.0E+00 | 2.7E−06 | 1.9E−06 | 5.6E−06 |
| 309 | 0.0E+00 | 1.8E−06 | 1.5E−06 | 0.0E+00 | 1.3E−05 | 6.9E−06 | 0.0E+00 |
| 310 | 1.9E−06 | 1.3E−06 | 0.0E+00 | 0.0E+00 | 2.2E−05 | 4.4E−06 | 0.0E+00 |
| 311 | 6.3E−07 | 1.3E−06 | 0.0E+00 | 0.0E+00 | 2.7E−06 | 0.0E+00 | 1.7E−06 |
| 312 | 2.5E−06 | 2.8E−04 | 3.0E−04 | 0.0E+00 | 5.8E−03 | 1.5E−03 | 3.5E−04 |
| 313 | 1.0E−05 | 0.0E+00 | 1.5E−05 | 0.0E+00 | 0.0E+00 | 5.6E−05 | 0.0E+00 |
| 314 | 1.6E−04 | 3.2E−04 | 6.8E−05 | 9.6E−06 | 7.5E−04 | 8.9E−05 | 3.9E−03 |
| 315 | 6.4E−04 | 5.6E−02 | 6.2E−03 | 3.1E−05 | 1.4E−01 | 2.7E−02 | 5.6E−02 |
| 316 | 0.0E+00 | 7.2E−05 | 6.1E−05 | 1.0E−06 | 1.5E−04 | 1.6E−04 | 6.7E−04 |
| 317 | 3.1E−07 | 0.0E+00 | 7.7E−07 | 0.0E+00 | 0.0E+00 | 0.0E+00 | 2.6E−06 |
| 318 | 0.0E+00 | 0.0E+00 | 0.0E+00 | 0.0E+00 | 6.8E−07 | 6.3E−07 | 0.0E+00 |
| 319 | 0.0E+00 | 0.0E+00 | 0.0E+00 | 0.0E+00 | 0.0E+00 | 0.0E+00 | 0.0E+00 |
| 320 | 0.0E+00 | 3.1E−06 | 1.2E−05 | 0.0E+00 | 1.7E−05 | 1.0E−05 | 8.1E−06 |
| 321 | 3.1E−07 | 0.0E+00 | 3.8E−07 | 0.0E+00 | 0.0E+00 | 0.0E+00 | 0.0E+00 |
| 322 | 0.0E+00 | 4.4E−07 | 0.0E+00 | 0.0E+00 | 6.8E−07 | 0.0E+00 | 1.3E−06 |
| 323 | 0.0E+00 | 0.0E+00 | 0.0E+00 | 0.0E+00 | 1.2E−05 | 3.1E−06 | 5.1E−06 |
| 324 | 0.0E+00 | 0.0E+00 | 0.0E+00 | 0.0E+00 | 0.0E+00 | 0.0E+00 | 0.0E+00 |
| 325 | 2.9E−04 | 4.3E−03 | 4.6E−04 | 7.0E−06 | 2.6E−03 | 4.5E−03 | 1.1E−02 |
| 326 | 5.0E−04 | 1.6E−03 | 1.6E−04 | 1.8E−06 | 2.8E−03 | 2.3E−03 | 4.3E−05 |
| 327 | 0.0E+00 | 0.0E+00 | 0.0E+00 | 0.0E+00 | 0.0E+00 | 0.0E+00 | 0.0E+00 |
| 328 | 0.0E+00 | 4.4E−07 | 0.0E+00 | 0.0E+00 | 1.0E−05 | 1.3E−06 | 3.8E−06 |
| 329 | 0.0E+00 | 0.0E+00 | 0.0E+00 | 0.0E+00 | 0.0E+00 | 0.0E+00 | 0.0E+00 |
| 330 | 1.3E−06 | 8.9E−07 | 0.0E+00 | 0.0E+00 | 0.0E+00 | 6.3E−07 | 4.3E−07 |
| 331 | 1.9E−05 | 3.8E−04 | 4.2E−06 | 1.0E−06 | 1.1E−04 | 1.3E−05 | 8.7E−05 |
| 332 | 0.0E+00 | 2.7E−04 | 3.8E−07 | 1.6E−06 | 4.2E−04 | 9.9E−05 | 1.3E−04 |
| 333 | 0.0E+00 | 8.9E−06 | 0.0E+00 | 0.0E+00 | 0.0E+00 | 0.0E+00 | 1.7E−06 |
| 334 | 4.5E−05 | 1.2E−03 | 2.4E−05 | 1.8E−06 | 4.3E−04 | 3.9E−04 | 2.8E−04 |
| 335 | 8.1E−06 | 5.4E−05 | 7.7E−07 | 2.6E−07 | 4.0E−05 | 3.5E−05 | 4.6E−05 |
| 336 | 0.0E+00 | 0.0E+00 | 0.0E+00 | 0.0E+00 | 0.0E+00 | 0.0E+00 | 0.0E+00 |
| 337 | 5.6E−01 | 6.2E−04 | 5.1E−04 | 1.0E+00 | 3.7E−03 | 5.5E−04 | 1.8E−03 |
| 338 | 4.1E−05 | 1.4E−04 | 1.0E−05 | 1.3E−06 | 1.7E−04 | 9.3E−05 | 2.7E−04 |
| 339 | 1.6E−06 | 8.9E−07 | 0.0E+00 | 0.0E+00 | 0.0E+00 | 3.8E−06 | 0.0E+00 |
| 340 | 5.6E−06 | 0.0E+00 | 0.0E+00 | 1.0E−06 | 6.4E−05 | 0.0E+00 | 0.0E+00 |
| 341 | 0.0E+00 | 1.1E−05 | 0.0E+00 | 0.0E+00 | 0.0E+00 | 0.0E+00 | 0.0E+00 |

-continued

| | | | | | | | |
|---|---|---|---|---|---|---|---|
| 342 | 0.0E+00 | 0.0E+00 | 0.0E+00 | 0.0E+00 | 0.0E+00 | 0.0E+00 | 0.0E+00 |
| 343 | 2.8E−06 | 0.0E+00 | 0.0E+00 | 6.0E−06 | 0.0E+00 | 0.0E+00 | 0.0E+00 |
| 344 | 0.0E+00 | 6.2E−06 | 0.0E+00 | 0.0E+00 | 1.6E−05 | 0.0E+00 | 4.7E−06 |
| 345 | 1.3E−06 | 0.0E+00 | 0.0E+00 | 1.6E−06 | 0.0E+00 | 6.3E−07 | 0.0E+00 |
| 346 | 0.0E+00 | 0.0E+00 | 0.0E+00 | 0.0E+00 | 3.4E−06 | 0.0E+00 | 0.0E+00 |
| 347 | 1.5E−05 | 8.3E−05 | 2.7E−05 | 0.0E+00 | 2.5E−05 | 6.3E−05 | 7.7E−05 |
| 348 | 3.1E−07 | 0.0E+00 | 0.0E+00 | 0.0E+00 | 0.0E+00 | 0.0E+00 | 0.0E+00 |
| 349 | 6.9E−03 | 1.6E−02 | 2.4E−02 | 1.0E−06 | 9.4E−04 | 3.5E−05 | 9.0E−03 |
| 350 | 0.0E+00 | 8.9E−07 | 0.0E+00 | 0.0E+00 | 0.0E+00 | 0.0E+00 | 0.0E+00 |
| 351 | 1.7E−02 | 9.4E−03 | 1.4E−02 | 5.2E−07 | 2.5E−03 | 1.8E−04 | 5.4E−03 |
| 352 | 6.6E−06 | 0.0E+00 | 0.0E+00 | 0.0E+00 | 2.6E−04 | 0.0E+00 | 0.0E+00 |
| 353 | 0.0E+00 | 1.6E−05 | 0.0E+00 | 0.0E+00 | 0.0E+00 | 0.0E+00 | 1.3E−06 |
| 354 | 4.5E−03 | 5.5E−02 | 6.3E−04 | 0.0E+00 | 8.6E−04 | 6.3E−07 | 1.7E−03 |
| 355 | 0.0E+00 | 4.0E−06 | 0.0E+00 | 0.0E+00 | 0.0E+00 | 0.0E+00 | 0.0E+00 |
| 356 | 0.0E+00 | 4.4E−06 | 3.8E−07 | 0.0E+00 | 0.0E+00 | 0.0E+00 | 8.5E−07 |
| 357 | 3.1E−07 | 8.9E−07 | 1.9E−06 | 2.6E−07 | 1.4E−06 | 1.9E−06 | 1.6E−05 |
| 358 | 0.0E+00 | 0.0E+00 | 0.0E+00 | 0.0E+00 | 0.0E+00 | 0.0E+00 | 0.0E+00 |
| 359 | 1.9E−06 | 0.0E+00 | 0.0E+00 | 2.6E−07 | 0.0E+00 | 0.0E+00 | 5.6E−06 |
| 360 | 0.0E+00 | 0.0E+00 | 0.0E+00 | 2.6E−07 | 0.0E+00 | 0.0E+00 | 0.0E+00 |
| 361 | 1.1E−05 | 1.3E−05 | 1.0E−05 | 0.0E+00 | 2.2E−04 | 4.6E−05 | 4.9E−04 |
| 362 | 4.1E−06 | 1.1E−04 | 1.5E−06 | 0.0E+00 | 2.5E−05 | 6.3E−07 | 4.3E−05 |
| 363 | 0.0E+00 | 0.0E+00 | 0.0E+00 | 0.0E+00 | 0.0E+00 | 0.0E+00 | 0.0E+00 |
| 364 | 0.0E+00 | 0.0E+00 | 0.0E+00 | 0.0E+00 | 0.0E+00 | 0.0E+00 | 0.0E+00 |
| 365 | 0.0E+00 | 2.5E−05 | 3.8E−07 | 0.0E+00 | 0.0E+00 | 0.0E+00 | 2.1E−05 |
| 366 | 0.0E+00 | 0.0E+00 | 0.0E+00 | 0.0E+00 | 0.0E+00 | 0.0E+00 | 0.0E+00 |
| 367 | 0.0E+00 | 1.9E−04 | 0.0E+00 | 0.0E+00 | 0.0E+00 | 0.0E+00 | 0.0E+00 |
| 368 | 9.4E−07 | 2.6E−05 | 1.2E−06 | 0.0E+00 | 1.3E−05 | 2.5E−05 | 1.2E−05 |
| 369 | 0.0E+00 | 0.0E+00 | 0.0E+00 | 0.0E+00 | 0.0E+00 | 1.4E−05 | 0.0E+00 |
| 370 | 0.0E+00 | 0.0E+00 | 0.0E+00 | 0.0E+00 | 0.0E+00 | 0.0E+00 | 5.1E−06 |
| 371 | 0.0E+00 | 7.1E−06 | 0.0E+00 | 0.0E+00 | 0.0E+00 | 1.9E−06 | 4.3E−06 |
| 372 | 1.9E−05 | 1.3E−05 | 0.0E+00 | 0.0E+00 | 5.3E−05 | 2.5E−06 | 4.7E−05 |
| 373 | 2.9E−01 | 2.6E−01 | 6.2E−04 | 5.3E−05 | 1.2E−01 | 1.8E−02 | 1.1E−01 |
| 374 | 0.0E+00 | 0.0E+00 | 8.8E−06 | 0.0E+00 | 1.2E−04 | 0.0E+00 | 0.0E+00 |
| 375 | 0.0E+00 | 4.4E−07 | 0.0E+00 | 0.0E+00 | 0.0E+00 | 0.0E+00 | 8.5E−07 |
| 376 | 0.0E+00 | 4.4E−06 | 0.0E+00 | 0.0E+00 | 0.0E+00 | 0.0E+00 | 4.3E−07 |
| 377 | 0.0E+00 | 1.3E−06 | 0.0E+00 | 0.0E+00 | 0.0E+00 | 0.0E+00 | 0.0E+00 |
| 378 | 2.3E−05 | 7.3E−04 | 1.3E−05 | 3.1E−06 | 2.4E−04 | 3.2E−04 | 2.6E−04 |

| Taxon ID | RM Atm−/− Small Intestine | | | |
|---|---|---|---|---|
| 1 | 4.2E−02 | 2.5E−03 | 6.3E−04 | 8.7E−04 |
| 2 | 0.0E+00 | 0.0E+00 | 0.0E+00 | 0.0E+00 |
| 3 | 0.0E+00 | 0.0E+00 | 0.0E+00 | 0.0E+00 |
| 4 | 7.1E−04 | 2.6E−04 | 5.2E−05 | 1.9E−05 |
| 5 | 0.0E+00 | 0.0E+00 | 0.0E+00 | 0.0E+00 |
| 6 | 1.6E−04 | 7.8E−06 | 0.0E+00 | 6.5E−07 |
| 7 | 1.7E−04 | 2.0E−05 | 0.0E+00 | 9.1E−06 |
| 8 | 1.9E−06 | 0.0E+00 | 0.0E+00 | 0.0E+00 |
| 9 | 1.5E−04 | 1.0E−06 | 0.0E+00 | 1.6E−06 |
| 10 | 3.3E−04 | 0.0E+00 | 0.0E+00 | 1.9E−06 |
| 11 | 1.8E−04 | 0.0E+00 | 0.0E+00 | 0.0E+00 |
| 12 | 0.0E+00 | 0.0E+00 | 0.0E+00 | 0.0E+00 |
| 13 | 9.3E−06 | 0.0E+00 | 0.0E+00 | 0.0E+00 |
| 14 | 0.0E+00 | 0.0E+00 | 0.0E+00 | 0.0E+00 |
| 15 | 0.0E+00 | 0.0E+00 | 0.0E+00 | 0.0E+00 |
| 16 | 0.0E+00 | 0.0E+00 | 0.0E+00 | 0.0E+00 |
| 17 | 1.3E−05 | 0.0E+00 | 1.6E−06 | 0.0E+00 |
| 18 | 0.0E+00 | 0.0E+00 | 0.0E+00 | 0.0E+00 |
| 19 | 8.3E−04 | 0.0E+00 | 0.0E+00 | 0.0E+00 |
| 20 | 0.0E+00 | 0.0E+00 | 0.0E+00 | 0.0E+00 |
| 21 | 0.0E+00 | 0.0E+00 | 3.1E−07 | 0.0E+00 |
| 22 | 2.7E−04 | 0.0E+00 | 0.0E+00 | 0.0E+00 |
| 23 | 0.0E+00 | 3.4E−06 | 0.0E+00 | 3.2E−07 |
| 24 | 3.7E−06 | 3.4E−07 | 0.0E+00 | 0.0E+00 |
| 25 | 0.0E+00 | 0.0E+00 | 0.0E+00 | 0.0E+00 |
| 26 | 1.2E−05 | 0.0E+00 | 0.0E+00 | 0.0E+00 |
| 27 | 0.0E+00 | 0.0E+00 | 0.0E+00 | 0.0E+00 |
| 28 | 9.6E−05 | 0.0E+00 | 0.0E+00 | 0.0E+00 |
| 29 | 0.0E+00 | 0.0E+00 | 0.0E+00 | 0.0E+00 |
| 30 | 2.9E−04 | 0.0E+00 | 0.0E+00 | 0.0E+00 |
| 31 | 3.1E−06 | 0.0E+00 | 0.0E+00 | 0.0E+00 |
| 32 | 1.3E−03 | 0.0E+00 | 1.6E−06 | 3.2E−07 |
| 33 | 2.4E−03 | 9.4E−05 | 9.4E−07 | 1.3E−06 |
| 34 | 8.8E−05 | 0.0E+00 | 0.0E+00 | 0.0E+00 |
| 35 | 0.0E+00 | 0.0E+00 | 0.0E+00 | 0.0E+00 |
| 36 | 0.0E+00 | 0.0E+00 | 0.0E+00 | 0.0E+00 |
| 37 | 1.9E−04 | 0.0E+00 | 0.0E+00 | 0.0E+00 |
| 38 | 1.1E−04 | 0.0E+00 | 0.0E+00 | 0.0E+00 |
| 39 | 0.0E+00 | 0.0E+00 | 0.0E+00 | 0.0E+00 |

-continued

| | | | | |
|---|---|---|---|---|
| 40 | 1.5E−05 | 0.0E+00 | 0.0E+00 | 0.0E+00 |
| 41 | 0.0E+00 | 0.0E+00 | 0.0E+00 | 0.0E+00 |
| 42 | 0.0E+00 | 0.0E+00 | 0.0E+00 | 0.0E+00 |
| 43 | 5.1E−05 | 0.0E+00 | 0.0E+00 | 0.0E+00 |
| 44 | 1.2E−06 | 0.0E+00 | 0.0E+00 | 0.0E+00 |
| 45 | 0.0E+00 | 0.0E+00 | 0.0E+00 | 1.6E−06 |
| 46 | 4.2E−04 | 0.0E+00 | 0.0E+00 | 0.0E+00 |
| 47 | 0.0E+00 | 0.0E+00 | 0.0E+00 | 0.0E+00 |
| 48 | 0.0E+00 | 0.0E+00 | 0.0E+00 | 0.0E+00 |
| 49 | 0.0E+00 | 0.0E+00 | 0.0E+00 | 6.5E−07 |
| 50 | 0.0E+00 | 3.8E−05 | 8.1E−05 | 2.0E−05 |
| 51 | 0.0E+00 | 1.4E−04 | 2.6E−05 | 1.7E−05 |
| 52 | 0.0E+00 | 0.0E+00 | 5.7E−06 | 0.0E+00 |
| 53 | 0.0E+00 | 1.2E−05 | 3.5E−06 | 7.1E−06 |
| 54 | 1.3E−04 | 6.8E−07 | 0.0E+00 | 0.0E+00 |
| 55 | 4.3E−05 | 0.0E+00 | 0.0E+00 | 0.0E+00 |
| 56 | 0.0E+00 | 0.0E+00 | 0.0E+00 | 0.0E+00 |
| 57 | 1.9E−06 | 6.8E−07 | 9.4E−07 | 0.0E+00 |
| 58 | 2.2E−05 | 1.8E−04 | 2.2E−04 | 6.8E−05 |
| 59 | 1.2E−06 | 2.4E−06 | 9.4E−07 | 9.7E−07 |
| 60 | 2.3E−05 | 1.8E−05 | 1.4E−05 | 2.6E−05 |
| 61 | 0.0E+00 | 0.0E+00 | 0.0E+00 | 0.0E+00 |
| 62 | 3.6E−05 | 3.4E−05 | 3.4E−05 | 5.5E−06 |
| 63 | 1.4E−05 | 8.1E−05 | 6.3E−05 | 8.0E−05 |
| 64 | 6.2E−07 | 5.4E−06 | 2.5E−06 | 6.5E−07 |
| 65 | 1.9E−06 | 3.4E−06 | 3.1E−06 | 2.6E−06 |
| 66 | 0.0E+00 | 1.4E−06 | 6.3E−07 | 3.2E−07 |
| 67 | 6.2E−07 | 1.4E−06 | 9.4E−07 | 1.3E−06 |
| 68 | 0.0E+00 | 0.0E+00 | 0.0E+00 | 0.0E+00 |
| 69 | 2.2E−04 | 5.1E−03 | 5.4E−03 | 1.2E−02 |
| 70 | 4.3E−06 | 6.1E−06 | 7.2E−06 | 7.5E−06 |
| 71 | 5.6E−06 | 4.8E−05 | 3.6E−05 | 5.5E−05 |
| 72 | 0.0E+00 | 6.8E−07 | 6.3E−07 | 3.2E−07 |
| 73 | 0.0E+00 | 0.0E+00 | 0.0E+00 | 0.0E+00 |
| 74 | 0.0E+00 | 3.4E−06 | 2.2E−06 | 3.9E−06 |
| 75 | 0.0E+00 | 0.0E+00 | 0.0E+00 | 0.0E+00 |
| 76 | 8.6E−06 | 1.0E−06 | 6.3E−04 | 2.8E−04 |
| 77 | 4.1E−05 | 5.4E−06 | 7.9E−06 | 6.8E−06 |
| 78 | 0.0E+00 | 1.4E−06 | 6.3E−07 | 1.3E−06 |
| 79 | 8.6E−06 | 4.1E−06 | 3.8E−06 | 5.2E−06 |
| 80 | 5.0E−04 | 8.4E−05 | 1.9E−06 | 3.9E−06 |
| 81 | 0.0E+00 | 0.0E+00 | 0.0E+00 | 0.0E+00 |
| 82 | 8.8E−03 | 5.2E−02 | 4.8E−02 | 4.8E−02 |
| 83 | 4.5E−03 | 1.2E−03 | 5.6E−02 | 2.7E−02 |
| 84 | 5.6E−06 | 0.0E+00 | 0.0E+00 | 0.0E+00 |
| 85 | 8.6E−06 | 2.5E−02 | 4.8E−02 | 4.7E−02 |
| 86 | 4.5E−02 | 2.9E−01 | 2.6E−01 | 3.5E−01 |
| 87 | 6.2E−07 | 5.8E−06 | 3.1E−06 | 6.8E−06 |
| 88 | 1.9E−06 | 0.0E+00 | 6.3E−07 | 0.0E+00 |
| 89 | 6.2E−07 | 6.8E−07 | 2.2E−06 | 0.0E+00 |
| 90 | 0.0E+00 | 0.0E+00 | 0.0E+00 | 0.0E+00 |
| 91 | 6.8E−06 | 1.4E−06 | 0.0E+00 | 0.0E+00 |
| 92 | 6.2E−07 | 0.0E+00 | 0.0E+00 | 0.0E+00 |
| 93 | 0.0E+00 | 0.0E+00 | 0.0E+00 | 0.0E+00 |
| 94 | 5.1E−05 | 2.9E−04 | 2.2E−04 | 3.0E−04 |
| 95 | 0.0E+00 | 0.0E+00 | 0.0E+00 | 0.0E+00 |
| 96 | 6.2E−07 | 3.7E−06 | 1.4E−03 | 7.0E−04 |
| 97 | 0.0E+00 | 1.0E−06 | 3.1E−07 | 6.5E−07 |
| 98 | 0.0E+00 | 0.0E+00 | 0.0E+00 | 0.0E+00 |
| 99 | 0.0E+00 | 0.0E+00 | 0.0E+00 | 0.0E+00 |
| 100 | 6.1E−05 | 6.8E−07 | 3.1E−07 | 0.0E+00 |
| 101 | 1.7E−03 | 8.8E−05 | 3.0E−05 | 2.1E−05 |
| 102 | 2.0E−05 | 3.4E−06 | 0.0E+00 | 0.0E+00 |
| 103 | 0.0E+00 | 0.0E+00 | 0.0E+00 | 0.0E+00 |
| 104 | 0.0E+00 | 0.0E+00 | 0.0E+00 | 0.0E+00 |
| 105 | 1.9E−06 | 1.7E−06 | 3.1E−07 | 2.6E−06 |
| 106 | 1.2E−06 | 0.0E+00 | 0.0E+00 | 0.0E+00 |
| 107 | 2.5E−06 | 1.0E−05 | 6.3E−06 | 8.4E−06 |
| 108 | 0.0E+00 | 0.0E+00 | 0.0E+00 | 0.0E+00 |
| 109 | 0.0E+00 | 0.0E+00 | 0.0E+00 | 0.0E+00 |
| 110 | 0.0E+00 | 0.0E+00 | 0.0E+00 | 0.0E+00 |
| 111 | 0.0E+00 | 1.4E−06 | 0.0E+00 | 0.0E+00 |
| 112 | 0.0E+00 | 1.3E−05 | 0.0E+00 | 0.0E+00 |
| 113 | 0.0E+00 | 0.0E+00 | 0.0E+00 | 0.0E+00 |
| 114 | 1.4E−04 | 0.0E+00 | 0.0E+00 | 1.3E−06 |
| 115 | 2.1E−03 | 2.0E−04 | 8.8E−05 | 6.8E−06 |
| 116 | 0.0E+00 | 0.0E+00 | 0.0E+00 | 0.0E+00 |
| 117 | 0.0E+00 | 0.0E+00 | 0.0E+00 | 0.0E+00 |
| 118 | 6.2E−04 | 0.0E+00 | 0.0E+00 | 0.0E+00 |

-continued

| | | | | |
|---|---|---|---|---|
| 119 | 0.0E+00 | 0.0E+00 | 0.0E+00 | 0.0E+00 |
| 120 | 0.0E+00 | 0.0E+00 | 3.1E−07 | 0.0E+00 |
| 121 | 0.0E+00 | 0.0E+00 | 3.1E−07 | 0.0E+00 |
| 122 | 6.4E−05 | 0.0E+00 | 0.0E+00 | 0.0E+00 |
| 123 | 0.0E+00 | 0.0E+00 | 0.0E+00 | 0.0E+00 |
| 124 | 0.0E+00 | 0.0E+00 | 0.0E+00 | 3.2E−07 |
| 125 | 1.5E−04 | 2.0E−05 | 3.1E−07 | 0.0E+00 |
| 126 | 2.5E−06 | 0.0E+00 | 0.0E+00 | 0.0E+00 |
| 127 | 0.0E+00 | 0.0E+00 | 0.0E+00 | 0.0E+00 |
| 128 | 1.8E−03 | 4.7E−04 | 7.1E−05 | 1.1E−05 |
| 129 | 9.9E−06 | 0.0E+00 | 0.0E+00 | 0.0E+00 |
| 130 | 0.0E+00 | 0.0E+00 | 0.0E+00 | 0.0E+00 |
| 131 | 7.4E−06 | 3.4E−07 | 0.0E+00 | 0.0E+00 |
| 132 | 0.0E+00 | 0.0E+00 | 0.0E+00 | 0.0E+00 |
| 133 | 0.0E+00 | 0.0E+00 | 0.0E+00 | 0.0E+00 |
| 134 | 1.0E−03 | 1.0E−06 | 6.0E−06 | 3.2E−07 |
| 135 | 0.0E+00 | 0.0E+00 | 0.0E+00 | 0.0E+00 |
| 136 | 0.0E+00 | 3.1E−06 | 3.1E−06 | 3.2E−07 |
| 137 | 1.0E−03 | 6.8E−07 | 0.0E+00 | 0.0E+00 |
| 138 | 0.0E+00 | 0.0E+00 | 0.0E+00 | 0.0E+00 |
| 139 | 4.9E−05 | 4.5E−05 | 6.3E−07 | 9.7E−07 |
| 140 | 2.8E−03 | 7.6E−05 | 7.8E−05 | 3.1E−05 |
| 141 | 0.0E+00 | 0.0E+00 | 0.0E+00 | 0.0E+00 |
| 142 | 0.0E+00 | 0.0E+00 | 0.0E+00 | 6.5E−07 |
| 143 | 0.0E+00 | 0.0E+00 | 0.0E+00 | 0.0E+00 |
| 144 | 0.0E+00 | 0.0E+00 | 0.0E+00 | 0.0E+00 |
| 145 | 0.0E+00 | 0.0E+00 | 0.0E+00 | 0.0E+00 |
| 146 | 6.8E−03 | 0.0E+00 | 0.0E+00 | 0.0E+00 |
| 147 | 0.0E+00 | 0.0E+00 | 0.0E+00 | 0.0E+00 |
| 148 | 5.2E−03 | 6.2E−05 | 1.6E−05 | 6.8E−06 |
| 149 | 0.0E+00 | 0.0E+00 | 0.0E+00 | 0.0E+00 |
| 150 | 6.2E−07 | 5.0E−05 | 3.6E−04 | 2.3E−04 |
| 151 | 0.0E+00 | 0.0E+00 | 0.0E+00 | 0.0E+00 |
| 152 | 0.0E+00 | 0.0E+00 | 0.0E+00 | 0.0E+00 |
| 153 | 0.0E+00 | 0.0E+00 | 0.0E+00 | 0.0E+00 |
| 154 | 4.7E−02 | 6.1E−06 | 2.5E−06 | 5.5E−06 |
| 155 | 0.0E+00 | 1.0E−05 | 0.0E+00 | 3.2E−07 |
| 156 | 2.0E−03 | 1.9E−05 | 2.2E−06 | 1.1E−05 |
| 157 | 4.5E−05 | 0.0E+00 | 0.0E+00 | 0.0E+00 |
| 158 | 0.0E+00 | 0.0E+00 | 0.0E+00 | 0.0E+00 |
| 159 | 2.9E−03 | 1.3E−04 | 4.4E−06 | 2.7E−05 |
| 160 | 0.0E+00 | 2.0E−05 | 0.0E+00 | 0.0E+00 |
| 161 | 0.0E+00 | 2.0E−06 | 0.0E+00 | 0.0E+00 |
| 162 | 4.3E−04 | 1.4E−05 | 0.0E+00 | 0.0E+00 |
| 163 | 1.9E−06 | 6.8E−07 | 9.4E−07 | 0.0E+00 |
| 164 | 7.8E−05 | 7.5E−06 | 2.5E−06 | 1.9E−06 |
| 165 | 0.0E+00 | 0.0E+00 | 0.0E+00 | 0.0E+00 |
| 166 | 8.0E−06 | 0.0E+00 | 0.0E+00 | 0.0E+00 |
| 167 | 4.6E−01 | 1.7E−01 | 1.0E−03 | 2.7E−03 |
| 168 | 0.0E+00 | 3.4E−07 | 0.0E+00 | 0.0E+00 |
| 169 | 1.2E−06 | 1.0E−06 | 2.2E−06 | 0.0E+00 |
| 170 | 0.0E+00 | 0.0E+00 | 0.0E+00 | 0.0E+00 |
| 171 | 0.0E+00 | 0.0E+00 | 0.0E+00 | 0.0E+00 |
| 172 | 2.4E−02 | 2.8E−01 | 2.2E−01 | 6.5E−02 |
| 173 | 0.0E+00 | 0.0E+00 | 0.0E+00 | 0.0E+00 |
| 174 | 1.5E−05 | 9.9E−06 | 1.1E−05 | 1.1E−05 |
| 175 | 0.0E+00 | 0.0E+00 | 0.0E+00 | 0.0E+00 |
| 176 | 0.0E+00 | 0.0E+00 | 0.0E+00 | 0.0E+00 |
| 177 | 0.0E+00 | 0.0E+00 | 0.0E+00 | 0.0E+00 |
| 178 | 1.2E−05 | 6.1E−06 | 1.6E−06 | 0.0E+00 |
| 179 | 0.0E+00 | 0.0E+00 | 0.0E+00 | 0.0E+00 |
| 180 | 0.0E+00 | 0.0E+00 | 0.0E+00 | 0.0E+00 |
| 181 | 0.0E+00 | 0.0E+00 | 0.0E+00 | 0.0E+00 |
| 182 | 0.0E+00 | 3.4E−07 | 6.3E−07 | 6.5E−07 |
| 183 | 0.0E+00 | 0.0E+00 | 0.0E+00 | 0.0E+00 |
| 184 | 0.0E+00 | 0.0E+00 | 0.0E+00 | 6.5E−07 |
| 185 | 6.5E−04 | 2.5E−04 | 0.0E+00 | 2.3E−06 |
| 186 | 2.5E−06 | 1.7E−06 | 0.0E+00 | 0.0E+00 |
| 187 | 0.0E+00 | 0.0E+00 | 0.0E+00 | 0.0E+00 |
| 188 | 6.8E−06 | 1.0E−06 | 0.0E+00 | 0.0E+00 |
| 189 | 0.0E+00 | 2.1E−05 | 0.0E+00 | 0.0E+00 |
| 190 | 1.3E−03 | 6.0E−05 | 3.5E−06 | 1.0E−05 |
| 191 | 1.0E−03 | 1.3E−04 | 6.3E−05 | 2.6E−06 |
| 192 | 3.1E−04 | 4.4E−06 | 0.0E+00 | 0.0E+00 |
| 193 | 0.0E+00 | 0.0E+00 | 0.0E+00 | 3.2E−07 |
| 194 | 2.4E−03 | 1.2E−05 | 0.0E+00 | 0.0E+00 |
| 195 | 0.0E+00 | 1.1E−05 | 0.0E+00 | 1.3E−06 |
| 196 | 0.0E+00 | 0.0E+00 | 0.0E+00 | 0.0E+00 |
| 197 | 0.0E+00 | 0.0E+00 | 0.0E+00 | 0.0E+00 |

-continued

| | | | | |
|---|---|---|---|---|
| 198 | 0.0E+00 | 0.0E+00 | 0.0E+00 | 0.0E+00 |
| 199 | 1.2E−03 | 8.5E−04 | 6.5E−02 | 2.2E−05 |
| 200 | 0.0E+00 | 1.0E−06 | 0.0E+00 | 0.0E+00 |
| 201 | 1.2E−06 | 6.8E−07 | 6.3E−07 | 0.0E+00 |
| 202 | 0.0E+00 | 0.0E+00 | 0.0E+00 | 0.0E+00 |
| 203 | 0.0E+00 | 2.9E−04 | 8.5E−06 | 0.0E+00 |
| 204 | 1.2E−06 | 3.7E−06 | 1.6E−06 | 0.0E+00 |
| 205 | 1.9E−06 | 1.0E−06 | 0.0E+00 | 0.0E+00 |
| 206 | 0.0E+00 | 1.4E−06 | 1.3E−06 | 0.0E+00 |
| 207 | 1.1E−02 | 9.9E−05 | 2.6E−05 | 1.2E−05 |
| 208 | 3.2E−02 | 1.6E−03 | 3.3E−04 | 8.4E−05 |
| 209 | 0.0E+00 | 0.0E+00 | 0.0E+00 | 5.2E−06 |
| 210 | 2.7E−03 | 6.5E−05 | 1.4E−05 | 3.6E−06 |
| 211 | 0.0E+00 | 0.0E+00 | 0.0E+00 | 6.5E−07 |
| 212 | 0.0E+00 | 0.0E+00 | 0.0E+00 | 0.0E+00 |
| 213 | 1.2E−05 | 0.0E+00 | 0.0E+00 | 5.2E−06 |
| 214 | 0.0E+00 | 0.0E+00 | 0.0E+00 | 0.0E+00 |
| 215 | 1.5E−04 | 5.4E−06 | 0.0E+00 | 0.0E+00 |
| 216 | 2.7E−03 | 5.3E−05 | 4.3E−05 | 1.5E−05 |
| 217 | 0.0E+00 | 0.0E+00 | 0.0E+00 | 0.0E+00 |
| 218 | 4.9E−04 | 4.8E−05 | 9.4E−07 | 1.9E−06 |
| 219 | 0.0E+00 | 0.0E+00 | 0.0E+00 | 0.0E+00 |
| 220 | 1.1E−03 | 4.6E−05 | 1.9E−06 | 0.0E+00 |
| 221 | 1.2E−06 | 3.4E−07 | 6.3E−07 | 0.0E+00 |
| 222 | 0.0E+00 | 0.0E+00 | 0.0E+00 | 0.0E+00 |
| 223 | 0.0E+00 | 3.4E−07 | 0.0E+00 | 0.0E+00 |
| 224 | 0.0E+00 | 0.0E+00 | 0.0E+00 | 0.0E+00 |
| 225 | 9.3E−04 | 2.0E−05 | 2.5E−05 | 3.6E−06 |
| 226 | 0.0E+00 | 0.0E+00 | 0.0E+00 | 0.0E+00 |
| 227 | 0.0E+00 | 0.0E+00 | 0.0E+00 | 0.0E+00 |
| 228 | 0.0E+00 | 0.0E+00 | 0.0E+00 | 0.0E+00 |
| 229 | 0.0E+00 | 0.0E+00 | 0.0E+00 | 0.0E+00 |
| 230 | 0.0E+00 | 0.0E+00 | 0.0E+00 | 0.0E+00 |
| 231 | 0.0E+00 | 1.7E−06 | 0.0E+00 | 0.0E+00 |
| 232 | 3.1E−04 | 3.5E−05 | 3.6E−05 | 2.3E−05 |
| 233 | 0.0E+00 | 1.7E−06 | 0.0E+00 | 0.0E+00 |
| 234 | 0.0E+00 | 0.0E+00 | 0.0E+00 | 0.0E+00 |
| 235 | 0.0E+00 | 5.4E−06 | 2.5E−06 | 3.2E−07 |
| 236 | 1.2E−03 | 7.7E−05 | 3.3E−05 | 1.6E−06 |
| 237 | 1.2E−04 | 6.5E−06 | 4.4E−06 | 0.0E+00 |
| 238 | 0.0E+00 | 0.0E+00 | 0.0E+00 | 0.0E+00 |
| 239 | 0.0E+00 | 0.0E+00 | 0.0E+00 | 0.0E+00 |
| 240 | 1.2E−06 | 0.0E+00 | 0.0E+00 | 0.0E+00 |
| 241 | 0.0E+00 | 0.0E+00 | 0.0E+00 | 0.0E+00 |
| 242 | 0.0E+00 | 0.0E+00 | 0.0E+00 | 0.0E+00 |
| 243 | 2.7E−03 | 8.5E−05 | 4.4E−06 | 3.2E−07 |
| 244 | 4.8E−05 | 0.0E+00 | 0.0E+00 | 0.0E+00 |
| 245 | 0.0E+00 | 0.0E+00 | 0.0E+00 | 0.0E+00 |
| 246 | 0.0E+00 | 0.0E+00 | 0.0E+00 | 0.0E+00 |
| 247 | 0.0E+00 | 0.0E+00 | 0.0E+00 | 0.0E+00 |
| 248 | 0.0E+00 | 3.4E−07 | 0.0E+00 | 0.0E+00 |
| 249 | 0.0E+00 | 0.0E+00 | 0.0E+00 | 0.0E+00 |
| 250 | 0.0E+00 | 0.0E+00 | 0.0E+00 | 0.0E+00 |
| 251 | 7.0E−03 | 3.2E−04 | 6.8E−05 | 9.7E−06 |
| 252 | 6.3E−02 | 1.5E−01 | 2.4E−01 | 1.5E−01 |
| 253 | 0.0E+00 | 0.0E+00 | 3.1E−07 | 1.9E−06 |
| 254 | 2.0E−03 | 1.6E−04 | 2.9E−05 | 5.8E−05 |
| 255 | 0.0E+00 | 0.0E+00 | 0.0E+00 | 0.0E+00 |
| 256 | 0.0E+00 | 0.0E+00 | 6.3E−07 | 0.0E+00 |
| 257 | 0.0E+00 | 0.0E+00 | 0.0E+00 | 0.0E+00 |
| 258 | 2.0E−03 | 3.4E−07 | 2.2E−06 | 6.5E−07 |
| 259 | 7.8E−04 | 8.3E−04 | 3.9E−03 | 1.4E−03 |
| 260 | 1.8E−03 | 1.8E−04 | 3.2E−04 | 3.1E−05 |
| 261 | 3.1E−05 | 1.9E−05 | 1.5E−02 | 2.6E−01 |
| 262 | 1.3E−04 | 2.5E−03 | 1.3E−02 | 4.9E−03 |
| 263 | 0.0E+00 | 2.2E−05 | 0.0E+00 | 0.0E+00 |
| 264 | 1.1E−02 | 6.7E−04 | 2.2E−04 | 1.1E−05 |
| 265 | 3.7E−04 | 3.4E−07 | 0.0E+00 | 0.0E+00 |
| 266 | 0.0E+00 | 0.0E+00 | 3.1E−07 | 0.0E+00 |
| 267 | 0.0E+00 | 0.0E+00 | 0.0E+00 | 0.0E+00 |
| 268 | 0.0E+00 | 2.4E−06 | 6.3E−07 | 6.5E−07 |
| 269 | 7.7E−05 | 8.8E−05 | 3.0E−04 | 3.3E−05 |
| 270 | 0.0E+00 | 8.8E−06 | 0.0E+00 | 0.0E+00 |
| 271 | 3.3E−02 | 1.7E−02 | 1.5E−02 | 3.0E−02 |
| 272 | 1.2E−05 | 0.0E+00 | 0.0E+00 | 0.0E+00 |
| 273 | 0.0E+00 | 0.0E+00 | 0.0E+00 | 0.0E+00 |
| 274 | 1.8E−04 | 0.0E+00 | 0.0E+00 | 0.0E+00 |
| 275 | 5.2E−05 | 0.0E+00 | 0.0E+00 | 0.0E+00 |
| 276 | 6.1E−05 | 0.0E+00 | 0.0E+00 | 0.0E+00 |

-continued

| | | | | |
|---|---|---|---|---|
| 277 | 3.7E−05 | 6.5E−06 | 0.0E+00 | 0.0E+00 |
| 278 | 6.7E−05 | 1.0E−06 | 0.0E+00 | 0.0E+00 |
| 279 | 0.0E+00 | 0.0E+00 | 0.0E+00 | 0.0E+00 |
| 280 | 3.5E−05 | 0.0E+00 | 0.0E+00 | 0.0E+00 |
| 281 | 0.0E+00 | 1.4E−06 | 1.6E−06 | 6.5E−07 |
| 282 | 0.0E+00 | 0.0E+00 | 0.0E+00 | 0.0E+00 |
| 283 | 0.0E+00 | 0.0E+00 | 0.0E+00 | 0.0E+00 |
| 284 | 1.3E−04 | 0.0E+00 | 0.0E+00 | 0.0E+00 |
| 285 | 0.0E+00 | 0.0E+00 | 0.0E+00 | 0.0E+00 |
| 286 | 0.0E+00 | 0.0E+00 | 0.0E+00 | 0.0E+00 |
| 287 | 0.0E+00 | 0.0E+00 | 0.0E+00 | 0.0E+00 |
| 288 | 1.2E−06 | 0.0E+00 | 0.0E+00 | 0.0E+00 |
| 289 | 0.0E+00 | 0.0E+00 | 0.0E+00 | 0.0E+00 |
| 290 | 2.1E−05 | 0.0E+00 | 0.0E+00 | 0.0E+00 |
| 291 | 0.0E+00 | 0.0E+00 | 0.0E+00 | 0.0E+00 |
| 292 | 0.0E+00 | 0.0E+00 | 0.0E+00 | 0.0E+00 |
| 293 | 0.0E+00 | 1.4E−06 | 1.6E−06 | 1.9E−06 |
| 294 | 1.2E−06 | 0.0E+00 | 0.0E+00 | 0.0E+00 |
| 295 | 1.1E−01 | 1.5E−03 | 7.5E−05 | 1.7E−04 |
| 296 | 2.4E−04 | 3.4E−06 | 0.0E+00 | 0.0E+00 |
| 297 | 1.3E−05 | 0.0E+00 | 0.0E+00 | 0.0E+00 |
| 298 | 0.0E+00 | 0.0E+00 | 0.0E+00 | 0.0E+00 |
| 299 | 5.4E−05 | 0.0E+00 | 0.0E+00 | 0.0E+00 |
| 300 | 4.8E−05 | 0.0E+00 | 0.0E+00 | 0.0E+00 |
| 301 | 1.2E−06 | 3.4E−07 | 0.0E+00 | 0.0E+00 |
| 302 | 0.0E+00 | 0.0E+00 | 0.0E+00 | 0.0E+00 |
| 303 | 6.9E−04 | 9.2E−06 | 0.0E+00 | 0.0E+00 |
| 304 | 0.0E+00 | 2.4E−06 | 0.0E+00 | 0.0E+00 |
| 305 | 0.0E+00 | 0.0E+00 | 0.0E+00 | 0.0E+00 |
| 306 | 0.0E+00 | 1.7E−06 | 3.1E−07 | 0.0E+00 |
| 307 | 0.0E+00 | 0.0E+00 | 0.0E+00 | 0.0E+00 |
| 308 | 0.0E+00 | 3.4E−07 | 3.1E−07 | 0.0E+00 |
| 309 | 0.0E+00 | 2.0E−06 | 0.0E+00 | 0.0E+00 |
| 310 | 3.7E−06 | 5.8E−06 | 0.0E+00 | 0.0E+00 |
| 311 | 5.6E−06 | 3.4E−07 | 0.0E+00 | 0.0E+00 |
| 312 | 0.0E+00 | 0.0E+00 | 0.0E+00 | 0.0E+00 |
| 313 | 0.0E+00 | 0.0E+00 | 0.0E+00 | 0.0E+00 |
| 314 | 0.0E+00 | 0.0E+00 | 1.3E−06 | 6.5E−07 |
| 315 | 1.7E−05 | 9.2E−06 | 1.1E−05 | 1.3E−05 |
| 316 | 0.0E+00 | 0.0E+00 | 0.0E+00 | 0.0E+00 |
| 317 | 0.0E+00 | 0.0E+00 | 0.0E+00 | 0.0E+00 |
| 318 | 0.0E+00 | 0.0E+00 | 0.0E+00 | 0.0E+00 |
| 319 | 0.0E+00 | 0.0E+00 | 0.0E+00 | 0.0E+00 |
| 320 | 0.0E+00 | 1.8E−04 | 3.3E−04 | 7.1E−05 |
| 321 | 0.0E+00 | 0.0E+00 | 0.0E+00 | 0.0E+00 |
| 322 | 0.0E+00 | 0.0E+00 | 6.3E−07 | 0.0E+00 |
| 323 | 0.0E+00 | 0.0E+00 | 0.0E+00 | 0.0E+00 |
| 324 | 0.0E+00 | 0.0E+00 | 0.0E+00 | 0.0E+00 |
| 325 | 1.1E−05 | 6.8E−06 | 4.7E−06 | 4.5E−06 |
| 326 | 1.2E−06 | 2.0E−06 | 3.5E−06 | 1.6E−06 |
| 327 | 0.0E+00 | 0.0E+00 | 0.0E+00 | 0.0E+00 |
| 328 | 0.0E+00 | 0.0E+00 | 0.0E+00 | 0.0E+00 |
| 329 | 0.0E+00 | 0.0E+00 | 0.0E+00 | 0.0E+00 |
| 330 | 0.0E+00 | 0.0E+00 | 0.0E+00 | 0.0E+00 |
| 331 | 2.3E−03 | 7.1E−06 | 9.4E−07 | 0.0E+00 |
| 332 | 2.0E−03 | 6.7E−05 | 6.6E−06 | 0.0E+00 |
| 333 | 0.0E+00 | 0.0E+00 | 0.0E+00 | 0.0E+00 |
| 334 | 6.7E−03 | 1.4E−04 | 2.2E−06 | 7.5E−06 |
| 335 | 2.4E−04 | 5.4E−06 | 6.3E−07 | 6.5E−07 |
| 336 | 7.0E−04 | 0.0E+00 | 0.0E+00 | 0.0E+00 |
| 337 | 3.9E−03 | 1.1E−04 | 6.3E−05 | 5.9E−05 |
| 338 | 3.6E−03 | 5.4E−05 | 2.8E−06 | 9.7E−07 |
| 339 | 0.0E+00 | 1.0E−06 | 6.3E−07 | 0.0E+00 |
| 340 | 2.5E−04 | 1.3E−05 | 1.9E−06 | 0.0E+00 |
| 341 | 0.0E+00 | 0.0E+00 | 0.0E+00 | 0.0E+00 |
| 342 | 2.7E−03 | 3.4E−07 | 0.0E+00 | 0.0E+00 |
| 343 | 0.0E+00 | 0.0E+00 | 0.0E+00 | 0.0E+00 |
| 344 | 0.0E+00 | 0.0E+00 | 0.0E+00 | 3.2E−07 |
| 345 | 0.0E+00 | 0.0E+00 | 0.0E+00 | 0.0E+00 |
| 346 | 0.0E+00 | 0.0E+00 | 0.0E+00 | 0.0E+00 |
| 347 | 1.6E−03 | 7.8E−06 | 1.6E−06 | 6.5E−07 |
| 348 | 7.3E−04 | 0.0E+00 | 0.0E+00 | 0.0E+00 |
| 349 | 2.5E−06 | 2.0E−06 | 1.3E−06 | 0.0E+00 |
| 350 | 0.0E+00 | 0.0E+00 | 0.0E+00 | 0.0E+00 |
| 351 | 1.2E−06 | 1.4E−06 | 6.3E−07 | 3.2E−07 |
| 352 | 0.0E+00 | 0.0E+00 | 0.0E+00 | 0.0E+00 |
| 353 | 0.0E+00 | 0.0E+00 | 0.0E+00 | 0.0E+00 |
| 354 | 6.2E−07 | 3.7E−06 | 1.3E−06 | 6.5E−07 |
| 355 | 1.2E−05 | 3.4E−07 | 0.0E+00 | 0.0E+00 |

-continued

| | | | | |
|---|---|---|---|---|
| 356 | 0.0E+00 | 0.0E+00 | 0.0E+00 | 0.0E+00 |
| 357 | 2.5E−06 | 2.0E−06 | 1.6E−06 | 0.0E+00 |
| 358 | 0.0E+00 | 0.0E+00 | 0.0E+00 | 0.0E+00 |
| 359 | 6.2E−05 | 1.0E−06 | 3.1E−07 | 3.2E−07 |
| 360 | 2.0E−05 | 0.0E+00 | 0.0E+00 | 0.0E+00 |
| 361 | 0.0E+00 | 0.0E+00 | 0.0E+00 | 0.0E+00 |
| 362 | 3.9E−04 | 5.1E−06 | 3.1E−07 | 6.5E−07 |
| 363 | 9.0E−05 | 0.0E+00 | 0.0E+00 | 0.0E+00 |
| 364 | 1.2E−06 | 0.0E+00 | 0.0E+00 | 0.0E+00 |
| 365 | 9.0E−04 | 1.1E−05 | 2.2E−06 | 0.0E+00 |
| 366 | 0.0E+00 | 0.0E+00 | 0.0E+00 | 0.0E+00 |
| 367 | 8.6E−06 | 6.8E−07 | 0.0E+00 | 0.0E+00 |
| 368 | 0.0E+00 | 0.0E+00 | 9.4E−07 | 3.2E−07 |
| 369 | 1.2E−06 | 2.0E−06 | 2.5E−06 | 5.5E−06 |
| 370 | 0.0E+00 | 0.0E+00 | 0.0E+00 | 0.0E+00 |
| 371 | 1.2E−04 | 0.0E+00 | 1.5E−05 | 0.0E+00 |
| 372 | 0.0E+00 | 0.0E+00 | 0.0E+00 | 0.0E+00 |
| 373 | 3.3E−05 | 1.8E−05 | 1.1E−05 | 9.7E−06 |
| 374 | 0.0E+00 | 0.0E+00 | 0.0E+00 | 0.0E+00 |
| 375 | 2.5E−06 | 6.8E−07 | 6.3E−07 | 1.3E−06 |
| 376 | 0.0E+00 | 6.8E−07 | 0.0E+00 | 3.2E−07 |
| 377 | 0.0E+00 | 0.0E+00 | 0.0E+00 | 0.0E+00 |
| 378 | 6.3E−03 | 3.6E−05 | 6.0E−06 | 4.5E−06 |

| Taxon ID | CM Atm−/− Colon | | | | | | |
|---|---|---|---|---|---|---|---|
| 1 | 3.9E−03 | 2.5E−03 | 2.7E−03 | 9.4E−04 | 3.9E−03 | 3.6E−03 | 1.3E−03 |
| 2 | 0.0E+00 | 0.0E+00 | 0.0E+00 | 0.0E+00 | 0.0E+00 | 0.0E+00 | 0.0E+00 |
| 3 | 6.8E−07 | 5.1E−07 | 0.0E+00 | 0.0E+00 | 7.7E−07 | 0.0E+00 | 4.2E−06 |
| 4 | 1.0E−04 | 1.8E−05 | 4.3E−05 | 0.0E+00 | 0.0E+00 | 2.1E−05 | 1.8E−05 |
| 5 | 0.0E+00 | 0.0E+00 | 0.0E+00 | 0.0E+00 | 0.0E+00 | 0.0E+00 | 0.0E+00 |
| 6 | 0.0E+00 | 5.1E−07 | 0.0E+00 | 0.0E+00 | 1.3E−05 | 0.0E+00 | 0.0E+00 |
| 7 | 8.9E−06 | 0.0E+00 | 0.0E+00 | 1.2E−06 | 6.1E−06 | 1.4E−05 | 0.0E+00 |
| 8 | 8.2E−06 | 9.7E−06 | 1.1E−04 | 0.0E+00 | 1.8E−05 | 1.6E−06 | 6.1E−06 |
| 9 | 2.7E−06 | 0.0E+00 | 0.0E+00 | 0.0E+00 | 9.9E−06 | 5.4E−07 | 4.7E−07 |
| 10 | 1.0E−05 | 0.0E+00 | 3.4E−06 | 0.0E+00 | 1.1E−05 | 5.4E−07 | 2.8E−06 |
| 11 | 0.0E+00 | 0.0E+00 | 0.0E+00 | 0.0E+00 | 0.0E+00 | 0.0E+00 | 0.0E+00 |
| 12 | 0.0E+00 | 0.0E+00 | 0.0E+00 | 0.0E+00 | 0.0E+00 | 0.0E+00 | 0.0E+00 |
| 13 | 0.0E+00 | 0.0E+00 | 0.0E+00 | 0.0E+00 | 0.0E+00 | 0.0E+00 | 0.0E+00 |
| 14 | 0.0E+00 | 0.0E+00 | 2.3E−06 | 0.0E+00 | 2.3E−06 | 1.2E−05 | 0.0E+00 |
| 15 | 0.0E+00 | 0.0E+00 | 0.0E+00 | 0.0E+00 | 0.0E+00 | 0.0E+00 | 0.0E+00 |
| 16 | 7.5E−06 | 0.0E+00 | 0.0E+00 | 3.0E−07 | 0.0E+00 | 0.0E+00 | 0.0E+00 |
| 17 | 4.8E−06 | 1.4E−05 | 9.1E−06 | 0.0E+00 | 2.3E−06 | 4.3E−06 | 7.0E−06 |
| 18 | 0.0E+00 | 4.1E−06 | 0.0E+00 | 0.0E+00 | 0.0E+00 | 0.0E+00 | 0.0E+00 |
| 19 | 0.0E+00 | 0.0E+00 | 0.0E+00 | 0.0E+00 | 0.0E+00 | 0.0E+00 | 0.0E+00 |
| 20 | 2.7E−06 | 4.1E−06 | 4.5E−06 | 0.0E+00 | 5.4E−06 | 5.4E−07 | 3.8E−06 |
| 21 | 2.0E−04 | 1.4E−04 | 4.1E−04 | 7.7E−05 | 1.6E−04 | 2.3E−04 | 2.7E−04 |
| 22 | 0.0E+00 | 0.0E+00 | 0.0E+00 | 0.0E+00 | 0.0E+00 | 0.0E+00 | 0.0E+00 |
| 23 | 0.0E+00 | 2.0E−06 | 0.0E+00 | 0.0E+00 | 3.1E−06 | 0.0E+00 | 0.0E+00 |
| 24 | 9.5E−06 | 6.1E−06 | 9.1E−06 | 0.0E+00 | 0.0E+00 | 1.1E−06 | 5.6E−06 |
| 25 | 0.0E+00 | 0.0E+00 | 0.0E+00 | 0.0E+00 | 0.0E+00 | 0.0E+00 | 0.0E+00 |
| 26 | 0.0E+00 | 0.0E+00 | 0.0E+00 | 0.0E+00 | 0.0E+00 | 0.0E+00 | 0.0E+00 |
| 27 | 0.0E+00 | 1.0E−06 | 0.0E+00 | 0.0E+00 | 0.0E+00 | 5.4E−07 | 3.3E−06 |
| 28 | 0.0E+00 | 0.0E+00 | 0.0E+00 | 0.0E+00 | 0.0E+00 | 0.0E+00 | 0.0E+00 |
| 29 | 0.0E+00 | 0.0E+00 | 0.0E+00 | 0.0E+00 | 0.0E+00 | 0.0E+00 | 9.4E−07 |
| 30 | 0.0E+00 | 0.0E+00 | 0.0E+00 | 0.0E+00 | 7.7E−07 | 5.4E−07 | 0.0E+00 |
| 31 | 0.0E+00 | 0.0E+00 | 0.0E+00 | 0.0E+00 | 0.0E+00 | 5.4E−07 | 0.0E+00 |
| 32 | 8.2E−06 | 0.0E+00 | 0.0E+00 | 0.0E+00 | 9.9E−06 | 1.0E−05 | 0.0E+00 |
| 33 | 2.5E−04 | 1.0E−06 | 6.4E−05 | 2.1E−06 | 2.2E−05 | 8.1E−06 | 4.7E−07 |
| 34 | 0.0E+00 | 0.0E+00 | 0.0E+00 | 0.0E+00 | 0.0E+00 | 0.0E+00 | 0.0E+00 |
| 35 | 6.1E−06 | 2.6E−06 | 3.4E−06 | 0.0E+00 | 4.6E−06 | 2.7E−06 | 9.4E−06 |
| 36 | 7.5E−06 | 0.0E+00 | 0.0E+00 | 4.5E−06 | 0.0E+00 | 0.0E+00 | 0.0E+00 |
| 37 | 0.0E+00 | 0.0E+00 | 0.0E+00 | 0.0E+00 | 0.0E+00 | 0.0E+00 | 0.0E+00 |
| 38 | 0.0E+00 | 0.0E+00 | 0.0E+00 | 0.0E+00 | 0.0E+00 | 0.0E+00 | 0.0E+00 |
| 39 | 0.0E+00 | 0.0E+00 | 0.0E+00 | 1.2E−06 | 0.0E+00 | 0.0E+00 | 0.0E+00 |
| 40 | 0.0E+00 | 0.0E+00 | 0.0E+00 | 0.0E+00 | 2.7E−05 | 0.0E+00 | 0.0E+00 |
| 41 | 0.0E+00 | 0.0E+00 | 0.0E+00 | 1.0E−05 | 0.0E+00 | 0.0E+00 | 0.0E+00 |
| 42 | 0.0E+00 | 0.0E+00 | 0.0E+00 | 0.0E+00 | 0.0E+00 | 0.0E+00 | 0.0E+00 |
| 43 | 0.0E+00 | 0.0E+00 | 0.0E+00 | 0.0E+00 | 0.0E+00 | 0.0E+00 | 0.0E+00 |
| 44 | 4.1E−06 | 4.1E−06 | 6.8E−06 | 0.0E+00 | 6.1E−06 | 1.1E−06 | 9.4E−07 |
| 45 | 0.0E+00 | 0.0E+00 | 0.0E+00 | 0.0E+00 | 3.1E−06 | 0.0E+00 | 0.0E+00 |
| 46 | 0.0E+00 | 0.0E+00 | 0.0E+00 | 0.0E+00 | 0.0E+00 | 0.0E+00 | 0.0E+00 |
| 47 | 3.4E−06 | 1.0E−06 | 0.0E+00 | 0.0E+00 | 0.0E+00 | 0.0E+00 | 2.3E−06 |
| 48 | 2.7E−06 | 5.1E−07 | 0.0E+00 | 6.0E−07 | 7.7E−07 | 0.0E+00 | 4.7E−07 |
| 49 | 0.0E+00 | 0.0E+00 | 0.0E+00 | 0.0E+00 | 9.9E−06 | 0.0E+00 | 0.0E+00 |
| 50 | 2.5E−04 | 9.7E−05 | 4.4E−05 | 6.0E−06 | 1.3E−04 | 4.6E−05 | 5.6E−05 |
| 51 | 6.6E−05 | 0.0E+00 | 3.4E−06 | 3.0E−07 | 1.5E−06 | 0.0E+00 | 1.3E−05 |
| 52 | 3.1E−05 | 0.0E+00 | 1.1E−06 | 1.4E−05 | 1.3E−04 | 7.5E−06 | 0.0E+00 |
| 53 | 8.2E−06 | 4.1E−06 | 0.0E+00 | 0.0E+00 | 4.4E−05 | 1.1E−06 | 0.0E+00 |

-continued

| | | | | | | | |
|---|---|---|---|---|---|---|---|
| 54 | 1.2E−05 | 5.1E−06 | 4.3E−05 | 1.0E−05 | 9.9E−06 | 5.4E−07 | 6.6E−06 |
| 55 | 1.2E−04 | 1.4E−04 | 1.9E−04 | 0.0E+00 | 2.0E−04 | 3.5E−05 | 1.1E−04 |
| 56 | 0.0E+00 | 0.0E+00 | 0.0E+00 | 0.0E+00 | 0.0E+00 | 0.0E+00 | 0.0E+00 |
| 57 | 0.0E+00 | 0.0E+00 | 0.0E+00 | 1.5E−06 | 7.7E−07 | 0.0E+00 | 0.0E+00 |
| 58 | 1.4E−02 | 9.4E−03 | 2.5E−02 | 4.8E−03 | 1.4E−02 | 1.6E−02 | 1.6E−02 |
| 59 | 5.5E−05 | 8.5E−04 | 2.2E−03 | 1.0E−04 | 4.7E−03 | 8.5E−03 | 4.1E−03 |
| 60 | 3.2E−04 | 7.3E−04 | 5.9E−03 | 6.9E−04 | 1.1E−02 | 2.5E−02 | 1.7E−03 |
| 61 | 1.5E−04 | 2.9E−04 | 2.4E−04 | 1.8E−04 | 9.5E−04 | 2.7E−04 | 1.9E−04 |
| 62 | 4.1E−03 | 2.1E−03 | 9.4E−03 | 1.2E−03 | 4.8E−03 | 1.1E−03 | 1.9E−03 |
| 63 | 1.4E−06 | 8.9E−05 | 1.0E−05 | 1.1E−05 | 8.2E−05 | 1.9E−04 | 8.0E−05 |
| 64 | 3.4E−03 | 5.0E−04 | 1.2E−02 | 7.3E−03 | 1.0E−02 | 3.6E−03 | 2.9E−03 |
| 65 | 5.1E−04 | 2.8E−03 | 1.0E−03 | 2.7E−04 | 4.1E−02 | 2.2E−04 | 1.7E−02 |
| 66 | 1.3E−04 | 9.7E−04 | 7.1E−04 | 1.2E−04 | 1.5E−03 | 1.9E−03 | 4.9E−04 |
| 67 | 4.7E−03 | 2.0E−03 | 2.3E−02 | 4.0E−03 | 1.7E−02 | 4.7E−03 | 5.8E−03 |
| 68 | 0.0E+00 | 0.0E+00 | 0.0E+00 | 0.0E+00 | 0.0E+00 | 0.0E+00 | 0.0E+00 |
| 69 | 1.0E−05 | 6.7E−06 | 2.1E−03 | 3.0E−06 | 9.2E−06 | 1.1E−05 | 1.2E−05 |
| 70 | 0.0E+00 | 7.7E−06 | 2.3E−06 | 3.0E−07 | 1.1E−05 | 8.6E−06 | 5.2E−06 |
| 71 | 6.8E−07 | 3.4E−05 | 5.7E−06 | 4.8E−06 | 6.3E−05 | 7.5E−05 | 6.6E−05 |
| 72 | 0.0E+00 | 0.0E+00 | 1.1E−06 | 0.0E+00 | 0.0E+00 | 0.0E+00 | 0.0E+00 |
| 73 | 0.0E+00 | 0.0E+00 | 0.0E+00 | 0.0E+00 | 0.0E+00 | 0.0E+00 | 9.4E−07 |
| 74 | 1.4E−06 | 1.5E−06 | 0.0E+00 | 0.0E+00 | 3.1E−06 | 5.4E−07 | 3.3E−06 |
| 75 | 3.7E−05 | 0.0E+00 | 1.5E−05 | 1.6E−04 | 6.3E−05 | 2.3E−05 | 9.9E−06 |
| 76 | 4.3E−05 | 6.7E−04 | 5.4E−04 | 1.9E−04 | 1.8E−03 | 8.2E−04 | 6.0E−04 |
| 77 | 8.9E−06 | 3.4E−05 | 2.4E−05 | 2.1E−06 | 4.6E−05 | 3.8E−05 | 6.5E−05 |
| 78 | 0.0E+00 | 4.1E−06 | 0.0E+00 | 0.0E+00 | 2.3E−06 | 1.1E−05 | 9.4E−07 |
| 79 | 8.1E−05 | 1.3E−05 | 2.1E−03 | 1.5E−04 | 3.7E−03 | 1.3E−02 | 1.5E−04 |
| 80 | 1.1E−05 | 1.1E−05 | 0.0E+00 | 1.2E−06 | 4.7E−05 | 0.0E+00 | 1.5E−05 |
| 81 | 8.2E−06 | 3.1E−06 | 3.4E−06 | 1.6E−05 | 1.5E−05 | 1.2E−05 | 7.5E−06 |
| 82 | 2.3E−04 | 4.3E−02 | 4.5E−02 | 6.5E−04 | 2.2E−02 | 9.6E−02 | 1.5E−02 |
| 83 | 2.0E−03 | 8.5E−04 | 1.2E−03 | 1.5E−03 | 4.2E−03 | 1.9E−03 | 8.9E−03 |
| 84 | 0.0E+00 | 0.0E+00 | 1.1E−06 | 0.0E+00 | 0.0E+00 | 0.0E+00 | 4.7E−07 |
| 85 | 4.5E−04 | 3.3E−04 | 5.1E−03 | 6.9E−04 | 5.0E−03 | 2.3E−02 | 9.5E−04 |
| 86 | 7.1E−03 | 2.4E−01 | 2.8E−02 | 2.9E−02 | 3.5E−01 | 3.5E−01 | 2.8E−01 |
| 87 | 6.8E−07 | 9.7E−06 | 3.4E−06 | 1.2E−05 | 1.1E−05 | 1.1E−05 | 1.5E−05 |
| 88 | 0.0E+00 | 2.8E−03 | 4.0E−03 | 3.0E−07 | 0.0E+00 | 0.0E+00 | 0.0E+00 |
| 89 | 4.8E−06 | 5.1E−06 | 0.0E+00 | 0.0E+00 | 1.1E−05 | 0.0E+00 | 9.4E−06 |
| 90 | 3.7E−05 | 2.8E−05 | 1.0E−04 | 3.7E−04 | 9.9E−05 | 1.9E−05 | 6.3E−05 |
| 91 | 6.8E−07 | 0.0E+00 | 0.0E+00 | 0.0E+00 | 2.3E−06 | 0.0E+00 | 4.7E−07 |
| 92 | 0.0E+00 | 0.0E+00 | 0.0E+00 | 0.0E+00 | 7.7E−07 | 0.0E+00 | 4.7E−07 |
| 93 | 0.0E+00 | 0.0E+00 | 0.0E+00 | 3.0E−07 | 0.0E+00 | 5.4E−07 | 0.0E+00 |
| 94 | 5.9E−04 | 8.4E−03 | 1.7E−02 | 2.9E−03 | 3.2E−02 | 4.5E−02 | 2.0E−02 |
| 95 | 0.0E+00 | 1.5E−06 | 0.0E+00 | 0.0E+00 | 7.7E−07 | 2.2E−06 | 0.0E+00 |
| 96 | 1.0E−04 | 3.7E−04 | 1.1E−03 | 4.1E−04 | 2.9E−03 | 1.4E−03 | 1.8E−03 |
| 97 | 6.8E−07 | 1.5E−02 | 3.2E−02 | 0.0E+00 | 7.7E−07 | 5.4E−07 | 6.9E−03 |
| 98 | 1.3E−04 | 1.8E−04 | 1.5E−04 | 0.0E+00 | 9.9E−05 | 3.5E−05 | 2.3E−04 |
| 99 | 6.1E−06 | 0.0E+00 | 1.1E−06 | 3.3E−06 | 1.5E−06 | 1.6E−06 | 0.0E+00 |
| 100 | 0.0E+00 | 0.0E+00 | 0.0E+00 | 0.0E+00 | 0.0E+00 | 0.0E+00 | 0.0E+00 |
| 101 | 8.9E−05 | 2.4E−05 | 2.5E−05 | 1.7E−05 | 2.6E−05 | 8.6E−06 | 1.7E−05 |
| 102 | 0.0E+00 | 0.0E+00 | 1.6E−05 | 0.0E+00 | 0.0E+00 | 0.0E+00 | 0.0E+00 |
| 103 | 3.4E−06 | 0.0E+00 | 1.1E−06 | 0.0E+00 | 0.0E+00 | 0.0E+00 | 4.7E−07 |
| 104 | 0.0E+00 | 0.0E+00 | 0.0E+00 | 0.0E+00 | 0.0E+00 | 0.0E+00 | 0.0E+00 |
| 105 | 3.7E−03 | 1.5E−03 | 4.9E−03 | 6.2E−05 | 1.0E−03 | 3.4E−04 | 5.4E−04 |
| 106 | 5.4E−06 | 1.5E−06 | 2.3E−06 | 0.0E+00 | 3.1E−06 | 0.0E+00 | 1.9E−06 |
| 107 | 2.0E−06 | 9.7E−06 | 1.2E−05 | 3.6E−06 | 1.6E−05 | 2.9E−05 | 1.3E−05 |
| 108 | 0.0E+00 | 0.0E+00 | 0.0E+00 | 0.0E+00 | 0.0E+00 | 0.0E+00 | 5.6E−06 |
| 109 | 6.8E−07 | 2.0E−06 | 2.3E−06 | 0.0E+00 | 1.5E−06 | 1.1E−06 | 1.4E−06 |
| 110 | 1.3E−04 | 9.3E−05 | 1.6E−04 | 9.9E−05 | 6.7E−05 | 2.8E−05 | 1.0E−04 |
| 111 | 0.0E+00 | 0.0E+00 | 0.0E+00 | 0.0E+00 | 0.0E+00 | 0.0E+00 | 0.0E+00 |
| 112 | 0.0E+00 | 0.0E+00 | 0.0E+00 | 0.0E+00 | 0.0E+00 | 0.0E+00 | 0.0E+00 |
| 113 | 0.0E+00 | 0.0E+00 | 0.0E+00 | 0.0E+00 | 0.0E+00 | 0.0E+00 | 0.0E+00 |
| 114 | 1.4E−06 | 5.1E−07 | 0.0E+00 | 0.0E+00 | 0.0E+00 | 7.5E−06 | 0.0E+00 |
| 115 | 1.4E−03 | 2.5E−04 | 6.4E−03 | 7.5E−06 | 5.4E−06 | 3.1E−04 | 3.2E−04 |
| 116 | 0.0E+00 | 0.0E+00 | 6.7E−05 | 0.0E+00 | 0.0E+00 | 0.0E+00 | 0.0E+00 |
| 117 | 0.0E+00 | 0.0E+00 | 0.0E+00 | 0.0E+00 | 0.0E+00 | 0.0E+00 | 0.0E+00 |
| 118 | 0.0E+00 | 0.0E+00 | 0.0E+00 | 0.0E+00 | 0.0E+00 | 0.0E+00 | 0.0E+00 |
| 119 | 0.0E+00 | 0.0E+00 | 0.0E+00 | 0.0E+00 | 0.0E+00 | 0.0E+00 | 0.0E+00 |
| 120 | 1.8E−04 | 9.6E−05 | 1.8E−04 | 0.0E+00 | 3.6E−04 | 4.8E−05 | 4.7E−06 |
| 121 | 9.5E−05 | 3.1E−05 | 5.7E−05 | 1.5E−06 | 6.1E−06 | 1.6E−06 | 3.8E−06 |
| 122 | 7.0E−05 | 2.1E−05 | 1.8E−05 | 1.9E−05 | 3.1E−06 | 3.8E−05 | 5.2E−04 |
| 123 | 1.4E−06 | 0.0E+00 | 0.0E+00 | 0.0E+00 | 0.0E+00 | 0.0E+00 | 0.0E+00 |
| 124 | 0.0E+00 | 0.0E+00 | 0.0E+00 | 0.0E+00 | 0.0E+00 | 0.0E+00 | 0.0E+00 |
| 125 | 9.7E−05 | 5.6E−05 | 1.2E−04 | 2.1E−06 | 1.8E−04 | 4.3E−06 | 3.0E−04 |
| 126 | 0.0E+00 | 0.0E+00 | 0.0E+00 | 0.0E+00 | 0.0E+00 | 0.0E+00 | 0.0E+00 |
| 127 | 1.0E−05 | 0.0E+00 | 0.0E+00 | 0.0E+00 | 0.0E+00 | 8.6E−06 | 0.0E+00 |
| 128 | 1.3E−02 | 1.6E−04 | 3.0E−03 | 3.8E−05 | 1.7E−04 | 4.1E−04 | 1.0E−04 |
| 129 | 3.4E−06 | 2.0E−06 | 2.3E−06 | 0.0E+00 | 3.8E−06 | 5.4E−07 | 3.3E−06 |
| 130 | 0.0E+00 | 0.0E+00 | 1.1E−06 | 0.0E+00 | 8.4E−06 | 0.0E+00 | 0.0E+00 |
| 131 | 0.0E+00 | 0.0E+00 | 0.0E+00 | 0.0E+00 | 0.0E+00 | 0.0E+00 | 0.0E+00 |
| 132 | 0.0E+00 | 0.0E+00 | 0.0E+00 | 0.0E+00 | 0.0E+00 | 0.0E+00 | 0.0E+00 |

-continued

| | | | | | | | |
|---|---|---|---|---|---|---|---|
| 133 | 7.6E−05 | 0.0E+00 | 0.0E+00 | 0.0E+00 | 0.0E+00 | 0.0E+00 | 0.0E+00 |
| 134 | 1.4E−02 | 9.5E−04 | 1.3E−03 | 7.2E−06 | 6.3E−03 | 4.6E−04 | 1.2E−04 |
| 135 | 0.0E+00 | 0.0E+00 | 0.0E+00 | 0.0E+00 | 0.0E+00 | 0.0E+00 | 0.0E+00 |
| 136 | 2.9E−05 | 4.1E−06 | 4.7E−05 | 0.0E+00 | 9.2E−06 | 2.2E−06 | 8.0E−06 |
| 137 | 0.0E+00 | 0.0E+00 | 0.0E+00 | 0.0E+00 | 0.0E+00 | 0.0E+00 | 4.7E−07 |
| 138 | 0.0E+00 | 1.4E−05 | 0.0E+00 | 0.0E+00 | 0.0E+00 | 0.0E+00 | 0.0E+00 |
| 139 | 1.2E−04 | 1.7E−05 | 5.1E−03 | 5.1E−06 | 6.9E−06 | 1.1E−06 | 1.5E−04 |
| 140 | 1.6E−03 | 1.1E−03 | 9.5E−04 | 1.6E−05 | 1.3E−04 | 3.1E−04 | 3.1E−05 |
| 141 | 0.0E+00 | 0.0E+00 | 0.0E+00 | 0.0E+00 | 0.0E+00 | 0.0E+00 | 0.0E+00 |
| 142 | 0.0E+00 | 0.0E+00 | 0.0E+00 | 0.0E+00 | 0.0E+00 | 0.0E+00 | 0.0E+00 |
| 143 | 0.0E+00 | 0.0E+00 | 0.0E+00 | 0.0E+00 | 0.0E+00 | 0.0E+00 | 0.0E+00 |
| 144 | 0.0E+00 | 0.0E+00 | 0.0E+00 | 0.0E+00 | 0.0E+00 | 0.0E+00 | 0.0E+00 |
| 145 | 3.4E−06 | 0.0E+00 | 0.0E+00 | 0.0E+00 | 0.0E+00 | 0.0E+00 | 0.0E+00 |
| 146 | 0.0E+00 | 0.0E+00 | 0.0E+00 | 0.0E+00 | 0.0E+00 | 0.0E+00 | 0.0E+00 |
| 147 | 0.0E+00 | 0.0E+00 | 0.0E+00 | 0.0E+00 | 0.0E+00 | 1.0E−04 | 0.0E+00 |
| 148 | 3.4E−04 | 8.1E−04 | 2.4E−03 | 1.9E−05 | 3.7E−03 | 7.7E−04 | 9.5E−04 |
| 149 | 0.0E+00 | 0.0E+00 | 0.0E+00 | 0.0E+00 | 0.0E+00 | 0.0E+00 | 5.6E−06 |
| 150 | 0.0E+00 | 5.1E−07 | 0.0E+00 | 0.0E+00 | 3.1E−06 | 6.5E−06 | 5.2E−06 |
| 151 | 0.0E+00 | 0.0E+00 | 0.0E+00 | 0.0E+00 | 0.0E+00 | 0.0E+00 | 4.7E−07 |
| 152 | 0.0E+00 | 0.0E+00 | 0.0E+00 | 0.0E+00 | 0.0E+00 | 0.0E+00 | 0.0E+00 |
| 153 | 4.0E−05 | 0.0E+00 | 0.0E+00 | 0.0E+00 | 0.0E+00 | 0.0E+00 | 0.0E+00 |
| 154 | 2.0E−06 | 2.0E−06 | 4.5E−06 | 6.0E−07 | 1.5E−06 | 4.5E−05 | 1.9E−06 |
| 155 | 0.0E+00 | 1.5E−06 | 0.0E+00 | 0.0E+00 | 4.6E−06 | 0.0E+00 | 0.0E+00 |
| 156 | 6.8E−07 | 1.3E−05 | 3.5E−05 | 4.5E−06 | 3.0E−04 | 1.8E−05 | 0.0E+00 |
| 157 | 0.0E+00 | 0.0E+00 | 0.0E+00 | 3.0E−07 | 0.0E+00 | 0.0E+00 | 0.0E+00 |
| 158 | 0.0E+00 | 0.0E+00 | 0.0E+00 | 0.0E+00 | 0.0E+00 | 0.0E+00 | 0.0E+00 |
| 159 | 4.3E−05 | 5.0E−05 | 0.0E+00 | 4.2E−06 | 2.5E−04 | 0.0E+00 | 0.0E+00 |
| 160 | 4.4E−05 | 0.0E+00 | 3.4E−05 | 0.0E+00 | 0.0E+00 | 7.0E−06 | 0.0E+00 |
| 161 | 0.0E+00 | 5.1E−07 | 0.0E+00 | 0.0E+00 | 0.0E+00 | 0.0E+00 | 0.0E+00 |
| 162 | 0.0E+00 | 0.0E+00 | 0.0E+00 | 0.0E+00 | 0.0E+00 | 1.2E−05 | 0.0E+00 |
| 163 | 6.6E−03 | 1.5E−06 | 5.4E−05 | 1.0E−02 | 1.5E−06 | 2.2E−06 | 5.3E−05 |
| 164 | 7.5E−06 | 9.4E−05 | 6.4E−05 | 2.2E−05 | 3.1E−05 | 1.0E−04 | 1.3E−05 |
| 165 | 0.0E+00 | 0.0E+00 | 0.0E+00 | 0.0E+00 | 0.0E+00 | 0.0E+00 | 0.0E+00 |
| 166 | 0.0E+00 | 0.0E+00 | 4.5E−06 | 0.0E+00 | 7.7E−07 | 0.0E+00 | 0.0E+00 |
| 167 | 3.0E−02 | 3.5E−02 | 2.6E−02 | 5.6E−03 | 2.4E−02 | 1.5E−02 | 4.1E−03 |
| 168 | 6.8E−07 | 0.0E+00 | 6.8E−06 | 0.0E+00 | 0.0E+00 | 1.1E−06 | 1.9E−06 |
| 169 | 0.0E+00 | 0.0E+00 | 1.1E−06 | 0.0E+00 | 0.0E+00 | 0.0E+00 | 0.0E+00 |
| 170 | 6.8E−06 | 0.0E+00 | 0.0E+00 | 0.0E+00 | 0.0E+00 | 0.0E+00 | 0.0E+00 |
| 171 | 0.0E+00 | 0.0E+00 | 0.0E+00 | 0.0E+00 | 0.0E+00 | 0.0E+00 | 0.0E+00 |
| 172 | 5.9E−03 | 1.4E−04 | 1.9E−02 | 1.4E−04 | 7.7E−04 | 4.3E−03 | 6.3E−03 |
| 173 | 0.0E+00 | 0.0E+00 | 0.0E+00 | 0.0E+00 | 0.0E+00 | 0.0E+00 | 0.0E+00 |
| 174 | 4.7E−02 | 2.7E−03 | 3.2E−02 | 8.7E−04 | 8.5E−04 | 1.5E−02 | 2.6E−03 |
| 175 | 0.0E+00 | 0.0E+00 | 0.0E+00 | 0.0E+00 | 0.0E+00 | 0.0E+00 | 0.0E+00 |
| 176 | 0.0E+00 | 0.0E+00 | 0.0E+00 | 0.0E+00 | 0.0E+00 | 0.0E+00 | 0.0E+00 |
| 177 | 2.0E−06 | 3.1E−06 | 4.5E−06 | 0.0E+00 | 0.0E+00 | 0.0E+00 | 9.4E−07 |
| 178 | 1.4E−06 | 8.2E−06 | 1.1E−06 | 0.0E+00 | 7.7E−07 | 5.4E−07 | 1.4E−05 |
| 179 | 0.0E+00 | 0.0E+00 | 0.0E+00 | 0.0E+00 | 0.0E+00 | 0.0E+00 | 0.0E+00 |
| 180 | 2.6E−04 | 1.0E−06 | 0.0E+00 | 0.0E+00 | 1.5E−06 | 5.4E−07 | 9.4E−07 |
| 181 | 4.1E−06 | 6.1E−06 | 3.4E−06 | 0.0E+00 | 3.8E−06 | 0.0E+00 | 8.4E−06 |
| 182 | 0.0E+00 | 5.1E−06 | 0.0E+00 | 0.0E+00 | 2.3E−06 | 0.0E+00 | 4.7E−07 |
| 183 | 0.0E+00 | 1.2E−05 | 0.0E+00 | 0.0E+00 | 0.0E+00 | 1.1E−06 | 0.0E+00 |
| 184 | 0.0E+00 | 0.0E+00 | 0.0E+00 | 0.0E+00 | 1.1E−05 | 0.0E+00 | 0.0E+00 |
| 185 | 4.7E−04 | 3.3E−03 | 7.3E−03 | 4.2E−06 | 8.5E−04 | 9.8E−04 | 2.2E−04 |
| 186 | 0.0E+00 | 0.0E+00 | 0.0E+00 | 0.0E+00 | 0.0E+00 | 0.0E+00 | 0.0E+00 |
| 187 | 0.0E+00 | 0.0E+00 | 0.0E+00 | 0.0E+00 | 0.0E+00 | 0.0E+00 | 0.0E+00 |
| 188 | 1.4E−06 | 0.0E+00 | 0.0E+00 | 0.0E+00 | 0.0E+00 | 0.0E+00 | 0.0E+00 |
| 189 | 0.0E+00 | 0.0E+00 | 0.0E+00 | 0.0E+00 | 0.0E+00 | 0.0E+00 | 0.0E+00 |
| 190 | 1.2E−02 | 1.1E−04 | 7.0E−05 | 4.5E−06 | 1.5E−04 | 1.1E−04 | 1.8E−05 |
| 191 | 7.6E−05 | 6.8E−05 | 4.8E−05 | 0.0E+00 | 9.9E−05 | 1.7E−04 | 8.4E−05 |
| 192 | 3.2E−05 | 3.8E−05 | 1.1E−04 | 0.0E+00 | 1.5E−05 | 0.0E+00 | 2.0E−05 |
| 193 | 8.4E−04 | 1.9E−05 | 2.3E−06 | 3.0E−07 | 6.9E−06 | 0.0E+00 | 0.0E+00 |
| 194 | 2.5E−05 | 3.1E−06 | 1.0E−05 | 0.0E+00 | 2.3E−06 | 0.0E+00 | 0.0E+00 |
| 195 | 0.0E+00 | 0.0E+00 | 0.0E+00 | 0.0E+00 | 6.1E−06 | 0.0E+00 | 7.5E−06 |
| 196 | 6.8E−06 | 0.0E+00 | 0.0E+00 | 0.0E+00 | 0.0E+00 | 0.0E+00 | 4.0E−05 |
| 197 | 7.5E−06 | 4.6E−06 | 9.9E−05 | 7.2E−06 | 3.6E−05 | 8.1E−06 | 7.5E−06 |
| 198 | 0.0E+00 | 0.0E+00 | 0.0E+00 | 0.0E+00 | 0.0E+00 | 1.4E−04 | 5.6E−06 |
| 199 | 2.6E−03 | 8.1E−05 | 1.4E−03 | 7.2E−06 | 1.7E−05 | 1.4E−04 | 3.1E−05 |
| 200 | 1.4E−06 | 0.0E+00 | 0.0E+00 | 0.0E+00 | 0.0E+00 | 0.0E+00 | 0.0E+00 |
| 201 | 2.8E−05 | 9.7E−06 | 1.2E−04 | 1.8E−06 | 1.6E−05 | 2.2E−06 | 1.9E−06 |
| 202 | 0.0E+00 | 0.0E+00 | 0.0E+00 | 0.0E+00 | 0.0E+00 | 1.1E−05 | 0.0E+00 |
| 203 | 6.6E−04 | 0.0E+00 | 5.5E−04 | 1.2E−04 | 0.0E+00 | 1.9E−04 | 0.0E+00 |
| 204 | 2.7E−06 | 3.1E−06 | 7.9E−06 | 0.0E+00 | 0.0E+00 | 0.0E+00 | 0.0E+00 |
| 205 | 0.0E+00 | 0.0E+00 | 0.0E+00 | 0.0E+00 | 0.0E+00 | 0.0E+00 | 0.0E+00 |
| 206 | 0.0E+00 | 0.0E+00 | 0.0E+00 | 0.0E+00 | 0.0E+00 | 0.0E+00 | 0.0E+00 |
| 207 | 2.5E−05 | 8.7E−05 | 3.4E−06 | 7.2E−06 | 6.1E−06 | 1.4E−03 | 1.6E−04 |
| 208 | 1.3E−02 | 8.2E−03 | 2.6E−02 | 9.0E−04 | 5.2E−03 | 8.6E−04 | 5.8E−03 |
| 209 | 0.0E+00 | 0.0E+00 | 0.0E+00 | 0.0E+00 | 0.0E+00 | 2.9E−05 | 0.0E+00 |
| 210 | 7.7E−03 | 6.1E−03 | 2.2E−02 | 1.7E−04 | 3.2E−03 | 9.4E−04 | 1.6E−03 |
| 211 | 0.0E+00 | 0.0E+00 | 0.0E+00 | 0.0E+00 | 0.0E+00 | 0.0E+00 | 8.9E−06 |

| | | | | | | | |
|---|---|---|---|---|---|---|---|
| 212 | 2.3E−05 | 0.0E+00 | 3.4E−06 | 1.6E−05 | 1.5E−05 | 2.7E−05 | 0.0E+00 |
| 213 | 0.0E+00 | 0.0E+00 | 0.0E+00 | 0.0E+00 | 0.0E+00 | 0.0E+00 | 0.0E+00 |
| 214 | 0.0E+00 | 0.0E+00 | 0.0E+00 | 0.0E+00 | 0.0E+00 | 0.0E+00 | 0.0E+00 |
| 215 | 0.0E+00 | 1.5E−06 | 0.0E+00 | 0.0E+00 | 3.1E−06 | 0.0E+00 | 0.0E+00 |
| 216 | 3.9E−03 | 1.1E−03 | 9.8E−05 | 4.3E−05 | 2.2E−03 | 1.0E−04 | 2.5E−04 |
| 217 | 0.0E+00 | 0.0E+00 | 0.0E+00 | 0.0E+00 | 0.0E+00 | 0.0E+00 | 0.0E+00 |
| 218 | 2.2E−03 | 4.0E−04 | 9.7E−04 | 1.1E−04 | 7.5E−05 | 8.5E−05 | 8.2E−05 |
| 219 | 0.0E+00 | 0.0E+00 | 0.0E+00 | 0.0E+00 | 2.1E−05 | 5.4E−07 | 0.0E+00 |
| 220 | 1.3E−03 | 1.2E−03 | 2.8E−03 | 1.1E−04 | 1.2E−03 | 1.4E−04 | 3.8E−04 |
| 221 | 2.0E−06 | 0.0E+00 | 0.0E+00 | 0.0E+00 | 0.0E+00 | 0.0E+00 | 0.0E+00 |
| 222 | 3.5E−05 | 6.7E−06 | 0.0E+00 | 0.0E+00 | 1.5E−06 | 0.0E+00 | 0.0E+00 |
| 223 | 4.8E−06 | 0.0E+00 | 0.0E+00 | 0.0E+00 | 5.6E−05 | 0.0E+00 | 0.0E+00 |
| 224 | 1.4E−06 | 2.6E−06 | 5.7E−06 | 1.8E−06 | 1.5E−06 | 5.4E−07 | 3.8E−06 |
| 225 | 8.1E−03 | 1.5E−03 | 6.4E−03 | 5.2E−05 | 8.8E−04 | 4.0E−04 | 5.1E−04 |
| 226 | 1.7E−04 | 0.0E+00 | 9.2E−05 | 0.0E+00 | 0.0E+00 | 0.0E+00 | 0.0E+00 |
| 227 | 2.7E−05 | 9.2E−06 | 9.1E−06 | 3.0E−07 | 0.0E+00 | 1.1E−05 | 3.7E−05 |
| 228 | 6.1E−06 | 5.1E−07 | 0.0E+00 | 0.0E+00 | 0.0E+00 | 0.0E+00 | 0.0E+00 |
| 229 | 0.0E+00 | 2.0E−06 | 0.0E+00 | 0.0E+00 | 1.5E−06 | 1.6E−06 | 6.1E−06 |
| 230 | 0.0E+00 | 3.1E−06 | 0.0E+00 | 0.0E+00 | 7.7E−07 | 2.2E−06 | 0.0E+00 |
| 231 | 8.2E−06 | 1.5E−06 | 5.7E−06 | 3.9E−06 | 2.1E−05 | 6.5E−06 | 5.2E−06 |
| 232 | 2.5E−01 | 3.5E−01 | 2.4E−01 | 3.1E−05 | 2.1E−01 | 5.6E−02 | 4.5E−01 |
| 233 | 5.4E−06 | 2.9E−05 | 2.3E−06 | 0.0E+00 | 1.5E−06 | 1.1E−05 | 4.7E−06 |
| 234 | 0.0E+00 | 0.0E+00 | 0.0E+00 | 0.0E+00 | 0.0E+00 | 6.2E−05 | 0.0E+00 |
| 235 | 8.8E−04 | 5.9E−04 | 2.2E−03 | 3.9E−06 | 1.4E−03 | 6.9E−05 | 3.2E−04 |
| 236 | 9.4E−03 | 1.8E−03 | 7.1E−03 | 5.3E−04 | 1.5E−03 | 9.4E−04 | 8.6E−04 |
| 237 | 0.0E+00 | 0.0E+00 | 1.1E−04 | 2.1E−05 | 1.1E−05 | 1.2E−05 | 1.1E−05 |
| 238 | 2.0E−06 | 0.0E+00 | 0.0E+00 | 0.0E+00 | 0.0E+00 | 5.4E−07 | 1.3E−04 |
| 239 | 4.3E−04 | 5.6E−05 | 7.4E−05 | 3.6E−06 | 4.7E−05 | 1.9E−05 | 3.8E−05 |
| 240 | 1.1E−05 | 1.0E−06 | 4.5E−06 | 1.2E−06 | 2.3E−06 | 0.0E+00 | 2.3E−06 |
| 241 | 2.7E−04 | 4.1E−06 | 3.0E−05 | 8.2E−06 | 0.0E+00 | 1.7E−04 | 1.4E−06 |
| 242 | 4.1E−06 | 3.1E−06 | 0.0E+00 | 0.0E+00 | 7.7E−07 | 1.1E−06 | 6.1E−06 |
| 243 | 3.2E−02 | 2.0E−03 | 2.8E−03 | 2.1E−04 | 1.0E−03 | 4.0E−04 | 2.4E−04 |
| 244 | 0.0E+00 | 0.0E+00 | 0.0E+00 | 0.0E+00 | 0.0E+00 | 1.2E−05 | 0.0E+00 |
| 245 | 0.0E+00 | 0.0E+00 | 0.0E+00 | 0.0E+00 | 0.0E+00 | 0.0E+00 | 0.0E+00 |
| 246 | 0.0E+00 | 0.0E+00 | 0.0E+00 | 0.0E+00 | 0.0E+00 | 0.0E+00 | 0.0E+00 |
| 247 | 6.8E−07 | 5.1E−07 | 0.0E+00 | 0.0E+00 | 7.7E−07 | 0.0E+00 | 5.2E−06 |
| 248 | 0.0E+00 | 0.0E+00 | 0.0E+00 | 0.0E+00 | 0.0E+00 | 1.1E−04 | 9.4E−07 |
| 249 | 0.0E+00 | 0.0E+00 | 3.7E−04 | 0.0E+00 | 0.0E+00 | 0.0E+00 | 0.0E+00 |
| 250 | 2.2E−04 | 5.4E−05 | 2.7E−05 | 0.0E+00 | 1.7E−05 | 1.8E−05 | 0.0E+00 |
| 251 | 1.4E−02 | 7.6E−03 | 4.6E−03 | 3.5E−04 | 1.3E−03 | 2.8E−03 | 3.6E−03 |
| 252 | 1.7E−04 | 2.2E−03 | 2.0E−04 | 3.4E−05 | 2.9E−04 | 7.7E−03 | 2.6E−03 |
| 253 | 0.0E+00 | 0.0E+00 | 0.0E+00 | 0.0E+00 | 0.0E+00 | 0.0E+00 | 0.0E+00 |
| 254 | 3.4E−06 | 8.2E−05 | 7.9E−05 | 4.3E−05 | 9.9E−05 | 1.5E−04 | 5.8E−05 |
| 255 | 0.0E+00 | 0.0E+00 | 0.0E+00 | 0.0E+00 | 0.0E+00 | 0.0E+00 | 0.0E+00 |
| 256 | 6.1E−06 | 5.7E−03 | 5.5E−04 | 0.0E+00 | 1.7E−03 | 4.9E−04 | 2.0E−04 |
| 257 | 0.0E+00 | 0.0E+00 | 0.0E+00 | 0.0E+00 | 0.0E+00 | 0.0E+00 | 2.6E−05 |
| 258 | 5.3E−05 | 2.3E−03 | 4.1E−03 | 9.7E−05 | 1.4E−02 | 1.3E−02 | 4.6E−03 |
| 259 | 1.3E−04 | 6.0E−05 | 1.1E−06 | 3.9E−06 | 9.6E−04 | 3.9E−04 | 5.1E−05 |
| 260 | 4.1E−06 | 2.5E−05 | 5.2E−05 | 3.6E−05 | 4.4E−04 | 8.5E−04 | 6.3E−03 |
| 261 | 1.7E−03 | 1.4E−05 | 2.0E−04 | 1.0E−05 | 6.0E−05 | 2.7E−02 | 1.3E−05 |
| 262 | 6.8E−07 | 5.1E−07 | 3.4E−06 | 1.8E−06 | 4.6E−06 | 5.4E−07 | 0.0E+00 |
| 263 | 9.8E−04 | 1.4E−03 | 3.9E−03 | 8.2E−06 | 1.3E−03 | 2.3E−04 | 1.4E−04 |
| 264 | 2.5E−02 | 1.9E−02 | 5.5E−02 | 3.6E−04 | 1.1E−02 | 4.1E−03 | 7.9E−03 |
| 265 | 1.2E−03 | 3.1E−05 | 3.5E−03 | 3.3E−06 | 1.3E−04 | 5.9E−06 | 6.3E−05 |
| 266 | 0.0E+00 | 0.0E+00 | 0.0E+00 | 0.0E+00 | 0.0E+00 | 0.0E+00 | 0.0E+00 |
| 267 | 0.0E+00 | 0.0E+00 | 0.0E+00 | 0.0E+00 | 0.0E+00 | 0.0E+00 | 0.0E+00 |
| 268 | 4.1E−05 | 7.9E−05 | 4.8E−05 | 1.3E−05 | 1.2E−04 | 1.5E−04 | 1.6E−04 |
| 269 | 6.1E−06 | 1.1E−05 | 2.0E−05 | 3.0E−07 | 9.2E−06 | 2.3E−05 | 1.9E−06 |
| 270 | 0.0E+00 | 0.0E+00 | 0.0E+00 | 0.0E+00 | 0.0E+00 | 0.0E+00 | 0.0E+00 |
| 271 | 2.0E−02 | 8.4E−03 | 4.3E−02 | 3.7E−03 | 1.6E−02 | 1.5E−02 | 9.1E−03 |
| 272 | 2.4E−05 | 2.3E−05 | 4.7E−05 | 9.1E−07 | 2.2E−05 | 5.4E−06 | 3.5E−05 |
| 273 | 0.0E+00 | 0.0E+00 | 0.0E+00 | 0.0E+00 | 2.3E−06 | 0.0E+00 | 0.0E+00 |
| 274 | 0.0E+00 | 0.0E+00 | 0.0E+00 | 0.0E+00 | 6.9E−06 | 0.0E+00 | 0.0E+00 |
| 275 | 0.0E+00 | 0.0E+00 | 0.0E+00 | 0.0E+00 | 0.0E+00 | 0.0E+00 | 0.0E+00 |
| 276 | 0.0E+00 | 0.0E+00 | 0.0E+00 | 0.0E+00 | 0.0E+00 | 0.0E+00 | 0.0E+00 |
| 277 | 6.4E−04 | 9.4E−05 | 4.1E−04 | 1.5E−05 | 1.0E−04 | 1.6E−05 | 8.9E−05 |
| 278 | 2.0E−06 | 0.0E+00 | 0.0E+00 | 0.0E+00 | 0.0E+00 | 0.0E+00 | 0.0E+00 |
| 279 | 0.0E+00 | 0.0E+00 | 0.0E+00 | 0.0E+00 | 0.0E+00 | 0.0E+00 | 0.0E+00 |
| 280 | 0.0E+00 | 0.0E+00 | 0.0E+00 | 0.0E+00 | 0.0E+00 | 0.0E+00 | 0.0E+00 |
| 281 | 0.0E+00 | 0.0E+00 | 0.0E+00 | 0.0E+00 | 0.0E+00 | 0.0E+00 | 0.0E+00 |
| 282 | 0.0E+00 | 5.1E−07 | 1.1E−06 | 0.0E+00 | 0.0E+00 | 0.0E+00 | 0.0E+00 |
| 283 | 0.0E+00 | 0.0E+00 | 0.0E+00 | 0.0E+00 | 0.0E+00 | 0.0E+00 | 0.0E+00 |
| 284 | 0.0E+00 | 0.0E+00 | 0.0E+00 | 0.0E+00 | 0.0E+00 | 0.0E+00 | 0.0E+00 |
| 285 | 0.0E+00 | 0.0E+00 | 0.0E+00 | 0.0E+00 | 0.0E+00 | 0.0E+00 | 0.0E+00 |
| 286 | 0.0E+00 | 0.0E+00 | 0.0E+00 | 0.0E+00 | 0.0E+00 | 0.0E+00 | 0.0E+00 |
| 287 | 0.0E+00 | 0.0E+00 | 0.0E+00 | 0.0E+00 | 0.0E+00 | 0.0E+00 | 0.0E+00 |
| 288 | 0.0E+00 | 0.0E+00 | 1.1E−06 | 0.0E+00 | 0.0E+00 | 0.0E+00 | 0.0E+00 |
| 289 | 0.0E+00 | 0.0E+00 | 0.0E+00 | 0.0E+00 | 0.0E+00 | 0.0E+00 | 0.0E+00 |
| 290 | 3.4E−06 | 0.0E+00 | 0.0E+00 | 1.2E−06 | 0.0E+00 | 1.6E−06 | 1.4E−06 |

-continued

| | | | | | | | |
|---|---|---|---|---|---|---|---|
| 291 | 1.2E−05 | 0.0E+00 | 1.0E−05 | 1.2E−06 | 0.0E+00 | 4.3E−06 | 1.5E−05 |
| 292 | 0.0E+00 | 0.0E+00 | 0.0E+00 | 0.0E+00 | 0.0E+00 | 0.0E+00 | 0.0E+00 |
| 293 | 3.4E−06 | 2.8E−05 | 4.4E−05 | 2.1E−06 | 3.1E−05 | 6.9E−05 | 3.7E−05 |
| 294 | 0.0E+00 | 0.0E+00 | 0.0E+00 | 0.0E+00 | 0.0E+00 | 0.0E+00 | 0.0E+00 |
| 295 | 2.3E−03 | 1.2E−03 | 6.6E−04 | 5.0E−04 | 1.4E−03 | 2.6E−03 | 5.7E−04 |
| 296 | 4.1E−06 | 1.5E−06 | 1.1E−06 | 2.4E−06 | 6.1E−06 | 3.2E−06 | 1.4E−06 |
| 297 | 0.0E+00 | 0.0E+00 | 0.0E+00 | 0.0E+00 | 0.0E+00 | 0.0E+00 | 0.0E+00 |
| 298 | 0.0E+00 | 0.0E+00 | 0.0E+00 | 0.0E+00 | 0.0E+00 | 0.0E+00 | 0.0E+00 |
| 299 | 0.0E+00 | 1.0E−06 | 0.0E+00 | 0.0E+00 | 0.0E+00 | 0.0E+00 | 2.3E−06 |
| 300 | 0.0E+00 | 0.0E+00 | 0.0E+00 | 0.0E+00 | 0.0E+00 | 0.0E+00 | 0.0E+00 |
| 301 | 2.7E−06 | 6.7E−06 | 9.1E−06 | 6.0E−07 | 3.8E−06 | 5.4E−07 | 8.9E−06 |
| 302 | 0.0E+00 | 4.6E−06 | 4.5E−06 | 0.0E+00 | 0.0E+00 | 0.0E+00 | 3.3E−06 |
| 303 | 0.0E+00 | 0.0E+00 | 0.0E+00 | 0.0E+00 | 0.0E+00 | 0.0E+00 | 0.0E+00 |
| 304 | 0.0E+00 | 0.0E+00 | 0.0E+00 | 0.0E+00 | 0.0E+00 | 0.0E+00 | 0.0E+00 |
| 305 | 0.0E+00 | 0.0E+00 | 0.0E+00 | 0.0E+00 | 7.7E−06 | 0.0E+00 | 0.0E+00 |
| 306 | 0.0E+00 | 0.0E+00 | 3.4E−06 | 0.0E+00 | 0.0E+00 | 0.0E+00 | 0.0E+00 |
| 307 | 6.8E−06 | 0.0E+00 | 0.0E+00 | 6.0E−07 | 0.0E+00 | 0.0E+00 | 0.0E+00 |
| 308 | 3.4E−06 | 1.1E−05 | 1.0E−05 | 0.0E+00 | 5.4E−05 | 1.4E−05 | 5.5E−05 |
| 309 | 0.0E+00 | 0.0E+00 | 0.0E+00 | 1.2E−06 | 6.9E−06 | 0.0E+00 | 0.0E+00 |
| 310 | 2.0E−06 | 0.0E+00 | 0.0E+00 | 0.0E+00 | 0.0E+00 | 0.0E+00 | 0.0E+00 |
| 311 | 6.8E−07 | 3.1E−06 | 1.2E−05 | 0.0E+00 | 7.7E−07 | 1.1E−06 | 9.9E−06 |
| 312 | 1.5E−04 | 1.8E−04 | 1.9E−03 | 3.0E−06 | 1.7E−03 | 5.2E−04 | 1.2E−04 |
| 313 | 3.6E−05 | 0.0E+00 | 0.0E+00 | 0.0E+00 | 0.0E+00 | 0.0E+00 | 0.0E+00 |
| 314 | 1.6E−02 | 1.1E−03 | 5.0E−03 | 4.7E−03 | 1.9E−03 | 5.9E−04 | 4.7E−03 |
| 315 | 6.2E−02 | 5.1E−02 | 1.7E−01 | 2.1E−02 | 9.8E−02 | 2.4E−02 | 2.9E−02 |
| 316 | 0.0E+00 | 7.4E−04 | 2.4E−03 | 8.5E−04 | 2.4E−04 | 3.8E−04 | 8.3E−04 |
| 317 | 1.5E−04 | 2.6E−06 | 5.6E−05 | 9.1E−07 | 2.0E−05 | 4.8E−06 | 9.4E−07 |
| 318 | 6.8E−07 | 0.0E+00 | 1.1E−06 | 0.0E+00 | 7.7E−07 | 5.4E−07 | 0.0E+00 |
| 319 | 0.0E+00 | 0.0E+00 | 0.0E+00 | 0.0E+00 | 0.0E+00 | 1.6E−06 | 3.8E−06 |
| 320 | 0.0E+00 | 5.3E−05 | 1.0E−05 | 9.7E−06 | 4.3E−05 | 7.6E−05 | 6.1E−05 |
| 321 | 1.7E−05 | 3.6E−06 | 1.4E−05 | 0.0E+00 | 0.0E+00 | 0.0E+00 | 0.0E+00 |
| 322 | 6.8E−07 | 2.0E−06 | 1.1E−06 | 0.0E+00 | 5.4E−06 | 0.0E+00 | 2.8E−06 |
| 323 | 0.0E+00 | 3.6E−06 | 1.1E−05 | 3.6E−06 | 2.8E−05 | 4.8E−06 | 1.3E−05 |
| 324 | 0.0E+00 | 0.0E+00 | 5.7E−06 | 0.0E+00 | 2.3E−06 | 0.0E+00 | 0.0E+00 |
| 325 | 2.0E−02 | 1.3E−01 | 5.5E−02 | 6.9E−04 | 3.1E−02 | 1.8E−01 | 7.9E−02 |
| 326 | 4.2E−02 | 1.8E−02 | 5.4E−03 | 9.0E−05 | 1.9E−02 | 2.0E−02 | 7.0E−04 |
| 327 | 6.8E−07 | 3.1E−06 | 3.4E−06 | 1.8E−06 | 3.1E−06 | 1.1E−06 | 6.6E−06 |
| 328 | 0.0E+00 | 2.6E−06 | 1.2E−05 | 0.0E+00 | 2.3E−06 | 0.0E+00 | 1.4E−06 |
| 329 | 0.0E+00 | 0.0E+00 | 0.0E+00 | 0.0E+00 | 0.0E+00 | 0.0E+00 | 0.0E+00 |
| 330 | 6.8E−07 | 0.0E+00 | 0.0E+00 | 6.0E−06 | 2.3E−06 | 0.0E+00 | 9.4E−07 |
| 331 | 1.4E−05 | 2.4E−05 | 9.1E−06 | 1.3E−05 | 5.0E−05 | 8.4E−05 | 1.0E−05 |
| 332 | 2.2E−05 | 5.5E−05 | 1.2E−05 | 5.1E−06 | 7.0E−05 | 5.4E−06 | 1.5E−05 |
| 333 | 0.0E+00 | 0.0E+00 | 0.0E+00 | 0.0E+00 | 0.0E+00 | 0.0E+00 | 0.0E+00 |
| 334 | 2.2E−04 | 5.4E−05 | 3.5E−05 | 2.8E−05 | 1.1E−04 | 1.0E−04 | 8.5E−05 |
| 335 | 0.0E+00 | 5.6E−06 | 3.4E−06 | 1.5E−06 | 1.8E−05 | 4.3E−06 | 8.4E−06 |
| 336 | 0.0E+00 | 5.1E−06 | 0.0E+00 | 0.0E+00 | 0.0E+00 | 0.0E+00 | 0.0E+00 |
| 337 | 2.7E−01 | 1.1E−04 | 2.3E−04 | 8.9E−01 | 3.9E−04 | 1.9E−04 | 1.8E−04 |
| 338 | 1.0E−04 | 5.5E−05 | 3.0E−05 | 9.4E−06 | 4.7E−05 | 1.8E−04 | 4.5E−05 |
| 339 | 0.0E+00 | 3.1E−06 | 0.0E+00 | 0.0E+00 | 0.0E+00 | 7.0E−06 | 0.0E+00 |
| 340 | 0.0E+00 | 0.0E+00 | 0.0E+00 | 7.2E−06 | 2.3E−06 | 2.2E−06 | 2.8E−06 |
| 341 | 0.0E+00 | 0.0E+00 | 0.0E+00 | 0.0E+00 | 0.0E+00 | 0.0E+00 | 0.0E+00 |
| 342 | 0.0E+00 | 0.0E+00 | 0.0E+00 | 0.0E+00 | 0.0E+00 | 0.0E+00 | 0.0E+00 |
| 343 | 0.0E+00 | 0.0E+00 | 0.0E+00 | 3.6E−06 | 0.0E+00 | 0.0E+00 | 0.0E+00 |
| 344 | 0.0E+00 | 0.0E+00 | 0.0E+00 | 0.0E+00 | 3.1E−06 | 2.4E−05 | 0.0E+00 |
| 345 | 0.0E+00 | 0.0E+00 | 0.0E+00 | 3.3E−06 | 0.0E+00 | 0.0E+00 | 0.0E+00 |
| 346 | 6.8E−07 | 5.1E−07 | 0.0E+00 | 0.0E+00 | 7.7E−07 | 0.0E+00 | 4.7E−07 |
| 347 | 1.9E−05 | 2.5E−05 | 7.9E−06 | 3.0E−07 | 3.4E−05 | 5.7E−05 | 1.4E−06 |
| 348 | 0.0E+00 | 0.0E+00 | 0.0E+00 | 0.0E+00 | 0.0E+00 | 0.0E+00 | 0.0E+00 |
| 349 | 1.2E−03 | 3.1E−05 | 2.4E−04 | 1.4E−05 | 0.0E+00 | 1.1E−06 | 1.4E−06 |
| 350 | 0.0E+00 | 0.0E+00 | 0.0E+00 | 2.4E−06 | 0.0E+00 | 0.0E+00 | 0.0E+00 |
| 351 | 4.2E−03 | 6.7E−06 | 1.7E−04 | 1.7E−05 | 1.8E−05 | 5.4E−07 | 3.3E−06 |
| 352 | 0.0E+00 | 1.1E−05 | 3.4E−06 | 2.7E−06 | 3.1E−05 | 0.0E+00 | 0.0E+00 |
| 353 | 0.0E+00 | 0.0E+00 | 0.0E+00 | 0.0E+00 | 0.0E+00 | 0.0E+00 | 0.0E+00 |
| 354 | 1.0E−03 | 9.2E−06 | 4.1E−05 | 4.8E−06 | 2.3E−06 | 1.1E−06 | 4.7E−06 |
| 355 | 1.4E−06 | 0.0E+00 | 0.0E+00 | 0.0E+00 | 0.0E+00 | 0.0E+00 | 0.0E+00 |
| 356 | 0.0E+00 | 0.0E+00 | 0.0E+00 | 0.0E+00 | 0.0E+00 | 0.0E+00 | 0.0E+00 |
| 357 | 6.8E−07 | 5.1E−07 | 6.8E−06 | 3.0E−07 | 0.0E+00 | 5.4E−07 | 4.7E−07 |
| 358 | 0.0E+00 | 0.0E+00 | 0.0E+00 | 0.0E+00 | 0.0E+00 | 0.0E+00 | 0.0E+00 |
| 359 | 1.4E−06 | 0.0E+00 | 0.0E+00 | 3.0E−07 | 0.0E+00 | 5.4E−07 | 4.7E−07 |
| 360 | 0.0E+00 | 0.0E+00 | 0.0E+00 | 0.0E+00 | 0.0E+00 | 0.0E+00 | 0.0E+00 |
| 361 | 1.6E−03 | 4.9E−05 | 4.1E−04 | 3.1E−04 | 2.2E−04 | 2.2E−04 | 1.9E−04 |
| 362 | 1.5E−05 | 2.6E−06 | 5.7E−06 | 1.8E−06 | 6.9E−06 | 1.6E−05 | 1.4E−06 |
| 363 | 0.0E+00 | 0.0E+00 | 0.0E+00 | 0.0E+00 | 0.0E+00 | 0.0E+00 | 0.0E+00 |
| 364 | 0.0E+00 | 0.0E+00 | 0.0E+00 | 0.0E+00 | 0.0E+00 | 0.0E+00 | 0.0E+00 |
| 365 | 1.8E−05 | 3.6E−05 | 0.0E+00 | 0.0E+00 | 6.9E−06 | 0.0E+00 | 2.6E−05 |
| 366 | 0.0E+00 | 0.0E+00 | 0.0E+00 | 0.0E+00 | 0.0E+00 | 0.0E+00 | 0.0E+00 |
| 367 | 0.0E+00 | 0.0E+00 | 0.0E+00 | 0.0E+00 | 0.0E+00 | 0.0E+00 | 0.0E+00 |
| 368 | 2.0E−06 | 5.1E−06 | 1.2E−05 | 0.0E+00 | 1.7E−05 | 2.2E−05 | 1.4E−05 |
| 369 | 0.0E+00 | 5.1E−07 | 0.0E+00 | 0.0E+00 | 0.0E+00 | 7.5E−05 | 0.0E+00 |

-continued

| | | | | | | | |
|---|---|---|---|---|---|---|---|
| 370 | 0.0E+00 | 1.0E−06 | 0.0E+00 | 0.0E+00 | 0.0E+00 | 0.0E+00 | 0.0E+00 |
| 371 | 1.2E−05 | 2.5E−04 | 0.0E+00 | 0.0E+00 | 1.5E−06 | 0.0E+00 | 0.0E+00 |
| 372 | 1.1E−04 | 9.5E−05 | 0.0E+00 | 6.2E−05 | 2.0E−04 | 3.5E−05 | 4.6E−05 |
| 373 | 1.2E−03 | 7.9E−04 | 6.9E−05 | 7.4E−04 | 1.9E−03 | 4.3E−04 | 2.7E−04 |
| 374 | 0.0E+00 | 0.0E+00 | 1.8E−04 | 3.1E−05 | 1.5E−04 | 1.1E−05 | 0.0E+00 |
| 375 | 0.0E+00 | 0.0E+00 | 0.0E+00 | 0.0E+00 | 0.0E+00 | 0.0E+00 | 0.0E+00 |
| 376 | 0.0E+00 | 1.0E−06 | 0.0E+00 | 0.0E+00 | 0.0E+00 | 0.0E+00 | 0.0E+00 |
| 377 | 0.0E+00 | 2.6E−06 | 4.5E−06 | 0.0E+00 | 0.0E+00 | 0.0E+00 | 0.0E+00 |
| 378 | 1.0E−04 | 4.6E−05 | 3.9E−05 | 9.4E−06 | 6.9E−05 | 4.2E−04 | 1.7E−05 |

| Taxon ID | RM Atm−/− Colon | | | |
|---|---|---|---|---|
| 1 | 2.3E−03 | 3.1E−03 | 2.6E−03 | 1.7E−03 |
| 2 | 3.8E−07 | 0.0E+00 | 0.0E+00 | 0.0E+00 |
| 3 | 0.0E+00 | 0.0E+00 | 0.0E+00 | 0.0E+00 |
| 4 | 1.1E−04 | 2.0E−05 | 5.1E−05 | 3.4E−05 |
| 5 | 3.0E−05 | 0.0E+00 | 0.0E+00 | 0.0E+00 |
| 6 | 0.0E+00 | 8.8E−06 | 0.0E+00 | 0.0E+00 |
| 7 | 1.1E−05 | 2.3E−06 | 2.9E−06 | 2.6E−06 |
| 8 | 7.5E−07 | 0.0E+00 | 5.7E−07 | 8.5E−07 |
| 9 | 3.8E−07 | 0.0E+00 | 0.0E+00 | 0.0E+00 |
| 10 | 4.1E−06 | 1.4E−06 | 5.7E−07 | 0.0E+00 |
| 11 | 0.0E+00 | 0.0E+00 | 0.0E+00 | 0.0E+00 |
| 12 | 0.0E+00 | 0.0E+00 | 0.0E+00 | 0.0E+00 |
| 13 | 0.0E+00 | 0.0E+00 | 0.0E+00 | 0.0E+00 |
| 14 | 7.9E−06 | 0.0E+00 | 0.0E+00 | 0.0E+00 |
| 15 | 0.0E+00 | 0.0E+00 | 0.0E+00 | 0.0E+00 |
| 16 | 0.0E+00 | 0.0E+00 | 0.0E+00 | 0.0E+00 |
| 17 | 5.3E−06 | 5.6E−06 | 5.7E−07 | 2.6E−06 |
| 18 | 3.8E−07 | 0.0E+00 | 0.0E+00 | 4.3E−07 |
| 19 | 0.0E+00 | 0.0E+00 | 0.0E+00 | 0.0E+00 |
| 20 | 0.0E+00 | 0.0E+00 | 0.0E+00 | 0.0E+00 |
| 21 | 0.0E+00 | 9.3E−06 | 0.0E+00 | 0.0E+00 |
| 22 | 0.0E+00 | 0.0E+00 | 0.0E+00 | 0.0E+00 |
| 23 | 0.0E+00 | 1.9E−06 | 0.0E+00 | 0.0E+00 |
| 24 | 5.6E−06 | 6.0E−06 | 1.1E−06 | 5.1E−06 |
| 25 | 0.0E+00 | 0.0E+00 | 0.0E+00 | 0.0E+00 |
| 26 | 4.9E−06 | 0.0E+00 | 0.0E+00 | 0.0E+00 |
| 27 | 0.0E+00 | 0.0E+00 | 0.0E+00 | 0.0E+00 |
| 28 | 0.0E+00 | 0.0E+00 | 0.0E+00 | 0.0E+00 |
| 29 | 0.0E+00 | 0.0E+00 | 0.0E+00 | 0.0E+00 |
| 30 | 1.9E−06 | 0.0E+00 | 5.7E−07 | 0.0E+00 |
| 31 | 0.0E+00 | 0.0E+00 | 0.0E+00 | 0.0E+00 |
| 32 | 1.5E−04 | 1.8E−04 | 7.9E−05 | 2.8E−05 |
| 33 | 1.1E−05 | 2.0E−05 | 1.2E−05 | 3.0E−06 |
| 34 | 0.0E+00 | 0.0E+00 | 0.0E+00 | 0.0E+00 |
| 35 | 0.0E+00 | 0.0E+00 | 0.0E+00 | 0.0E+00 |
| 36 | 0.0E+00 | 1.4E−06 | 0.0E+00 | 0.0E+00 |
| 37 | 0.0E+00 | 0.0E+00 | 0.0E+00 | 0.0E+00 |
| 38 | 0.0E+00 | 0.0E+00 | 0.0E+00 | 0.0E+00 |
| 39 | 0.0E+00 | 3.3E−06 | 0.0E+00 | 0.0E+00 |
| 40 | 0.0E+00 | 0.0E+00 | 0.0E+00 | 0.0E+00 |
| 41 | 0.0E+00 | 0.0E+00 | 0.0E+00 | 0.0E+00 |
| 42 | 0.0E+00 | 0.0E+00 | 0.0E+00 | 0.0E+00 |
| 43 | 0.0E+00 | 9.3E−07 | 0.0E+00 | 0.0E+00 |
| 44 | 3.8E−07 | 0.0E+00 | 0.0E+00 | 0.0E+00 |
| 45 | 4.5E−06 | 5.1E−06 | 0.0E+00 | 1.7E−06 |
| 46 | 0.0E+00 | 0.0E+00 | 0.0E+00 | 0.0E+00 |
| 47 | 0.0E+00 | 0.0E+00 | 0.0E+00 | 0.0E+00 |
| 48 | 0.0E+00 | 0.0E+00 | 0.0E+00 | 0.0E+00 |
| 49 | 0.0E+00 | 0.0E+00 | 0.0E+00 | 0.0E+00 |
| 50 | 2.5E−04 | 1.6E−04 | 1.1E−04 | 5.2E−05 |
| 51 | 6.7E−05 | 1.1E−04 | 5.4E−05 | 5.9E−05 |
| 52 | 1.1E−06 | 0.0E+00 | 5.1E−06 | 0.0E+00 |
| 53 | 2.3E−05 | 0.0E+00 | 1.7E−06 | 1.3E−05 |
| 54 | 3.8E−07 | 4.7E−07 | 4.0E−06 | 1.3E−06 |
| 55 | 0.0E+00 | 0.0E+00 | 0.0E+00 | 0.0E+00 |
| 56 | 0.0E+00 | 0.0E+00 | 0.0E+00 | 0.0E+00 |
| 57 | 4.9E−06 | 1.9E−06 | 1.1E−06 | 2.1E−06 |
| 58 | 8.9E−03 | 1.4E−03 | 4.7E−03 | 1.8E−03 |
| 59 | 7.5E−07 | 5.0E−03 | 5.9E−03 | 4.3E−07 |
| 60 | 3.3E−05 | 5.0E−03 | 3.4E−03 | 3.5E−05 |
| 61 | 0.0E+00 | 0.0E+00 | 0.0E+00 | 0.0E+00 |
| 62 | 2.7E−03 | 2.2E−04 | 1.1E−03 | 4.8E−04 |
| 63 | 1.2E−04 | 1.0E−04 | 1.2E−04 | 1.3E−04 |
| 64 | 6.9E−05 | 2.8E−05 | 5.5E−05 | 9.4E−06 |
| 65 | 9.4E−06 | 5.1E−06 | 2.9E−06 | 2.6E−06 |
| 66 | 1.9E−06 | 1.7E−04 | 1.5E−03 | 4.3E−07 |
| 67 | 1.1E−06 | 1.9E−06 | 2.9E−06 | 2.1E−06 |

-continued

| | | | | |
|---|---|---|---|---|
| 68 | 0.0E+00 | 0.0E+00 | 0.0E+00 | 0.0E+00 |
| 69 | 6.5E−03 | 4.6E−03 | 8.6E−03 | 7.5E−03 |
| 70 | 1.2E−05 | 1.0E−05 | 7.4E−06 | 1.1E−05 |
| 71 | 8.5E−05 | 8.1E−05 | 7.4E−05 | 1.0E−04 |
| 72 | 3.8E−07 | 1.9E−06 | 5.7E−07 | 4.3E−07 |
| 73 | 1.5E−06 | 4.7E−07 | 5.7E−07 | 8.5E−07 |
| 74 | 5.3E−06 | 3.7E−06 | 4.6E−06 | 7.4E−05 |
| 75 | 0.0E+00 | 0.0E+00 | 0.0E+00 | 0.0E+00 |
| 76 | 6.5E−04 | 5.0E−05 | 2.0E−04 | 2.2E−04 |
| 77 | 1.0E−04 | 1.4E−04 | 1.0E−04 | 7.1E−05 |
| 78 | 3.8E−07 | 1.4E−06 | 5.7E−07 | 0.0E+00 |
| 79 | 7.5E−06 | 6.0E−06 | 8.6E−06 | 4.7E−06 |
| 80 | 2.1E−05 | 6.0E−06 | 0.0E+00 | 5.5E−06 |
| 81 | 0.0E+00 | 0.0E+00 | 0.0E+00 | 0.0E+00 |
| 82 | 4.6E−02 | 4.1E−02 | 8.4E−02 | 3.6E−02 |
| 83 | 3.4E−02 | 2.3E−02 | 6.6E−03 | 2.1E−02 |
| 84 | 2.6E−06 | 1.4E−05 | 5.7E−07 | 1.7E−06 |
| 85 | 3.6E−02 | 4.6E−02 | 7.5E−03 | 3.0E−02 |
| 86 | 4.6E−01 | 3.8E−01 | 5.9E−01 | 5.6E−01 |
| 87 | 1.3E−05 | 7.4E−06 | 1.3E−05 | 1.4E−05 |
| 88 | 0.0E+00 | 4.7E−07 | 0.0E+00 | 4.3E−07 |
| 89 | 0.0E+00 | 1.8E−05 | 0.0E+00 | 0.0E+00 |
| 90 | 0.0E+00 | 0.0E+00 | 0.0E+00 | 0.0E+00 |
| 91 | 7.5E−07 | 0.0E+00 | 0.0E+00 | 1.3E−06 |
| 92 | 0.0E+00 | 0.0E+00 | 0.0E+00 | 0.0E+00 |
| 93 | 0.0E+00 | 0.0E+00 | 0.0E+00 | 0.0E+00 |
| 94 | 4.7E−04 | 3.5E−04 | 3.8E−03 | 4.9E−04 |
| 95 | 0.0E+00 | 0.0E+00 | 0.0E+00 | 0.0E+00 |
| 96 | 1.3E−03 | 1.3E−04 | 4.1E−04 | 5.4E−04 |
| 97 | 7.5E−07 | 9.3E−07 | 0.0E+00 | 1.3E−06 |
| 98 | 0.0E+00 | 0.0E+00 | 0.0E+00 | 0.0E+00 |
| 99 | 0.0E+00 | 0.0E+00 | 0.0E+00 | 0.0E+00 |
| 100 | 8.6E−06 | 1.6E−05 | 3.4E−06 | 1.4E−05 |
| 101 | 1.0E−04 | 4.7E−05 | 5.9E−05 | 3.8E−05 |
| 102 | 2.3E−06 | 0.0E+00 | 7.5E−05 | 6.6E−05 |
| 103 | 0.0E+00 | 0.0E+00 | 0.0E+00 | 0.0E+00 |
| 104 | 0.0E+00 | 0.0E+00 | 0.0E+00 | 0.0E+00 |
| 105 | 1.9E−06 | 2.8E−06 | 4.0E−06 | 4.3E−07 |
| 106 | 3.8E−07 | 9.3E−07 | 1.1E−06 | 4.3E−07 |
| 107 | 1.2E−05 | 1.0E−05 | 1.9E−05 | 8.5E−06 |
| 108 | 0.0E+00 | 0.0E+00 | 0.0E+00 | 0.0E+00 |
| 109 | 0.0E+00 | 0.0E+00 | 0.0E+00 | 0.0E+00 |
| 110 | 0.0E+00 | 0.0E+00 | 0.0E+00 | 0.0E+00 |
| 111 | 0.0E+00 | 0.0E+00 | 0.0E+00 | 0.0E+00 |
| 112 | 0.0E+00 | 0.0E+00 | 0.0E+00 | 0.0E+00 |
| 113 | 0.0E+00 | 0.0E+00 | 0.0E+00 | 0.0E+00 |
| 114 | 7.5E−07 | 4.7E−06 | 0.0E+00 | 4.3E−07 |
| 115 | 2.1E−03 | 1.8E−03 | 1.0E−03 | 1.6E−03 |
| 116 | 0.0E+00 | 0.0E+00 | 0.0E+00 | 0.0E+00 |
| 117 | 0.0E+00 | 0.0E+00 | 0.0E+00 | 0.0E+00 |
| 118 | 0.0E+00 | 0.0E+00 | 0.0E+00 | 0.0E+00 |
| 119 | 0.0E+00 | 0.0E+00 | 0.0E+00 | 0.0E+00 |
| 120 | 1.5E−06 | 3.3E−06 | 1.1E−06 | 8.5E−07 |
| 121 | 3.0E−06 | 9.3E−07 | 9.1E−06 | 0.0E+00 |
| 122 | 0.0E+00 | 2.3E−06 | 0.0E+00 | 8.5E−07 |
| 123 | 0.0E+00 | 0.0E+00 | 0.0E+00 | 0.0E+00 |
| 124 | 3.8E−07 | 0.0E+00 | 0.0E+00 | 0.0E+00 |
| 125 | 4.3E−05 | 2.8E−04 | 1.8E−04 | 1.4E−04 |
| 126 | 0.0E+00 | 0.0E+00 | 0.0E+00 | 0.0E+00 |
| 127 | 0.0E+00 | 0.0E+00 | 0.0E+00 | 0.0E+00 |
| 128 | 1.6E−03 | 2.5E−03 | 1.6E−03 | 1.6E−03 |
| 129 | 3.4E−06 | 7.0E−06 | 5.7E−07 | 4.3E−07 |
| 130 | 0.0E+00 | 0.0E+00 | 4.6E−06 | 0.0E+00 |
| 131 | 0.0E+00 | 9.3E−07 | 5.7E−07 | 8.5E−07 |
| 132 | 0.0E+00 | 0.0E+00 | 0.0E+00 | 0.0E+00 |
| 133 | 0.0E+00 | 0.0E+00 | 0.0E+00 | 0.0E+00 |
| 134 | 7.1E−04 | 5.6E−04 | 1.1E−06 | 4.3E−07 |
| 135 | 1.1E−05 | 0.0E+00 | 0.0E+00 | 0.0E+00 |
| 136 | 1.5E−04 | 2.6E−04 | 3.3E−05 | 3.2E−04 |
| 137 | 0.0E+00 | 0.0E+00 | 0.0E+00 | 0.0E+00 |
| 138 | 0.0E+00 | 0.0E+00 | 0.0E+00 | 0.0E+00 |
| 139 | 6.5E−05 | 1.9E−04 | 1.0E−04 | 3.8E−04 |
| 140 | 2.3E−03 | 1.5E−03 | 4.2E−03 | 3.2E−03 |
| 141 | 0.0E+00 | 0.0E+00 | 0.0E+00 | 1.1E−05 |
| 142 | 0.0E+00 | 0.0E+00 | 0.0E+00 | 0.0E+00 |
| 143 | 5.3E−06 | 0.0E+00 | 0.0E+00 | 0.0E+00 |
| 144 | 9.0E−06 | 0.0E+00 | 0.0E+00 | 0.0E+00 |
| 145 | 0.0E+00 | 0.0E+00 | 0.0E+00 | 0.0E+00 |
| 146 | 0.0E+00 | 0.0E+00 | 0.0E+00 | 0.0E+00 |

-continued

| | | | | |
|---|---|---|---|---|
| 147 | 0.0E+00 | 0.0E+00 | 0.0E+00 | 0.0E+00 |
| 148 | 1.4E−04 | 7.4E−04 | 1.2E−03 | 8.2E−04 |
| 149 | 0.0E+00 | 0.0E+00 | 0.0E+00 | 0.0E+00 |
| 150 | 7.3E−05 | 5.1E−05 | 3.2E−05 | 6.7E−05 |
| 151 | 0.0E+00 | 0.0E+00 | 0.0E+00 | 0.0E+00 |
| 152 | 0.0E+00 | 0.0E+00 | 0.0E+00 | 0.0E+00 |
| 153 | 0.0E+00 | 0.0E+00 | 0.0E+00 | 0.0E+00 |
| 154 | 3.8E−07 | 1.4E−06 | 1.3E−05 | 8.5E−06 |
| 155 | 7.5E−06 | 1.4E−06 | 0.0E+00 | 0.0E+00 |
| 156 | 1.9E−05 | 7.0E−06 | 7.4E−06 | 7.2E−06 |
| 157 | 0.0E+00 | 0.0E+00 | 0.0E+00 | 0.0E+00 |
| 158 | 1.4E−05 | 0.0E+00 | 0.0E+00 | 0.0E+00 |
| 159 | 9.7E−05 | 4.7E−05 | 4.0E−05 | 1.1E−05 |
| 160 | 8.3E−06 | 0.0E+00 | 5.7E−07 | 0.0E+00 |
| 161 | 1.8E−05 | 0.0E+00 | 1.2E−05 | 0.0E+00 |
| 162 | 0.0E+00 | 0.0E+00 | 0.0E+00 | 0.0E+00 |
| 163 | 3.8E−07 | 0.0E+00 | 5.7E−07 | 4.3E−07 |
| 164 | 3.1E−04 | 1.0E−03 | 1.7E−04 | 1.1E−03 |
| 165 | 0.0E+00 | 0.0E+00 | 0.0E+00 | 0.0E+00 |
| 166 | 0.0E+00 | 0.0E+00 | 4.0E−06 | 0.0E+00 |
| 167 | 7.4E−03 | 5.7E−03 | 2.7E−02 | 2.6E−03 |
| 168 | 0.0E+00 | 0.0E+00 | 1.8E−05 | 0.0E+00 |
| 169 | 1.1E−06 | 0.0E+00 | 0.0E+00 | 4.3E−07 |
| 170 | 0.0E+00 | 0.0E+00 | 0.0E+00 | 0.0E+00 |
| 171 | 0.0E+00 | 0.0E+00 | 0.0E+00 | 0.0E+00 |
| 172 | 1.5E−01 | 6.6E−02 | 1.2E−02 | 4.0E−02 |
| 173 | 0.0E+00 | 2.3E−06 | 0.0E+00 | 2.6E−06 |
| 174 | 3.6E−05 | 7.0E−06 | 3.8E−03 | 1.1E−05 |
| 175 | 0.0E+00 | 0.0E+00 | 0.0E+00 | 0.0E+00 |
| 176 | 0.0E+00 | 0.0E+00 | 0.0E+00 | 0.0E+00 |
| 177 | 0.0E+00 | 0.0E+00 | 0.0E+00 | 0.0E+00 |
| 178 | 9.0E−06 | 3.7E−05 | 3.1E−05 | 2.1E−06 |
| 179 | 0.0E+00 | 0.0E+00 | 0.0E+00 | 0.0E+00 |
| 180 | 0.0E+00 | 0.0E+00 | 0.0E+00 | 0.0E+00 |
| 181 | 0.0E+00 | 0.0E+00 | 5.7E−07 | 0.0E+00 |
| 182 | 0.0E+00 | 0.0E+00 | 1.2E−05 | 0.0E+00 |
| 183 | 0.0E+00 | 0.0E+00 | 0.0E+00 | 0.0E+00 |
| 184 | 1.2E−05 | 0.0E+00 | 7.4E−06 | 1.7E−06 |
| 185 | 7.5E−07 | 7.5E−04 | 7.7E−04 | 7.9E−04 |
| 186 | 3.8E−06 | 4.1E−05 | 0.0E+00 | 1.2E−05 |
| 187 | 0.0E+00 | 0.0E+00 | 0.0E+00 | 0.0E+00 |
| 188 | 0.0E+00 | 0.0E+00 | 5.7E−07 | 0.0E+00 |
| 189 | 0.0E+00 | 1.8E−05 | 9.1E−06 | 0.0E+00 |
| 190 | 9.1E−05 | 3.0E−05 | 3.7E−05 | 1.1E−05 |
| 191 | 2.2E−04 | 1.2E−03 | 7.5E−04 | 2.8E−04 |
| 192 | 6.8E−06 | 4.7E−06 | 2.3E−05 | 6.8E−06 |
| 193 | 0.0E+00 | 0.0E+00 | 0.0E+00 | 0.0E+00 |
| 194 | 0.0E+00 | 4.2E−06 | 3.6E−05 | 2.6E−06 |
| 195 | 8.3E−06 | 1.1E−05 | 0.0E+00 | 6.4E−06 |
| 196 | 0.0E+00 | 0.0E+00 | 0.0E+00 | 0.0E+00 |
| 197 | 0.0E+00 | 0.0E+00 | 0.0E+00 | 0.0E+00 |
| 198 | 3.8E−07 | 0.0E+00 | 0.0E+00 | 0.0E+00 |
| 199 | 3.4E−03 | 6.8E−04 | 1.0E−04 | 2.0E−05 |
| 200 | 7.5E−07 | 0.0E+00 | 0.0E+00 | 0.0E+00 |
| 201 | 6.4E−06 | 2.3E−06 | 0.0E+00 | 0.0E+00 |
| 202 | 0.0E+00 | 0.0E+00 | 0.0E+00 | 0.0E+00 |
| 203 | 4.7E−04 | 4.7E−04 | 1.9E−03 | 8.1E−05 |
| 204 | 9.8E−06 | 6.5E−06 | 1.1E−06 | 4.3E−07 |
| 205 | 3.4E−06 | 0.0E+00 | 0.0E+00 | 0.0E+00 |
| 206 | 0.0E+00 | 9.3E−07 | 0.0E+00 | 0.0E+00 |
| 207 | 3.0E−04 | 5.0E−04 | 6.4E−04 | 3.9E−04 |
| 208 | 1.0E−02 | 2.0E−02 | 5.4E−02 | 1.9E−02 |
| 209 | 0.0E+00 | 0.0E+00 | 0.0E+00 | 0.0E+00 |
| 210 | 1.9E−03 | 1.9E−03 | 1.4E−03 | 1.4E−03 |
| 211 | 5.3E−06 | 1.4E−06 | 9.7E−06 | 0.0E+00 |
| 212 | 0.0E+00 | 1.1E−05 | 0.0E+00 | 0.0E+00 |
| 213 | 0.0E+00 | 0.0E+00 | 1.7E−06 | 0.0E+00 |
| 214 | 0.0E+00 | 0.0E+00 | 0.0E+00 | 0.0E+00 |
| 215 | 0.0E+00 | 0.0E+00 | 0.0E+00 | 0.0E+00 |
| 216 | 5.5E−04 | 8.9E−04 | 8.1E−04 | 4.3E−04 |
| 217 | 0.0E+00 | 0.0E+00 | 0.0E+00 | 0.0E+00 |
| 218 | 4.9E−04 | 7.7E−04 | 7.4E−03 | 1.0E−03 |
| 219 | 0.0E+00 | 0.0E+00 | 0.0E+00 | 0.0E+00 |
| 220 | 9.4E−05 | 7.0E−04 | 2.9E−04 | 7.1E−05 |
| 221 | 3.8E−07 | 1.4E−06 | 2.3E−06 | 8.5E−07 |
| 222 | 0.0E+00 | 0.0E+00 | 0.0E+00 | 0.0E+00 |
| 223 | 2.6E−05 | 1.9E−05 | 0.0E+00 | 3.5E−05 |
| 224 | 0.0E+00 | 0.0E+00 | 8.6E−06 | 0.0E+00 |
| 225 | 2.6E−03 | 2.1E−03 | 3.8E−03 | 8.1E−04 |

-continued

| | | | | |
|---|---|---|---|---|
| 226 | 0.0E+00 | 0.0E+00 | 0.0E+00 | 0.0E+00 |
| 227 | 0.0E+00 | 1.0E−05 | 0.0E+00 | 0.0E+00 |
| 228 | 0.0E+00 | 0.0E+00 | 0.0E+00 | 0.0E+00 |
| 229 | 0.0E+00 | 0.0E+00 | 2.3E−06 | 4.3E−07 |
| 230 | 0.0E+00 | 1.5E−05 | 2.3E−05 | 2.0E−05 |
| 231 | 2.1E−05 | 1.6E−04 | 1.5E−05 | 2.3E−05 |
| 232 | 1.3E−04 | 9.6E−05 | 4.7E−05 | 4.5E−05 |
| 233 | 2.7E−05 | 1.3E−05 | 7.4E−06 | 1.3E−06 |
| 234 | 0.0E+00 | 0.0E+00 | 0.0E+00 | 0.0E+00 |
| 235 | 3.0E−04 | 6.6E−04 | 8.3E−04 | 9.7E−04 |
| 236 | 3.7E−03 | 2.4E−03 | 1.2E−03 | 1.6E−03 |
| 237 | 1.6E−04 | 2.1E−04 | 3.2E−05 | 9.8E−05 |
| 238 | 2.6E−06 | 0.0E+00 | 2.9E−06 | 4.3E−07 |
| 239 | 0.0E+00 | 0.0E+00 | 0.0E+00 | 0.0E+00 |
| 240 | 0.0E+00 | 0.0E+00 | 0.0E+00 | 0.0E+00 |
| 241 | 0.0E+00 | 0.0E+00 | 0.0E+00 | 0.0E+00 |
| 242 | 0.0E+00 | 0.0E+00 | 0.0E+00 | 0.0E+00 |
| 243 | 5.1E−04 | 5.9E−04 | 6.0E−04 | 7.6E−04 |
| 244 | 1.2E−05 | 2.8E−06 | 5.7E−06 | 0.0E+00 |
| 245 | 0.0E+00 | 0.0E+00 | 0.0E+00 | 0.0E+00 |
| 246 | 0.0E+00 | 0.0E+00 | 0.0E+00 | 0.0E+00 |
| 247 | 0.0E+00 | 0.0E+00 | 0.0E+00 | 0.0E+00 |
| 248 | 0.0E+00 | 0.0E+00 | 0.0E+00 | 0.0E+00 |
| 249 | 0.0E+00 | 0.0E+00 | 0.0E+00 | 0.0E+00 |
| 250 | 0.0E+00 | 0.0E+00 | 0.0E+00 | 0.0E+00 |
| 251 | 1.7E−03 | 3.1E−03 | 4.3E−03 | 3.0E−03 |
| 252 | 1.2E−01 | 2.3E−02 | 5.3E−02 | 3.6E−02 |
| 253 | 0.0E+00 | 4.2E−06 | 0.0E+00 | 2.1E−06 |
| 254 | 9.1E−04 | 1.0E−04 | 3.3E−04 | 1.7E−04 |
| 255 | 0.0E+00 | 0.0E+00 | 0.0E+00 | 0.0E+00 |
| 256 | 7.5E−07 | 0.0E+00 | 0.0E+00 | 4.3E−07 |
| 257 | 0.0E+00 | 0.0E+00 | 0.0E+00 | 0.0E+00 |
| 258 | 2.3E−06 | 2.4E−04 | 4.7E−05 | 7.7E−05 |
| 259 | 3.4E−03 | 4.4E−03 | 1.1E−02 | 8.2E−04 |
| 260 | 1.4E−02 | 5.7E−03 | 7.1E−03 | 4.4E−03 |
| 261 | 1.5E−02 | 2.8E−01 | 4.9E−05 | 1.8E−01 |
| 262 | 1.2E−02 | 2.3E−02 | 3.7E−02 | 2.9E−03 |
| 263 | 9.0E−06 | 0.0E+00 | 9.1E−06 | 0.0E+00 |
| 264 | 1.6E−02 | 1.3E−02 | 1.1E−02 | 7.5E−03 |
| 265 | 2.6E−06 | 0.0E+00 | 2.5E−04 | 5.1E−05 |
| 266 | 6.8E−06 | 0.0E+00 | 0.0E+00 | 0.0E+00 |
| 267 | 0.0E+00 | 0.0E+00 | 0.0E+00 | 0.0E+00 |
| 268 | 1.2E−04 | 1.6E−04 | 1.3E−04 | 1.1E−04 |
| 269 | 4.5E−05 | 1.4E−05 | 5.7E−06 | 1.1E−05 |
| 270 | 0.0E+00 | 0.0E+00 | 0.0E+00 | 0.0E+00 |
| 271 | 2.5E−02 | 2.1E−02 | 3.0E−02 | 2.9E−02 |
| 272 | 3.8E−06 | 4.7E−06 | 2.9E−06 | 1.3E−06 |
| 273 | 0.0E+00 | 0.0E+00 | 0.0E+00 | 0.0E+00 |
| 274 | 0.0E+00 | 0.0E+00 | 0.0E+00 | 0.0E+00 |
| 275 | 0.0E+00 | 0.0E+00 | 0.0E+00 | 0.0E+00 |
| 276 | 0.0E+00 | 0.0E+00 | 0.0E+00 | 0.0E+00 |
| 277 | 1.6E−05 | 2.1E−05 | 1.6E−04 | 0.0E+00 |
| 278 | 1.1E−06 | 9.3E−07 | 0.0E+00 | 0.0E+00 |
| 279 | 0.0E+00 | 1.4E−06 | 0.0E+00 | 0.0E+00 |
| 280 | 0.0E+00 | 0.0E+00 | 0.0E+00 | 0.0E+00 |
| 281 | 3.8E−07 | 0.0E+00 | 0.0E+00 | 0.0E+00 |
| 282 | 0.0E+00 | 0.0E+00 | 0.0E+00 | 0.0E+00 |
| 283 | 0.0E+00 | 0.0E+00 | 0.0E+00 | 0.0E+00 |
| 284 | 0.0E+00 | 0.0E+00 | 0.0E+00 | 4.3E−07 |
| 285 | 0.0E+00 | 0.0E+00 | 0.0E+00 | 0.0E+00 |
| 286 | 0.0E+00 | 0.0E+00 | 0.0E+00 | 0.0E+00 |
| 287 | 0.0E+00 | 0.0E+00 | 0.0E+00 | 0.0E+00 |
| 288 | 3.4E−06 | 1.9E−06 | 0.0E+00 | 0.0E+00 |
| 289 | 0.0E+00 | 0.0E+00 | 0.0E+00 | 0.0E+00 |
| 290 | 7.5E−07 | 1.9E−06 | 0.0E+00 | 0.0E+00 |
| 291 | 0.0E+00 | 0.0E+00 | 0.0E+00 | 0.0E+00 |
| 292 | 0.0E+00 | 0.0E+00 | 0.0E+00 | 0.0E+00 |
| 293 | 5.3E−06 | 1.2E−05 | 8.0E−06 | 5.1E−06 |
| 294 | 0.0E+00 | 0.0E+00 | 0.0E+00 | 0.0E+00 |
| 295 | 1.3E−03 | 8.5E−04 | 6.0E−04 | 2.1E−04 |
| 296 | 7.5E−07 | 4.7E−07 | 1.1E−06 | 0.0E+00 |
| 297 | 0.0E+00 | 0.0E+00 | 0.0E+00 | 0.0E+00 |
| 298 | 0.0E+00 | 0.0E+00 | 0.0E+00 | 0.0E+00 |
| 299 | 3.8E−07 | 0.0E+00 | 5.7E−07 | 4.3E−07 |
| 300 | 0.0E+00 | 0.0E+00 | 0.0E+00 | 0.0E+00 |
| 301 | 1.5E−06 | 4.7E−06 | 0.0E+00 | 2.6E−06 |
| 302 | 0.0E+00 | 0.0E+00 | 0.0E+00 | 0.0E+00 |
| 303 | 0.0E+00 | 0.0E+00 | 0.0E+00 | 0.0E+00 |
| 304 | 0.0E+00 | 0.0E+00 | 0.0E+00 | 1.3E−06 |

-continued

| | | | | |
|---|---|---|---|---|
| 305 | 0.0E+00 | 0.0E+00 | 0.0E+00 | 0.0E+00 |
| 306 | 7.5E-07 | 0.0E+00 | 0.0E+00 | 0.0E+00 |
| 307 | 0.0E+00 | 0.0E+00 | 0.0E+00 | 0.0E+00 |
| 308 | 1.5E-06 | 7.4E-06 | 2.3E-06 | 2.1E-06 |
| 309 | 4.1E-06 | 0.0E+00 | 5.7E-07 | 0.0E+00 |
| 310 | 0.0E+00 | 4.7E-07 | 0.0E+00 | 0.0E+00 |
| 311 | 3.8E-07 | 1.4E-06 | 5.7E-07 | 0.0E+00 |
| 312 | 0.0E+00 | 0.0E+00 | 0.0E+00 | 0.0E+00 |
| 313 | 3.8E-07 | 0.0E+00 | 7.4E-06 | 0.0E+00 |
| 314 | 1.1E-06 | 4.7E-07 | 5.7E-07 | 4.3E-07 |
| 315 | 1.7E-05 | 1.2E-05 | 2.2E-05 | 9.4E-06 |
| 316 | 0.0E+00 | 0.0E+00 | 0.0E+00 | 0.0E+00 |
| 317 | 0.0E+00 | 0.0E+00 | 0.0E+00 | 0.0E+00 |
| 318 | 0.0E+00 | 0.0E+00 | 0.0E+00 | 0.0E+00 |
| 319 | 0.0E+00 | 0.0E+00 | 0.0E+00 | 0.0E+00 |
| 320 | 9.8E-05 | 3.1E-05 | 2.1E-05 | 3.6E-05 |
| 321 | 0.0E+00 | 0.0E+00 | 0.0E+00 | 0.0E+00 |
| 322 | 3.8E-07 | 0.0E+00 | 1.7E-06 | 2.6E-06 |
| 323 | 0.0E+00 | 0.0E+00 | 1.1E-06 | 0.0E+00 |
| 324 | 3.8E-07 | 0.0E+00 | 5.7E-07 | 0.0E+00 |
| 325 | 1.4E-05 | 8.8E-06 | 6.3E-06 | 8.1E-06 |
| 326 | 2.6E-06 | 9.3E-07 | 1.1E-06 | 1.7E-06 |
| 327 | 0.0E+00 | 0.0E+00 | 5.7E-07 | 0.0E+00 |
| 328 | 0.0E+00 | 0.0E+00 | 0.0E+00 | 0.0E+00 |
| 329 | 0.0E+00 | 2.1E-05 | 0.0E+00 | 0.0E+00 |
| 330 | 0.0E+00 | 0.0E+00 | 0.0E+00 | 0.0E+00 |
| 331 | 1.7E-05 | 1.1E-05 | 1.1E-05 | 3.4E-06 |
| 332 | 1.6E-05 | 1.2E-05 | 2.3E-05 | 6.8E-06 |
| 333 | 0.0E+00 | 0.0E+00 | 0.0E+00 | 0.0E+00 |
| 334 | 8.3E-05 | 6.7E-05 | 5.4E-05 | 1.0E-05 |
| 335 | 5.6E-06 | 4.7E-07 | 2.9E-06 | 1.7E-06 |
| 336 | 0.0E+00 | 0.0E+00 | 0.0E+00 | 0.0E+00 |
| 337 | 1.0E-04 | 1.1E-04 | 1.4E-04 | 7.7E-05 |
| 338 | 2.1E-05 | 1.9E-05 | 1.7E-05 | 8.5E-07 |
| 339 | 0.0E+00 | 0.0E+00 | 0.0E+00 | 8.5E-07 |
| 340 | 1.5E-05 | 4.2E-06 | 1.1E-05 | 3.4E-06 |
| 341 | 0.0E+00 | 0.0E+00 | 0.0E+00 | 0.0E+00 |
| 342 | 0.0E+00 | 0.0E+00 | 0.0E+00 | 0.0E+00 |
| 343 | 0.0E+00 | 0.0E+00 | 0.0E+00 | 0.0E+00 |
| 344 | 0.0E+00 | 0.0E+00 | 4.6E-06 | 0.0E+00 |
| 345 | 0.0E+00 | 0.0E+00 | 0.0E+00 | 0.0E+00 |
| 346 | 0.0E+00 | 0.0E+00 | 0.0E+00 | 0.0E+00 |
| 347 | 1.1E-06 | 1.0E-05 | 1.0E-05 | 8.9E-06 |
| 348 | 0.0E+00 | 0.0E+00 | 0.0E+00 | 0.0E+00 |
| 349 | 7.5E-07 | 4.7E-07 | 5.7E-07 | 4.3E-07 |
| 350 | 0.0E+00 | 0.0E+00 | 0.0E+00 | 0.0E+00 |
| 351 | 0.0E+00 | 9.3E-07 | 5.7E-07 | 8.5E-07 |
| 352 | 5.6E-06 | 0.0E+00 | 1.1E-05 | 1.3E-06 |
| 353 | 0.0E+00 | 0.0E+00 | 0.0E+00 | 0.0E+00 |
| 354 | 1.9E-06 | 9.3E-07 | 4.0E-06 | 2.1E-06 |
| 355 | 0.0E+00 | 0.0E+00 | 0.0E+00 | 0.0E+00 |
| 356 | 0.0E+00 | 0.0E+00 | 0.0E+00 | 0.0E+00 |
| 357 | 1.1E-06 | 1.4E-06 | 0.0E+00 | 8.5E-07 |
| 358 | 0.0E+00 | 0.0E+00 | 0.0E+00 | 0.0E+00 |
| 359 | 3.8E-07 | 0.0E+00 | 0.0E+00 | 0.0E+00 |
| 360 | 0.0E+00 | 0.0E+00 | 0.0E+00 | 0.0E+00 |
| 361 | 0.0E+00 | 4.7E-07 | 0.0E+00 | 0.0E+00 |
| 362 | 0.0E+00 | 1.4E-06 | 4.0E-06 | 0.0E+00 |
| 363 | 0.0E+00 | 0.0E+00 | 0.0E+00 | 0.0E+00 |
| 364 | 0.0E+00 | 4.7E-07 | 0.0E+00 | 4.3E-07 |
| 365 | 1.5E-04 | 1.7E-04 | 5.1E-05 | 1.2E-04 |
| 366 | 7.5E-07 | 4.7E-07 | 0.0E+00 | 0.0E+00 |
| 367 | 0.0E+00 | 0.0E+00 | 0.0E+00 | 0.0E+00 |
| 368 | 5.6E-06 | 2.3E-06 | 4.6E-06 | 1.3E-05 |
| 369 | 6.8E-06 | 7.9E-06 | 1.1E-06 | 4.3E-06 |
| 370 | 0.0E+00 | 0.0E+00 | 0.0E+00 | 0.0E+00 |
| 371 | 6.6E-04 | 2.4E-04 | 8.5E-05 | 0.0E+00 |
| 372 | 0.0E+00 | 0.0E+00 | 0.0E+00 | 0.0E+00 |
| 373 | 1.4E-05 | 1.3E-05 | 1.3E-05 | 1.5E-05 |
| 374 | 0.0E+00 | 0.0E+00 | 0.0E+00 | 0.0E+00 |
| 375 | 1.5E-06 | 0.0E+00 | 5.7E-07 | 0.0E+00 |
| 376 | 7.5E-07 | 0.0E+00 | 1.1E-06 | 0.0E+00 |
| 377 | 1.1E-06 | 3.7E-06 | 1.1E-06 | 4.3E-07 |
| 378 | 4.6E-05 | 2.3E-05 | 1.6E-05 | 1.7E-05 |

Example E. *Lactobacillus johnsonii* Decreases Systemic Inflammation and Genotoxicity in Atm$^{-/-}$ Mice To verify whether individual bacteria were contributing to the differential systemic genotoxicity detected in CM and RM mice, Koch's postulates experiments were performed. The high throughput sequence analysis identified numerous phylotypes exhibiting higher populations in RM than CM mice—a feature that makes them potentially beneficial organisms. It was attempted to culture two of the most abundant of these (FIGS. 4B and 4C), and successfully isolated and grew *L. johnsonii* from RM mice in pure culture.

Figure 6:
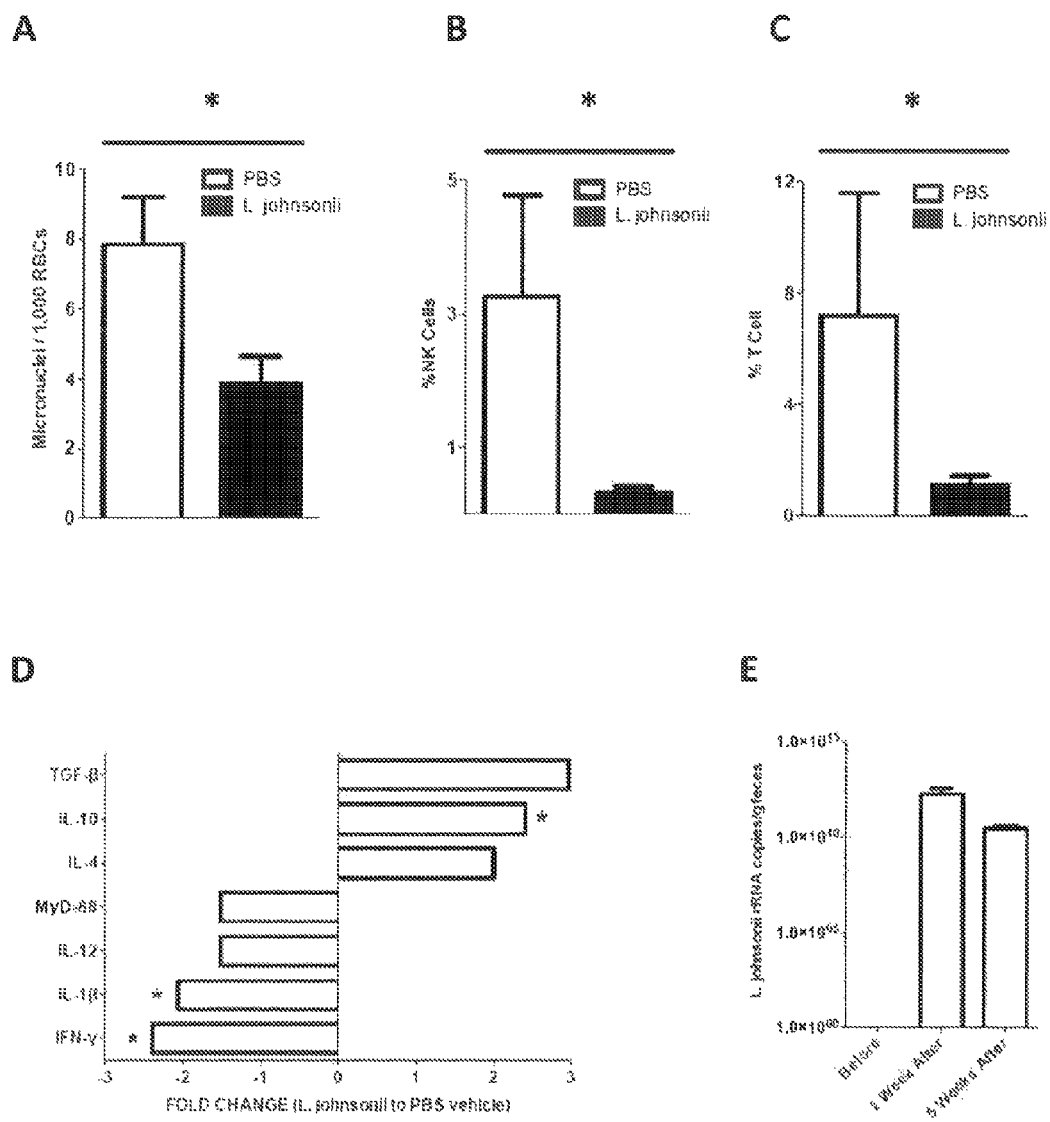
FIG. 6 depicts the effect of oral administration of *L. johnsonii* on genotoxicity and inflammation in CM Atm$^{-/-}$ mice. (A) Systemic genotoxicity was measured by RBC micronuclei quantitation. (B, C) Levels of hepatic NK (B) and T cells (C) were quantitated by flow cytometry for CD335 and CD3 cells, respectively. (D) Hepatic tissue levels of cytokines were measured by ELISA, and fold-change was calculated for *L. johnsonii* relative to vehicle (PBS) control groups. (E) Fecal pellet levels of *L. johnsonii* were quantitated by qPCR. Error bars indicate SE. *=P<0.05 by Student's t tests. Details are described herein, e.g., in Example E.

CM Atm$^{-/-}$ mice were orally gavaged with 109 CFU of *L. johnsonii* every other day for 4 weeks. Fecal qPCR targeting *L. johnsonii* demonstrated the deficiency of this taxon in CM Atm$^{-/-}$ mice, and that this periodic administration resulted in successful establishment and maintenance of high enteric levels *L. johnsonii* (FIG. 6E). After this 4-week period, *L. johnsonii* but not the vehicle control (PBS) resulted in reduced genotoxicity levels (FIG. 6A). This was time dependent, as no difference was observed after only 1 or 2 weeks of treatment (data not shown).

Figure 7:
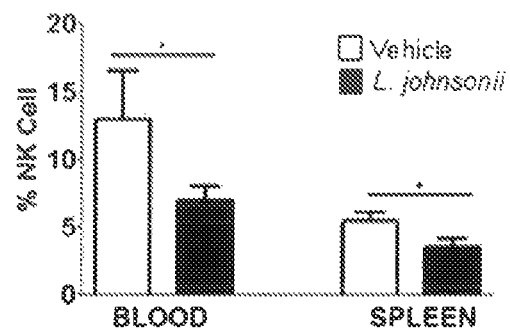
FIG. 7 depicts the effect of oral administration of *L. johnsonii* on inflammation. (A, B) Levels of NK (A) and T cells (B) in blood or spleen were quantitated by flow cytometry for CD335 and CD3 cells, respectively. (C) Blood (serum) levels of cytokines were measured by ELISA, and fold-change was calculated for *L. johnsonii* relative to vehicle (PBS) control groups. Error bars indicate SE. Details are described herein, e.g., in Example E.
Figure 7:
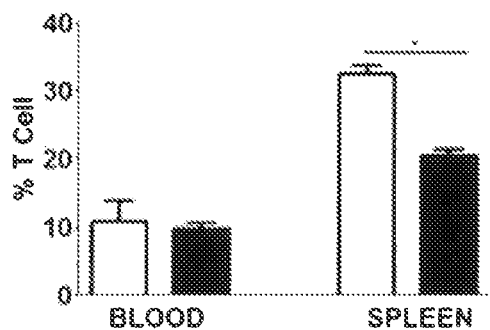
Figure 7:
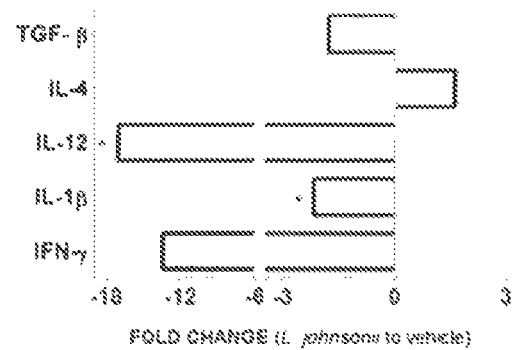
Figure 13:
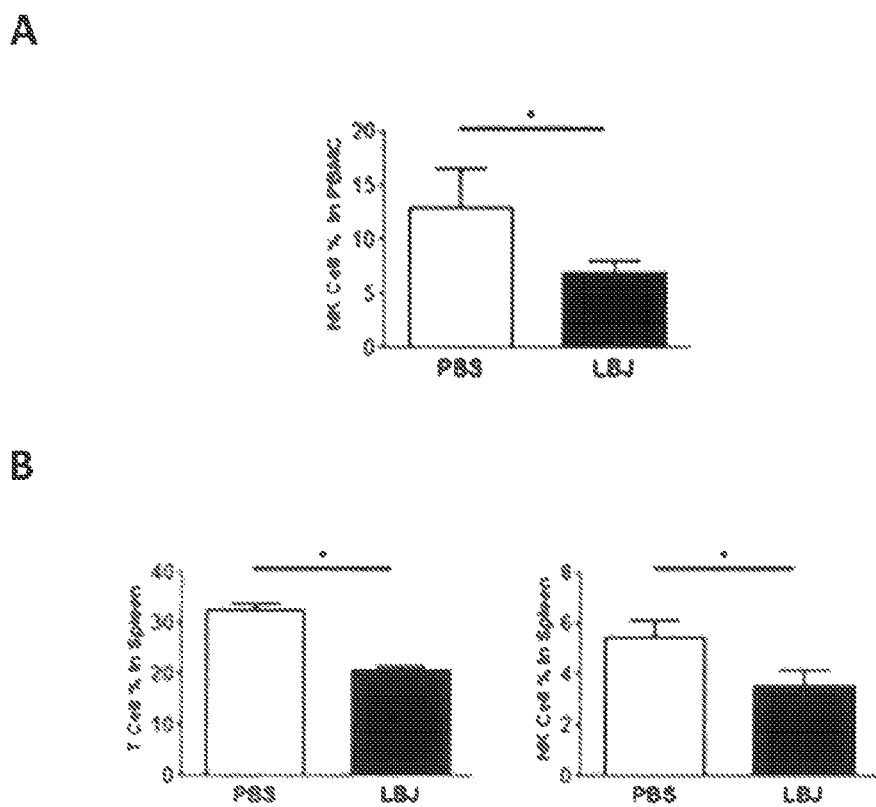
FIG. 13 depicts that inoculation with *L. johnsonii* affects immune cell composition. (A) iNKT cells are decreased in mice inoculated with *L. johnsonii*. Both iNKT and overall T cell ratios are decreased in the spleen (B) of mice inoculated with *L. johnsonii*. n=3 for PBS-inoculated mice and n=6 for *L. johnsonii*-inoculated mice. * indicates p<0.05. Error bars represent the SEM. Details are described in Example E.

Since systemic genotoxicity is induced by innate inflammatory mediators (Westbrook et al., 2009, *Cancer Res* 69:4827-4834, Westbrook et al., 2012, *Mutagenesis* 27:77-86), the effect of *L. johnsonii* administration on basal systemic inflammatory parameters in these mice was analyzed. In the liver, *L. johnsonii* significantly reduced the abundance of both hepatic NK and T cells (FIG. 6B, 6C). A comparable reduction of these leucocyte subsets was also observed in the splenic and blood compartments (FIGS. 7A, B; see also FIG. 13). With respect to molecular mediators, *L. johnsonii* treatment significantly reduced levels of the pro-inflammatory cytokines IL-1β and IFN-γ, and elevated the levels of the anti-inflammatory cytokines TGF-β and IL-10 (FIG. 6D). Similar changes were also observed in the blood compartment (FIG. 7C; see also FIG. 13).

These findings indicate that short-term administration of the single RM-associated bacterium, *L. johnsonii*, recapitulated the reduction of systemic genotoxicity observed in RM mice, a host effect associated with reduced systemic inflammatory activity.

Figure 11:
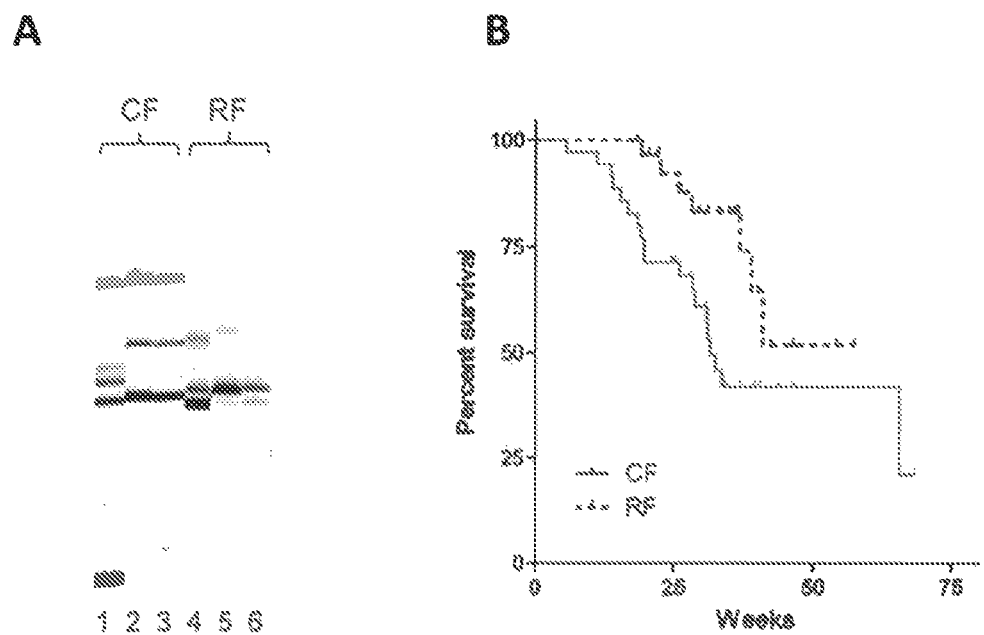
FIG. 11 depicts that CM mice have a shorter lifespan than RM mice. (A) Lanes 1-3 represent samples from RF mice, lanes 4-6 represent samples from conventionalized mice. Each lane represents a different mouse. (B) The Kaplan Meier survival curve of CM and RM mice is significantly different (p<0.05). n=35 and 30 for CM and RM mice, respectively. Details are described in Example F.

Example F. Specifically Altering the Intestinal Microbiota, Creating a Restricted Microbiota Colony and a Conventional Colony Causes a Change in Lifespan in Atm$^{-/-}$ Mice To confirm that the effects we found were due to a change in the intestinal microbiota, more rigorous methods to alter the microbiota were used. Mice from the sterile (SPF-S) facility were used to form two colonies: one with a restricted microbiota (RM, Table 4) and one with a conventional microbiota (CM, Table 4). To form the RM colony, mice were re-derived into an RM colony described previously (Fujiwara et al., 2008, *J Immunol* 180:5843-5852). Since most of the gut colonization occurs within the first few days after birth (Savage, 1977, *Annu Rev Microbiol* 31:107-133), re-derivation ensures that the pups incorporate the microbiome of the foster mother (bacterial rRNA gene spectrum shown in FIG. 11A, lanes 1-3). To form the CM colony, mice were treated with a cocktail of antibiotics for 4 weeks to clear the gut of native microbiota, as described previously (Rakoff-Nahoum et al., 2004; *Cell* 118:229-241). Then the mice were re-inoculated with fecal samples from conventional mice to create conventionalized mice (FIG. 11A, lanes 4-6). The procedure changed their fecal rRNA gene spectrum by both RISA and sequencing analyses; implying that their microbiome was altered (data not shown; e.g., see FIG. 1D).

It was found that the lifespan of conventionalized Atm$^{-/-}$ mice was significantly shorter than the lifespan of sterile-treated mice (SPF-S) (previously reported from our lab (Reliene and Schiestl, 2006a, *DNA Repair* (Amst) 5:852-859, p<0.05) and the RM mice (p<0.05, FIG. 11B). The median survival of conventional mice was 32 weeks versus 51 weeks in the sterile facility (SPF-S) and 80 weeks for the RF mice (FIG. 11B). The median lifespan of mice in the SPF-N colony was 44 weeks, in between the sterile (SPF-S) and CM colonies. Therefore, as microbiota restriction and sterility decrease, lifespan also decreases indicating a positive correlation with life expectancy. Thus, the intestinal microbiota may be responsible for the significant inter- and intra-laboratory differences discussed by Reliene and Schiestl (Reliene and Schiestl, 2006b, *DNA Repair* (Amst) 5:651-653) for Atm and possibly other cancer predisposed mice. By simply exposing isogenic mice from a sterile SPF-S facility to conventional mice, or by more rigorously altering intestinal microbiota, it was possible to affect median lifespan.

Example G. DNA Damage is Increased in Older CM Mice Compared to RM Mice

Figure 12:
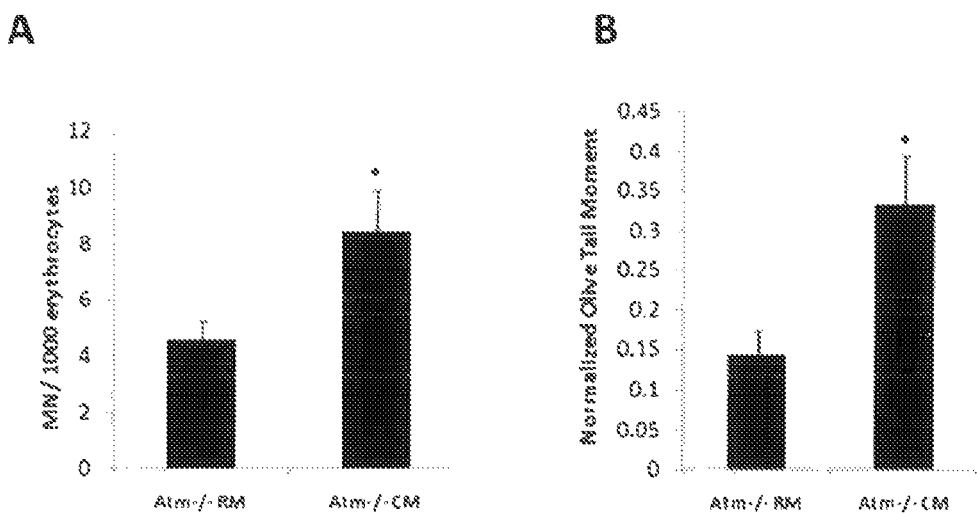
FIG. 12 depicts that CM mice have higher levels of spontaneous DNA damage compared to RM mice. (A) Micronuclei are increased in CM mice compared to RM mice. n=6 for RM mice and n=5 for CM mice. (B) Olive tail moments are increased in CM mice compared to RM mice. n=5 for both groups. * indicates p<0.05 for both figures. Error bars represent the SEM. Details are described in Example G.

To determine if DNA damage was affected by altering the intestinal microbiota, DNA strand breaks and clastogenic damage in the peripheral blood of CM and RM Atm$^{-/-}$ mice was measured. It was found that DNA damage was increased in older (~6 months) CM Atm$^{-/-}$ mice compared to RM mice. These differences were not seen in younger, 8 week old mice or in SPF-N Atm$^{-/-}$ mice compared to SPF-S Atm$^{-/-}$ mice (data not shown). Specifically, it was found that micronuclei and DNA strand breaks were increased in CM Atm$^{-/-}$ mice compared to RM Atm$^{-/-}$ mice (FIG. 12). Micronuclei in peripheral blood erythrocytes were almost 85% higher in CM mice compared to RM mice (FIG. 12A, p<0.05). DNA strand breaks were measured by the alkaline comet assay. Olive Tail Moments which are a ratio of % tail DNA: % comet head DNA were also higher in CM mice compared to RM mice (FIG. 12B, p<0.05). As an additional measure, % tail DNA at the 80th percentile, indicating the more damaged cells, was also assessed and were increased in CM mice compared to RM mice as well (data not shown). Therefore, DNA damage may accumulate and/or be induced to a greater extent in mice with conventional microbiota compared to those with a restricted microbiota which likely contributes to their decreased lifespan.

Figure 14:
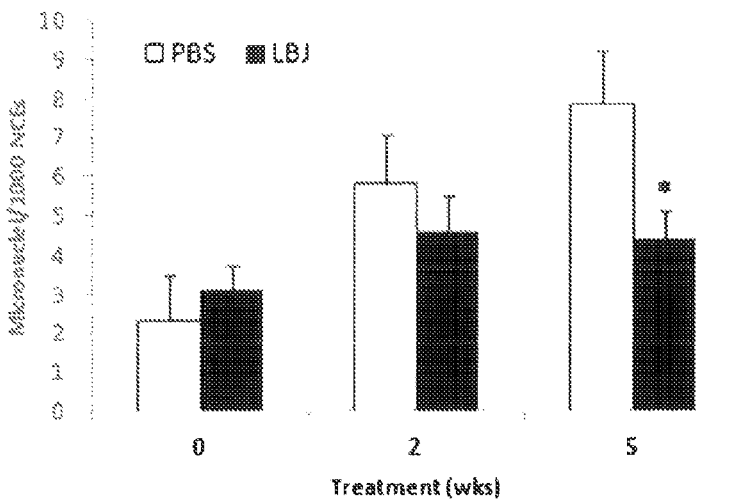
FIG. 14 depicts that inoculation with *L. Johnsonii* decreases MN formation. n=3 for PBS-inoculated mice and n=6 for *L. johnsonii*-inoculated mice. * indicates p<0.05. Error bars represent the SEM. Details are described in Example H.

Example H. Inoculating Mice with *L. johnsonii* Decreases Micronucleus Formation To determine whether inoculation with the protective bacteria, *L. johnsonii*, can affect carcinogenesis, levels of DNA damage were measured. It was found that at the end of a 4-week treatment with *L. johnsonii*, micronucleus formation was decreased by more than 40% compared to PBS-treated Atm-/- mice (FIG. 14, p<0.05).

Example I. *Lactobacillus johnsonii* 456 can be Transferred and Induces Beneficial Effects in Mice Experiments utilizing gradient analysis strategy identified one strong candidate bacterium (*Lactobacillus johnsonii*)

that was protective (Presley et al., 2010, *Appl Environ Microbiol* 76(3):936-41). It has also been shown to have a positive effect on oxidative stress and inflammation in the intestines and prolongs development of diabetes in rats (Valladares et al., 2010, *PLoS One* 5(5):e10507). As described herein, an antibiotic treatment for 7 days followed by daily inoculations of *L. johnsonii* 456 ($10^7$-$10^9$ CFUs) for 14 days showed a trend towards increased levels of the bacteria in the intestines of the mice tested (p=0.099). It was also found that mice treated with $10^7$ CFUs of *L. johnsonii* had a trend towards lower levels of chromosomal breaks as measured by the micronucleus assay (p=0.083 not shown).

Example J. Bacteria which are More Prevalent in RM Mice can be Differentiated from Bacteria which are More Prevalent in CM Mice and Provide Candidates to Target with Pre-, Pro-, and Antibiotics Illumina and ITS rRNA gene analyses have identified candidate bacteria which may have positive effects on longevity and cancer latency (Table 7, left column (A)) as well as candidate bacteria which may have negative effects (Table 7, right column (B)). These lists provide a starting point to narrow down the types and/or species of bacteria which are detrimental or beneficial to the health of people.

TABLE 7

Candidate bacteria having a positive (A) or negative effect (B) on carcinogenesis and longevity.

| A. Bacteria more abundant in RM than CM mice (p < 0.0001) (Potentially beneficial bacteria) | B. Bacteria more abundant in CM than RM mice (p < 0.0001) (Potentially detrimental bacteria) |
|---|---|
| 1. *Lactobacillus johnsonii* | 1. *Dysgonomonas gadei* |
| 2. *Clostridium polysaccharolyticum* | 2. *Prevotellaceae bacterium* P4P_62 |
| 3. *Clostridium populeti* | 3. *Belliella* sp. MIM10 |
| 4. *Eubacterium hadrum* | 4. *Parabacteroides merdae* |
| 5. *Clostridium oroticum* | 5. *Clostridium* sp. AN-AS17 |
| 6. *Barnesiella intestinihominis* | 6. *Capnocytophaga ochracea* |
| 7. *Clostridium fimetarium* | 7. *Pedobacter koreensis* |
| 8. *Acetanaerobacterium elongatum* | 8. *Eubacterium* sp. BU014 |
| 9. *Porphyromonadaceae bacterium* C941 | 9. *Riemerella anatipestifer* |
| 10. *Butyrivibrio crossotus* | 10. *Helicobacter typhlonicus* |
| 11. *Butyricimonas synergistica* | 11. *Petrimonas sulfuriphila* |
| 12. *Clostridium chauvoei* | 12. *Caminicella sporogenes* |
| 13. *Lachnospiraceae bacterium* DJF_VP30 | 13. *Nubsella zeaxanthinifaciens* |
| 14. *Porphyromonas* sp. C1075 | 14. *Porphyromonas* sp. MI10-1288x |
| 15. *Prevotella* sp. oral clone CY006 | 15. *Sphingobacterium* sp. NBRC 15338 |
| 16. *Rumen bacterium* NK4A66 | 16. *Proteiniphilum acetatigenes* |
| 17. *Filifactor alocis* | 17. *Parabacteroides goldsteinii* |
| 18. *Cyanobacterium* sp. MS-B-20 | 18. *Bacteroidetes bacterium* P073B |
| 19. *Clostridium tyrobutyricum* | 19. *Porphyromonas catoniae* |
| 20. *Alistipes onderdonkii* | 20. *Bacteroides nordii*. |
| 21. *Barnesiella vischericola* | |

Example K. Conventional Wildtype Mice (CM) have More Chromosomal Aberrations than Mice in Sterile Conditions (SPF-S)

Figure 16:
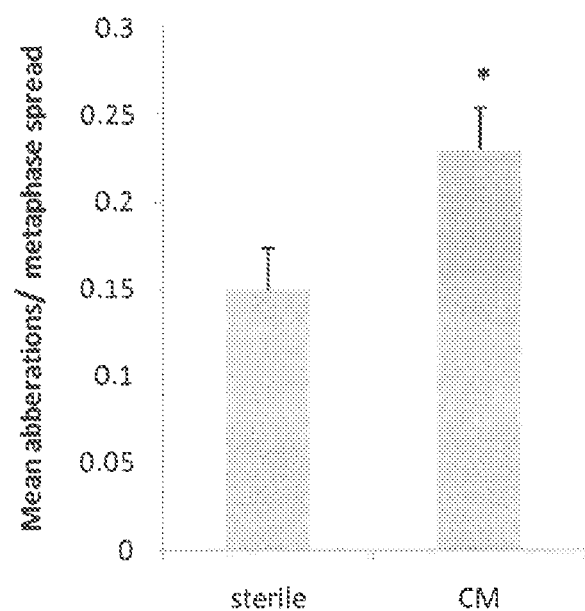
FIG. 16 schematically depicts that the frequency of chromosomal aberrations is increased in CM mice compared to mice housed in sterile (SPF-S) conditions. n=6 mice/group. * indicates p<0.05. Details are described in Example I.

Chromosome and chromatid-type aberrations were determined in bone marrow metaphase cells from CM mice and mice housed in sterile (SPF-S) conditions as described previously Kadhim et al., 1992, *Nature* 355(6362):738-40; Watson et al., 2001, *Int J Radiat Biol* 77(4):409-17). CM mice and mice in sterile (SPF-S) conditions also have differences in microbial composition as determined by RISA (data not shown). CM mice spontaneously displayed 35% more aberrations than RM mice (p<0.05, FIG. 16). This finding provides evidence that CM mice may have a spontaneously increased risk of carcinogenesis.

Figure 17:
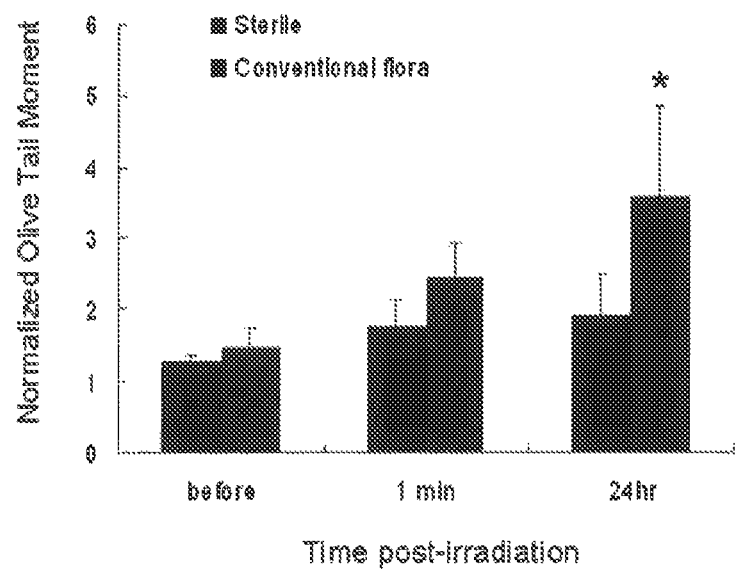
FIG. 17 schematically depicts that DNA Strand breaks and oxidative DNA damage are increased in CF mice 24 hours after 1 Gy γ-irradiation using the modified comet assay with hOGG1. Olive tail moments (comet assay) were normalized to an internal control to account for inter-experimental differences. Statistics was done by ANOVA and repeated measures ANOVA, n=4, sterile (SPF-S) mice, and n=5, CM mice, *, p<0.05. Details are described in Example J.

Example L. DNA Strand Breaks and Oxidative DNA Damage are Increased in CM Mice 24 Hours after Radiation Treatment but not in SPF-S Mice It was also found that oxidative DNA damage is increased in peripheral blood lymphocytes of CM mice compared to those housed in sterile (SPF-S) conditions 24 hours after exposure to 1 Gy γ rays (p<0.05, FIG. 17) as measured by the modified comet assay with hOGG1 (p<0.05), which detects both DNA strand breaks and oxidative DNA damage that can be excised by the enzyme hOGG1. No significant differences were found in sterile (SPF-S) mice using the modified comet assay or in either set of mice using the standard alkaline comet assay. This data indicates that there are differences in the CM mice, which exacerbates DNA damage caused by radiation after 24 hours.

These findings suggest that intestinal microbiota may play a significant role in damage response to ionizing radiation and can both mitigate and enhance the damage depending on the microbial titer and composition.

Example M. Survival of p53-/- Mice Developing Lymphoma

Figure 15:
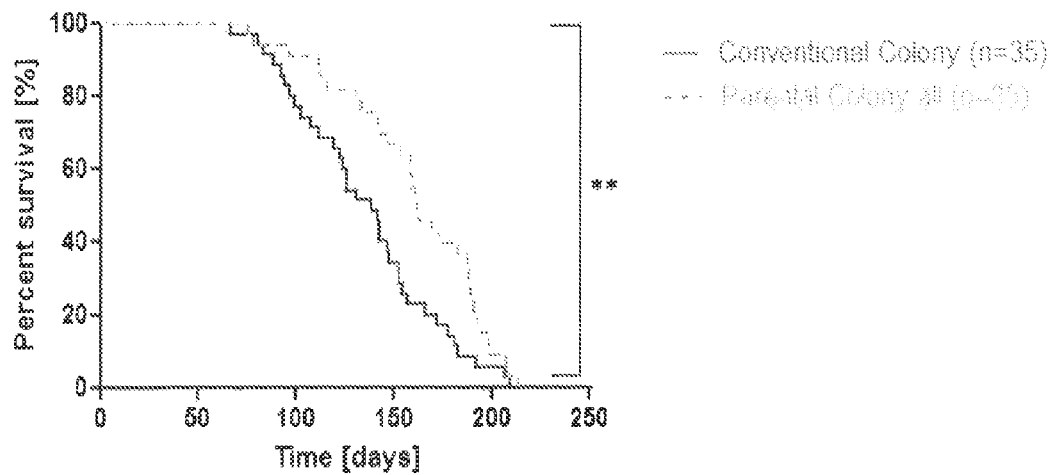
FIG. 15 schematically depicts the survival of p53-/- mice developing lymphoma using methods and compositions of the present invention. Solid line, conventional colony (CM) (n=35); dotted line, parental=restricted microbiota (RM) colony (see above) (n=33); p<0.01. Details are described in Example M.

The first p53 knock-out mice, which were derived from UCLA with a "medium life expectancy", were called the parental colony (PC). The conventional colony (CC) was established by treating a few mice of the parental colony for four weeks with an antibiotic cocktail (ampicillin: 1 g/L; vancomycin: 500 mg/L; neomycin sulphate: 1 g/L and metronidazole: 1 g/L) and subsequently inoculated them with an aqueous fecal suspension from a colony kept conventionally at the in-house animal facility. The PC and CC were housed in the same mouse room, but maintained differently (Table 1). The parental colony received sterile water and autoclaved food, the conventionalized mice tap water and normal food to sustain different microbial community. To generate the restricted colony (RC) the PC additionally was treated with antibiotics for three weeks and inoculated orally with the intestinal microbiota of a "long-lived, late tumor developing, limited flora" from UCLA. These mice were maintained in individually ventilated cages (IVCs) and received sterile water and food. Cages, food and water were changed once a week from animal caretakers. Pups were weaned at the age between 18 to 20 days. In this period they were earmarked with the use of an ear punch. Ear punches or tail tip biopsies were used for DNA isolation and genotyping. There was a highly significant difference in survival between the tumor free survival of the parental colony (PC) and the conventional colony (CC) which is the same as the RM and CM explained as above (see FIG. 15).

Example N. Intestinal Bacteria Modify Lymphoma Penetrance Via Inflammation-Mediated Genotoxicity The results described herein are believed to be the first to show a relationship between intestinal microbiota and lymphoma penetrance. In addition, the investigations described herein generated a detailed catalog of bacterial phylotypes that are differentially abundant between CM and RM mice, thereby providing candidates that may influence a wide range of traits from systemic genotoxicity (as described herein), oxidative stress (as described herein), colitis resistance (Aranda et al., 1997, *J Immunol* 158:3464-3473), pathogen clearance (Chang and Miller, 2006, *Infect Immun* 74:5261-5271) and selective reduction of marginal zone (MZ) B cells (Wei et al., 2008, *Eur J Immunol* 38:3411-3425), plasmacytoid dendritic cells (pDC) (Fujiwara et al., 2008, *J Immunol* 180:5843-5852), and invariant natural killer (iNK) T cells (Wei et al., 2010, *J Immunol* 184:1218-1226). Moreover, Applicants isolated *L. johnsonii* from RM mice and subsequently demonstrated its ability to decrease systemic inflammation and genotoxicity in $Atm^{-/-}$ mice via Koch's postulates experiments. Herein, and without being bound by theory, Applicants propose several mechanistic hypotheses of how *L. johnsonii* might influence these important host traits.

First, *L. johnsonii* may reduce systemic genotoxicity by inhibition of basal intestinal inflammatory activity and its systemic sequelae. Applicants recent work revealed that intestinal inflammation-associated genotoxicity occurred not only locally, but also systemically. Using either a model chemical inflammatory agent, dextran sodium sulfate (DSS), or immune-mediated genetic models to induce local intestinal inflammation, Applicants found that systemic genotoxicity was elevated in peripheral lymphocytes, an effect amplified in $Atm^{-/-}$ vs. wildtype mice (Westbrook et al., 2009, *Cancer Res* 69:4827-4834). Moreover, such lymphocyte genotoxicity is particularly abundant in the B lymphocyte subset, the progenitor cell type for B lymphoma (the predominant cancer in A-T patients) (Westbrook et al., 2011, *Int J Cancer* 129:1815-1825). Genetic and interventional studies revealed that one factor is systemic dispersal of the intestinal cytokine TNFα, that permits genotoxicity in TNFα receptor-bearing lymphocytes remote from the intestinal compartment, in a process dependent on cell-autonomous, NFkB and AP-1 induction of reactive oxygen and nitrogen species (RONS) (Westbrook et al., 2012, *Mutagenesis* 27:77-86).

The present study documents the reduction of several systemic measures of inflammatory activity after *L. johnsonii* restoration in $Atm^{-/-}$ CM mice. There are several known anti-inflammatory mechanisms of *Lactobacillus* sp. that may account for this host response, including products that directly modulate the NFkB inflammatory program of mucosal epithelial and hematopoietic cell types, or indirectly by ecologically changing the composition or functional activity of enteric microbial community (Resta-Lenert and Barrett, 2006, *Gastroenterology* 130:731-746; van Baarlen et al., 2011, *Proc Natl Acad Sci USA* 108 Suppl 1:4562-4569; McNulty et al., 2011, *Sci Transl Med* 3:106ra106; Jounai et al., 2012, *PLoS One* 7:e32588).

The results presented herein also documented that enteric *L. johnsonii* resulted in a reduction in the abundance of hepatic and migratory (blood, splenic) NK and T cells, a reduction also concordant with their reduced levels in CM (Wei et al., 2008, *Eur J Immunol* 38:3411-3425; Fujiwara et al., 2008, *J immunol* 180:5843-5852). The control of NK and T cells in these compartments is complex, integrating a diversity of chemoattractant and trophic cytokines (Brady et al., 2010, *J Immunol* 185:6679-6688; Malamut et al., 2010, *J Clin Invest* 120:2131-2143; Satoh-Takayama et al., 2010, *J Exp Med* 207:273-280; Pachynski et al., 2012, *J Exp Med* 209:1427-1435). *Lactobacillus* sp. may both augment or reduce the production of these key cytokines by parenchymal epithelial and hematopoietic cells, due to differences in host compartment and *Lactobacillus* taxon (Vanderpool et al., 2008, *Bowel Dis* 14:1585-1596; Jounai et al., 2012, *PLoS One* 7:e32588). The present study suggests that enteric (dietary) administration of *L. johnsonii* may represent a viable strategy to reduce inflammation-induced genotoxicity.

The ability of *L. johnsonii* to reduce pathogen-associated inflammation has been demonstrated in several prior in vivo investigations, including two involving *H. pylori*, a known cancer-promoting bacterium. In experiments examining *H. pylori* infection in C57BL/6 mice, oral administration of *L. johnsonii* over a 3-month-period reduced the amounts of lymphocytic and neutrophilic infiltration of the lamina propria as well as proinflammatory chemokines (Sgouras et al., 2005, *Clin Diagn Lab Immunol* 12:1378-1386). Similarly, *L. johnsonii* reduced both *H. pylori* populations and gastritis in Mongolian gerbils (Isobe et al., 2012, *Biosci Biotechnol Biochem* 76:850-852). A single inoculation of 1-day-old chickens with *L. johnsonii* inhibited the colonization and persistence of *Clostridium perfringens*, a poultry pathogen that causes necrotic enteritis (La Ragione et al., 2004, *Lett Appl Microbiol* 38:197-205). Finally, prior inoculation of gerbils with *L. johnsonii* prevented a persistent infection by the protozoan parasite, *Giardia intestinalis* (Humen et al., 2005, *Infect Immun* 73:1265-1269)

Second, analysis of the literature suggests that *L. johnsonii* reduces immune-mediated oxidative stress and systemic genotoxicity by decreasing $NF-k_B$ activation. Linked to cancer and various inflammatory disorders, $NF-k_B$ is involved in managing responses to a wide range of potentially deleterious stimuli. Consistent with an agent that down-regulates $NF-k_B$ activation, *L. johnsonii* and other CM-RM associated microbiota may affect lymphoma penetrance by altering systemic genotoxicity caused by immune-mediated oxidative stress. The results described herein and others demonstrated that oral administration of *L. johnsonii* reduced both oxidative stress (Valladares et al., 2010, *PLoS One* 5:e10507; Joo et al., 2011, *Int Immunopharmacol* 11:1758-1765) and systemic genotoxicity (as described herein). Mechanistically, there are precedents that microbial environments modulate cancer formation in part through oxidative stress mediated by inflammatory or carcinogenic bacterial metabolites on local epithelial cells (Parsonnet, 1995, *Environ Health Perspect* 103 Suppl 8:263-268; Zha et al., 2008, *Proc Natl Acad Sci USA* 105:9302-9306). For example, inflammation that accompanies *H. pylori* infection, *S. haematobium* infection, or human inflammatory bowel disease is associated with elevated risk of stomach, bladder, or colon cancer, respectively (Parsonnet, 1995, *Environ Health Perspect* 103 Suppl 8:263-268; Mostafa et al., 1999, *Clin Microbiol Rev* 12:97-111; Pohl et al., 2000, *Hepatogastroenterology* 47:57-70). In an experimental system examining vaginal infection of mice with the bacterium *Gardnerella vaginalis*, oral administration of *L. johnsonii* reduced levels of proinflammatory cytokines, oxidative stress (iNOS), and activation of NF-kB (Joo et al., 2011, *Immunopharmacol* 11:1758-1765). An important factor linking inflammation to neoplasia is genotoxicity from inflammation-associated oxidative products, created either in trans (due to local oxidative products of inflammatory cells), and cell-autonomously (due to endogenous intracellular oxidative products induced by receptors to TNFα and other cytokines) (Kaser et al., 2008, *Cell* 134:743-756; Todd et al., 2008, *Nat Rev Immunol* 8:663-674). In disease models, enteric colonization of *H. hepaticus* elicits innate immune activation, which via TNF-α and iNOS induction yields host oxidative products required for neoplasia (Rao et al., 2006, *Cancer Res* 66:7395-7400; Erdman et al., 2009, *Proc Natl Acad Sci USA* 106:1027-1032).

Genomic analysis of L. johnsonii revealed several features that may contribute to a superior colonizing ability in the mucosa, and to its ability to outcompete pathogens and other proinflammatory organisms (Pridmore et al., 2004, Proc Natl Acad Sci USA 101:2512-2517). Attachment to the host is often a key feature of mucosa-associated microbes. Putative cell-surface proteins in L. johnsonii have similarity to the mucin binding protein (MUB) from Lactobacillus reuteri (Roos and Jonsson, 2002, Microbiology 148:433-442). In addition, similarities to Fap1 and GspB from Streptococcus species suggest L. johnsonii encodes adhesive and fimbrial proteins, respectively (Bensing and Sullam, 2002, Mol Microbiol 44:1081-1094; Stephenson et al., 2002, Mol Microbiol 43:147-157). Lactobacillus johnsonii also produces a putative cell-surface protein with similarity to an IgA protease, which could enable it to avoid a key host defense mechanism. In addition, L. johnsonii may inhibit potential microbial competitors by producing the bacteriocin Lactacin F and by increasing Paneth cell numbers, which are a host cell type that produces antimicrobial compounds (Allison et al., 1994, J Bacteriol 176:2235-2241; Kingma et al., 2011, J Nutr 141:1023-1028).

Given that intestinal microbiota is a potentially modifiable trait, experiments described herein and insights gained therefrom hold considerable promise for translational intervention of B cell lymphoma and other diseases driven by immune-mediated oxidative stress and its resulting systemic genotoxicity. The translational promise of this approach, exemplified by the studies described herein, suggest that simple interventions such as sustaining enteric levels of L. johnsonii, may favorably shift microbial composition and function to reduce basal levels of genotoxicity in a manner that may reduce cancer risk in susceptible individuals, such as those bearing the A-T genotype.

Applicants describe herein that intestinal microbiota has a (likely direct) effect on the lifespan of Atm-deficient mice. Results indicated that isogenic mice derived from the same colony in which the microbiota had been altered have different lifespans. Restricted microbiota mice were re-derived from the mice in sterile (SPF-S) conditions into a restricted microbiota colony. Applicants' non-sterile (SPF-N) and conventional mice (CM) were also derived from the sterile (SPF-S) colony, and placed in non-sterile (SPF-N) conditions. The conventional microbiota mice, however, were treated with antibiotics followed by re-inoculation with conventional microbiota. In summary, Applicants found that changes in sterility of animal husbandry and direct changes in intestinal microbiota affects the population of microbiota in mice and correlates with a prolonged lifespan and delayed lymphoma onset. Surprisingly, Applicants also found that changes in the sterility, which affect intestinal microbiota, alter DNA deletions in Atm-deficient mice. DNA deletions are a measure of genetic instability and can result in cancer. The Atm-deficient mice were originally located at Harvard University and were housed there in non-sterile (SPF-N) conditions. Upon arriving at UCLA, mice were housed in sterile (SPF-S) conditions until they were moved to non-sterile (SPF-N) conditions as described in Example B. DNA deletions were increased in Atm-deficient mice at Harvard, compared to their wildtype littermates, however, decreased overtime in sterile (SPF-S) conditions until there was no difference between Atm-deficient mice and wildtype mice. Remarkably, once mice were moved to non-sterile (SPF-N) conditions, Atm-deficient mice again had more DNA deletions compared to their wildtype littermates.

Using the description provided herein it is now possible to characterize which bacteria are helpful and harmful. Since each mouse represents its own endpoint with respect to longevity and onset of lymphoma, exact distribution of intestinal microbiota can then be correlated with the cancer phenotype to characterize which bacteria are beneficial and which are detrimental to our health. A similar approach was successfully used in identifying bacterial species involved in intestinal inflammation. In addition it is possible to test how changing microbiota, e.g., as described in Vrese et al. (Adv Biochem Eng Biotechnol 111 (2008) 1-66), can affect lifespan of other cancer-prone as well as wildtype mice.

All publications, including but not limited to patents and patent applications, cited in this specification, to the extent that they provide exemplary procedural or other details supplementary to those set forth herein, are specifically incorporated herein by reference as if each individual publication were specifically and individually indicated to be incorporated by reference herein as though fully set forth.

The invention claimed is:

1. A method for treating, preventing, or delaying the onset of an ataxia telangiectasia (AT)-associated condition, a p53 deficiency, a cancerous condition in a subject having a p53 deficiency, a lung cancer, a sarcoma, a gastrointestinal cancer, a cancer of the genitourinary tract, a liver cancer, a skin cancer, a gynecological cancer, a bone cancer, a cancer of the nervous system, a hematologic cancer, a cancer of the adrenal glands, or a cancer associated with Li Fraumeni Disease, and/or exposure to radiation, in a subject, the method comprising:

administering to the subject a therapeutically effective amount of a composition comprising Lactobacillus johnsonii 456 as deposited at ATCC Deposit Designation No. PTA-124205;

whereby the disease related to genome instability, the ataxia telangiectasia (AT)-associated condition, the p53 deficiency, the cancerous condition in the subject having a p53 deficiency, and/or the exposure to radiation, in the subject is treated or, prevented, or its onset is delayed.

2. The method according to claim 1, wherein the AT-associated condition is selected from a neurological degeneration a condition selected from inability or difficulty of the subject to walk, inability or difficulty of the subject to move, inability or difficulty of the subject to swallow, an immunodeficiency, an inflammatory condition a substantially increased expression level of transforming growth factor type beta, a substantially increased expression level of interleukin (IL)-10, a substantially increased expression level of IL-4, a substantially decreased expression level of myeloid differentiation primary response 88, a substantially decreased expression level of IL-12, a substantially decreased expression level IL-1β, or a substantially decreased expression level of interferon gamma; wherein the substantially increased and substantially decreased expression levels are in comparison to the respective expression levels in a subject not having AT, an inflammation-induced genotoxicity, a radiation sensitivity, an abundance of hepatic and/or migratory cells, a genetic instability, Nijmegen Breakage Syndrome, Fanconi's anemia, Werner Syndrome, Blooms Syndrome, or Li Fraumeni Disease a cancerous condition, hematologic cancer or a lymphoid malignancy.

3. A method for treating, mitigating, or preventing normal tissue damage in a subject being exposed to radiation in a subject, the method comprising:

administering to the subject a therapeutically effective amount of a composition comprising Lactobacillus Johnsonii 456 as deposited at ATCC Deposit Designation No. PTA-124205.

4. The method according to claim 3, comprising both:
(a) administering to the subject a therapeutically effective amount of a composition comprising *Lactobacillus johnsonii* 456; and
(b) inhibiting the growth of one or more detrimental microorganisms in the subject.

5. The method according to claim 1, comprising both:
(a) administering to the subject a therapeutically effective amount of a composition comprising *Lactobacillus johnsonii* 456; and
(b) inhibiting the growth of one or more detrimental microorganisms in the subject.

6. The method according to claim 5, wherein step (b) comprises administering to the subject a therapeutically effective amount of an antibiotic.

7. The method according to claim 5, wherein step (b) comprises administering to the subject a therapeutically effective amount of one or more bacteriophages.

8. The method according to claim 7, wherein the one or more bacteriophages target a detrimental microorganism in *Enterobacter*, *Helicobacter*, *Pseudomonas*, *Escherichia*, *Klebsiella*, *Staphylococcus*, *Proteus*, *Salmonella*, or *Shigella* genera, or *Dysgonomonas gadei*, *Prevotellaceae bacterium* P4P_62, *Belliella* sp. MIM10, *Parabacteroides merdae*, *Clostridium* sp. AN-AS17, *Capnocytophaga ochracea*, *Pedobacter koreensis*, *Eubacterium* sp. BU014, *Riemerella anatipestifer*, *Helicobacter typhlonicus*, *Petrimonas sulfuriphila*, *Caminicella sporogenes*, *Nubsella zeaxanthinifaciens*, *Porphyromonas* sp. MI10-1288x, *Sphingobacterium* sp. NBRC 15338, *Proteiniphilum acetatigenes*, *Parabacteroides goldsteinii*, *Bacteroidetes bacterium* P073B, *Porphyromonas catoniae*, and *Bacteroides nordii*.

9. The method according to claim 7, wherein step (b) comprises administering to the subject a therapeutically effective amount of a combination of bacteriophages.

10. The method according to claim 9, wherein the combination of bacteriophages targets the same detrimental microorganism.

11. The method according to any one of claim 7, wherein the probiotic microorganism and the one or more bacteriophages are administered in the same composition.

12. A composition comprising a therapeutically effective amount of *Lactobacillus johnsonii* 456 as deposited at ATCC Deposit Designation No. PTA-124205 and one or more bacteriophages, wherein the therapeutically effective amount of the probiotic microorganism and one or more bacteriophages, is an amount sufficient to treat, prevent, or delay the onset of an ataxia telangiectasia (AT)-associated condition, a p53 deficiency, or exposure to radiation.

13. The composition according to claim 12, wherein the one or more bacteriophages target a detrimental microorganism in *Enterobacter*, *Helicobacter*, *Pseudomonas*, *Escherichia*, *Klebsiella*, *Staphylococcus*, *Proteus*, *Salmonella*, or *Shigella* genera, or *Dysgonomonas gadei*, *Prevotellaceae bacterium* P4P_62, *Belliella* sp. MIM10, *Parabacteroides merdae*, *Clostridium* sp. AN-AS17, *Capnocytophaga ochracea*, *Pedobacter koreensis*, *Eubacterium* sp. BU014, *Riemerella anatipestifer*, *Helicobacter typhlonicus*, *Petrimonas sulfuriphila*, *Caminicella sporogenes*, *Nubsella zeaxanthinifaciens*, *Porphyromonas* sp. MI10-1288x, *Sphingobacterium* sp. NBRC 15338, *Proteiniphilum acetatigenes*, *Parabacteroides goldsteinii*, *Bacteroidetes bacterium* P073B, *Porphyromonas catoniae*, and *Bacteroides nordii*.

14. The method according to claim 8, wherein the detrimental microorganism is *Enterobacter cloacae*, *Helicobacter acinonychis*, *Helicobacter anseris*, *Helicobacter aurati*, *Helicobacter bilis*, *Helicobacter bizzozeronii*, *Helicobacter brantae*, *Helicobacter canadensis*, *Helicobacter canis*, *Helicobacter cetorum*, *Helicobacter cholecystus*, *Helicobacter cinaedi*, *Helicobacter cynogastricus*, *Helicobacter felis*, *Helicobacter fennelliae*, *Helicobacter ganmani*, *Helicobacter hepaticus*, *Helicobacter mesocricetorum*, *Helicobacter marmotae*, *Helicobacter muridarum*, *Helicobacter mustelae*, *Helicobacter pametensis*, *Helicobacter pullorum*, *Helicobacter pylori*, *Helicobacter rappini*, *Helicobacter rodentium*, *Helicobacter salomonis*, *Helicobacter trogontum*, *Helicobacter typhlonius*, *Helicobacter winghamensis*, *Salmonella enterica*, *Salmonella bongori*, *Salmonella subterranean*, *Salmonella typhimurium*, *Shigella dysenteriae*, *Shigella flexneri*, *Shigella boydii*, and *Shigella sonnei*.

15. The method according to claim 14, wherein the detrimental microorganism is *Enterobacter cloacae*, *Helicobacter acinonychis*, *Helicobacter anseris*, *Helicobacter aurati*, *Helicobacter bilis*, *Helicobacter bizzozeronii*, *Helicobacter brantae*, *Helicobacter canadensis*, *Helicobacter canis*, *Helicobacter cetorum*, *Helicobacter cholecystus*, *Helicobacter cinaedi*, *Helicobacter cynogastricus*, *Helicobacter fells*, *Helicobacter fennelliae*, *Helicobacter ganmani*, *Helicobacter hepaticus*, *Helicobacter mesocricetorum*, *Helicobacter marmotae*, *Helicobacter muridarum*, *Helicobacter mustelae*, *Helicobacter pametensis*, *Helicobacter pullorum*, *Helicobacter pylori*, *Helicobacter rappini*, *Helicobacter rodentium*, *Helicobacter salomonis*, *Helicobacter trogontum*, *Helicobacter typhlonius*, *Helicobacter winghamensis*, *Salmonella enterica*, *Salmonella bongori*, *Salmonella subterranean*, *Salmonella typhimurium*, *Shigella dysenteriae*, *Shigella flexneri*, *Shigella boydii*, and *Shigella sonnei*.

\* \* \* \* \*

UNITED STATES PATENT AND TRADEMARK OFFICE
CERTIFICATE OF CORRECTION

PATENT NO. : 10,028,983 B2
APPLICATION NO. : 14/769734
DATED : July 24, 2018
INVENTOR(S) : Mitsuko L. Yamamoto et al.

It is certified that error appears in the above-identified patent and that said Letters Patent is hereby corrected as shown below:

In Claim 15 (Column 2, Line number 40):
"Helicobacter fells"
Should read:
-- Helicobacter felis --

Signed and Sealed this
Thirtieth Day of October, 2018

Andrei Iancu
*Director of the United States Patent and Trademark Office*